US012576599B2

(12) United States Patent
Cole et al.

(10) Patent No.: US 12,576,599 B2
(45) Date of Patent: Mar. 17, 2026

(54) SYSTEMS, DEVICES, AND METHODS FOR AN ANALYTE SENSOR

(71) Applicant: ABBOTT DIABETES CARE INC., Alameda, CA (US)

(72) Inventors: Jean-Pierre Cole, Tracy, CA (US); Peter Voit, Dublin, CA (US); Edward Kupa, Alameda, CA (US); Matthew Simmons, Pleasanton, CA (US); Steven Mitchell, Pleasant Hill, CA (US); Timothy Frederick Smith, San Ramon, CA (US); Vivek Rao, Alameda, CA (US); Peter Robinson, Alamo, CA (US); Theodore Kunich, Pleasanton, CA (US); Anthony Joseph San Nicolas, Reno, NV (US); Louis Pace, San Carlos, CA (US); Steve Nierlich, Berkley, CA (US); Dharmendra Patel, Oxfordshire (GB); Thomas Michael Meyer, Fremont, CA (US); Byron J. Lambert, Temecula, CA (US); Stephen T. Pudjijanto, San Ramon, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 0 days.

(21) Appl. No.: 17/475,111

(22) Filed: Sep. 14, 2021

(65) Prior Publication Data

US 2022/0080678 A1      Mar. 17, 2022

Related U.S. Application Data

(60) Provisional application No. 63/081,223, filed on Sep. 21, 2020, provisional application No. 63/078,681, filed on Sep. 15, 2020.

(51) Int. Cl.
B29C 65/48          (2006.01)
A61B 5/00           (2006.01)
(Continued)

(52) U.S. Cl.
CPC ............ B29C 65/48 (2013.01); A61B 5/6849 (2013.01); B29C 65/4835 (2013.01);
(Continued)

(58) Field of Classification Search
CPC ................ B29C 65/48; B29C 65/4835; B29C 65/4845; B29C 65/82; A61B 5/6849;
(Continued)

(56) References Cited

U.S. PATENT DOCUMENTS 2,892,990 A      6/1959   Werndl
3,517,670 A      6/1970   Speelman
(Continued)

FOREIGN PATENT DOCUMENTS

CA              2291105          12/1998
CA              2 766 693 A1      9/2011
(Continued)

OTHER PUBLICATIONS

Swanson, "Advances in Light Curing Adhesives and Coatings Lead to Process and Quality Benefits in Electronics Manufacturing", Intertronics, 2017. (Year: 2017).*

(Continued)

*Primary Examiner* — Christopher W Raimund
(74) *Attorney, Agent, or Firm* — ONE LLP

(57)                    ABSTRACT

A method includes assembling a sensor subassembly that includes a sensor, a sensor mount, a collar, a sharp, and a sensor cap. The method includes loading a sensor in a sensor mount; dispensing adhesive into a mount channel of the sensor mount; clamping a collar to the sensor mount; and curing the adhesive to fix the collar to the sensor mount. The
(Continued)

method can also include inserting a sharp into the sensor mount over the sensor an attaching a sensor cap to the sensor and sensor sharp to provide a sealed sensor subassembly. Methods of assembling an on-body sensor puck assembly and an applicator assembly, and a sensor including a tail, a flag, and a neck that interconnects the tail and the flag and methods of configuring a sensor are also disclosed.

16 Claims, 82 Drawing Sheets

(51) Int. Cl.
  *B29C 65/82*        (2006.01)
  *B29L 31/00*        (2006.01)
(52) U.S. Cl.
  CPC .......... *B29C 65/4845* (2013.01); *B29C 65/82*
      (2013.01); *A61B 2562/12* (2013.01); *B29L*
      *2031/752* (2013.01)
(58) Field of Classification Search
  CPC ..... A61B 2562/12; A61B 5/6848; A61B 5/01;
      A61B 5/0205; A61B 5/021; A61B 5/024;
      A61B 5/1118; A61B 5/1451; A61B
      5/14532; A61B 5/14542; A61B 5/14546;
      A61B 5/14503; B29L 2031/752
  See application file for complete search history.

(56)            References Cited

U.S. PATENT DOCUMENTS

| | | | |
|---|---|---|---|
| 3,960,497 | A | 6/1976 | Acord et al. |
| 4,033,330 | A | 7/1977 | Willis et al. |
| 4,464,170 | A | 8/1984 | Clemens et al. |
| 4,553,541 | A | 11/1985 | Burns |
| 4,561,963 | A | 12/1985 | Owen et al. |
| 4,592,745 | A | 6/1986 | Rex et al. |
| 4,627,445 | A | 12/1986 | Garcia et al. |
| 4,639,062 | A | 1/1987 | Taniguchi et al. |
| 4,752,935 | A | 6/1988 | Beck |
| 4,847,785 | A | 7/1989 | Stephens |
| 4,861,454 | A | 8/1989 | Ushizawa et al. |
| 4,924,879 | A | 5/1990 | O'Brien |
| 4,985,142 | A | 1/1991 | Laycock et al. |
| 5,086,246 | A | 2/1992 | Dymond et al. |
| 5,089,112 | A | 2/1992 | Skotheim et al. |
| 5,165,407 | A | 11/1992 | Wilson et al. |
| 5,188,534 | A | 2/1993 | Bertho et al. |
| 5,193,545 | A | 3/1993 | Marsoner et al. |
| 5,204,264 | A | 4/1993 | Kaminer et al. |
| 5,231,988 | A | 8/1993 | Wernicke et al. |
| 5,243,696 | A | 9/1993 | Carr et al. |
| 5,251,126 | A | 10/1993 | Kahn et al. |
| 5,259,793 | A | 11/1993 | Yamada et al. |
| 5,267,963 | A | 12/1993 | Bachynsky |
| 5,318,583 | A | 6/1994 | Rabenau et al. |
| 5,322,063 | A | 6/1994 | Allen et al. |
| 5,356,420 | A | 10/1994 | Czernecki et al. |
| 5,384,547 | A | 1/1995 | Lynk et al. |
| 5,390,671 | A | 2/1995 | Lord et al. |
| 5,391,250 | A | 2/1995 | Cheney et al. |
| 5,407,431 | A | 4/1995 | Botich et al. |
| 5,438,983 | A | 8/1995 | Falcone |
| 5,482,473 | A | 1/1996 | Lord et al. |
| 5,484,403 | A | 1/1996 | Yoakum et al. |
| 5,529,676 | A | 6/1996 | Maley et al. |
| 5,555,190 | A | 9/1996 | Derby et al. |
| 5,564,434 | A | 10/1996 | Halperin et al. |
| 5,568,806 | A | 10/1996 | Cheney, II et al. |
| 5,569,186 | A | 10/1996 | Lord et al. |
| 5,584,813 | A | 12/1996 | Livingston et al. |
| 5,586,553 | A | 12/1996 | Halili et al. |
| 5,591,137 | A | 1/1997 | Stevens |
| 5,593,852 | A | 1/1997 | Heller et al. |
| 5,626,566 | A | 5/1997 | Petersen et al. |
| 5,660,163 | A | 8/1997 | Schulman et al. |
| 5,669,543 | A | 9/1997 | Ueno |
| 5,700,360 | A | 12/1997 | Chan et al. |
| 5,726,646 | A | 3/1998 | Bane et al. |
| 5,738,220 | A | 4/1998 | Geszler |
| 5,746,217 | A | 5/1998 | Erickson et al. |
| 5,786,439 | A | 7/1998 | Van Antwerp et al. |
| 5,807,375 | A | 9/1998 | Gross et al. |
| 5,820,570 | A | 10/1998 | Erickson et al. |
| 5,849,174 | A | 12/1998 | Sanghera et al. |
| 5,865,804 | A | 2/1999 | Bachynsky |
| 5,879,311 | A | 3/1999 | Duchon et al. |
| 5,914,026 | A | 6/1999 | Blubaugh, Jr. et al. |
| 5,919,141 | A | 7/1999 | Money et al. |
| 5,921,963 | A | 7/1999 | Erez et al. |
| 5,951,492 | A | 9/1999 | Douglas et al. |
| 5,954,643 | A | 9/1999 | VanAntwerp et al. |
| 5,971,941 | A | 10/1999 | Simons et al. |
| 6,001,067 | A | 12/1999 | Shults et al. |
| 6,048,352 | A | 4/2000 | Douglas et al. |
| 6,066,243 | A | 5/2000 | Anderson et al. |
| 6,081,736 | A | 6/2000 | Colvin et al. |
| 6,088,605 | A | 7/2000 | Griffith et al. |
| 6,088,608 | A | 7/2000 | Schulman et al. |
| 6,093,172 | A | 7/2000 | Funderburk et al. |
| 6,099,484 | A | 8/2000 | Douglas et al. |
| 6,102,896 | A | 8/2000 | Roser |
| 6,103,033 | A | 8/2000 | Say et al. |
| 6,106,484 | A | 8/2000 | Terwilliger et al. |
| 6,132,449 | A | 10/2000 | Lum et al. |
| 6,134,461 | A | 10/2000 | Say et al. |
| 6,149,626 | A | 11/2000 | Bachynsky et al. |
| 6,157,850 | A | 12/2000 | Diab et al. |
| 6,159,181 | A | 12/2000 | Crossman et al. |
| 6,175,752 | B1 | 1/2001 | Say et al. |
| 6,180,221 | B1 | 1/2001 | Crotzer et al. |
| 6,192,891 | B1 | 2/2001 | Gravel et al. |
| 6,203,354 | B1 | 3/2001 | Kuwahara et al. |
| 6,212,417 | B1 | 4/2001 | Ikeda et al. |
| 6,223,283 | B1 | 4/2001 | Chaiken et al. |
| 6,233,471 | B1 | 5/2001 | Berner et al. |
| 6,237,394 | B1 | 5/2001 | Harris et al. |
| 6,248,067 | B1 | 6/2001 | Causey, III et al. |
| 6,275,717 | B1 | 8/2001 | Gross et al. |
| 6,283,982 | B1 | 9/2001 | Levaughn et al. |
| 6,293,925 | B1 | 9/2001 | Safabash et al. |
| 6,340,588 | B1 | 1/2002 | Nova et al. |
| 6,359,270 | B1 | 3/2002 | Bridson |
| 6,364,890 | B1 | 4/2002 | Lum et al. |
| 6,377,829 | B1 | 4/2002 | Al-Ali |
| 6,400,974 | B1 | 6/2002 | Lesho |
| 6,424,847 | B1 | 7/2002 | Mastrototaro et al. |
| 6,458,109 | B1 | 10/2002 | Henley et al. |
| 6,471,689 | B1 | 10/2002 | Joseph et al. |
| 6,537,242 | B1 | 3/2003 | Palmer |
| 6,546,268 | B1 | 4/2003 | Ishikawa et al. |
| 6,560,471 | B1 | 5/2003 | Heller et al. |
| 6,565,509 | B1 | 5/2003 | Say et al. |
| 6,574,490 | B2 | 6/2003 | Abbink et al. |
| 6,575,895 | B1 | 6/2003 | Blair |
| 6,579,690 | B1 | 6/2003 | Bonnecaze et al. |
| 6,602,268 | B2 | 8/2003 | Kuhr et al. |
| 6,607,543 | B2 | 8/2003 | Purcell et al. |
| 6,631,281 | B1 | 10/2003 | Kastle |
| 6,637,611 | B2 | 10/2003 | Luch |
| 6,673,022 | B1 | 1/2004 | Bobo et al. |
| 6,695,860 | B1 | 2/2004 | Ward et al. |
| 6,721,582 | B2 | 4/2004 | Trepagnier et al. |
| 6,730,025 | B1 | 5/2004 | Platt |
| 6,741,877 | B1 | 5/2004 | Shults et al. |
| 6,758,835 | B2 | 7/2004 | Close et al. |
| 6,809,653 | B1 | 10/2004 | Mann et al. |
| 6,850,859 | B1 | 2/2005 | Schuh |
| 6,923,763 | B1 | 8/2005 | Kovatchev et al. |
| 6,931,327 | B2 | 8/2005 | Goode, Jr. et al. |
| 6,954,662 | B2 | 10/2005 | Freger et al. |
| 6,960,192 | B1 | 11/2005 | Flaherty et al. |

(56) References Cited

U.S. PATENT DOCUMENTS

| | | | |
|---|---|---|---|
| 6,965,791 B1 | 11/2005 | Hitchcock et al. |
| 6,990,366 B2 | 1/2006 | Say et al. |
| 6,999,854 B2 | 2/2006 | Roth |
| 7,003,341 B2 | 2/2006 | Say et al. |
| 7,015,817 B2 | 3/2006 | Copley et al. |
| 7,016,713 B2 | 3/2006 | Gardner et al. |
| 7,022,219 B2 | 4/2006 | Mansouri et al. |
| 7,027,848 B2 | 4/2006 | Robinson et al. |
| 7,027,859 B1 | 4/2006 | McNichols et al. |
| 7,041,057 B1 | 5/2006 | Faupel et al. |
| 7,046,153 B2 | 5/2006 | Oja et al. |
| 7,110,803 B2 | 9/2006 | Shults et al. |
| 7,120,483 B2 | 10/2006 | Russel et al. |
| 7,123,950 B2 | 10/2006 | Mannheimer |
| 7,134,999 B2 | 11/2006 | Brauker et al. |
| 7,144,384 B2 | 12/2006 | Gorman et al. |
| 7,169,600 B2 | 1/2007 | Hoss et al. |
| 7,174,199 B2 | 2/2007 | Berner et al. |
| 7,179,226 B2 | 2/2007 | Crothall et al. |
| 7,207,974 B2 | 4/2007 | Safabash et al. |
| 7,223,276 B2 | 5/2007 | List et al. |
| 7,299,082 B2 | 11/2007 | Feldman et al. |
| 7,310,544 B2 | 12/2007 | Brister et al. |
| 7,323,142 B2 | 1/2008 | Pendo et al. |
| 7,344,500 B2 | 3/2008 | Talbot et al. |
| 7,381,184 B2 | 6/2008 | Funderburk et al. |
| 7,407,493 B2 | 8/2008 | Cane |
| 7,433,727 B2 | 10/2008 | Ward |
| 7,468,125 B2 | 12/2008 | Kraft et al. |
| 7,481,819 B2 | 1/2009 | Koeppel et al. |
| 7,525,315 B2 | 4/2009 | Fredette et al. |
| 7,582,059 B2 | 9/2009 | Funderburk et al. |
| 7,585,287 B2 | 9/2009 | Bresina et al. |
| 7,635,594 B2 | 12/2009 | Holmes et al. |
| 7,651,845 B2 | 1/2010 | Doyle, III et al. |
| 7,660,615 B2 | 2/2010 | VanAntwerp et al. |
| 7,699,775 B2 | 4/2010 | Desai et al. |
| 7,699,807 B2 | 4/2010 | Faust et al. |
| 7,715,893 B2 | 5/2010 | Kamath et al. |
| 7,725,148 B2 | 5/2010 | Shah et al. |
| 7,729,737 B2 | 6/2010 | Ward |
| 7,731,691 B2 | 6/2010 | Cote et al. |
| 7,736,310 B2 | 6/2010 | Taub et al. |
| 7,811,231 B2 | 10/2010 | Jin et al. |
| 7,837,633 B2 | 11/2010 | Conway et al. |
| 7,846,132 B2 | 12/2010 | Gravesen et al. |
| 7,850,652 B2 | 12/2010 | Liniger et al. |
| 7,867,244 B2 | 1/2011 | Lathrop et al. |
| 7,883,473 B2 | 2/2011 | LeVaughn et al. |
| 7,896,844 B2 | 3/2011 | Thalmann et al. |
| 7,899,545 B2 | 3/2011 | John |
| 7,920,906 B2 | 4/2011 | Goode, Jr. et al. |
| 7,938,797 B2 | 5/2011 | Estes |
| 7,941,200 B2 | 5/2011 | Weinart et al. |
| 7,946,984 B2 | 5/2011 | Brister et al. |
| 7,955,297 B2 | 6/2011 | Radmer et al. |
| 7,970,449 B2 | 6/2011 | Ward |
| 7,972,296 B2 | 7/2011 | Braig et al. |
| 7,985,203 B2 | 7/2011 | Haueter et al. |
| 7,996,158 B2 | 8/2011 | Hayter et al. |
| 8,005,524 B2 | 8/2011 | Brauker et al. |
| 8,010,256 B2 | 8/2011 | Oowada |
| 8,016,774 B2 | 9/2011 | Freeman et al. |
| 8,028,837 B2 | 10/2011 | Gerstle et al. |
| 8,029,442 B2 | 10/2011 | Funderburk et al. |
| 8,103,471 B2 | 1/2012 | Hayter |
| 8,140,312 B2 | 3/2012 | Hayter et al. |
| 8,160,670 B2 | 4/2012 | Quyang et al. |
| 8,160,900 B2 | 4/2012 | Taub et al. |
| 8,172,805 B2 | 5/2012 | Mogensen et al. |
| 8,175,673 B2 | 5/2012 | Say et al. |
| 8,192,394 B2 | 6/2012 | Estes et al. |
| 8,216,138 B1 | 7/2012 | McGaraugh et al. |
| 8,221,332 B2 | 7/2012 | Robbins et al. |
| 8,224,410 B2 | 7/2012 | Hadvary et al. |
| 8,239,166 B2 | 8/2012 | Hayter et al. |
| 8,255,026 B1 | 8/2012 | Al-Ali |
| 8,260,558 B2 | 9/2012 | Hayter et al. |
| 8,262,618 B2 | 9/2012 | Scheurer |
| 8,268,143 B2 | 9/2012 | Liu et al. |
| 8,280,474 B2 | 10/2012 | Liu et al. |
| 8,282,549 B2 | 10/2012 | Brauker et al. |
| 8,346,335 B2 | 1/2013 | Harper et al. |
| 8,346,337 B2 | 1/2013 | Heller et al. |
| 8,374,668 B1 | 2/2013 | Hayter et al. |
| 8,376,945 B2 | 2/2013 | Hayter et al. |
| 8,377,271 B2 | 2/2013 | Mao et al. |
| 8,382,671 B2 | 2/2013 | Anthony et al. |
| 8,382,681 B2 | 2/2013 | Escutia et al. |
| 8,398,664 B2 | 3/2013 | Lamps et al. |
| 8,409,093 B2 | 4/2013 | Bugler |
| 8,409,145 B2 | 4/2013 | Raymond et al. |
| 8,444,560 B2 | 5/2013 | Hayter et al. |
| 8,461,985 B2 | 6/2013 | Fennell et al. |
| 8,469,986 B2 | 6/2013 | Schraga |
| 8,515,519 B2 | 8/2013 | Brister et al. |
| 8,560,038 B2 | 10/2013 | Hayter et al. |
| 8,571,808 B2 | 10/2013 | Hayter |
| 8,583,205 B2 | 11/2013 | Budiman et al. |
| 8,597,570 B2 | 12/2013 | Terashima et al. |
| 8,600,681 B2 | 12/2013 | Hayter et al. |
| 8,612,163 B2 | 12/2013 | Hayter et al. |
| 8,671,237 B2 | 3/2014 | Ma et al. |
| 8,682,408 B2 | 3/2014 | Boock et al. |
| 8,682,615 B2 | 3/2014 | Hayter et al. |
| 8,710,993 B2 | 4/2014 | Hayter et al. |
| 8,747,363 B2 | 6/2014 | Nielsen et al. |
| 8,750,955 B2 | 6/2014 | Brister et al. |
| 8,834,366 B2 | 9/2014 | Hayter et al. |
| 8,845,536 B2 | 9/2014 | Brauker et al. |
| 8,870,822 B2 | 10/2014 | Thalmann et al. |
| 8,880,138 B2 | 11/2014 | Cho |
| 8,945,056 B2 | 2/2015 | Lio et al. |
| 9,060,719 B2 | 6/2015 | Hayter et al. |
| 9,186,098 B2 | 11/2015 | Lee et al. |
| 9,241,631 B2 | 1/2016 | Valdes et al. |
| 9,265,453 B2 | 2/2016 | Curry et al. |
| 9,289,179 B2 | 3/2016 | Hayter et al. |
| 9,295,786 B2 | 3/2016 | Gottlieb et al. |
| 9,357,951 B2 | 6/2016 | Simpson et al. |
| 9,398,872 B2 | 7/2016 | Hayter et al. |
| 9,402,544 B2 | 8/2016 | Yee et al. |
| 9,439,586 B2 | 9/2016 | Bugler |
| 9,474,479 B2 | 10/2016 | Pusey et al. |
| 9,480,421 B2 | 11/2016 | Stafford |
| 9,483,608 B2 | 11/2016 | Hayter et al. |
| 9,504,471 B2 | 11/2016 | Vaitekunas et al. |
| 9,558,325 B2 | 1/2017 | Hayter et al. |
| 9,566,384 B2 | 2/2017 | Gyrn et al. |
| 9,615,779 B2 | 4/2017 | Pryor et al. |
| 9,668,682 B2 | 6/2017 | Brister et al. |
| 9,743,876 B2 | 8/2017 | Gelfand et al. |
| 9,788,766 B2 | 10/2017 | Simpson et al. |
| 9,808,574 B2 | 11/2017 | Yodfat et al. |
| 10,213,139 B2 | 2/2019 | Rao et al. |
| 10,292,632 B2 | 5/2019 | Lee et al. |
| 10,772,547 B1 | 9/2020 | Lee et al. |
| 10,820,842 B2 | 11/2020 | Harper |
| 10,827,954 B2 | 11/2020 | Hoss et al. |
| 10,874,338 B2 | 12/2020 | Stafford |
| 10,881,341 B1 | 1/2021 | Curry et al. |
| 10,945,647 B2 | 3/2021 | Mazza et al. |
| 10,945,649 B2 | 3/2021 | Lee et al. |
| 10,952,653 B2 | 3/2021 | Harper |
| 10,959,654 B2 | 3/2021 | Curry et al. |
| 10,966,644 B2 | 4/2021 | Stafford |
| 10,973,443 B2 | 4/2021 | Funderburk et al. |
| 10,980,461 B2 | 4/2021 | Simpson et al. |
| 11,000,213 B2 | 5/2021 | Kamath et al. |
| 11,000,216 B2 | 5/2021 | Curry et al. |
| 11,013,440 B2 | 5/2021 | Lee et al. |
| 11,064,917 B2 | 7/2021 | Simpson et al. |
| 11,116,430 B2 | 9/2021 | Funderburk et al. |
| 11,141,084 B2 | 10/2021 | Funderburk et al. |

(56) References Cited

U.S. PATENT DOCUMENTS

| | | |
|---|---|---|
| 11,202,591 B2 | 12/2021 | Yee et al. |
| 11,246,519 B2 | 2/2022 | Donnay et al. |
| 11,266,335 B2 | 3/2022 | Donnay et al. |
| 11,298,056 B2 | 4/2022 | Harper |
| 11,510,625 B2 | 11/2022 | Gray et al. |
| 2001/0034479 A1 | 10/2001 | Ring et al. |
| 2002/0002344 A1 | 1/2002 | Douglas et al. |
| 2002/0016534 A1 | 2/2002 | Trepagnier et al. |
| 2002/0022855 A1 | 2/2002 | Bobroff et al. |
| 2002/0032386 A1 | 3/2002 | Sackner et al. |
| 2002/0032531 A1 | 3/2002 | Mansky et al. |
| 2002/0057993 A1 | 5/2002 | Maisey et al. |
| 2002/0072720 A1 | 6/2002 | Hague et al. |
| 2002/0095076 A1 | 7/2002 | Krausman et al. |
| 2002/0117639 A1 | 8/2002 | Paolini et al. |
| 2002/0120186 A1 | 8/2002 | Keimel |
| 2002/0147135 A1 | 10/2002 | Schnell |
| 2002/0150959 A1 | 10/2002 | Lejeune et al. |
| 2002/0161288 A1 | 10/2002 | Shin et al. |
| 2002/0169369 A1 | 11/2002 | Ward et al. |
| 2002/0169439 A1 | 11/2002 | Flaherty |
| 2003/0023189 A1 | 1/2003 | Kuo |
| 2003/0032077 A1 | 2/2003 | Itoh et al. |
| 2003/0042137 A1 | 3/2003 | Mao et al. |
| 2003/0050546 A1 | 3/2003 | Desai et al. |
| 2003/0054428 A1 | 3/2003 | Monfre et al. |
| 2003/0055380 A1 | 3/2003 | Flaherty |
| 2003/0069509 A1 | 4/2003 | Matzinger et al. |
| 2003/0097082 A1 | 5/2003 | Purdy et al. |
| 2003/0100040 A1 | 5/2003 | Bonnecaze et al. |
| 2003/0100821 A1 | 5/2003 | Heller et al. |
| 2003/0114836 A1 | 6/2003 | Estes et al. |
| 2003/0135127 A1 | 7/2003 | Sackner et al. |
| 2003/0187338 A1 | 10/2003 | Say et al. |
| 2003/0199744 A1 | 10/2003 | Buse et al. |
| 2003/0225361 A1 | 12/2003 | Sabra |
| 2003/0225373 A1 | 12/2003 | Bobroff et al. |
| 2003/0225474 A1 | 12/2003 | Bobroff et al. |
| 2003/0236489 A1 | 12/2003 | Jacobson et al. |
| 2004/0002682 A1 | 1/2004 | Kovelman et al. |
| 2004/0010207 A1 | 1/2004 | Flaherty et al. |
| 2004/0015131 A1 | 1/2004 | Flaherty et al. |
| 2004/0030726 A1 | 2/2004 | Baxter et al. |
| 2004/0034289 A1 | 2/2004 | Teller et al. |
| 2004/0061232 A1 | 4/2004 | Shah et al. |
| 2004/0087876 A1 | 5/2004 | Eskuri |
| 2004/0098684 A1 | 5/2004 | Amekawa |
| 2004/0098685 A1 | 5/2004 | Higuchi |
| 2004/0106858 A1 | 6/2004 | Say et al. |
| 2004/0107971 A1 | 6/2004 | De |
| 2004/0111017 A1 | 6/2004 | Say et al. |
| 2004/0117204 A1 | 6/2004 | Mazar et al. |
| 2004/0133164 A1 | 7/2004 | Funderburk et al. |
| 2004/0133390 A1 | 7/2004 | Osorio et al. |
| 2004/0135571 A1 | 7/2004 | Uutela et al. |
| 2004/0142403 A1 | 7/2004 | Hetzel et al. |
| 2004/0147872 A1 | 7/2004 | Thompson |
| 2004/0162521 A1 | 8/2004 | Bengtsson et al. |
| 2004/0162678 A1 | 8/2004 | Hetzel et al. |
| 2004/0186365 A1 | 9/2004 | Jin et al. |
| 2004/0204673 A1 | 10/2004 | Flaherty |
| 2004/0204687 A1 | 10/2004 | Mogensen et al. |
| 2004/0206916 A1 | 10/2004 | Colvin, Jr. et al. |
| 2004/0249253 A1 | 12/2004 | Racchini et al. |
| 2005/0009379 A1 | 1/2005 | Huang et al. |
| 2005/0027181 A1 | 2/2005 | Goode, Jr. et al. |
| 2005/0027463 A1 | 2/2005 | Goode, Jr. et al. |
| 2005/0033132 A1 | 2/2005 | Shults et al. |
| 2005/0037184 A1 | 2/2005 | Halsey, IV et al. |
| 2005/0038332 A1 | 2/2005 | Saidara et al. |
| 2005/0038465 A1 | 2/2005 | Shraga |
| 2005/0049179 A1 | 3/2005 | Davidson et al. |
| 2005/0051427 A1 | 3/2005 | Brauker et al. |
| 2005/0051440 A1 | 3/2005 | Simpson et al. |
| 2005/0056552 A1 | 3/2005 | Simpson et al. |
| 2005/0070774 A1 | 3/2005 | Addison et al. |
| 2005/0070819 A1 | 3/2005 | Poux et al. |
| 2005/0092177 A1 | 5/2005 | Bonchonsky et al. |
| 2005/0096516 A1 | 5/2005 | Soykan et al. |
| 2005/0101912 A1 | 5/2005 | Faust et al. |
| 2005/0101932 A1 | 5/2005 | Cote et al. |
| 2005/0113648 A1 | 5/2005 | Yang et al. |
| 2005/0115832 A1 | 6/2005 | Simpson et al. |
| 2005/0131346 A1 | 6/2005 | Douglas |
| 2005/0134731 A1 | 6/2005 | Lee et al. |
| 2005/0154271 A1 | 7/2005 | Rasdal et al. |
| 2005/0159678 A1 | 7/2005 | Taniike et al. |
| 2005/0161346 A1 | 7/2005 | Simpson et al. |
| 2005/0176136 A1 | 8/2005 | Burd et al. |
| 2005/0187442 A1 | 8/2005 | Cho et al. |
| 2005/0192557 A1 | 9/2005 | Brauker et al. |
| 2005/0197793 A1 | 9/2005 | Baker |
| 2005/0214892 A1 | 9/2005 | Kovatchev et al. |
| 2005/0215871 A1 | 9/2005 | Feldman et al. |
| 2005/0239154 A1 | 10/2005 | Feldman et al. |
| 2005/0245799 A1 | 11/2005 | Brauker et al. |
| 2005/0269214 A1 | 12/2005 | Lee |
| 2005/0277912 A1 | 12/2005 | John |
| 2005/0283114 A1 | 12/2005 | Bresina et al. |
| 2006/0001024 A1 | 1/2006 | Makimura et al. |
| 2006/0011474 A1 | 1/2006 | Schulein et al. |
| 2006/0015024 A1 | 1/2006 | Brister et al. |
| 2006/0015922 A1 | 1/2006 | Lee et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020191 A1 | 1/2006 | Brister et al. |
| 2006/0036142 A1 | 2/2006 | Brister et al. |
| 2006/0036144 A1 | 2/2006 | Brister et al. |
| 2006/0036145 A1 | 2/2006 | Brister et al. |
| 2006/0040402 A1 | 2/2006 | Brauker et al. |
| 2006/0061354 A1 | 3/2006 | Wallance et al. |
| 2006/0068208 A1 | 3/2006 | Tapsak et al. |
| 2006/0081469 A1 | 4/2006 | Lee |
| 2006/0086624 A1 | 4/2006 | Tapsak et al. |
| 2006/0094944 A1 | 5/2006 | Chuang |
| 2006/0095014 A1 | 5/2006 | Ethelfeld |
| 2006/0108809 A1 | 5/2006 | Scalzi |
| 2006/0116607 A1 | 6/2006 | Nakamura et al. |
| 2006/0142651 A1 | 6/2006 | Brister et al. |
| 2006/0155180 A1 | 7/2006 | Brister et al. |
| 2006/0178022 A1 | 8/2006 | Liu |
| 2006/0181695 A1 | 8/2006 | Sage |
| 2006/0183984 A1 | 8/2006 | Dobbles et al. |
| 2006/0183985 A1 | 8/2006 | Brister et al. |
| 2006/0189851 A1 | 8/2006 | Tvig et al. |
| 2006/0189863 A1 | 8/2006 | Peyser et al. |
| 2006/0200020 A1 | 9/2006 | Brister et al. |
| 2006/0200022 A1 | 9/2006 | Brauker et al. |
| 2006/0211921 A1 | 9/2006 | Brauker et al. |
| 2006/0224108 A1 | 10/2006 | Brauker et al. |
| 2006/0226985 A1 | 10/2006 | Goodnow et al. |
| 2006/0247895 A1 | 11/2006 | Liamos et al. |
| 2006/0257996 A1 | 11/2006 | Simpson et al. |
| 2006/0258939 A1 | 11/2006 | Pesach et al. |
| 2006/0258959 A1 | 11/2006 | Sode |
| 2006/0264888 A1 | 11/2006 | Moberg et al. |
| 2006/0270922 A1 | 11/2006 | Brauker et al. |
| 2006/0270923 A1 | 11/2006 | Brauker et al. |
| 2006/0276771 A1 | 12/2006 | Galley et al. |
| 2006/0281985 A1 | 12/2006 | Ward et al. |
| 2007/0007133 A1 | 1/2007 | Mang et al. |
| 2007/0016129 A1 | 1/2007 | Liniger et al. |
| 2007/0027381 A1 | 2/2007 | Stafford |
| 2007/0027384 A1 | 2/2007 | Brister et al. |
| 2007/0027385 A1 | 2/2007 | Brister et al. |
| 2007/0027788 A1 | 2/2007 | Bandman et al. |
| 2007/0032717 A1 | 2/2007 | Brister et al. |
| 2007/0032718 A1 | 2/2007 | Shults et al. |
| 2007/0038044 A1 | 2/2007 | Dobbles et al. |
| 2007/0041248 A1 | 2/2007 | Togami |
| 2007/0045902 A1 | 3/2007 | Brauker et al. |

(56)             References Cited

U.S. PATENT DOCUMENTS

| | | | |
|---|---|---|---|
| 2007/0053184 A1* | 3/2007 | Brukilacchio | A61N 5/062 |
| | | | 362/231 |
| 2007/0053832 A1 | 3/2007 | Frincke et al. | |
| 2007/0060801 A1 | 3/2007 | Neinast | |
| 2007/0060814 A1 | 3/2007 | Stafford | |
| 2007/0060869 A1 | 3/2007 | Tolle et al. | |
| 2007/0073129 A1 | 3/2007 | Shah et al. | |
| 2007/0078322 A1 | 4/2007 | Stafford | |
| 2007/0093704 A1 | 4/2007 | Brister et al. | |
| 2007/0093754 A1 | 4/2007 | Mogensen et al. | |
| 2007/0097754 A1 | 5/2007 | Spitz | |
| 2007/0110124 A1 | 5/2007 | Shiraki et al. | |
| 2007/0135696 A1 | 6/2007 | Ward | |
| 2007/0135774 A1 | 6/2007 | Turner et al. | |
| 2007/0149873 A1 | 6/2007 | Say et al. | |
| 2007/0153705 A1 | 7/2007 | Rosar et al. | |
| 2007/0156094 A1 | 7/2007 | Safabash et al. | |
| 2007/0173706 A1 | 7/2007 | Neinast et al. | |
| 2007/0173709 A1 | 7/2007 | Petisce et al. | |
| 2007/0173710 A1 | 7/2007 | Petisce et al. | |
| 2007/0191702 A1 | 8/2007 | Yodfat et al. | |
| 2007/0197889 A1 | 8/2007 | Brister et al. | |
| 2007/0202562 A1 | 8/2007 | Curry et al. | |
| 2007/0203407 A1 | 8/2007 | Hoss et al. | |
| 2007/0208244 A1 | 9/2007 | Brauker et al. | |
| 2007/0208245 A1 | 9/2007 | Brauker et al. | |
| 2007/0219480 A1 | 9/2007 | Kamen et al. | |
| 2007/0219496 A1 | 9/2007 | Kamen et al. | |
| 2007/0222609 A1 | 9/2007 | Duron et al. | |
| 2007/0232878 A1 | 10/2007 | Kovatchev et al. | |
| 2007/0255321 A1 | 11/2007 | Gerber et al. | |
| 2008/0004515 A1 | 1/2008 | Jennewine et al. | |
| 2008/0004601 A1 | 1/2008 | Jennewine et al. | |
| 2008/0009805 A1 | 1/2008 | Ethelfeld | |
| 2008/0027296 A1 | 1/2008 | Hadvary et al. | |
| 2008/0029390 A1 | 2/2008 | Roche et al. | |
| 2008/0031941 A1 | 2/2008 | Pettersson | |
| 2008/0033268 A1 | 2/2008 | Stafford | |
| 2008/0033273 A1 | 2/2008 | Zhou et al. | |
| 2008/0058773 A1 | 3/2008 | John | |
| 2008/0058830 A1 | 3/2008 | Cole et al. | |
| 2008/0061961 A1 | 3/2008 | John | |
| 2008/0064941 A1 | 3/2008 | Funderburk et al. | |
| 2008/0064944 A1 | 3/2008 | VanAntwerp et al. | |
| 2008/0081000 A1* | 4/2008 | MacLeod | G01M 3/329 |
| | | | 422/68.1 |
| 2008/0092911 A1 | 4/2008 | Schulman et al. | |
| 2008/0097246 A1 | 4/2008 | Stafford | |
| 2008/0114280 A1 | 5/2008 | Stafford | |
| 2008/0129486 A1 | 6/2008 | Jeckelmann et al. | |
| 2008/0146904 A1 | 6/2008 | Hunn | |
| 2008/0161666 A1 | 7/2008 | Feldman et al. | |
| 2008/0172205 A1 | 7/2008 | Breton et al. | |
| 2008/0177149 A1 | 7/2008 | Weinart et al. | |
| 2008/0177165 A1 | 7/2008 | Blomquist et al. | |
| 2008/0188731 A1 | 8/2008 | Brister et al. | |
| 2008/0201325 A1 | 8/2008 | Doniger et al. | |
| 2008/0208026 A1 | 8/2008 | Noujaim et al. | |
| 2008/0214900 A1 | 9/2008 | Fennell et al. | |
| 2008/0214910 A1 | 9/2008 | Buck | |
| 2008/0242961 A1 | 10/2008 | Brister et al. | |
| 2008/0242962 A1 | 10/2008 | Roesicke et al. | |
| 2008/0242963 A1 | 10/2008 | Essenpreis et al. | |
| 2008/0243051 A1 | 10/2008 | DeStefano | |
| 2008/0254544 A1 | 10/2008 | Modzelewski et al. | |
| 2008/0255440 A1 | 10/2008 | Eilersen et al. | |
| 2008/0269584 A1 | 10/2008 | Shekalim | |
| 2008/0269683 A1 | 10/2008 | Bikovsky | |
| 2008/0269687 A1 | 10/2008 | Chong et al. | |
| 2008/0269714 A1 | 10/2008 | Mastrototaro et al. | |
| 2008/0275313 A1 | 11/2008 | Brister et al. | |
| 2008/0278333 A1 | 11/2008 | Fennell et al. | |
| 2008/0281178 A1 | 11/2008 | Chuang et al. | |
| 2008/0281179 A1 | 11/2008 | Fennell et al. | |
| 2008/0294024 A1 | 11/2008 | Cosentino et al. | |
| 2008/0300476 A1 | 12/2008 | Stafford | |
| 2008/0300572 A1 | 12/2008 | Rankers et al. | |
| 2008/0308523 A1 | 12/2008 | Krulevitch et al. | |
| 2008/0319085 A1 | 12/2008 | Wright et al. | |
| 2008/0319414 A1 | 12/2008 | Yodfat et al. | |
| 2009/0005729 A1 | 1/2009 | Hendrixson et al. | |
| 2009/0006061 A1 | 1/2009 | Thukral et al. | |
| 2009/0012376 A1 | 1/2009 | Agus | |
| 2009/0028824 A1 | 1/2009 | Chiang et al. | |
| 2009/0030293 A1 | 1/2009 | Cooper et al. | |
| 2009/0040022 A1 | 2/2009 | Finkenzeller | |
| 2009/0048563 A1 | 2/2009 | Ethelfeld et al. | |
| 2009/0054745 A1 | 2/2009 | Jennewine et al. | |
| 2009/0054747 A1 | 2/2009 | Fennell | |
| 2009/0054753 A1 | 2/2009 | Robinson et al. | |
| 2009/0076360 A1 | 3/2009 | Brister et al. | |
| 2009/0093687 A1 | 4/2009 | Telfort et al. | |
| 2009/0099521 A1 | 4/2009 | Gravesen et al. | |
| 2009/0102678 A1 | 4/2009 | Mazza et al. | |
| 2009/0105568 A1 | 4/2009 | Bugler | |
| 2009/0105570 A1 | 4/2009 | Sloan et al. | |
| 2009/0105571 A1 | 4/2009 | Fennell et al. | |
| 2009/0124979 A1 | 5/2009 | Raymond et al. | |
| 2009/0163855 A1 | 6/2009 | Shin et al. | |
| 2009/0177068 A1 | 7/2009 | Stivoric et al. | |
| 2009/0178459 A1 | 7/2009 | Li et al. | |
| 2009/0197440 A1 | 8/2009 | Hirata et al. | |
| 2009/0198186 A1 | 8/2009 | Mernoe et al. | |
| 2009/0216215 A1 | 8/2009 | Thalmann et al. | |
| 2009/0234212 A1 | 9/2009 | Slomski et al. | |
| 2009/0240121 A1 | 9/2009 | Bickoff | |
| 2009/0247857 A1 | 10/2009 | Harper et al. | |
| 2009/0266573 A1 | 10/2009 | Engmark et al. | |
| 2009/0267269 A1* | 10/2009 | Lim | B29C 64/112 |
| | | | 264/401 |
| 2009/0277242 A1 | 11/2009 | Crane et al. | |
| 2009/0281406 A1 | 11/2009 | McGarraugh et al. | |
| 2009/0292185 A1 | 11/2009 | Funderburk et al. | |
| 2009/0299301 A1 | 12/2009 | Gottlieb et al. | |
| 2010/0014626 A1 | 1/2010 | Fennell et al. | |
| 2010/0022863 A1 | 1/2010 | Mogensen et al. | |
| 2010/0022988 A1 | 1/2010 | Wochner et al. | |
| 2010/0049129 A1 | 2/2010 | Yokoi et al. | |
| 2010/0069728 A1 | 3/2010 | Funderburk et al. | |
| 2010/0081953 A1 | 4/2010 | Syeda-Mahmood et al. | |
| 2010/0094251 A1 | 4/2010 | Estes et al. | |
| 2010/0121167 A1 | 5/2010 | McGarraugh et al. | |
| 2010/0137695 A1 | 6/2010 | Yodfat et al. | |
| 2010/0141656 A1 | 6/2010 | Krieftewirth | |
| 2010/0145377 A1 | 6/2010 | Lai et al. | |
| 2010/0160759 A1 | 6/2010 | Celentano et al. | |
| 2010/0174266 A1 | 7/2010 | Estes | |
| 2010/0198034 A1 | 8/2010 | Thomas et al. | |
| 2010/0230285 A1 | 9/2010 | Hoss et al. | |
| 2010/0274111 A1 | 10/2010 | Say et al. | |
| 2010/0275108 A1 | 10/2010 | Sloan et al. | |
| 2010/0324392 A1 | 12/2010 | Yee et al. | |
| 2011/0021889 A1 | 1/2011 | Hoss et al. | |
| 2011/0031986 A1 | 2/2011 | Bhat et al. | |
| 2011/0040163 A1 | 2/2011 | Telson et al. | |
| 2011/0054282 A1 | 3/2011 | Nekoomaram et al. | |
| 2011/0060530 A1 | 3/2011 | Fennell | |
| 2011/0077494 A1 | 3/2011 | Doniger et al. | |
| 2011/0077659 A1 | 3/2011 | Mandecki et al. | |
| 2011/0081726 A1 | 4/2011 | Berman et al. | |
| 2011/0112696 A1 | 5/2011 | Yodfat et al. | |
| 2011/0178378 A1 | 7/2011 | Mernoe et al. | |
| 2011/0282327 A1 | 11/2011 | Kellogg et al. | |
| 2011/0288574 A1 | 11/2011 | Curry et al. | |
| 2011/0289497 A1 | 11/2011 | Kiaie et al. | |
| 2011/0319729 A1 | 12/2011 | Donnay et al. | |
| 2011/0320130 A1 | 12/2011 | Valdes et al. | |
| 2012/0088995 A1 | 4/2012 | Fennell et al. | |
| 2012/0116190 A1 | 5/2012 | Iketani et al. | |
| 2012/0165626 A1 | 6/2012 | Irina et al. | |
| 2012/0165640 A1 | 6/2012 | Galley et al. | |
| 2012/0173200 A1 | 7/2012 | Breton et al. | |
| 2012/0179113 A1 | 7/2012 | Yokota et al. | |
| 2012/0184909 A1 | 7/2012 | Gyrn | |

(56) References Cited

U.S. PATENT DOCUMENTS

| | | | |
|---|---|---|---|
| 2012/0197098 A1 | 8/2012 | Donnay et al. | |
| 2012/0245447 A1 | 9/2012 | Karan et al. | |
| 2012/0265042 A1 | 10/2012 | Neinast et al. | |
| 2012/0303043 A1 | 11/2012 | Donnay | |
| 2013/0008486 A1 | 1/2013 | Ono | |
| 2013/0035575 A1 | 2/2013 | Mayou et al. | |
| 2013/0109940 A1 | 5/2013 | Yang et al. | |
| 2013/0150691 A1 | 6/2013 | Pace et al. | |
| 2013/0184547 A1 | 7/2013 | Taub et al. | |
| 2013/0225959 A1 | 8/2013 | Bugler | |
| 2013/0235166 A1 | 9/2013 | Jones et al. | |
| 2013/0253289 A1 | 9/2013 | Hadvary et al. | |
| 2013/0267812 A1 | 10/2013 | Pryor et al. | |
| 2014/0121480 A1 | 5/2014 | Budiman et al. | |
| 2014/0121989 A1 | 5/2014 | Kamath et al. | |
| 2014/0148667 A1 | 5/2014 | Boock et al. | |
| 2014/0171771 A1 | 6/2014 | Feldman et al. | |
| 2014/0188053 A1 | 7/2014 | Lundquist | |
| 2015/0005601 A1 | 1/2015 | Hoss et al. | |
| 2015/0018643 A1 | 1/2015 | Cole et al. | |
| 2015/0025338 A1* | 1/2015 | Lee | A61B 5/150427 |
| | | | 600/309 |
| 2015/0105644 A1 | 4/2015 | Yang et al. | |
| 2015/0173661 A1 | 6/2015 | Myles | |
| 2015/0241407 A1 | 8/2015 | Ou et al. | |
| 2016/0157759 A1 | 6/2016 | Yang | |
| 2016/0331283 A1 | 11/2016 | Rao et al. | |
| 2016/0331284 A1 | 11/2016 | Pace | |
| 2016/0338733 A1 | 11/2016 | Shah et al. | |
| 2017/0112531 A1 | 4/2017 | Schoonmaker et al. | |
| 2017/0127985 A1 | 5/2017 | Thompson et al. | |
| 2017/0128011 A1 | 5/2017 | Frey et al. | |
| 2017/0188912 A1 | 7/2017 | Halac et al. | |
| 2017/0290546 A1 | 10/2017 | Antonio et al. | |
| 2017/0368268 A1 | 12/2017 | Chopra | |
| 2018/0116572 A1 | 5/2018 | Simpson et al. | |
| 2018/0125464 A1 | 5/2018 | Kolb et al. | |
| 2018/0235520 A1 | 8/2018 | Rao et al. | |
| 2018/0360493 A1 | 12/2018 | Baker et al. | |
| 2019/0117133 A1* | 4/2019 | Halac | A61B 5/6801 |
| 2019/0133501 A1 | 5/2019 | Rao et al. | |
| 2019/0133638 A1 | 5/2019 | Ii et al. | |
| 2020/0113494 A1 | 4/2020 | Akiyama | |
| 2020/0178899 A1 | 6/2020 | Chae et al. | |
| 2020/0196919 A1 | 6/2020 | Rao et al. | |
| 2020/0330005 A1* | 10/2020 | Barry | A61B 5/1473 |
| 2021/0030969 A1 | 2/2021 | Huang et al. | |
| 2021/0161437 A1 | 6/2021 | Thomas et al. | |
| 2021/0177315 A1 | 6/2021 | Thomas et al. | |
| 2021/0196163 A1 | 7/2021 | Halac et al. | |
| 2021/0378592 A1 | 12/2021 | Rodriguez et al. | |
| 2022/0007973 A1 | 1/2022 | Rao et al. | |
| 2022/0125480 A1 | 4/2022 | Rao et al. | |

FOREIGN PATENT DOCUMENTS

| | | |
|---|---|---|
| CA | 2 766 685 A1 | 12/2011 |
| CA | 3050721 | 7/2018 |
| CN | 201370857 | 12/2009 |
| CN | 201828525 U | 5/2011 |
| CN | 113040761 A | 6/2021 |
| DK | PA 2004 01265 | 8/2004 |
| EP | 0838230 | 4/1998 |
| EP | 1 092 390 A1 | 4/2001 |
| EP | 1413245 | 4/2004 |
| EP | 1092390 | 7/2004 |
| EP | 2236077 A1 | 10/2010 |
| EP | 1789116 B1 | 5/2013 |
| EP | 1075209 | 10/2014 |
| EP | 2713879 B1 | 7/2017 |
| EP | 2393417 B1 | 1/2019 |
| EP | 3 632 315 A1 | 4/2020 |
| EP | 3 851 045 | 7/2021 |
| EP | 3730044 | 12/2021 |
| EP | 3730045 | 3/2022 |
| EP | 3766408 | 4/2022 |
| EP | 3928688 | 6/2022 |
| EP | 3831283 B1 | 4/2023 |
| EP | 3 977 921 B1 | 7/2023 |
| EP | 4 111 949 B1 | 7/2023 |
| EP | 3300658 B1 | 1/2024 |
| EP | 4238496 B1 | 2/2024 |
| GB | 1399192 | 6/1975 |
| GB | 2067764 | 7/1981 |
| JP | 07-10973 | 2/1995 |
| JP | 2004-103354 | 4/2004 |
| JP | 2004-358016 | 12/2004 |
| JP | 2005-122994 | 5/2005 |
| JP | 2008-62072 A | 3/2008 |
| JP | 2012-221588 A | 11/2012 |
| JP | 2014-056762 A | 3/2014 |
| JP | 5642611 | 12/2014 |
| JP | 2015-053232 | 3/2015 |
| KR | 10-2017-0068964 | 6/2017 |
| WO | WO 1995/13838 | 5/1995 |
| WO | WO 98/16975 A1 | 4/1998 |
| WO | WO 1998/56293 | 12/1998 |
| WO | WO 99/56613 A1 | 11/1999 |
| WO | WO 1999/056613 | 11/1999 |
| WO | WO 01/17875 A1 | 3/2001 |
| WO | WO 2001/52727 | 7/2001 |
| WO | WO 2002/058537 | 8/2002 |
| WO | WO 03/026728 | 4/2003 |
| WO | WO 2003/032411 | 4/2003 |
| WO | WO 2003/056319 | 7/2003 |
| WO | WO 2004/006982 | 1/2004 |
| WO | WO 2004/030726 | 4/2004 |
| WO | WO 2004/088275 | 10/2004 |
| WO | WO 2004/095648 | 11/2004 |
| WO | WO 2004/098682 | 11/2004 |
| WO | WO 2004/098684 | 11/2004 |
| WO | WO 2004/098685 | 11/2004 |
| WO | WO 2004/107971 | 12/2004 |
| WO | WO 2005/011779 | 2/2005 |
| WO | WO 2005/026689 | 3/2005 |
| WO | WO 2005/037184 | 4/2005 |
| WO | WO 2005/041766 | 5/2005 |
| WO | WO 2005/046780 | 5/2005 |
| WO | WO 2005/065542 | 7/2005 |
| WO | WO 2005/092177 | 10/2005 |
| WO | WO 2005/123186 | 12/2005 |
| WO | WO 2006/001024 | 1/2006 |
| WO | WO 2006/015922 | 2/2006 |
| WO | WO 2006/018447 A2 | 2/2006 |
| WO | WO 2006/061354 | 6/2006 |
| WO | WO 2006/086423 | 8/2006 |
| WO | WO 2006/121921 | 11/2006 |
| WO | WO 2007/002189 | 1/2007 |
| WO | WO 2007/120363 | 10/2007 |
| WO | WO 2008/065646 | 6/2008 |
| WO | WO 2008/073813 | 6/2008 |
| WO | WO 2008/114223 | 9/2008 |
| WO | WO 2008/115409 | 9/2008 |
| WO | WO 2008/129532 | 10/2008 |
| WO | WO 2008/147921 | 12/2008 |
| WO | WO 2008/155377 | 12/2008 |
| WO | WO 2008/157821 | 12/2008 |
| WO | WO 2009/001347 | 12/2008 |
| WO | WO 2009/007287 | 1/2009 |
| WO | WO 2009/016635 | 2/2009 |
| WO | WO 2009/016638 | 2/2009 |
| WO | WO 2009/035773 | 3/2009 |
| WO | WO 2009/039013 | 3/2009 |
| WO | WO 2009/066288 A1 | 5/2009 |
| WO | WO 2010/091005 | 8/2010 |
| WO | WO 2011/002815 A2 | 1/2011 |
| WO | WO 2011/011643 | 1/2011 |
| WO | WO 2011/025549 | 3/2011 |
| WO | WO 2011/041531 A1 | 4/2011 |
| WO | WO 2011/077893 A1 | 6/2011 |
| WO | WO 2011/119896 A1 | 9/2011 |
| WO | WO 2011/119898 | 9/2011 |
| WO | WO 2012/103429 | 8/2012 |

US 12,576,599 B2

Page 7

(56) References Cited

FOREIGN PATENT DOCUMENTS

| WO | WO 2012/118872 A2 | 9/2012 |
| WO | WO 2013/090215 | 6/2013 |
| WO | WO 2016/120920 | 8/2016 |
| WO | WO 2017/004576 A1 | 1/2017 |
| WO | WO 2017/027749 | 2/2017 |
| WO | WO2018/136898 A1 | 7/2018 |
| WO | WO 2019/005627 | 1/2019 |
| WO | WO 2019/236850 A1 | 12/2019 |
| WO | WO2019/236859 A1 | 12/2019 |
| WO | WO2019/236876 A1 | 12/2019 |
| WO | WO 2020/012837 A1 | 1/2020 |
| WO | WO 2020/231405 A1 | 11/2020 |

OTHER PUBLICATIONS

Intertronics, "Fisnar F1300N.2 Rotary Dispensing Table Benchtop Robot", Intertronics, Aug. 15, 2018, https://www.intertronics.co.uk/product/fisnar-f1300n-rotary-dispensing-table-benchtop-robot/. (Year: 2018).*
Masterbond, "Needle Bonding Adhesives", Sep. 14, 2011, https://www.masterbond.com/industrial-applications/needle-bonding-adhesives. (Year: 2011).*
U.S. Appl. No. 61/155,889, filed Feb. 26, 2009, Hoss, et al.
Brückel et al., "In Vivo Measurement of Subcutaneous Glucose Concentrations with an Enzymatic Glucose Sensor and a Wick Method", Klin Wochenschr, 67:491-495 (1989).
Guardian® REAL-Time, Continuous Glucose Monitoring System, User Guide, Medtronic MiniMed, Inc., 184 pages (2006).
Mastrototaro et al., "An electroenzymatic glucose sensor fabricated on a flexible substrate", Sensors and Actuators B, 5:139-144 (1991).
Accu-Chek® Compact Plus, Blood Glucose Meter, Owner's Booklet, 2008, 100 pages.
Chen et al., "A novel fault-tolerant sensor system for sensor drift compensation", Sensors and Actuators, A 147:623-632 (2008).
De Block et al., "Minimally-Invasive and Non-Invasive Continuous Glucose Monitoring Systems: Indications, Advantages, Limitations and Clinical Aspects", Current Diabetes Reviews, 2008, 4:159-168.
FDA, Premarket Approval (PMA), FreeStyle Navigator Continuous Glucose Monitor, 2008, 6 pages.
FreeStyle Navigator Continuous Glucose Monitoring System, Summary of Safety and Effectiveness Data in support of Pre-Market Approval (PMA) No. P050020, Abbott Diabetes Care, 27 pages (2008).
FreeStyle Navigator Continuous Glucose Monitoring System, User Guide, Abbott Diabetes Care Inc., 195 pages (2008).
Garibotto et al., "An Innovative Application of Shape Memory Alloy Technology Yields a Novel Therapeutic Approach to Diabetes Management," Insulet Corporation, A41 (2009).
Gerritsen et al., "Performance of subcutaneously implanted glucose sensors for continuous monitoring", The Netherlands Journal of Medicine, 54:167-179 (1999).
Guardian® REAL-Time, Continuous Glucose Monitoring System, User Guide, Medtronic MiniMed, Inc., 181 pages (2006).
Insulet OmniPod Insulin Management System 019 UST400 User Manual, 2011, 190 pages.
Kalivas et al., "Compensation for Drift and Interferences in Multicomponent Analysis", Laboratory for Chemometrics, Department of Chemistry, University of Washington, 38 pages (1982).
Klonoff, D., "A Review of Continuous Glucose Monitoring Technology", Diabetes Technology & Therapeutics, 2005, 5:7:770-775.
Sen-serter User Guide, Metronic MiniMed, 2006, 96 pages.
Sof-Serter Infusion Set Insertion System, REF MMT-300, Instructions for use, Apr. 12, 2001, 2 pages.
Thévenot et al., "Electrochemical Biosensors: Recommended Definitions and Classification (Technical Report)", Pure Appl. Chem. 71(12):2333-2348 (1999).
U.S. Appl. No. 60/424,099, filed Nov. 5, 2002, 63 pages.
U.S. Appl. No. 08/871,831, filed Jun. 9, 1997, 36 pages.
U.S. Appl. No. 12/842,013 Office Action dated Nov. 6, 2014.

U.S. Appl. No. 12/842,013 Office Action dated Aug. 26, 2015.
U.S. Appl. No. 12/842,013 Office Action dated Mar. 23, 2016.
Walt et al., "The chemistry of enzyme and protein immobilization with glutaraldehyde," Trends in Analytical Chemistry, 13, 10, 425-430 (1994).
Zhang, "Investigations of potentially implantable glucose sensors", University of Kansas, 24 pages (1991).
International Search Report and Written Opinion dated Feb. 1, 2022 in International Application No. PCT/US21/50142.
U.S. Appl. No. 60/490,208, filed Jul. 25, 2003, Simpson.
U.S. Appl. No. 60/614,683, filed Sep. 30, 2004, Brister et al.
Cho et al., "The TheraSense, Inc. Continuous Glucose Monitor: Preliminary Clinical Results from a Subcutaneous Sensor with a Wireless Connection to a Hand-Held Display/Alarm," Clinical Therapeutics/New Technology—Glucose Monitoring and Sensing, 392-P, A91 (2003).
COHRlastic Silicone Rubber Products, Saint-Gobain Performance Plastics, 7 pages (2002).
Craston et al., "Microband Electrodes Fabricated by Screen Printing Processes: Applications in Electroanalysis," Talanta, vol. 38, No. 1, 17-26 (1991).
Elastosil® RT 602, RTV-2 Silicone Encapsulant Specification Sheet, Wacker Chemie GmbH, Version 3.00, 2 pages (2004).
Elastosil® RTV-1 Silicone Rubber Specification Sheet, Wacker Chemie GmbH, 16 pages (2001).
Elastosil® LR 3162 A, B Specification Sheet, Wacker Chemie GmbH, Version 3.00, 3 pages (2004).
"GESilicones—Master Grade" retrieved from "https://web.archive.org/web/20031105083652/http://www.gesilicones.com:80/gesilicones/am1/en/grade/mastergrade_kit_one_part.jsp?masterGradeId=749&categoryId=12&typeId=21" General Electric Company, 2 pages (2003).
Silastic® 94-595, Product Information Liquid Silicone Rubber, Dow Corning, 4 pages (2002).
U.S. Appl. No. 60/614,764, filed Sep. 30, 2004, Kamath.
U.S. Appl. No. 60/587,787, filed Jul. 13, 2004, Brister.
U.S. Appl. No. 61/317,243, filed Mar. 24, 2010, Curry.
U.S. Appl. No. 61/345,562, filed May 17, 2010, Curry.
U.S. Appl. No. 61/361,374, filed Jul. 2, 2010, Donnay.
U.S. Appl. No. 61/411,262, filed Nov. 8, 2010, Donnay.
U.S. Appl. No. 12/250,760, filed Oct. 14, 2008, Gravesen.
Abbott's Continuous Blood Glucose Monitor Approval Soon, 3 pages (2006).
Accu-Chek Compact Plus Owner's Booklet, 2008, pp. 1-100.
Ahson, S., et al., RFID Handbook, Applications, Technology, Security, and Privacy, CRC Press, 6 pages (2008).
Application Note AN048, Compact Reach Xtend™ Bluetooth®, 802.11b/g WLAN Chip Antenna, Antenna Part No. FR05-S1-N-0-102, Texas Instruments, 13 pages (2008).
Application Note, Nordic Semiconductor, nRF9E5 RF antenna layout, nAN900-05, 13 pages (2006).
AVR2023-AT86RF231 PCB reference design for antenna diversity, Atmel® AVR Z Link, Application Note, 15 pages (2008).
Benkič, K., et al., Using RSSI value for distance estimation in Wireless sensor networks based on ZigBee, 4 pages (2000).
Black, J., et al., Handbook of Biomaterial Properties, Springer—Science+Business Media, B.V., 61 pages (1998).
Bluetooth Antenna Design, National Semiconductor Application Note, 16 pages (2005).
Bonnett, A.H., "Squirrel-Cage Rotor Options for AC Induction Motors", IEEE Transactions on Industry Applications, vol. 37, No. 4, Jul./Aug. 2001, pp. 1197-1209.
Callaway, E.H., Wireless Sensor Networks, Architectures and Protocols, 4 pages (2004).
Chen et al., "Defining the Period of Recovery of the Glucose Concentration after Its Local Perturbation by the Implantation of a Miniature Sensor," Clin Chem Lab Med, 40(8):786-789 (2002).
Children with Diabetes, Report from Diabetes Technology Meeting, 3 pages (2022) https://archive.childrenwithdiabetes.com/d_0j_129.htm.
Claremont, D.J., et al., In vivo chemical sensors and biosensors in clinical medicine, pp. 356-376 (1987).
Cleo 90 Infusion Set Training Guide. (2007).

(56) References Cited

OTHER PUBLICATIONS

Declaration of John Mastrototaro, Ph.D. (2022).

Dehez et al, Development of a Spherical Induction Motor with Two Degrees of Freedom, IEEE Transactions on Magnetics, vol. 42, No. 8, Aug. 2006, pp. 2077-2089.

DexCom CGM Resource Center References Bibliography (2011).

Dexcom Leading the Way, Seven Plus Continuous Glucose Monitoring System, 12 pages (2010).

DexCom™ STS™ Continuous Glucose Monitoring System User's Guide, 2006, pp. 1-57.

Diabetes Close Up—Conferences—#2, Diabetes Technology, pp. 1-8 (2003).

Dufresne, A.T., et al., How reliable are trial dates relied on by the PTAB in the Fintiv analysis?, Perkins Coie, 1600 PTAB & Beyond, 4 pages (2021).

FDA Premarket Approval (PMA), Freestyle Navigator Continuous Glucose Monitor, 6 pages (2005).

FDA—Notice-Determination of Regulatory Review Period for Purposes of Patent Extension, Federal Register vol. 86, No. 211 60827-60829 (2021).

Federal Register, vol. 86, No. 211, pp. 60827-60829 (2021).

Feldman, B., et al., A Continuous Glucose Sensor Based on Wired Enzyme™ Technology-Results from a 3-Day Trial in Patients with Type 1 Diabetes, Diabetes Technology & Therapeutics, vol. 5, No. 5, pp. 769-779 (2003).

FreeStyle Navigator Continuous Glucose Monitoring System, Original Premarket Approval Application, 61 pages (2005).

FreeStyle Navigator Continuous Glucose Monitoring System, Premarket Approval Application Amendment, 89 pages (2006).

FreeStyle Navigator, Continuous Glucose Monitoring System, User's Guide, 38 pages (2008).

Frenzel, L.E., Printed-Circuit-Board Antennas, Electronic Design, 4 pages (2005).

Fujipoly, New High Performance Silver Zebra® Connector, Fujipoly Data Sheet No. FPDS 01-34/Version 2, 7 pages (2002).

Fujipoly, New High Performance Silver Zebra® Connector, Fujipoly Data Sheet No. FPDS 01-34/Version 5, 7 pages (2006).

Fujipoly, New High Performance Silver Zebra® Connector, Fujipoly Data Sheet No. FPDS 01-34/Version 5, 7 pages (2007).

Fujipoly, Zebra® Elastomeric Connectors, Fujipoly America Corp—Zebra—Zebra Carbon, 3 pages (2003).

Gandrud et al., "Functionality of the MiniMed Continuous Glucose Monitoring System (CGMS) in Young Childen with Type 1 Diabetes," Abstracts of the 64th Scientific Sessions of the American Diabetes Association, vol. 50, Supplement 2 (2004).

Gonzalez, O.L., et al., Low-Cost Wireless Sensors, Designer Reference Manual, RS08 Microcontrollers, DRM094, Rv. 0, freescale™ semiconductor, 49 pages (2007).

Guardian RT Continuous Glucose Monitoring System REF MMT-7900, 2005, Medtronic MiniMed.

Güler, N.F., et al., Theory and Applications of Biotelemetry, Journal of Medical Systems, vol. 26, No. 2, pp. 159-178 (2002).

Heftman, G., Chip Antenna Reduces Cell-Phone Dimensions, Microwaves & RF, p. 182 (1999).

Heide, C., Silicone Rubber for Medical Device Applications, Medical Plastics and Biomaterials, Special Section, Medical Device & Diagnostic Industry, 7 pages (1999).

Heinemann et al., "Benefits and Limitations of MARD as a Performance Parameter for Continuous Glucose Monitoring in the Interstitial Space," Journal of Diabetes Science and Technology, vol. 14 (1) 135-150 (2020).

Heller et al., "Electrochemical Glucose Sensors and Their Applications in Diabetes Management," Chem. Rev., 108, 2482-2505 (2008).

Heller et al., "Electrochemistry in Diabetes Management," Accounts of Chemical Research, vol. 43, No. 7, 963-973 (2010).

Heller, "Integrated Medical Feedback Systems for Drug Delivery", AIChE Journal, vol. 51, No. 4, 1054-1066 (2005).

Huang, Y., et al., Antennas from Theory to Practice, Wiley, 5 pages (2008).

Jain, et al. "Wound Rotor Induction Generator with Sensorless Control and Integrated Active Filter for Feeding Nonlinear Loads in a Stand-Alone Grid", IEEE Transactions on Industrial Electronics, vol. 55, No. 1, Jan. 2008, pp. 218-228.

James, J.R., et al., Handbook of Microstrip Antennas, vol. 2, Peter Peregrinus Ltd., 8 pages (1989).

Johanson Technology, Chip Antenna Layout Considerations for 802.11 Applications, 5 pages (2007).

Kass, D., Fintiv Fails: PTAB Uses 'Remarkably Inaccurate' Trial Dates, Law 360, Portfolio Media, Inc., 1 page (2021).

Kovatchev, B., et al., Evaluating the Accuracy of Continuous Glucose-Monitoring Sensors, Diabetes Care, vol. 27, No. 8, pp. 1922-1928 (2004).

Kreith, F., The CRC Handbook of Mechanical Engineering, 3 pages (1998).

Krieth, Frank, et al., The CRC Handbook of Mechanical Engineer, Second Edition, CRC Press Inc. (2004).

Loy, M., et al., ISM-Band and Short Range Device Antennas, High-Speed and RF, Application Report, SWRA046A, Texas Instruments, 38 pages (2005).

MD+DI Qmed, Silicone Rubber for Medical Device Applications, 13 pages (1999).

Medtronic, User Guide, Guardian Real-Time, 2006, Medtronic MiniMed, Inc.

Microchip, MRF24J40MA Data Sheet, 2.4GHz IEEE Std. 802.15. 4™ RF Tranceiver Module, 30 pages (2008).

Moore, B., The Potential Use of Radio Frequency Identification Devices for Active Monitoring of Blood Glucose Levels, Journal of Diabetes Science and Technology, vol. 3, Issue 1, pp. 180-183 (2009).

Moussy, F., et al., 32.2: Implantable Glucose Sensor: Progress and Problems, IEEE, pp. 270-273 (2002).

Moussy, F., et al., Performance of Subcutaneously Implanted Needle-Type Glucose Sensors Employing a Novel Trilayer Coating, Analytical Chemistry, vol. 65, No. 15, pp. 2072-2077 (1993).

Murata Puts Antenna on a Chip, Electronic News, p. 44 (1999).

Princy, K.G., et al., Studies on Conductive Silicone Rubber Compounds, 8 pages (1998).

Reiterer et al., "Significance and Reliability of MARD for the Accuracy of CGM Systems," Journal of Diabetes Science and Technology, vol. 11 (1) 59-67 (2017).

Rotate—definition of rotor by The Free Dictionary (2010).

Rotor—definition of rotor by The Free Dictionary (2010).

Schoepke, E., Johanson Technology, Chip Antenna Layout Considerations for 802.11 Applications, 7 pages (2006).

Seal Design Guide, Apple Rubber Products Inc., 190 pages (1999).

Sharawi, M.S., Use of low-cost patch antennas in modern wireless technology, IEEE, 5 pages (2006).

Standard Test Method for Rubber Property-Durometer Hardness, ASTM International, Designation: D 2240-05, 13 pages (2005).

Summary of Safety and Effectiveness, Cleo90 Infusion Set, Aug. 10, 2004.

The Seal Design Guide of Apple Rubber Products, Apple Rubber Products, Inc. (2020).

The Wayback Machine, Accu-Chek, Compact Plus Blood Glucose Meter, 2009.

The Wayback Machine, Accu-Chek, Softclix Plus Lancet Device, 2006.

The Wayback Machine, MiniMed, Quick-Set, Apr. 12, 2001.

The Wayback Machine, MiniMed, Sof-set Micro QR, Apr. 12, 2001.

TheraSense Files Premarket Approval Application for Freestyle Navigator(TM) Cont, 3 pages (2003).

Therasense Navigated Continuous Glucose Monitor PMA, Prepares for Flash, The Gray Sheet, vol. 29; No. 37; p. 18 (2003).

U.S. Food & Drug Administration, Premarket Approval (PMA) for Freestyle Navigator Continuous Glucose Monitor, 6 pages, Notice Date: Apr. 1, 2008.

United States Securities and Exchange Commission, Form 10-K, 59 pages (2005).

United States Securities and Exchange Commission, Form S-1, 309 pages (2005).

User Guide, for PDM Model UST400, 2011, Insulet Corporation.

(56) References Cited

OTHER PUBLICATIONS

Ward, W.K., et al., A Wire-Based Dual-Analyte Sensor for Glucose and Lactane: In Vitro and in Vivo Evaluation, Military Metabolic Monitoring, edited by Friedl, C.K.E., Diabetes Technology & Therapeutics, vol. 6, No. 3, pp. 389-401 (2004).
Ward, W.K., et al., Rise in background current over time in a subcutaneous glucose sensor in the rabbit: relevance to calibration and accuracy, Biosensors & Bioelectronics, 15, pp. 53-61 (2000).
Waterhouse, R., Printed Antennas for Wireless Communications, Wiley, 14 pages (2007).
Wilson et al., "Introduction to the Glucose Sensing Problem," In Vivo Glucose Sensing, 1-27 (2010).
Wong, K., Planar Antennas for Wireless Communications, Wiley, 16 pages (2003).
Z-Carbon LCD Connector, 2 pages (2004).
Z-Silver Connector, 2 pages (2004).
Zisser, H. "The OmniPod Insulin Management System: The Latest Innovation in Insulin Pump Therapy", Diabetes Ther. (2010) 1(1): 10-24.
"Abbott Receives CE Mark for Freestyle® Libre, A Revolutionary Glucose Monitoring System for People with Diabetes," 8 pages (2023).
An Interview with Kevin Sayer, President and CEO of Dexcom About The New Dexcom G6, College Diabetes Network, 6 pages (2021).
Anderson, Foundations of Computer Technology, Chapman & Hall, 6 pages (1994).
Annex 1 Dexcom's Opening Skeleton Argument Trial C, Summary of Claim 1 of the Patent, Claim No. HP-2021-000025 (2023).
Annex 2 Dexcom's Opening Skeleton Argument Trial C, Summary of the operation of the G7 Applicator, Claim No. HP-2021-000025 (2023).
Annex 2 to Abbott's Closing Submission, Summary of operation of the G7 Applicator (Abbott's amendments) (2023).
Annex 2 to Abbott's Skeleton—Commercial devices and their key features (2023).
ATTD Program, $2^{nd}$ International Conference on Advanced Technologies & Treatments for Diabetes, Athens, Greece, 4 pages (2009).
Cambridge Dictionary of American English, for the word "recess," Cambridge University Press, 3 pages (2000).
Preliminary Amendment for U.S. Pat. No. 10,827,954, issued on Nov. 10, 2020, 7 pages.
Preliminary Amendment for U.S. Pat. No. 10,973,443, issued on Apr. 13, 2021, 22 pages.
CGMS Changing Diabetes Management: Kevin Sayer, DIC Interview Transcript, 11 pages (2019).
Deciding When to Submit a 510(k) for a Change to an Existing Device, Guidance for Industry and Food and Drug Administration Staff, U.S. Department of Health and Human Services, Food and Drug Administration, 78 pages (2017).
Deutscher Gesundheitsbericht Diabetes, 2023, German Health Report, Diabetes 2023, 13 pages (English abstract).
Dexcom (DXCM) Company Profile, 2017 /Q4 Earnings call transcript, 12 pages (2017).
DexCom (Dxcm) Q1 2018 Results—Earnings Call Transcript, 4 pages (2018).
Dexcom CEO—Prime Position in Our Market—Mad Money—CNBC.mp4, 4 pages (2023).
Dexcom G6 Continuous Glucose Monitoring System User Guide, 7 pages (2020).
Dexcom G6, Continuous Glucose Monitoring System, User Guide, 22 pages (2020).
Dexcom G6, Start Here Set Up, Dexcom G6 Continuous Glucose Monitoring (CGM) System (G6), 8 pages (2019).
Dexcom G6, Using Your G6, 7 pages (2020).
Dexcom G7, Start Here, Operational Manual, Dexcom, Inc. 9 pages (2022) (with an English abstract).
Dexcom G7, Receiver: Start Here, Operational Manual, Dexcom, Inc., 8 pages (2022).

Dexcom G7, Operational Manual, User Guide, Dexcom, Inc., 179 pages (2022) (with an English abstract).
Dexcom, Inserting Sensor, Instructions for Use, Dexcom, Inc., 2 pages (2021).
DexCom, Inc. NasdaqGS:DXCM, Company Conference Presentation, 10 pages (2020).
DexCom, Inc. NasdaqGS:DXCM, Company Conference Presentation, 11 pages (2019).
DexCom, Inc. NasdaqGS:DXCM, Company Conference Presentation, 17 pages (2021).
Email from Sophie Hood to Matthew Werdegar and Manuela Cabal re. Abbott Diabetes Care, Inc. et al v. DexCom, Inc. | Case No. 21-977-KAJ, dated Jan. 24, 2023.
Excerpts from Expert Report of Catharine M. Lawton—Ex. 36, Spruce Point Capital Management, Does Dexcom Really Have a Future if it Can't Match Abbott's Scale? 2 pages, Mar. 21, 2019.
Exhibit AV-31, To the Third Expert Report of Andrew Varde, Claim No. HP-2021-000025, Claim No. HP-2021-000026, May 11, 2023: Instructions for Use DexcomTM STSTM Sensor, DexCom (2006).
Exhibit AV-32, To the Third Expert Report of Andrew Varde, Claim No. HP-2021-000025, Claim No. HP-2021-000026, May 11, 2023: STS®—Seven Continuous Glucose Monitoring System, User's Guide, DexCom, Inc. (2007).
Exhibit AV-33, To the Third Expert Report of Andrew Varde, Claim No. HP-2021-000025, Claim No. HP-2021-000026, May 11, 2023: Guardian® REAL-Time, Continuous Glucose Monitoring System, User Guide, Medtronic MiniMed, Inc. (2006).
Exhibit AV-34, To the Third Expert Report of Andrew Varde, Claim No. HP-2021-000025, Claim No. HP-2021-000026, May 11, 2023: FreeStyle Navigator® Continuous Glucose Monitoring System, User's Guide, Abbott Diabetes Care, Inc. (2008).
Exhibit AV-35, To the Third Expert Report of Andrew Varde, Claim No. HP-2021-000025, Claim No. HP-2021-000026, May 11, 2023: Letter from Department of Health & Human Services to DexCom, Inc. re. P050012 DexComTM STSTM Continuous Glucose Monitoring System (Mar. 24, 2006).
Exhibit AV-36, To the Third Expert Report of Andrew Varde, Claim No. HP-2021-000025, Claim No. HP-2021-000026, May 11, 2023: Summary of Safety and Effectiveness Data, DexComTM STSTM Continuous Glucose Monitoring System, PMA No. P050012, Date of Notice of Approval: Mar. 24, 2006.
Exhibit AV-37, To the Third Expert Report of Andrew Varde, Claim No. HP-2021-000025, Claim No. HP-2021-000026, May 11, 2023: Letter from Department of Health & Human Services to DexCom, Inc. re. P050012/S001 STS-7 Continuous Glucose Monitoring System (May 31, 2007).
Exhibit AV-38, To the Third Expert Report of Andrew Varde, Claim No. HP-2021-000025, Claim No. HP-2021-000026, May 11, 2023: Summary of Safety and Effectiveness Data, STS®—7 Continuous Glucose Monitoring System, PMA No. P050012/S001, Date of Notice of Approval: May 31, 2007.
Exhibit AV-39, To the Third Expert Report of Andrew Varde, Claim No. HP-2021-000025, Claim No. HP-2021-000026, May 11, 2023: Letter from Department of Health & Human Services to Medtronic MiniMed re. P980022/S011 Guardian RT (Jul. 18, 2005).
Exhibit AV-40, To the Third Expert Report of Andrew Varde, Claim No. HP-2021-000025, Claim No. HP-2021-000026, May 11, 2023: Summary of Safety and Effectiveness Data, Guardian RT, PMA No. P980022/S011, Date of Notice of Approval: Jul. 18, 2005.
Exhibit AV-41, To the Third Expert Report of Andrew Varde, Claim No. HP-2021-000025, Claim No. HP-2021-000026, May 11, 2023: Letter from Department of Health & Human Services to Abbott Diabetes Care, Inc. re. P050020 FreeStyle Navigator Continuous Glucose Monitoring System (Mar. 12, 2008).
Exhibit AV-42, To the Third Expert Report of Andrew Varde, Claim No. HP-2021-000025, Claim No. HP-2021-000026, May 11, 2023: Summary of Safety and Effectiveness Data, FreeStyle Navigator® Continuous Glucose Monitoring System, PMA No. P050020, Date of Notice of Approval: Mar. 12, 2008.
Exhibit AV-43, To the Third Expert Report of Andrew Varde, Claim No. HP-2021-000025, Claim No. HP-2021-000026, May 11, 2023: Seven® Plus Continuous Glucose Monitoring System, User's Guide, Dexcom, Inc. (2011).

(56) References Cited

OTHER PUBLICATIONS

Exhibit AV-44, To the Third Expert Report of Andrew Varde, Claim No. HP-2021-000025, Claim No. HP-2021-000026, May 11, 2023: International Standard, ISO 14971, Medical devices—Application of risk management to medical devices (2007).

Exhibit AV-45, To the Third Expert Report of Andrew Varde, Claim No. HP-2021-000025, Claim No. HP-2021-000026, May 11, 2023: EN ISO 15197, In vitro diagnostic test systems—Requirements for blood-glucose monitoring systems for self-testing in managing diabetes mellitus (ISO 15 97:2003), CEN (2003).

Exhibit AV-46, To the Third Expert Report of Andrew Varde, Claim No. HP-2021-000025, Claim No. HP-2021-000026, May 11, 2023: Food and Drug Administration, HHS, pp. 147-148, Authenticated U.S. Government Information.

Exhibit AV-47, To the Third Expert Report of Andrew Varde, Claim No. HP-2021-000025, Claim No. HP-2021-000026, May 11, 2023: EN ISO 13485, Medical devices—Quality management systems—Requirements for regulatory purposes (ISO 13485: 003), CEN (2003).

Exhibit AV-48, To the Third Expert Report of Andrew Varde, Claim No. HP-2021-000025, Claim No. HP-2021-000026, May 11, 2023: Diglas, et al., Reduced pain perception with Pen MateTM, an automatic needle insertion device for use with an insulin pen, Practical Diabetes International, vol. 16, No. 2, pp. 39-41 (1999).

Exhibit AV-49, To the Third Expert Report of Andrew Varde, Claim No. HP-2021-000025, Claim No. HP-2021-000026, May 11, 2023: Authenticated U.S. Government Information, Occupational Safety and Health Admin., Labor, §1910.1030, 29 CFR Ch. XVII (Jul. 1, 2003 Edition), pp. 260-273.

Exhibit AV-50, To the Third Expert Report of Andrew Varde, Claim No. HP-2021-000025, Claim No. HP-2021-000026, May 11, 2023: Hemmerich, et al., Sterilization Methods Stand the Test of Time, Medical Device & Diagnostic Industry (2004).

Exhibit AV-51, To the Third Expert Report of Andrew Varde, Claim No. HP-2021-000025, Claim No. HP-2021-000026, May 11, 2023: Submission and Review of Sterility Information in Premarket Notification (510(k)) Submissions for Devices Labeled as Sterile Guidance for Industry and Food and Drug Administration Staff, U.S. Department of Health and Human Services, Food and Drug Administration, issued on Jan. 21, 2016.

Exhibit AV-52, To the Third Expert Report of Andrew Varde, Claim No. HP-2021-000025, Claim No. HP-2021-000026, May 11, 2023: EN ISO 11607-1, Packaging for terminally sterilized medical devices—Part 1: Requirements for materials, sterile barrier systems and packaging systems (ISO 11607-1: 006), CEN (2006).

Exhibit AV-53, To the Fourth Expert Report of Andrew Varde, Claim No. HP-2021-000025, Claim No. HP-2021-000026, Jun. 9, 2023: US 2006/0019327 A1, Brister et al. (Jan. 26, 2006).

Exhibit AV-54, To the Fourth Expert Report of Andrew Varde, Claim No. HP-2021-000025, Claim No. HP-2021-000026, Jun. 9, 2023: Sen-Serter® User Guide, Medtronic MiniMed (2006).

Exhibit AV-55, To the Fourth Expert Report of Andrew Varde, Claim No. HP-2021-000025, Claim No. HP-2021-000026, Jun. 9, 2023: Summary of Safety and Effectiveness Data (SSED), Freestyle Libre Pro Flash Glucose Monitoring System, PMA No. P150021, Date of FDA Notice of Approval: Sep. 23, 2016.

Exhibit AV-56, To the Fourth Expert Report of Andrew Varde, Claim No. HP-2021-000025, Claim No. HP-2021-000026, Jun. 9, 2023: The MiniMed Paradigm® REAL-Time Insulin Pump and Continuous Glucose Monitoring System, Insulin Pump User Guide, Paradigm® 522 and 722 Insulin Pumps, User Guide, Medtronic MiniMed, Inc. 2008.

Exhibit AV-57, To the Fifth Expert Report of Andrew Varde, Claim No. HP-2021-000025, Claim No. HP-2021-000026, Jun. 23, 2023: Hirsch, Realistic Expectations and Practical Use of Continuous Glucose Monitoring for the Endocrinologist, J. Clin. Endocrinol Metab., 94(7), pp. 2232-2238 (2009).

Exhibit AV-58, To the Fifth Expert Report of Andrew Varde, Claim No. HP-2021-000025, Claim No. HP-2021-000026, Jun. 23, 2023:

Hughes, The Business of Self-Monitoring of Blood Glucose: A Market Profile, J. Diabetes Sci Technol, vol. 3, Issue 5, pp. 1219-1223 (2009).

Exhibit DJ-4, Expert Report of Douglas Jennings, Claim No. HP-2021-000025, May 12, 2023: Guardian® REAL-Time, Continuous Glucose Monitoring System, User Guide, Medtronic MiniMed, Inc. (2006).

Exhibit DJ-5, Expert Report of Douglas Jennings, Claim No. HP-2021-000025, May 12, 2023: STS®—Seven Continuous Glucose Monitoring System, User's Guide, DexCom, Inc. (2007).

Exhibit DJ-6, Expert Report of Douglas Jennings, Claim No. HP-2021-000025, May 12, 2023: FreeStyle Navigator® Continuous Glucose Monitoring System, User's Guide, Abbott Diabetes Care, Inc. (2008).

Exhibit DJ-7, Expert Report of Douglas Jennings, Claim No. HP-2021-000025, May 12, 2023: Klueh, et al., Inflammation and Glucose Sensors: Use of Dexamethasone to Extend Glucose Sensor Function and Life Span in Vivo, Journal of Diabetes Science and Technology, vol. 1, Issue 4, pp. 496-504 (2007).

Exhibit DJ-8, Expert Report of Douglas Jennings, Claim No. HP-2021-000025, May 12, 2023: Klueh, et al., Blood-Induced Interference of Glucose Sensor Function in Vitro: Implications for in Vivo Sensor Function, Journal of Diabetes Science and Technology, vol. 1, Issue 6, pp. 842-849 (2007).

Exhibit PG-16, To the Third Expert Report of Pantelis Georgiou, Claim No. HP-2021-000025, Claim No. HP-2021-000026, May 10, 2023: STS®—Seven Continuous Glucose Monitoring System, User's Guide, DexCom, Inc. (2007).

Exhibit PG-17, To the Third Expert Report of Pantelis Georgiou, Claim No. HP-2021-000025, Claim No. HP-2021-000026, May 10, 2023: Guardian® REAL-Time, Continuous Glucose Monitoring System, User Guide, Medtronic MiniMed, Inc. (2006).

Exhibit PG-18, To the Third Expert Report of Pantelis Georgiou, Claim No. HP-2021-000025, Claim No. HP-2021-000026, May 10, 2023: FreeStyle Navigator® Continuous Glucose Monitoring System, User's Guide, Abbott Diabetes Care, Inc. (2008).

Exhibit PG-19, To the Third Expert Report of Pantelis Georgiou, Claim No. HP-2021-000025, Claim No. HP-2021-000026, May 10, 2023: Instructions for Use DexcomTM STSTM Sensor, DexCom (2006).

Exhibit PG-20, To the Third Expert Report of Pantelis Georgiou, Claim No. HP-2021-000025, Claim No. HP-2021-000026, May 10, 2023: OneTouch® UltraTM Blood Glucose Monitoring System, The Comfort of Control, Owner's Booklet, LifeScan, Inc. (2000).

Exhibit PG-21, To the Third Expert Report of Pantelis Georgiou, Claim No. HP-2021-000025, Claim No. HP-2021-000026, May 10, 2023: OneTouch® Ultra2 Blood Glucose Monitoring System, Link the Effects of Food to Glucose Results, Owner's Booklet, LifeScan, Inc. (2005).

Exhibit PG-22, To the Third Expert Report of Pantelis Georgiou, Claim No. HP-2021-000025, Claim No. HP-2021-000026, May 10, 2023: FreeStyle® Lite, Blood Glucose Monitoring System, Owner's Booklet, Abbott Diabetes Care, Inc. (2006).

FDA News Release, FDA authorizes first fully interoperable continuous glucose monitoring system, streamlines review pathway for similar devices, 3 pages (2018).

U.S. Appl. No. 60/587,787, filed Jul. 13, 2004.

Figures 13 and 12 of U.S. Pat. No. 10,973,443 B2 issued on Apr. 13, 2021.

FreeStyle Libre, Fact Sheet, Abbott, (2016), 3 pages, (English abstract).

FreeStyle Libre, Flash Glukose Messystem, Abbott, (2016), 11 pages (English abstract).

Funderburk et al., Joint Declaration for U.S. Appl. No. 15/963,828, 11 pages (2020).

Hoss et al., "Continuous Glucose Monitoring in Subcutaneous Tissue Using Factory-Calibrated Sensors: A Pilot Study", Diabetes Technology & Therapeutics, 12(8):591-597 (2010).

Hoss et al., "Feasibility of Factory Calibration for Subcutaneous Glucose Sensors in Subjects With Diabetes", Journal of Diabetes Science and Technology, 8(1):89-94 (2014).

(56)                    References Cited

OTHER PUBLICATIONS

Hoss, et al., Continuous glucose monitoring in the tissue: Do we really need to calibrate in-vivo?, Abbott Diabetes Care, 23 pages (2009).
IEEE 100, The Authoritative Dictionary of IEEE Standards Terms, 7th Ed., 3 pages (2000).
In Vivo Glucose Sensing, John Wiley & Sons, Inc., 5 pages (2010).
Interview with Dexcom CEO, Dexcom CEO Kevin Sayer Explains G6, Written By: Michelle Boise, 10 pages (2018).
Kal., S., Basic Electronics, Devices, Circuits and IT Fundamentals, Fifth printing, Chapter 13 Microcomputers and Microprocessors, 4 pages (2006).
Letter from the Department of Health & Human Services, Food and Drug Administration to Abbott Diabetes Care, Inc. dated Mar. 12, 2008, regarding the Premarket Approval Application (PMA) for the FreeStyle Navigator Continuous Glucose Monitoring System, 7 pages.
Merriam-Webster's Collegiate Dictionary, 10th Ed., 4 pages (1999)—Housing and recess.
Merriam-Webster's Collegiate Dictionary, 10th Ed., 4 pages (1999)—Release and retain.
Non-Final Office Action for U.S. Appl. No. 14/884,622 dated Jun. 13, 2018, 7 pages.
Non-Final Office Action for U.S. Appl. No. 17/030,030 dated Dec. 17, 2020, 7 pages.
Notice of Allowance for U.S. Appl. No. 15/963,828 dated Mar. 3, 2021, 32 pages.
Omnipod image, Exhibit 182, 2 pages (Sep. 22, 2022).
Original drawings for PCT/US2011/029881, filed Mar. 24, 2011, 99 pages.
Program Book, 2nd International Conference on Advanced Technologies & Treatments for Diabetes, Athens, Greece, 4 pages (2009).
Response to Non-Final Office Action for U.S. Appl. No. 15/963,828 filed on Dec. 8, 2020, 17 pages.
Response to Restriction Requirement for U.S. Appl. No. 14/884,622 filed on Apr. 5, 2018, 15 pages.
S&P Global Market Intelligence "DexCom, Inc. NasdaqGS:DXCM, Company Conference Presentation," 10 pages (2020).
S&P Global Market Intelligence "DexCom, Inc. NasdaqGS:DXCM, Company Conference Presentation," 11 pages (2019).
S&P Global Market Intelligence "DexCom, Inc. NasdaqGS:DXCM, Company Conference Presentation," 17 pages (2021).
Sonix, Dexcom CEO—Prime Position in Our Market—Mad Money—CNBC.mp4, 4 pages (2023).
Spruce Point Capital Management, Dexcom, Inc., Investment Research Report, Does Dexcom Really Have a Future if it Can't Match Abbott's Scale? 2 pages (Mar. 21, 2019).
"Standard Test Method for Rubber Property-Durometer Hardness", ASTM International Designation: D 2240-05, 2005, 13 pages.
Tegnestedt, et al., Levels and sources of sound in the intensive care unit—an observational study of three room types, Acta Anaesthesiol Scandinavica Foundation, 11 pages (2013).
The Chambers Dictionary, Chambers Harrap Publishers 4 pages (1998, 1999)—Retract.
The MiniMed Paradigm® Real-Time Insulin Pump and Continuous Glucose Monitoring System, Insulin Pump User Guide, Medtronic, Paradigm® 522 and 722 Insulin Pumps User Guide, 25 pages (2008).
The New Oxford American Dictionary, for the word "retract," Oxford University Press, 3 pages (2001).
The New Penguin English Dictionary, for the word "recess," Penguin Books, 4 pages (2000).
U.S. Food & Drug Administration, "Deciding When to Submit a 510(k) for a Change to an Existing Device, Guidance for Industry and Food and Drug Administration Staff," 32 pages (2017).
Watkin, "An Introduction to Flash Glucose Monitoring," 16 pages (2013).
Webster's II New College Dictionary, for the word "alcove," 2 pages (2001).

Webster's Third New International Dictionary of the English Language Unabridged, for the word "retract," Merriam-Webster Inc., 5 pages (1993).
Abbott Diabetes Care Inc. and Abbott Diabetes Care Limited v. Dexcom, Inc., Scheduling Order, Sep. 19, 2023, 14 pages.
Breton, et al., "Optimum Subcutaneous Glucose Sampling and Fourier Analysis of Continuous Glucose Monitors", Journal of Diabetes Science and Technology, 2(3):495-500 (2008).
Declaration of Gary D. Fletcher, Ph.D., 133 pages (2023).
Declaration of Gary D. Fletcher, Ph.D., 141 pages (2023).
Dexcom Inc. v. Abbott Diabetes Care Inc., Statement of Defense (Counterclaim), Sep. 1, 2023, 67 pages.
U.S. Appl. No. 13/071,461, filed Mar. 24, 2011.
U.S. Appl. No. 17/019,110, filed Sep. 11, 2020.
U.S. Appl. No. 17/221,154, filed Apr. 2, 2021.
U.S. Appl. No. 61/345,562, filed May 17, 2010.
U.S. Appl. No. 61/361,374, filed Jul. 2, 2010.
U.S. Appl. No. 61/411,262, filed Nov. 8, 2010.
McGraw-Hill Dictionary of Mechanical and Design Engineering, 4 pages (1984)—boss.
Panteleon, et al., "The Role of the Independent Variable to Glucose Sensor Calibration", Diabetes Technology & Therapeutics, 5(3):401-410 (2003).
Poitout, et al., "A glucose monitoring system for on line estimation in man of blood glucose concentration using a miniaturized glucose sensor implanted in the subcutaneous tissue and a wearable control unit", Diabetologia, 36:658-663 (1993).
Shenoi, "Introduction to Digital Signal Processing and Filter Design", John Wiley & Sons, Inc., 46 pages (2006).
Smith, "The Scientist and Engineer's Guide to Digital Signal Processing", Second Edition, 46 pages (1999).
Bisco® EC2265 Electrically Conductive Solid, Product Data Sheet, Rogers Corporation, 2 pages (Dec. 14, 2023).
Conductive—High Consistency Silicone Rubber (HCR), Type—Carbon filled. (C), Technical Data Sheet, Primasil Silicones Ltd., 1 page (Dec. 14, 2023).
Conductive Carbon Filled Silicone (ERC-225), retrieved from the internet: EMI Conductive Rubber, LLC (emiconductiverubberllc. com); EMI Conductive Rubber, LLC, 5 pages (Dec. 14, 2023).
Custom Medical-Grade Silicone Gasket, Manufacturer of Medical Silicone Potash Sealing Liners, Suconvey, 17 pages (Dec. 20, 2023) (with an English translation).
Custom Silicone Gasket in Medical Quality, Manufacturer of Medical Silicone Rubber Seal Rollers, Suconvey, 16 pages (Dec. 14, 2023) (with an English translation).
Electrically Conductive Elastomers, Data Sheet Material (Material Specifications), Euro Technologies, 6 pages (Dec. 14, 2023).
Electrically Conductive Silicone Sheet, retrieved from the internet: Electrically Conductive Silicone Sheet Silex UK; Silex Ltd., 3 pages (Dec. 14, 2023).
Medical Silicone Seal/Closing Rolls, Suconvey, 16 pages (Dec. 14, 2023) (with an English translation).
Opponent's Written Response in Opposition of EP 3 730 045, Sep. 27, 2023, 43 pages.
Sterling® C carbon black, Product Data Sheet, Cabot Corporation, 2 pages (Dec. 14, 2023).
Vulcan® XC72 carbon black, Product Data Sheet, Cabot Corporation, 2 pages (Dec. 14, 2023).
Abbott receives CE mark for Freestyle® Libre, a revolutionary glucose monitoring system for people with diabetes, 5 pages (2023).
Ar35, Drawings (Figures 1, 16 and 17), 3 pages (2024).
Ar36, Clearer Drawings (Figures 1, 16 and 17), 3 pages (2024).
Ar38, Claims 1-21, 4 pages (2024).
Certified Korean Patent Application No. 10-2017-0068964 filed on Jun. 2, 2017, 48 pages [Korean language (48 pages) & English translation (51 pages)].
Claim chart for U.S. Pat. No. 10,959,654 to Dexcom G6, 17 pages (2021) [Exhibit 1022; Exhibit T].
Claim chart for U.S. Pat. No. 11,013,440 to Dexcom G6, 19 pages (2021) [Exhibit 1038; Exhibit X].
Continuous Glucose Monitoring Systems, Product Reference Guide, Diabetes Health, 3 pages, (Dec. 2006-Jan. 2007).

(56)            References Cited

OTHER PUBLICATIONS

Das et al., Review-Electrochemistry and Other Emerging Technologies for Continuous Glucose Monitoring Devices, ECS Sensors Plus, 20 pages (2022).

Dexcom G6 Continuous Glucose Monitoring System User Guide, 346 pages (2022).

Englert et al., Skin and Adhesive Issues with Continuous Glucose Monitors: A Sticky Situation, Journal of Diabetes Science and Technology, vol. 8(4), pp. 745-751 (2014).

Freckmann, et al., Performance Evaluation of Three Continuous Glucose Monitoring Systems: Comparison of Six Sensors per Subject in Parallel, Journal of Diabetes Science and Technology. Vol. 7, No. 4, pp. 842-853 (2013).

Harris, et al., Common Causes of Glucose Oxidase Instability in In Vivo Biosensing: A Brief Review, Journal of Diabetes Science and Technology, vol. 7, No. 4, pp. 1030-1038 (2013).

IPro2 User Guide, Medtronic MiniMed, 108 pages (2010) [Exhibit 1013].

Nichols, et al., Biocompatible Materials for Continuous Glucose Monitoring Devices, Chem Rev., 113(4), pp. 1-42 (2013).

Plus Continuous Glucose Monitoring System, Users Guide, Dexcom, 145 pages (2010) [Exhibit 1012].

Rice, et al., Continuous Measurement of Glucose, Facts and Challenges, Anesthesiology, vol. 116, No. 1, pp. 199-204 (2012).

Rigo, et al., Cutaneous Reactions to Continuous Glucose Monitoring and Continuous Subcutaneous Insulin Infusion Devices in Type I Diabetes Mellitus, Journal of Diabetes Science and Technology, vol. 15(4), pp. 786-791 (2021).

Rocchitta, et al., Enzyme Biosensors for Biomedical Applications: Strategies for Safeguarding Analytical Performances in Biological Fluids, Sensors, 16, 780, 22 pages (2016).

STS® Seven Continuous Glucose Monitoring System User's Guide, 75 pages (2007).

U.S. Appl. No. 13/071,487, filed Mar. 24, 2011, 132 pages [Exhibit 1003].

U.S. Appl. No. 13/071,497, filed Mar. 24, 2011, 162 pages [Exhibit 1003].

U.S. Appl. No. 14/884,622, filed Oct. 15, 2015 [Exhibit 1024; Part 1 (257 pages) & Part 2 (231 pages)].

U.S. Appl. No. 15/963,828, filed Apr. 26, 2018, [Exhibit 1002; Part 1 (174 pages) & Part 2 (184 pages)].

U.S. Appl. No. 17/008,630, filed Aug. 31, 2020, 484 pages.

U.S. Appl. No. 17/017,590, filed Sep. 10, 2020, 486 pages.

U.S. Appl. No. 17/077,445, filed Oct. 22, 2020 [Exhibit 1002; Part 1 (125 pages), Part 1-2 (131 pages) & Part 2 (260 pages)].

Webster's Third New International Dictionary for "transcutaneous", 5 pages (2002).

Xu, et al., Anti-Biofouling Strategies for Long-Term Continuous Use of Implantable Biosensors, Chemosensors, 8, 66, 30 pages (2020).

U.S. Appl. No. 10/705,719, filed Jul. 7, 2020, Jakowtiz.

59th Annual Meeting, EASD, 326 pages, Oct. 2023.

Abbott Reports Fourth-Quarter and Full-Year 2023 Results; Issues 2024 Financial Outlook, News Release, Jan. 24, 2024, 20 pages.

Abbott v. Dexcom, Jack Griffis Direct Examination, dated Mar. 15, 2024, 38 pages.

Annex C1 GS1 User Guide, SIBIONICS (2023), 26 pages.

Annex C2 GS1 Product Insert, SIBIONICS, 4 pages (2023).

Annex C3 GS1 Quick Start Guide, SIBIONICS, (Nov. 1, 2023), 3 pages.

Annex C4—GS1 App User Guide, GS1 Continuous Glucose Monitoring System, App User Guide, 49 pages (2023).

Annex C6 Extract from EUDAMED registry in relation to the Second Defendant, Manufacturer, CN-MF-000017945, Shenzhen Sisensing Co., Ltd. China, (2023) 7 pages.

Annex D1 Excerpts from First Defendant's website: Sibionics GS1 Continuous Glucose Monitoring (CGM) System, 5 pages (Mar. 20, 2024).

Annex F2 Original Application of the Patent, EP Patent Application No. EP21152231.3, filed (Jan. 19, 2021), 133 pages.

Annex F3 Announcement on website of the Defendants, SIBIONICS is temporarily discontinuing CGM offerings in select European countries (2024), 7 pages.

Annex F3, Earlier Application of the Patent, Request for grant of European patent EP 17182379.2, 131 pages, Jul. 2017.

Annex F4, Earliest Application of the Patent, Entry into the European phase EP 12857506.5, 131 pages, Dec. 2013.

Annex F5 Oxford Dictionary—distal (2023), 2 pages.

Annex F6, Announcement on website of the Defendants temporary cease of sale GS1 Device in German with English Translation, 4 pages, Apr. 2024.

Annex F9, Court of appeal Brussels, Novartis v. Eurocjenerics, in German with English Translation, 23 pages, Sep. 2016.

Baltensperger, Feature Article, Vials. Caps, Septa & Various Products in Comparison, ILM, 3 pages (Apr. 9, 2020).

Beardsall, et al., The continuous glucose monitoring sensor in neonatal intensive care, Arch Dis Child Fetal Neonatal Ed, 90, pp. F307-F310 (2005).

Black, et al., Handbook of Biomaterial Properties, Springer, 5 pages (1998).

Cather, CGM Frustrations Survey, Dexcom, dated Jun. 2020, 37 pages.

Certified Copy U.S. Pat. No. 11,000,216, issued on May 11, 2021, 86 pages.

Certified Korean Patent Application No. 10-2017-0068964 filed on Jun. 2, 2017 [Part 1-Korean language (48 pages) & Part 2-English translation (52 pages)].

Choosing the Right Hamilton Syringe for Your Application, 4 pages (1998).

Clinical Trials Competitor and Ecosystem Players, Abbott, dated Jun. 25, 2020, 29 pages.

Declaration of Karl R. Leinsing, Msme, Pe, in Support of Abbott's Motion for Summary Judgment, executed on May 19, 2023, 81 pages.

Design Concepts, Project Status Update for Glucose Sensor Applicator, Dexcom, dated Apr. 21, 2014, 6 pages.

Direct Examination of Neil Sheehan, filed May 31, 2024, ADC-1 (30 pages) & ADC-2 (30 pages).

Email from Christopher Dougherty with slides re. Global Commercial Insights Meeting, Abbott, sent on Dec. 17, 2019 (69 pages).

Enlite, Serter User Guide, Medtronics, 26 pages (2012).

File History of U.S. Pat. No. 11,510,625, issued on Nov. 29, 2022 [Part 1 (179 pages), Part 2 (178 pages), Part 3 (220 pages) & Part 4 (86 pages).

File Wrapper for U.S. Appl. No. 62/524,247, filed Jun. 23, 2017, 532 pages.

FreeStyle Libre 2 HCP Pulse, Mar. 2021 Report, Abbott, dated Apr. 13, 2021, 14 pages.

Gender of connectors and fasteners, Wikipedia, 6 pages (2024).

Hager, Why Double Elecrocoat and Powder Coat?, 5 pages (1999).

Index of /sdg, The Wayback Machine, Apple Rubber Products Inc., Parts 1-8 (1999).

Mark, et al., Second Edition, Encyclopedia of Polymer Science and Engineering, vol. 15, Parts 1-16 (1989).

MD+DI Qmed, Medical Device and Diagnostic Industry, Silicone Rubber for Medical Device Applications, 8 pages (1999).

Meltsner, et al., Observations on rotating needle insertions using a brachytherapy robot, Physics in Medicine and Biology, 52, pp. 6027-6037 (2007).

Petition for Inter Partes Review of U.S. Pat. No. 11,510,625 under 35 U.S.C. §§ 311-319 and 37 C.F.R. § 42.100 et seq., Case No. IPR2024-00860, In the United States Patent and Trademark Office, Before the Patent Trial and Appeal Board, May 9, 2024, 78 pages.

Princy, et al., Studies on Conductive Silicone Rubber Compounds, Journal of Applied Polymer Science, vol. 69, pp. 1043-1050 (1998).

Sclater, et al., Mechanisms and Mechanical Devices Sourcebook, Fourth Edition, McGraw-Hill, 29 pages (2006).

Seagrove Partners, Globeview™M, International Diabetes Device 2022 Blue Book, 143 pages.

Silastic® MDX4-4210 BioMedical Grade Elastomer, Product Information, Dow Corning, 4 pages (2005).

(56)　　　　References Cited

OTHER PUBLICATIONS

SlimStack™ SMT Stacking, Board-to-Board Connectors, 0.40 to 1.00mm (.016 to .039") Pitch, 0.95 to 20.00mm (.037 to .787") Height, Molex®, 8 pages (2004).
Tsumura, et al., "Histological Evaluation of Tissue Damage Caused by Rotational Needle Insertion", Annu Int Conf IEEE Eng Med Biol Soc., pp. 5120-5123 (2016).
Wampler, et al., Carbon Black, Chapter 6 in Rubber Compounding, Chemistry and Applications, 48 pages (2004).
Z-Carbon Connector, Z-Axis Connector Company, 2 pages (Jun. 7, 2004-May 6, 2007).
Z-Silver Connector, Z-Axis Connector Company, 2 pages (Jul. 9, 2004-May 7, 2007).
"Abbott Receives CE Mark for Freestyle® Libre, A Revolutionary Glucose Monitoring System for People With Diabetes", 2014, 7 pages.
"Alcove", Webster's New College Dictionary, 2001, p. 26.
"An Interview with Kevin Sayer, President and CEO of Dexcom, About The New G6", 2021, 5 pages.
"Does Dexcom Really Have a Future If It Can't Match Abbott's Scale", 2019, retrieved from https://www.sprucepointcap.com/reports/dxcm_research_thesis_3-21-2019.pdf, p. 46.
"Housing" and "recess", The New Penguin English Dictionary, 2000, pp. 678 and 1167.
"Housing", "recess", "release", and "retain", Merriam-Webster's Collegiate Dictionary, Tenth Edition, 1999, pp. 563, 975, 987, and 999.
"Recess", Cambridge Dictionary of American English, 2000, pp. 710-711.
"Retract", The Chambers Dictionary, 1998, p. 1410.
"Retract", The New Oxford American Dictionary, 2001, p. 1455.
"Retract", Webster's Third New International Dictionary, 1993, pp. 1939-1940.
Submission and Review of Sterility Information in Premarket Notification (510(k)) Submissions for Devices Labeled as Sterile, Guidance for Industry and Food and Drug Administration Staff", 2016, pp. 1-11.
"Transcutaneous", Webster's Third New International Dictionary, 2002, p. 2426.
27 Winners Announced at the 19th Annual Medical Design Excellence Awards (MDEA) Award Ceremony, 4 pages, Jun. 13, 2017.
55 chosen as winners in annual big innovation awards, business intelligence group, big innovation 2018, 3 pages, Feb. 7, 2018.
Abbott 2023 Annual Report, 86 pages (2023).
Abbott Press Release—"Abbott's FreeStyle Libre® is Named Best Medical Technology in Last 50 Years by the Galien Foundation", 2 pages (2022).
Abbott Press Release—"Abbott's FreeStyle® Libre 2 ICGM Cleared in U.S. for Adults and Children with Diabetes, Achieving Highest Level of Accuracy and Performance Standards", 3 pages (2020).
Abbott Press Release—"FreeStyle Libre Honored by Prix Galien", 4 pages (2019).
Abbott Press Release—"Real-World Data Show Abbott's FreeStyle Libre® Systems and GLP-1 Medicines Work Better Together for People with Type 2 Diabetes", 2 pages (2024).
Abbott's FreeStyle Libre Flash Glucose Monitoring System Wins the IMSTA most innovative product multi-national award 2017, 2 pages, Oct. 2017.
Abbott's Freestyle Libre® 3 Receives U.S. FDA Clearance—Features World's Smallest, Thinnest and Most Accurate 14-Day Glucose Sensor, 3 pages, May 31, 2022.
Abbott's Freestyle® Libre 14 Day Flash Glucose Monitoring System Now Approved in U.S., 2 pages, Jul. 27, 2018.
Affidavit of Paul Neale signed on May 18, 2016, pp. 1-2.
Affidavit of Richard Paragas signed on May 18, 2016, pp. 1-4.
Ahn, Abbott's Euro approved wearable glucose monitor is different than anything on the market, 6 pages, Sep. 9, 2014.
Battery Connector, 1.20MM Height, 1.60MM Pitch, Double Row, Product Specification, Molex, 9 pages (2006).

Binaxnow, FreeStyle Libre 2 win BIG innovation honors, At-home COVID-19 test, groundbreaking glucose monitoring system among Business Intelligence Group's best of 2021, 6 pages, Jan. 12, 2021.
Blum, Freestyle Libre Glucose Monitoring System, Clinical Pharmacology Update, Clinical.DiabetesJournals. Org, vol. 36, No. 2, pp. 203-204 (2018).
Boise, M., "Dexcom CEO Kevin Sayer Explains G6", 2018, retrieved from https://beyondtype1.org/dexcom-ceo-kevin-sayer-explains-g6/, 9 pages.
Cambridge Dictionary of American English for "periphery", Cambridge University Press, 5 pages (2000).
Certified Copy of Priority Document, U.S. Appl. No. 62/272,983, filed Dec. 30, 2015, 171 pages.
Certified Copy of U.S. Appl. No. 60/424,099, filed Nov. 5, 2002.
Certified Korean Patent Application No. 10-2017-0068964 filed on Jun. 2, 2017, 48 pages [Part 1—Korean language (48 pages) & Part 2—English translation (50 pages)].
Certified True Copy of Preliminary Amendment filed on Apr. 20, 2018 for U.S. Pat. No. 10,827,954, 7 pages.
CES 2022 Innovation Award Product, Innovation Awards Honorees, FreeStyle Libre 3 System, 1 page (2022).
Chicago Innovation, Abbott Laboratories, 5 pages, captured on Jul. 8, 2024.
Choleau, C., et al., "Calibration of a Subcutaneous Amperometric Glucose Sensor Part 1. Effect of Measurement Uncertainties on the Determination of Sensor Sensitivity and Background Current", Biosensor & Bioelectronics, 2002, vol. 17, No. 8, pp. 641-646.
Choleau, C., et al., "Calibration of a Subcutaneous Amperometric Glucose Sensor Implanted for 7 Days in Diabetic Patients Part 2. Superiority of the One-Point Calibration Method", Biosensor & Bioelectronics, 2002, vol. 17, No. 8, pp. 647-654.
Compression Connectors, 1.60mm Pitch Compression Connector, 1.20mm Working Height, Dual-row, 4 Circuits, Molex, 2 pages (2014).
Deposition of Gary Fletcher, Ph.D., dated Jun. 26, 2024, 54 pages in Abbott Diabetes Care Inc., et al. v. Dexcom, Inc., Case No. 03946-82752US01, In the United States District Court for the District of Delaware.
Dexcom CEO—Prime Position in Our Market—Mad Money—CNBC.mp4, Transcript 2023 by Sonix, 2 pages.
Dexcom G5 Mobile, Continuous Glucose Monitoring System, Quick Start Guide, Dexcom, 36 pages (2020).
Dexcom G6, Start Here, Set up Guide, Dexcom, 20 pages (2022).
Dexcom G7 Inserting Sensor Instructions for Use, 2021, pp. 1-2.
Dexcom G7 Overview, The Dexcom G7. The most accurate CGM system., 20 pages (2024).
Dexcom G7 Release: The Most Exciting New Features, , 14 pages (2023).
Dexcom G7, User Guide, Dexcom, 196 pages (2024).
Dexcom Seven® Plus Continuous Glucose Monitoring System User's Guide, 2011, pp. 1-144.
Dexcom STS®-7 Continuous Glucose Monitoring System Summary of Safety and Effectiveness Data, 2007, 14 pages.
Dexcom STS-7 Continuous Glucose Monitoring System FDA Premarket Approval (PMA), 2007, pp. 1-7.
DexCom™ STS™ Continuous Glucose Monitoring System Summary of Safety and Effectiveness Data, 2006, 20 pages.
DexCom™ STS™ Sensor Instructions for Use, 2006, pp. 1-6.
Diabetes Product Review: Abbott FreeStyle Libre Flash Glucose Monitor, 6 pages, Jun. 1, 2021.
Diglas, J., et al., "Reduced pain perception with Pen Mate™M, an automatic needle insertion device for use with an insulin pen", Practical Diabetes International, 1999, vol. 16, No. 2, pp. 39-41.
Edison Awards Announces 2016 Gold, Silver, and Bronze Awards Winners, 9 pages, Apr. 22, 2016.
Edison Awards, Edison Best New Product Awards, 2021 Winners, 19 pages.
Edison Awards, Edison Best New Product Awards, 2022 Winners, 52 pages.
Edison Awards, Our Mission: To be a leader in globally recognizing, honoring and fostering innovation and innovators to create a positive impact in the world., 3 pages (2024).

(56)                References Cited

OTHER PUBLICATIONS

Email from John Shaw of Shaw & Keller dated May 16, 2023, 2 pages.
European Standard, ISO 11607-1, Packaging for terminally sterilized medical devices—Part 1: Requirements for materials, sterile barrier systems and packaging systems, 2006, 32 pages.
European Standard, ISO 13485, Medical devices—Quality management systems—Requirement for regulatory purposes, 2003, 69 pages.
European Standard, ISO 15197, In vitro diagnostic test systems—Requirements for blood glucose monitoring systems for self-testing in managing diabetes mellitus, 2003, 43 pages.
Ex Parte Reexamination Certificate for U.S. Pat. No. 10,959,654, certificate issued on Aug. 5, 2024, 2 pages.
Explore The Monroe Street Market Community, retrieved from https://www.monroestreetmarket.com/floor-plans/apartment/B-231 on May 10, 2023, 2 pages.
U.S. Appl. No. 10/633,367, filed Aug. 1, 2003.
U.S. Appl. No. 61/317,243, filed Mar. 24, 2010.
Food and Drug Administration, HHS, 2009, Code of Federal Regulation § 820.30, Subpart C-Design Controls, pp. 147-148.
FreeStyle Libre 14 day, "Your FreeStyle Libre 14 day System", In-Service Guide, Abbott, 28 pages (2021).
FreeStyle Libre 2, Get Started, "Your guide to the FreeStyle Libre 2 system", Abbott, 15 pages (2023).
FreeStyle Libre 3, Continuous Glucose Monitoring System, User's Manual [Part 1 (124 pages) & Part 2 (124 pages)] (2022-2023).
FreeStyle Libre 3, Flash Glucose Monitoring System, Get Started with the FreeStyle Libre 3 System, Abbott, 11 pages (2023).
FreeStyle Libre FAQs, retrieved from https://www. freestyle abbott/uk-en/support/faq/question-answer.html?q=UKFagquestion-SS#, 2 pages (2024).
Freestyle Libre Pro Flash Glucose Monitoring System Summary of Safety and Effectiveness Data, 2016, 31 pages.
FreeStyle Libre, "It Frees Your Patients from the Inconvenience of Routine Blood Glucose Testing", 4 pages (2016) (with an English translation).
FreeStyle Libre, "Why Punch When You Can Scan 1, 2?", 20 pages (2016) (with an English translation).
FreeStyle Lite Blood Glucose Monitoring System Owner's Booklet, 2006, 15 pages.
FreeStyle Navigator Continuous Glucose Monitoring System FDA Premarket Approval (PMA), 2008, pp. 1-7.
Galien Golden Jubilee Webpage—https://www.galienfoundation.org/galien-golden-jubilee, 3 pages (2022).
German Health Report, Diabetes 2023, German Diabetes Society, 23 pages (2022) (with an English translation).
German Innovation Award—FreeStyle Libre 2—Measure Sugar without Piercing Using a Sensor and App, 1 page (2020).
Gonzales, et al., "The Progress of Glucose Monitoring—A Review of Invasive to Minimally and Non-Invasive Techniques, Devices and Sensors", Sensors, 19(4):800, 45 pages (2019).
Good Design Award, 2017 Good Design Award, Free Style Libre, 9 pages, Jan. 17, 2017.
Gough, et al., "Perspectives in Diabetes, Development of the Implantable Glucose Sensor, What Are the Prospects and Why Is It Taking So Long?", Diabetes, vol. 44, pp. 1005-1009 (1995).
Guerci, B., et al., "Clinical Performance of CGMS in Type 1 Diabetic Patients Treated by Continuous Subcutaneous Insulin Infusion Using Insulin Analogs", Diabetes Care, 2003, vol. 26, No. 3, pp. 582-589.
Hemmerich, K. J., et al., "Sterilization Methods Stand the Test of Time", 2004, retrieved from https://www.mddionline.com/sterilization/sterilization-methods-stand-test-time, pp. 1-8.
Hermanides, et al., "Current Application of Continuous Glucose Monitoring in the Treatment of Diabetes", Diabetes Care, vol. 34, Supp. 2, pp. S197-S201 (2011).

Hirsch, I. B., "Realistic Expectations and Practical Use of Continuous Glucose Monitoring for the Endocrinologist", The Journal of Clinical Endocrinology & Metabolism, 2009, vol. 94, No. 7, pp. 2232-2238.
Hovorka, R., "Continuous glucose monitoring and closed-loop systems", Diabetic Medicine, 2005, vol. 23, pp. 1-12.
Hughes, M. D., "The Business of Self-Monitoring of Blood Glucose: A Market Profile", Journal of Diabetes Science and Technology, 2009, vol. 3, No. 5, pp. 1219-1223.
International Standard, ISO 14971, Medical devices—Application of risk management to medical devices, 2007, 90 pages.
Joseph, et al., "Glucose Sensing in the Subcutaneous Tissue: Attempting to Correlate the Immune Response with Continuous Glucose Monitoring Accuracy", Diabetes Technology & Therapeutics, vol. 20, No. 5, pp. 321-324 (2018).
Kal, S., "Basic Electronics - Devices, Circuits and IT Fundamentals", 2006, Chapter 13, Microcomputers and Microprocessors, p. 412.
Klueh, U., et al., "Blood-Induced Interference of Glucose Sensor Function in Vitro: Implications for in Vivo Sensor Function", Journal of Diabetes Science and Technology, 2007, vol. 1, No. 6, pp. 842-849.
Kovatchev, B. P., et al., "Evaluating the Accuracy of Continuous Glucose-Monitoring Sensors", Diabetes Care, 2004, vol. 27, No. 8, pp. 1922-1928.
Letter from the U.S. Food & Drug Administration to Dexcom, Inc. regarding the Dexcom G7 Continuous Glucose Monitoring (CGM) System, 510(k) Premarket Notification and 510(k) summary, 10 pages, Dec. 7, 2022.
Lovett, "What's Next for Dexcom? CEO, CTO Talk G6 for Inpatient Use, Expanding CGMs for Patients without Diabetes", 17 pages (2020).
Mauras, N., et al., "Lack of Accuracy of Continuous Sensors in Healthy, Nondiabetic Children: Results of the Diabetes Research in Children Network (DirecNet) Accuracy Study", Journal of Pediatrics, 2004, pp. 770-775.
MD+DI Qmed, Medical Device and Diagnostic Industry, 11 pages, Apr. 1, 1996.
Medtronic MiniMed Guardian RT FDA Premarket Approval (PMA), 2005, pp. 1-6.
Medtronic MiniMed Guardian RT Summary of Safety and Effectiveness Data, 2005, 13 pages.
Medtronic MiniMed iPro2 User Guide, 2010, pp. 1-99.
Medtronic MiniMed Paradigm® Real-Time 522 and 722 Insulin Pumps User Guide, 2008, pp. 1-262.
Medtronic MiniMed Sen-Serter® User Guide, 2006, pp. 1-96.
Nichols, S. P., et al., "Biocompatible Materials for Continuous Glucose Monitoring Devices", Chem Rev., 2013, vol. 113, No. 4, pp. 2528-2549.
Occupational Safety and Health Admin., Labor, 2003, 29 CFR § 1910.1030 Bloodborne pathogens, pp. 260-273.
Ólafsdóttir, et al., A Clinical Trial of the Accuracy and Treatment Experience of the Flash Glucose Monitor FreeStyle Libre in Adults with Type 1 Diabetes, Diabetes Technology & Therapeutics, vol. 19, No. 3, pp. 164-172 (2017).
OneTouch Ultra2 Blood Glucose Monitoring System Owner's Booklet, 2005, 34 pages.
OneTouch® Ultra™ Blood Glucose Monitoring System Owner's Booklet, 2000, 23 pages.
Order, Federal Communications Commission, 2006, pp. 1-8.
Parker, S. P., ed., McGraw-Hill Dictionary of Mechanical and Design Engineering, 1984 (excerpted), 4 pages.
Sales Drawing for Battery 1.2H 1.6MM Pitch Double Row Connector, Molex, 2 pages (2013).
Schmidtke, D. W., et al., "Accuracy of the One-Point In Vivo Calibration of "Wired" Glucose Oxidase Electrodes Implanted in Jugular Veins of Rats in Periods of Rapid Rise and Decline of the Glucose Concentration", Analytical Chemistry, 1998, vol. 70, No. 10, pp. 2149-2155.
Shenoi, B. A., ed., Introduction to Digital Signal Processing and Filter Design, 2006, "Introduction", Chapter 1, pp. 1-30.
Slomski, et al., U.S. Appl. No. 61/037,246, filed Mar. 17, 2008, 13 pages.

(56) References Cited

OTHER PUBLICATIONS

Smith, S. S., ed., The Scientist and Engineer's Guide to Digital Signal Processing, Second Edition, 1997-1999, "Digital Signal Processors", Chapter 28, pp. 503-534.
Tierney, M. J., et al., "Effect of Acetaminophen on the Accuracy of Glucose Measurements Obtained with the GlucoWatch Biographer", Diabetes Technology & Therapeutics, 2000, vol. 2, No. 2, pp. 199-207.
Tsalikian, E., et al., "Accuracy of the GlucoWatch G2® Biographer and the Continuous Glucose Moninting System During Hypoglycemia: Experience of the Diabetes Research in Children Network", Diabetes Care, 2004, vol. 27, No. 3, pp. 722-726.
Van den Boom, et al., Changes in the utilization of blood glucose test strips among patients using intermittent-scanning continuous glucose monitoring in Germany, Diabetes Obes Metab, vol. 22, pp. 922-928 (2020).
Wikipedia, The Free Encyclopedia, "Continuous glucose monitor", retrieved from https://en.wikipedia.org/w/index.php?title=Continuous glucose monitor&oldid=1224795 137, 12 pages (2024).
"Enabling the Devices that Drive Innovation in Healthcare", Molex, 12 pages (2013).
"Molex—Medical Capabilities—Certifications" available on YouTube since Jul. 1, 2015 (https://www.youtube.com/watch?v=wMQzhXBd8hw), 6 pages.
"Molex—Product of the Quarter Videos—Micro Products" available on YouTube since Oct. 7, 2013 (https://www.youtube.com/watch?v=CSV88TUYvy0), 11 pages.
Application Brief—Improved Healthcare Monitoring and Patient Safety: Compliant Integrated Solutions for Durable Medical Devices, Molex, 2 pages (2015).
Burge, et al., "Continuous Glucose Monitoring: The Future of Diabetes Management", Diabetes Spectrum, vol. 21, No. 2, pp. 112-119 (2008).
Cable Products for the Medical Industry, Molex, 4 pages (2010).
Clancy, et al., "A new device for assessing changes in skin viscoelasticity using indentation and optical measurement", Skin Research and Technology, 16:210-228 (2010).
Cleo® 90 Infusion Set, Product Literature, Smiths Medical, 2 pages (2022).
Cleo™ 90 Infusion Set Training Guide, Smiths Medical, 1 page (2006).
Connector Types and Technologies Poised for Growth, Research Report P-606-12, 215 pages (Part 1—162 pages and Part 2-53 pages) (2012).
Continuous Glucose Monitoring System (CGMS), Summary of Safety and Effectiveness Data, Pre-Market Approval (PMA) No. P980022, MiniMed Inc., 25 pages (1999).
DexCom™ STS™ Continuous Glucose Monitoring System, User's Guide, DexCom, Inc., 58 pages (2006).
DexCom™ STS™ Sensor, User Guide, 51 pages (2006).
Diabetes Patents, FreeStyle Libre® Glucose Monitoring System, FreeStyle Libre® 2 Glucose Monitoring System and FreeStyle Libre® 3 Glucose Monitoring System, Abbott, 6 pages (2024).
Dutt-Ballerstadt, et al., "A label-free fiber-optic Turbidity Affinity Sensor (TAS) for continuous glucose monitoring", Biosensors and Bioelectronics, 61:280-284 (2014).
Fda U.S. Food and Drug Administration, Premarket Approval (PMA), New Search, FreeStyle Navigator Continuous Glucose Monitor, 2 pages, Nov. 11, 2024.
Ferguson, et al., "Real-Time, Aptamer-Based Tracking of Circulating Therapeutic Agents in Living Animals", Science, vol. 5, Issue 213, pp. 1-9 (2013).
U.S. Pat. No. 7,731,691 issued Jun. 8, 2010, 739 pages.
US Trademark Registration No. 3154910 (CLEO), registered on Oct. 10, 2006, 67 pages.
FreeStyle Libre Flash Glucose Monitoring System, User's Manual, Abbott Diabetes Care Ltd., 126 pages (2017) Part 1 (63 pages) and Part 2 (63 pages).
FreeStyle Navigator Continuous Glucose Monitoring System, User's Guide, Abbott Diabetes Care Inc., 191 pages (2008).

Letter from the Department of Health & Human Services, Food and Drug Administration to Mr. David H. Short at Smiths Medical MD, Incorporated re the Cleo 90 Infusion Set, Section 510(k) No. K042172, Premarket Notification dated Oct. 7, 2004, 3 pages.
Mazze, et al., "Evaluating the Accuracy, Reliability, and Clinical Applicability of Continuous Glucose Monitoring (CGM): Is CGM Ready for Real Time", Diabetes Technology & Therapeutics, vol. 11, No. 1, pp. 11-18 (2009).
MD+DI Qmed, "Choosing Electronic Connectors for Medical Devices", retrieved from https://www.mddionline.com/components/choosing-electronic-connectors-for-medical-devices, 9 pages (2014).
MediSpec™ MID/LDS Capabilities for High-Density Medical and other Applications, Molex, 2 pages (2011).
Piper, et al., "Real-Time Continuous Glucose Monitoring in Pediatric Patients During and After Cardiac Surgery", Pediatrics, vol. 118, No. 3, pp. 1176-1184 (2006).
Rabiee, et al., "Numerical and Clinical Accuracy of a Continuous Glucose Monitoring System during Intravenous Insulin Therapy in the Surgical and Burn Intensive Care Units", Journal of Diabetes Science and Technology, vol. 3, Issue 4, pp. 951-959 (2009).
Sacks, et al., "Skin blood flow changes and tissue deformations produced by cylindrical indentors", Journal of Rehabilitation Research and Development, vol. 22, No. 3, pp. 1-6, 11 pages (1985).
Schneider, et al., "Evaluating the use of the Cleo® 90 infusion set for patients on a palliative care unit", International Journal of Palliative Nursing, vol. 15, No. 8, pp. 372-376 (2009).
Stay Connected, Affinity Medical™ Connectors and Cable Assemblies for Patient Critical Applications, Molex, 8 pages (2014).
The Wayback Machine, CleoTM 90 Infusion Set, Smiths Medical, 1 page (2006).
The Wayback Machine, DexCom Products and User Manuals—the Seven System and STS System Manuals, DexCom, 2 pages (2007).
The Wayback Machine, DexCom Products, The Seven System, DexCom, 2 pages (2007).
The Wayback Machine, FreeStyle Navigator Continuous Glucose Monitoring System, Introducing the new FreeStyle Navigator® Continuous Glucose Monitoring System, Abbott Laboratories, 2 pages (2008).
The Wayback Machine, FreeStyle Navigator Continuous Glucose Monitoring System, Answers to Frequently Asked Questions, Abbott Laboratories, 1 page (2008).
The Wayback Machine, FreeStyle Navigator® Continuous Glucose Monitoring System, Answers to Frequently Asked Questions, Abbott Laboratories, 2 pages (2007).
The Wayback Machine, Guardian® Real-Time System, Features and Components, Medtronic MiniMed, Inc., 4 pages (2007).
The Wayback Machine, Medtronic Main Webpage, Medtronic MiniMed, Inc., 1 page (2007).
The Wayback Machine, Medtronic Product Information, Introducing the Guardian® Real-Time Continuous Glucose Monitoring System, Medtronic MiniMed, Inc., 3 pages (2007).
The Wayback Machine, Medtronic Product Information, We are the Leader in Diabetes Management, Medtronic MiniMed, Inc., 2 pages (2007).
The Wayback Machine, News—Cleo™ 90 Infusion Set from Smiths wins medical design excellence award, Smiths Medical, 1 page (2006).
The Wayback Machine, News & Events, Smiths Medical, 1 page (2006).
The Wayback Machine, Products and Promotions, Smiths Medical, 1 page (2006).
The Wayback Machine, Smiths Medical Cleo 90 Infusion Set, Ambulatory Infusion Disposables, 2 pages (2022).
The Wayback Machine, Smiths Medical Latest News, Smiths Medical, 2 pages (2006).
The Wayback Machine, Smiths Medical Main Webpage, Smiths Medical, 2 pages (2022).
The Wayback Machine, The STS Seven Continuous Glucose Monitoring System, DexCom, 1 page (2007).
The Wayback Machine, U.S. Food and Drug Administration, Search Premarket Approval (PMA) Database, 1 page (2008).

(56) References Cited

OTHER PUBLICATIONS

U.S. Department of Veterans Affairs, Journal of Rehabilitation Research & Development (JRRD), "JRRD 1980-1989" vol. 17-26, 3 pages (1980-1989).

U.S. Food and Drug Administration, 510(k) Premarket Notification, Cleo 90 Infusion Set, 1 page (2004).

U.S. Food and Drug Administration, Premarket Approval (PMA) Search Database, 1 page (2024).

U.S. Food and Drug Administration, Premarket Approval (PMA) Search Results, 1 page (2024).

U.S. Food and Drug Administration, Premarket Approval (PMA) Search Results, 2 pages (2008).

U.S. Food and Drug Administration, Premarket Approval (PMA), DexCom STS Continuous Monitors, 2 pages (2006).

202180062699.2 First Office Action, May 30, 2025.

2023-516499 Office Action, Jul. 1, 2025.

21870036.7 Examination Report, Nov. 20, 2025.

\* cited by examiner

FIG. 2B

Sensor Electronics 160

ASIC 161

Power Mgmt. Circuitry 164

Processor 166

AFE 162

Communication Circuitry 168

Memory 163

Power Source 170

Analyte Sensor 104

171

Sensor Control Device 102

FIG. 2C

Sensor Electronics 160

Chip 174

Power Mgmt. Circuitry 164

Processor 166

Memory 165

Communication Circuitry 168

Power Source 170

AFE 162

Memory 163

ASIC 161

171

Analyte Sensor 104

Sensor Control Device 102

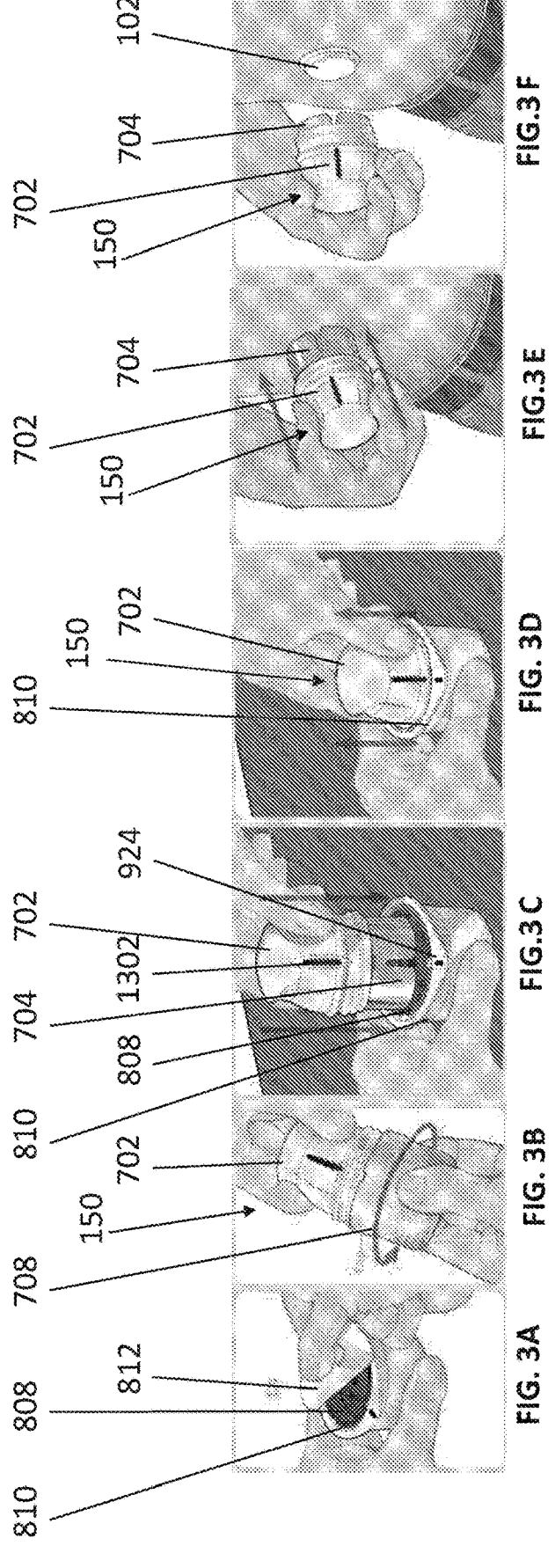

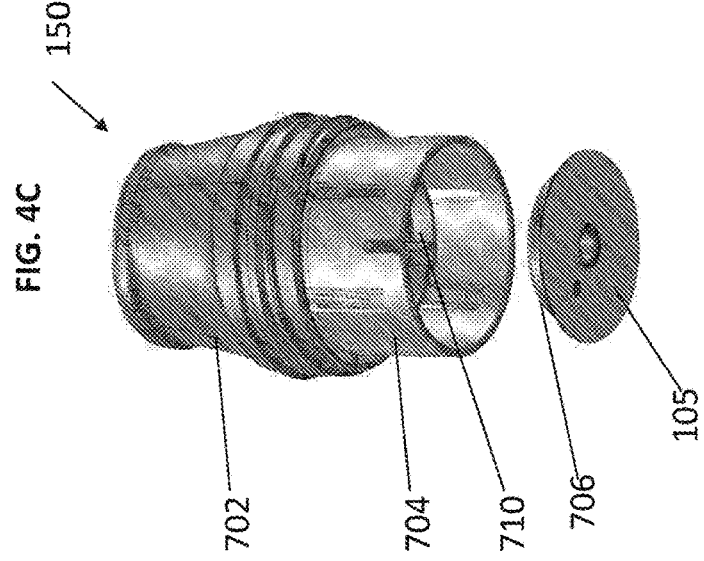
FIG. 4C
150
702
704
710
706
105
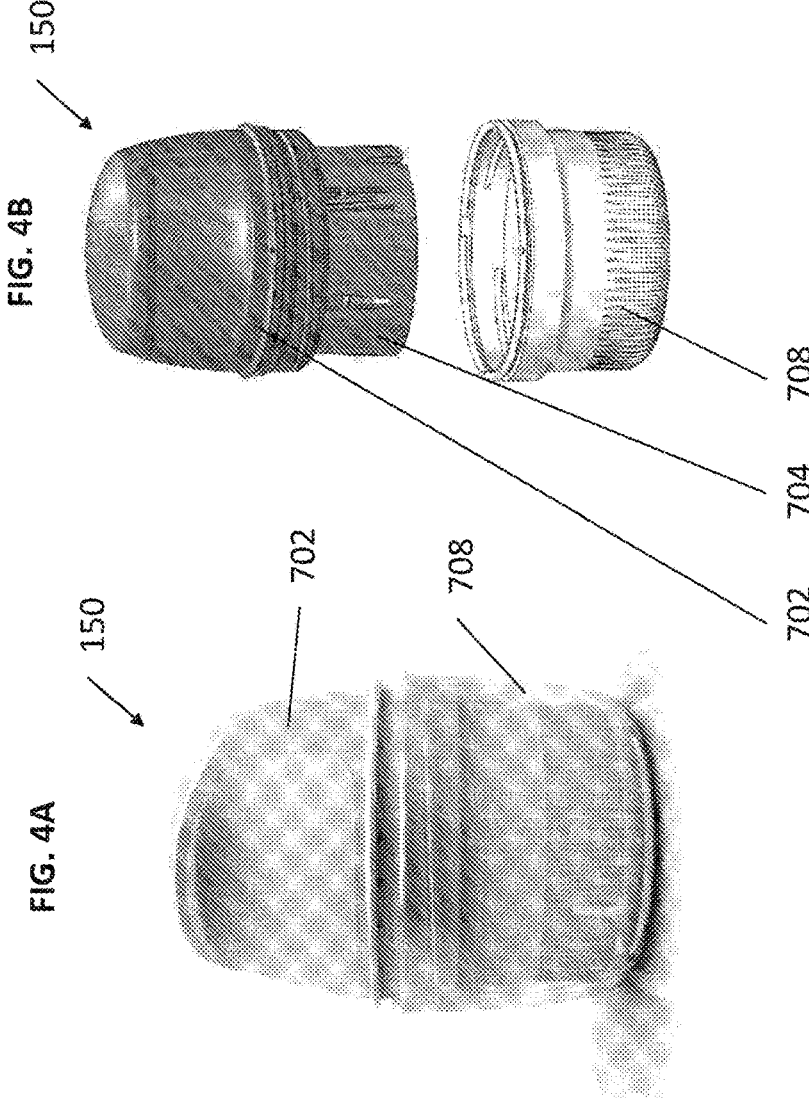
FIG. 4B
150
708
704
702
702
FIG. 4A
150
702
708

1318 Grip overhang

1316 Side grip zone

1314 Tamper ring protector

1320 Shark tooth

702

Housing orienting feature 1302

Tamper ring groove 1304

Tamper ring retainer 1306

Housing threads 1310

1336 Final lockout recess

1338 Sheath stopping ramp

1344 Firing detent

1334 Unlocked groove

1332 Locked groove

1330 Sheath snap lead-in feature

1340 Locking rib

702

Insertion hard stop 1322

Housing guide rib 1321

Sheath guide rail 1326

Sensor electronics carrier interface 1328

1346 central axis

1418 Guide rail

Detent snap 1402

1416 Lock arm interface

Detent clearance 1410

1414 Lock arm strengthening rib

1412 Lock arms

704

704

Sensor electronics carrier
travel limiter face 1420

Detent base 1436

Detent snap
stiffening feature 1422

Alignment notch 1424

Stiffening ribs 1426

1434 Tilt reducing ribs

1428 Housing guide rail clearance

704

1410

1424

704

1406 Detent snap flat

Detent snap bridge 1408

Detent snap Rounds 1404

Detent snap 1402

1448 Sheath rotation limiter

Backwall for guide rails 1446

704

1526 Sharp carrier retention feature

1524 Sharp carrier lock arms

1520 Sensor electronics retention feature

1518 Sensor electronics retention spring arm

1516 Spring alignment ridge

1510 Aperture

710

Lock interface 1502

Rotation limiter 1506

Sensor electronics
carrier shock lock 1534

710

1518 Sensor electronics
retention spring arm

1519 Retention
detent

6710

6519

1102

1610 Sharp carrier base chamfer

1608 Anti-rotation slot

1102

Sharp retention arms 1618

Sharp retention clip 1620

Sharp hub contact face 1622

2206 connector posts

Sharp slot 2208

Sensor ledge 2212

Sensor wall 2216

504

2202 module snaps

504

Sensor sway space 2204

2302 Contacts

2300

Seal
surfaces
2304

Seal
surfaces
2304

2308 Hinges

Locators 2306

2300

2418 Contacts

2404 Flag

2414 Bias Fulcrum

104

Biasing tower 2412

Service Loop 2420

Bias adjuster 2416

Neck 2406

Tail 2408

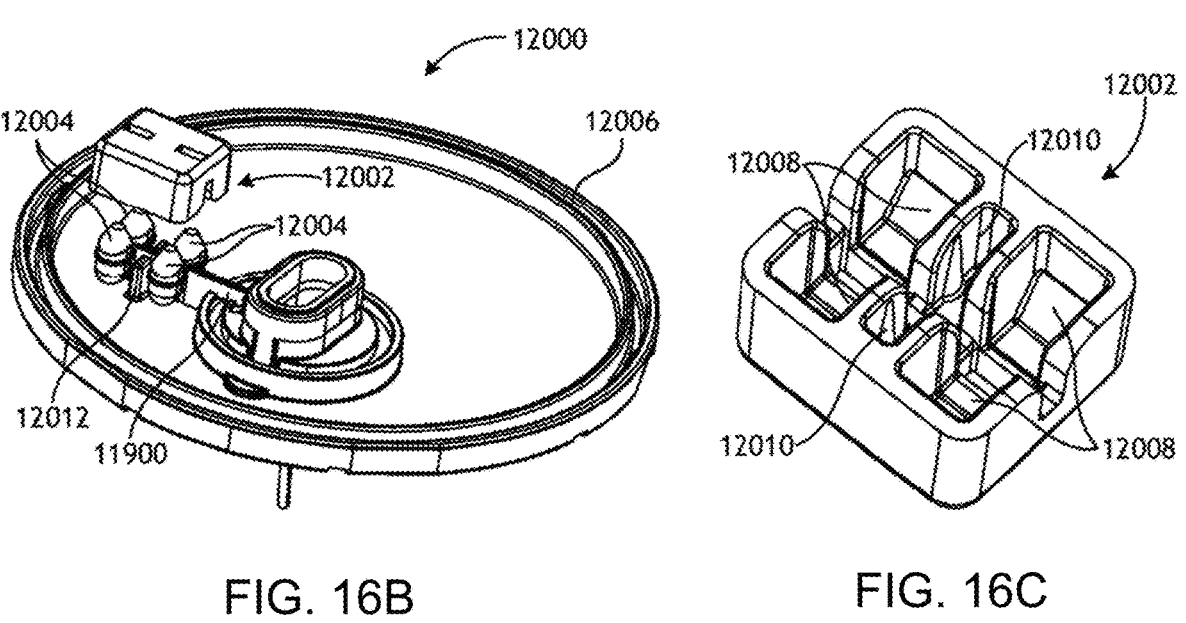
FIG. 16B
FIG. 16C
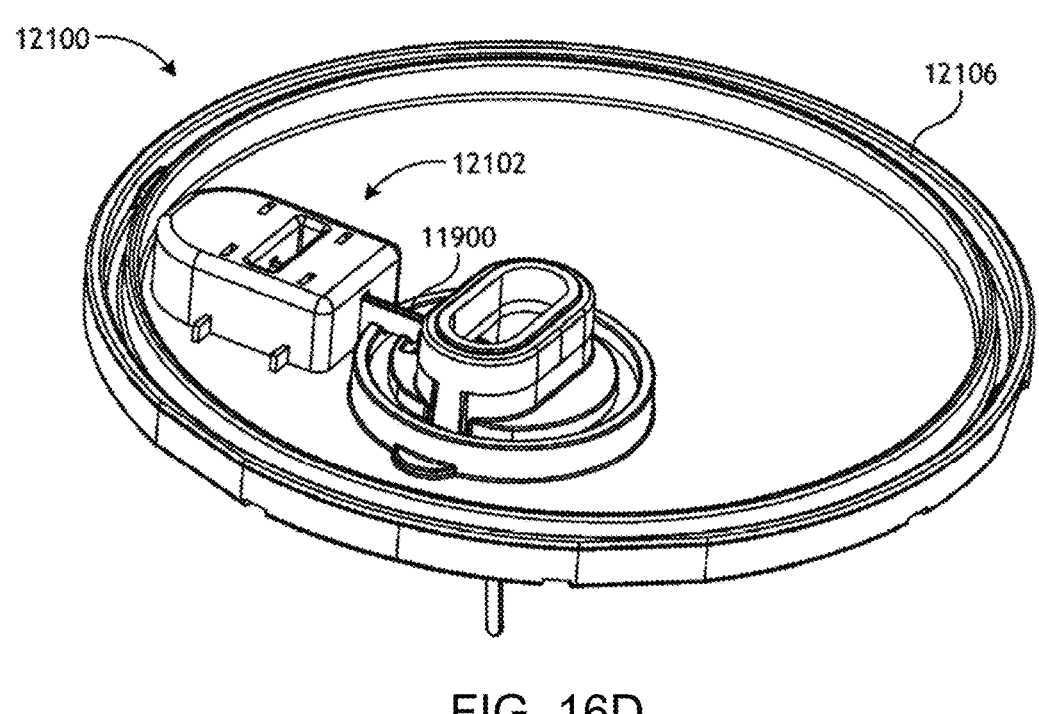
FIG. 16D

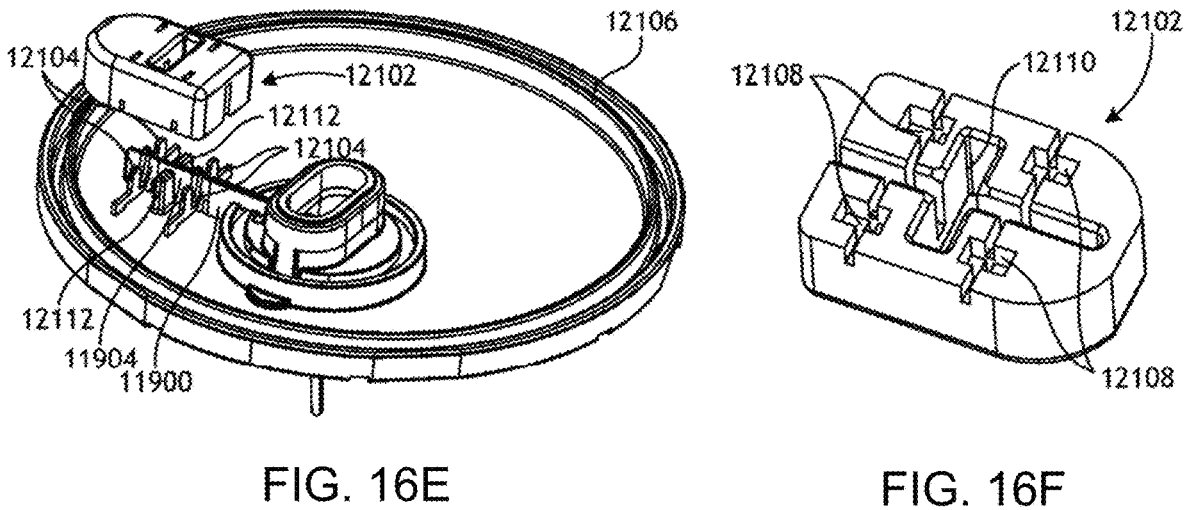
FIG. 16E                    FIG. 16F 2514 hubsnap pawl locating cylinder 2516 hub snap pawl 2512 hub small cylinder 2508 hub push cylinder 2502 sharp

2500 shaft 2504 distal tip 2506

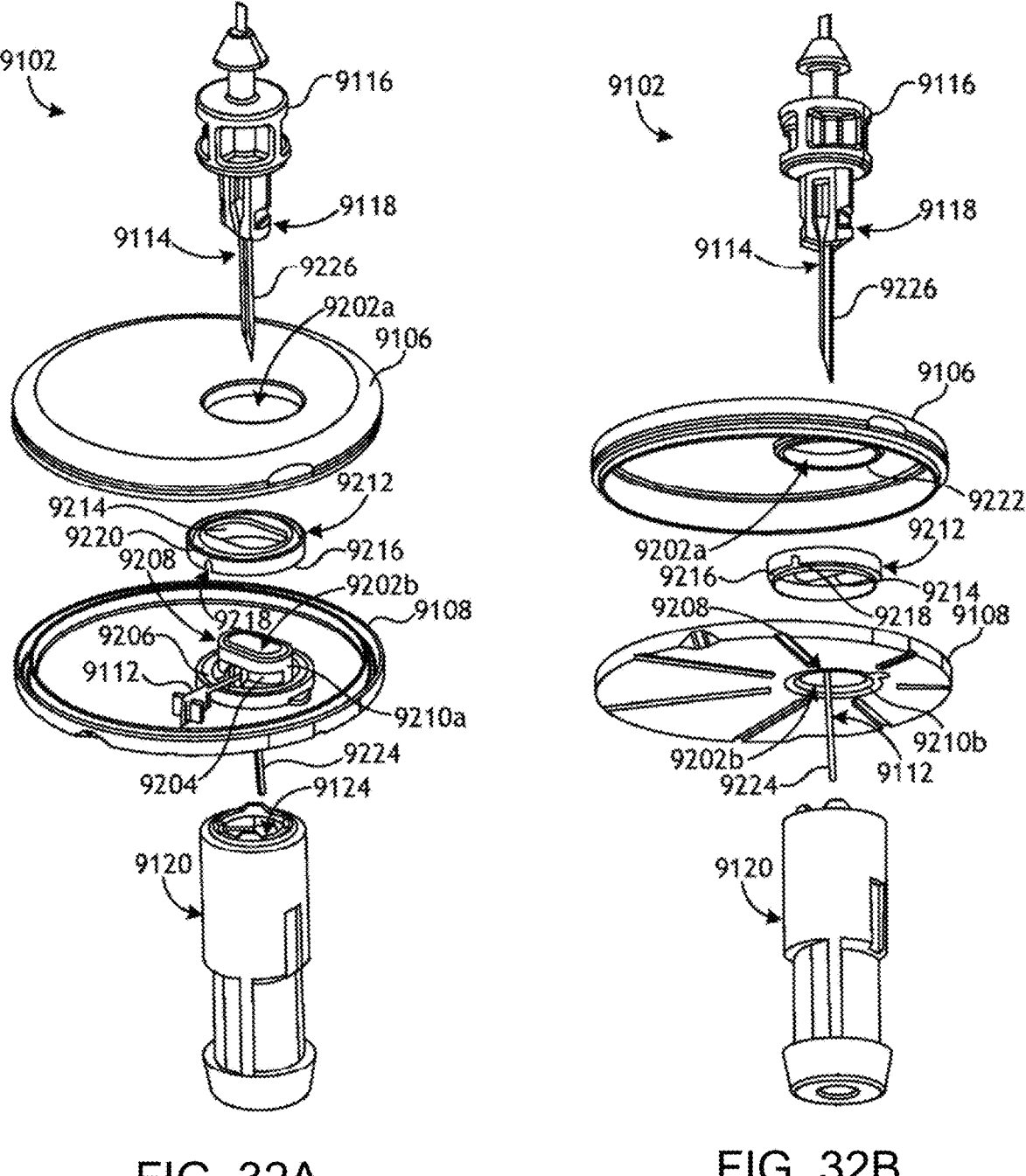
FIG. 32A                    FIG. 32B

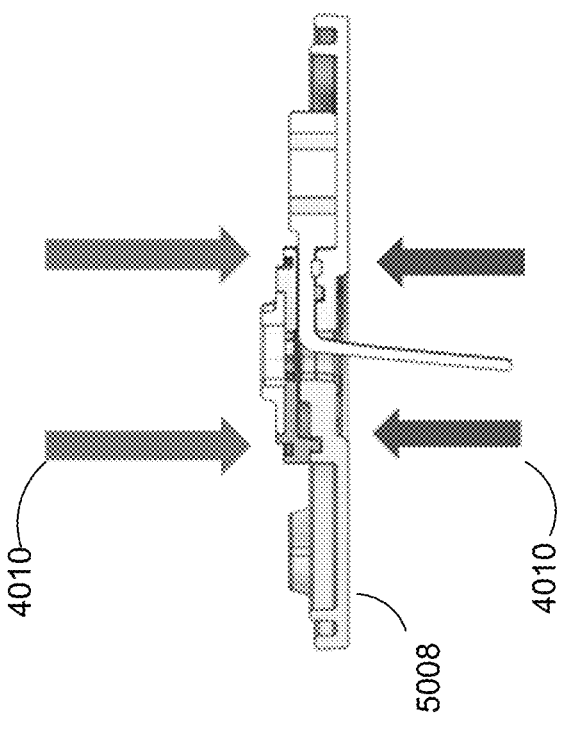
FIG. 40D
4010
4010
5008
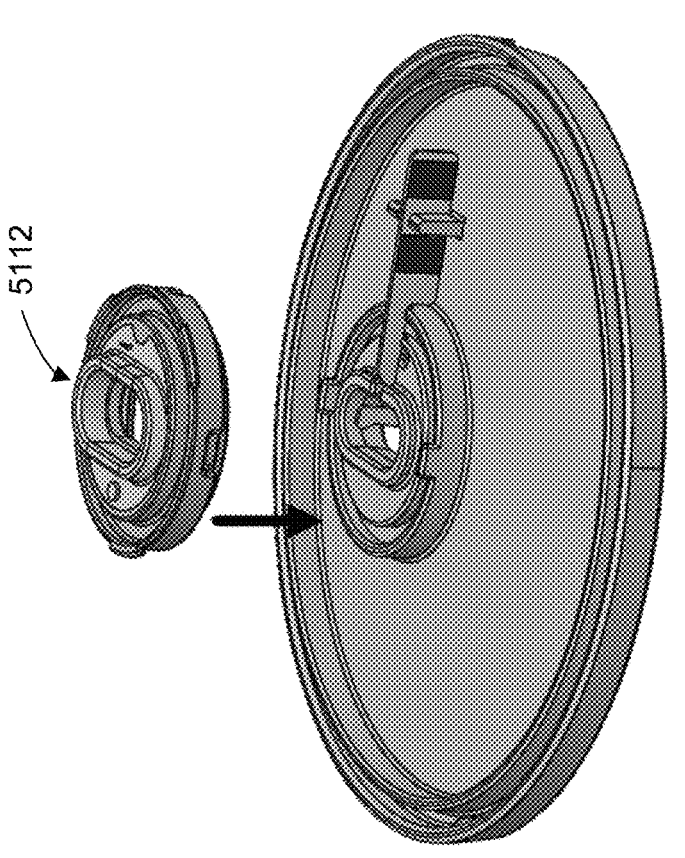
5112
FIG. 40C

702

708

702

708

SYSTEMS, DEVICES, AND METHODS FOR AN ANALYTE SENSOR

CROSS-REFERENCE TO RELATED APPLICATIONS

This application claims the benefit, under 35 U.S.C. § 119(e), of U.S. Provisional Patent Application No. 63/078,681, filed 15 Sep. 2020, and U.S. Provisional Patent Application No. 63/081,223, filed 21 Sep. 2020, which are incorporated herein by reference.

FIELD

The subject matter described herein relates generally to systems, devices, and methods for analyte sensors. For example, methods for assembling a sensor subassembly, an on-body sensor puck assembly, and an applicator assembly are disclosed. A sensor including a tail, a flag, and a neck that interconnects the tail and the flag and methods of configuring a sensor are also disclosed.

BACKGROUND

The detection and/or monitoring of analyte levels, such as glucose, ketones, lactate, oxygen, hemoglobin AIC, or the like, can be vitally important to the health of an individual having diabetes. Patients suffering from diabetes mellitus can experience complications including loss of consciousness, cardiovascular disease, retinopathy, neuropathy, and nephropathy. Diabetics are generally required to monitor their glucose levels to ensure that they are being maintained within a clinically safe range, and may also use this information to determine if and/or when insulin is needed to reduce glucose levels in their bodies, or when additional glucose is needed to raise the level of glucose in their bodies.

Growing clinical data demonstrates a strong correlation between the frequency of glucose monitoring and glycemic control. Despite such correlation, however, many individuals diagnosed with a diabetic condition do not monitor their glucose levels as frequently as they should due to a combination of factors including convenience, testing discretion, pain associated with glucose testing, and cost.

To increase patient adherence to a plan of frequent glucose monitoring, in vivo analyte monitoring systems can be utilized, in which a sensor control device may be worn on the body of an individual who requires analyte monitoring. To increase comfort and convenience for the individual, the sensor control device may have a small form-factor, and can be assembled and applied by the individual with a sensor applicator. The application process includes inserting a sensor, such as a dermal sensor that senses a user's analyte level in a bodily fluid located in the dermal layer of the human body, using an applicator or insertion mechanism, such that the sensor comes into contact with a bodily fluid. The sensor control device may also be configured to transmit analyte data to another device, from which the individual or her health care provider ("HCP") can review the data and make therapy decisions.

While current sensors can be convenient for users, they are also susceptible to malfunctions due to improper insertion. These malfunctions can be caused by user error, lack of proper training, poor user coordination, overly complicated procedures, and other issues. This can be particularly true for analyte monitoring systems having dermal sensors, which are typically of smaller scale relative to sensors used to measure an analyte level in an interstitial fluid ("ISF"), and which are inserted using sharps (also known as "introducers" or "needles") that are shorter than those used for ISF sensors. Some prior art systems, for example, may rely too much on the precision assembly and deployment of a sensor control device and an applicator by the individual user. Other prior art systems may utilize sharp insertion and retraction mechanisms that are susceptible to premature withdrawal before the sensor can be properly implanted. In addition, with respect to dermal sensors, some prior art systems may utilize sharps that are not optimally configured to create an insertion path in the dermal layer without creating trauma to surrounding tissue. These challenges and others described herein can lead to improperly inserted or damaged sensors, and consequently, a failure to properly monitor the patient's analyte level.

Thus, a need exists for more reliable sensor insertion devices, systems and methods, particularly for use in conjunction with dermal sensors, that are easy to use by the patient and less prone to error. A need also exists for manufacturing methods that provide reliable and reproducible sensors and are suitable for scale up.

SUMMARY

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve these and other advantages and in accordance with the purpose of the disclosed subject matter, as embodied and broadly described, the disclosed subject matter is directed to a method of assembling a sensor subassembly including a sensor, a sensor mount, a collar, a sharp, and a sensor cap. The method includes loading a sensor in a sensor mount, dispensing adhesive into a mount channel of the sensor mount, clamping a collar to the sensor mount, curing the adhesive to fix the collar to the sensor mount, inserting a sharp into the sensor mount over the sensor, and attaching a sensor cap to the sensor and sensor sharp to provide a sealed sensor subassembly. The adhesive can be a chemically-curable adhesive and the method can include curing the adhesive by exposing the adhesive to one or more chemical bonding catalysts. The adhesive can be a heat-curable adhesive and the method can include curing the adhesive by exposing the adhesive to heat suitable to cure the adhesive. The adhesive can be an ultra-violet (UV)-curable adhesive and the method can include curing the adhesive using one or more UV light sources. The sensor can be shielded from the one or more UV light sources while curing the adhesive. The one or more UV light sources can include a UV light emitting diode with light pipe and multiple angled spot light emitting diodes. The method can include loading the collar onto the sensor mount. The sharp can be attached to a sharp hub and inserting the sharp into the sensor mount can include coupling the sharp hub to the sensor mount. The method can include dispensing adhesive to a top surface of the sharp hub and curing the adhesive to seal incidental leaks between the sharp hub and the sharp. The method can include testing the sealed sensor subassembly for leaks using a pressure-decay leak test, vacuum-decay leak test, tracer gas leak test, signature analysis test, or mass-flow leak test. The method can include discarding the sealed sensor subassembly when leaks are detected that exceed a predetermined threshold. The method can include sterilizing the sensor subassembly via heat treatment, radiation, electronic-beam sterilization, gamma sterilization, x-ray sterilization, ethylene oxide sterilization, autoclave steam sterilization, chlorine dioxide gas sterilization, or hydrogen peroxide sterilization. The sensor can include a body temperature sensor, blood pressure sensor, pulse or heart-rate sensor, glucose level sensor, analyte sensor, or physical activity sensor. The method can include inspecting the sharp for imperfections prior to inserting the sharp into the sensor mount. The method can include discarding the inspected sharp when imperfections are detected that exceed a predetermined threshold. Attaching the sensor cap to the sensor and sensor sharp to provide a sealed subassembly can include twisting the sensor cap into position. The method can include inserting a desiccant into a plug and inserting the plug into the sensor cap prior to attaching the sensor cap to the sensor and sensor sharp.

The disclosed subject matter is further directed to a method of assembling an on-body sensor puck assembly including a printed circuit board (PCB), a puck shell cap, and a sensor subassembly, the sensor subassembly including a sensor, a sensor mount, a collar, and a sensor cap. The method can include dispensing a first adhesive to a sensor mount of the sensor subassembly, loading a PCB onto the sensor mount of the sensor subassembly after aligning the PCB with the sensor and the sensor subassembly, curing the first adhesive to fix the PCB to the sensor mount, dispensing a second adhesive onto an outer diameter of the sensor mount and inner diameter of a collar of the sensor subassembly, attaching the puck shell cap to the sensor subassembly, and curing the second adhesive to form the on-body sensor puck assembly. The PCB can be a flexible PCB and the method can include folding the PCB to fit a footprint of the on-body sensor puck assembly. Dispensing the first adhesive can further include dispensing the first adhesive at a location of the fold, a battery location, or a PCB connector location. The PCB can further include a radio component and the method can further include writing data to the radio component by reading sensor data from the sensor subassembly, PCB, a puck shell cap, or a mount carrying the sensor subassembly and writing the sensor data to the radio component of the PCB. Dispensing the second adhesive onto the outer diameter of the sensor mount and inner diameter of the collar of the sensor subassembly can include tilting the sensor mount along an axis to a predetermined angle, dispensing the adhesive to the inner diameter of the collar of the sensor subassembly, returning the sensor mount to a substantially horizontal position by tilting the sensor mount along the axis, and dispensing the adhesive to the outer diameter of the sensor mount. The method can further include testing the on-body sensor puck assembly for leaks using a pressure-decay leak test, vacuum-decay leak test, tracer gas leak test, signature analysis test, or mass-flow leak test. The method can further include discarding the on-body sensor puck when leaks are detected that exceed a predetermined threshold. The first adhesive or the second adhesive can be a chemically-curable adhesive and curing the first adhesive or the second adhesive can include exposing the adhesive to one or more chemical bonding catalysts. The first adhesive or the second adhesive can be a heat-curable adhesive and curing the first adhesive or the second adhesive can include exposing the adhesive heat suitable to cure the adhesive. The first adhesive or the second adhesive is an ultra-violet (UV)-curable adhesive and curing the first adhesive or the second adhesive can include using one or more UV light sources.

The disclosed subject matter is further directed to a method of assembling an applicator assembly comprising an inserter, on-body sensor puck assembly coupled to a puck carrier, a sheath, an applicator housing, and a cap. The method includes assembling the inserter by loading a spring to a sharp carrier, lowering a puck carrier to the sharp carrier and compressing the spring until seated within the sharp carrier, and locking one or more retention features of the sharp carrier to retain spring compression, coupling the on-body sensor puck assembly to the puck carrier, applying an adhesive patch to the on-body sensor puck assembly, attaching a sheath to the puck carrier, attaching the sheath to the applicator housing, and coupling the cap to the applicator housing. Attaching the sheath to the puck carrier can include loading the sheath into a fixture nest and lowering the puck carrier with compressed spring into the sheath. Attaching the sheath to the applicator housing can include loading the applicator housing into a fixture nest and engaging an alignment rib of the applicator housing with a notch in the fixture nest and lowering the sheath onto the applicator housing and engaging the alignment rib of the applicator housing. Coupling the cap to the applicator housing can include lowering the cap onto the applicator housing and screwing the cap to the applicator housing to a pre-determined torque. The method can include loading a desiccant into the cap. The method can include applying a tamper-proof sticker to the applicator assembly.

The disclosed subject matter is further directed to a sensor including a tail, a flag, and a neck that interconnects the tail and the flag. The tail, the flag, and the neck are aligned along a planar surface having a vertical axis and a horizontal axis, between the tail and the flag, the neck includes at least two turns in relation to the vertical axis defining a spring structure, and the flag includes a generally planar surface having one or more sensor contacts. The at least two turns of the neck can be formed by bending the neck of the sensor. The at least two turns of the neck can be formed by laser cutting the sensor. The at least two turns of the neck can be formed by stamping the sensor from a sheet of material comprising the sensor. The at least two turns of the neck can be formed by printing the sensor to include the two turns. The at least two turns, in relation to the vertical axis, can provide overlapping layers of the neck. The overlapping layers of the neck can be vertically-oriented. The overlapping layers of the neck can be horizontally-oriented.

The disclosed subject matter is further directed to a method of configuring a sensor including a tail, a flag, and a neck that interconnects the tail and the flag. The method can include heating a portion of the neck of the sensor to a predetermined temperature and bending the neck of the sensor to form a first angle between the tail of the sensor and the flag of the sensor. The predetermined temperature can be sufficient to improve malleability of the neck of the sensor. The predetermined temperature can be any suitable range, inclusive, including for example between 50 and 60° C., or a particular target temperature within that range. The method can further include verifying integrity of the sensor after bending by checking the neck for microfractures in the neck of the sensor. The method can further include disposing of the sensor if microfractures detected in the neck of the sensor exceed a predetermined threshold of microfractures. The heating can be performed by a first component of a heated-bending apparatus and the bending can be performed by a second component of the heated-bending apparatus. Heating the portion of the neck can include heating the first component of the heated-bending apparatus with a heating element and contacting the portion of the neck with the heated first component of the heated-bending apparatus. The heating can be performed by a heating element integrated into a heated-bending apparatus. The heat can be applied during the bending. The intensity of the heat applied to the neck can vary during the bending process.

BRIEF DESCRIPTION OF THE FIGURES

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

FIGS. 2B and 2C are block diagrams depicting example embodiments of sensor control devices.

FIG. 3A is a proximal perspective view depicting an example embodiment of a user preparing a tray for an assembly.

FIG. 3B is a side view depicting an example embodiment of a user preparing an applicator device for an assembly.

FIG. 3C is a proximal perspective view depicting an example embodiment of a user inserting an applicator device into a tray during an assembly.

FIG. 3D is a proximal perspective view depicting an example embodiment of a user removing an applicator device from a tray during an assembly.

FIG. 3E is a proximal perspective view depicting an example embodiment of a patient applying a sensor using an applicator device.

FIG. 3F is a proximal perspective view depicting an example embodiment of a patient with an applied sensor and a used applicator device.

FIG. 4A is a side view depicting an example embodiment of an applicator device coupled with a cap.

FIG. 4B is a side perspective view depicting an example embodiment of an applicator device and cap decoupled.

FIG. 4C is a perspective view depicting an example embodiment of a distal end of an applicator device and electronics housing.

FIGS. 16A and 16B are isometric and partially exploded isometric views of an example connector assembly, according to one or more embodiments.

FIG. 16C is an isometric bottom view of the connector of FIGS. 16A-16B.

FIGS. 16D and 16E are isometric and partially exploded isometric views of another example connector assembly, according to one or more embodiments.

FIG. 16F is an isometric bottom view of the connector of FIGS. 16D-16E.

FIGS. 32A and 32B are exploded, isometric top and bottom views, respectively, of the sensor control device of FIG. 2, according to one or more embodiments.

FIGS. 40A-40H illustrate steps of a process for assembling a sensor subassembly.

DETAILED DESCRIPTION

Figure 1:
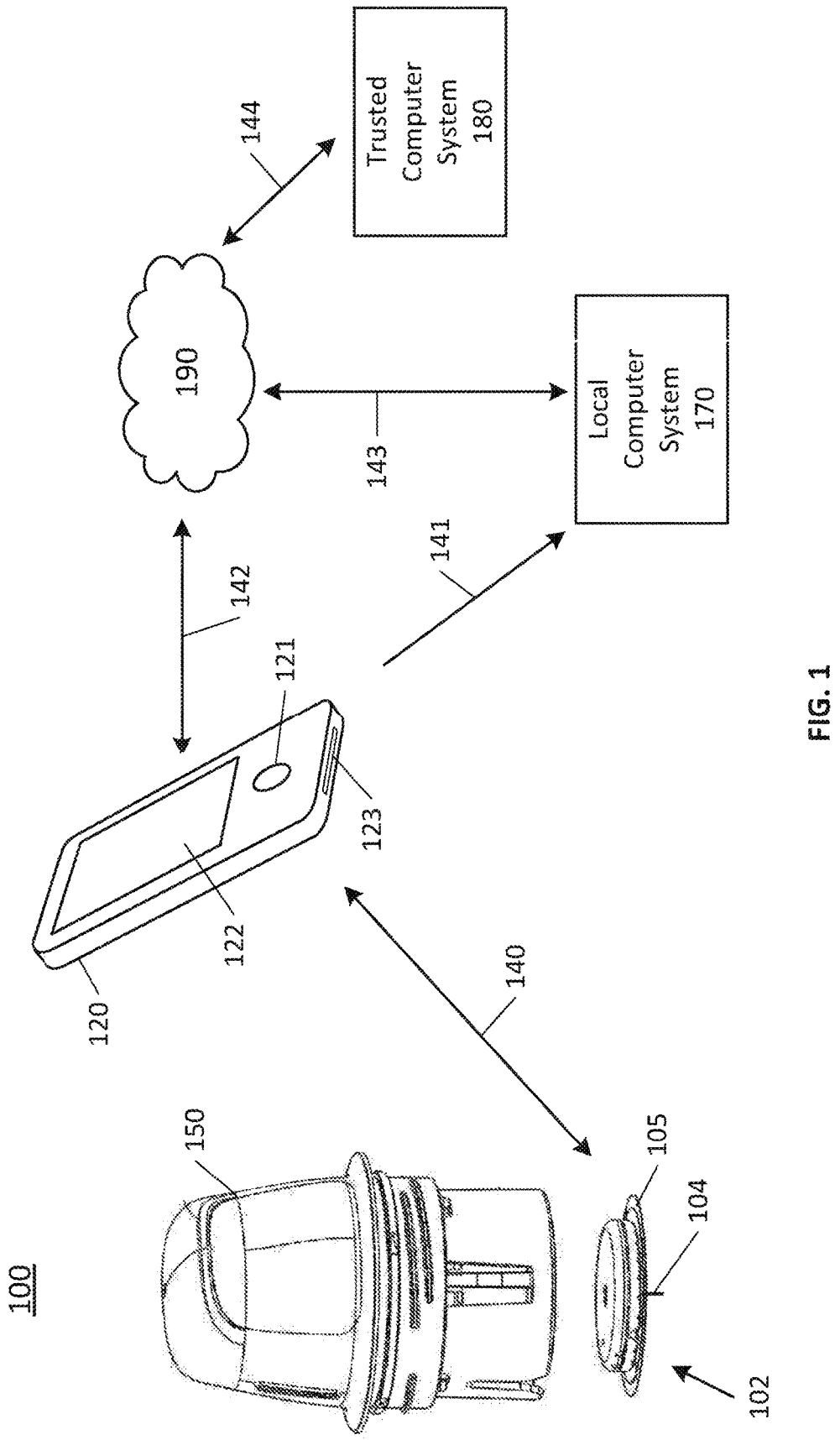
FIG. 1 is a system overview of a sensor applicator, reader device, monitoring system, network, and remote system.

Before the present subject matter is described in detail, it is to be understood that this disclosure is not limited to the particular embodiments described, as such may, of course, vary. It is also to be understood that the terminology used herein is for the purpose of describing particular embodiments only, and is not intended to be limiting, since the scope of the present disclosure will be limited only by the appended claims.

As used herein and in the appended claims, the singular forms "a," "an," and "the" include plural referents unless the context clearly dictates otherwise.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

Generally, embodiments of the present disclosure include systems, devices, and methods for the use of analyte sensor insertion applicators for use with in vivo analyte monitoring systems. An applicator can be provided to the user in a sterile package with an electronics housing of the sensor control device contained therein. According to some embodiments, a structure separate from the applicator, such as a container, can also be provided to the user as a sterile package with a sensor module and a sharp module contained therein. The user can couple the sensor module to the electronics housing, and can couple the sharp to the applicator with an assembly process that involves the insertion of the applicator into the container in a specified manner. In other embodiments, the applicator, sensor control device, sensor module, and sharp module can be provided in a single package. The applicator can be used to position the sensor control device on a human body with a sensor in contact with the wearer's bodily fluid. The embodiments provided herein are improvements to reduce the likelihood that a sensor is improperly inserted or damaged, or elicits an adverse physiological response. Other improvements and advantages are provided as well. The various configurations of these devices are described in detail by way of the embodiments which are only examples.

Furthermore, many embodiments include in vivo analyte sensors structurally configured so that at least a portion of the sensor is, or can be, positioned in the body of a user to obtain information about at least one analyte of the body. It should be noted, however, that the embodiments disclosed herein can be used with in vivo analyte monitoring systems that incorporate in vitro capability, as well as purely in vitro or ex vivo analyte monitoring systems, including systems that are entirely non-invasive.

Furthermore, for each and every embodiment of a method disclosed herein, systems and devices capable of performing each of those embodiments are covered within the scope of the present disclosure. For example, embodiments of sensor control devices are disclosed and these devices can have one or more sensors, analyte monitoring circuits (e.g., an analog circuit), memories (e.g., for storing instructions), power sources, communication circuits, transmitters, receivers, processors and/or controllers (e.g., for executing instructions) that can perform any and all method steps or facilitate the execution of any and all method steps. These sensor control device embodiments can be used and can be capable of use to implement those steps performed by a sensor control device from any and all of the methods described herein.

As mentioned, a number of embodiments of systems, devices, and methods are described herein that provide for the improved assembly and use of dermal sensor insertion devices for use with in vivo analyte monitoring systems. In particular, several embodiments of the present disclosure are designed to improve the method of sensor insertion with respect to in vivo analyte monitoring systems and, in particular, to prevent the premature retraction of an insertion sharp during a sensor insertion process. Some embodiments, for example, include a dermal sensor insertion mechanism with an increased firing velocity and a delayed sharp retraction. In other embodiments, the sharp retraction mechanism can be motion-actuated such that the sharp is not retracted until the user pulls the applicator away from the skin. Consequently, these embodiments can reduce the likelihood of prematurely withdrawing an insertion sharp during a sensor insertion process; decrease the likelihood of improper sensor insertion; and decrease the likelihood of damaging a sensor during the sensor insertion process, to name a few advantages. Several embodiments of the present disclosure also provide for improved insertion sharp modules to account for the small scale of dermal sensors and the relatively shallow insertion path present in a subject's dermal layer. In addition, several embodiments of the present disclosure are designed to prevent undesirable axial and/or rotational movement of applicator components during sensor insertion. Accordingly, these embodiments can reduce the likelihood of instability of a positioned dermal sensor, irritation at the insertion site, damage to surrounding tissue, and breakage of capillary blood vessels resulting in fouling of the dermal fluid with blood, to name a few advantages. In addition, to mitigate inaccurate sensor readings which can be caused by trauma at the insertion site, several embodiments of the present disclosure can reduce the end-depth penetration of the needle relative to the sensor tip during insertion.

Before describing these aspects of the embodiments in detail, however, it is first desirable to describe examples of devices that can be present within, for example, an in vivo analyte monitoring system, as well as examples of their operation, all of which can be used with the embodiments described herein.

There are various types of in vivo analyte monitoring systems. "Continuous Analyte Monitoring" systems (or "Continuous Glucose Monitoring" systems), for example, can transmit data from a sensor control device to a reader device continuously without prompting, e.g., automatically according to a schedule. "Flash Analyte Monitoring" systems (or "Flash Glucose Monitoring" systems or simply "Flash" systems), as another example, can transfer data from a sensor control device in response to a scan or request for data by a reader device, such as with a Near Field Communication (NFC) or Radio Frequency Identification (RFID) protocol. In vivo analyte monitoring systems can also operate without the need for finger stick calibration.

In vivo analyte monitoring systems can be differentiated from "in vitro" systems that contact a biological sample outside of the body (or "ex vivo") and that typically include a meter device that has a port for receiving an analyte test strip carrying bodily fluid of the user, which can be analyzed to determine the user's blood sugar level.

In vivo monitoring systems can include a sensor that, while positioned in vivo, makes contact with the bodily fluid of the user and senses the analyte levels contained therein. The sensor can be part of the sensor control device that resides on the body of the user and contains the electronics and power supply that enable and control the analyte sensing. The sensor control device, and variations thereof, can also be referred to as a "sensor control unit," an "on-body electronics" device or unit, an "on-body" device or unit, or a "sensor data communication" device or unit, to name a few.

In vivo monitoring systems can also include a device that receives sensed analyte data from the sensor control device and processes and/or displays that sensed analyte data, in any number of forms, to the user. This device, and variations thereof, can be referred to as a "handheld reader device," "reader device" (or simply a "reader"), "handheld electronics" (or simply a "handheld"), a "portable data processing" device or unit, a "data receiver," a "receiver" device or unit (or simply a "receiver"), or a "remote" device or unit, to name a few. Other devices such as personal computers have also been utilized with or incorporated into in vivo and in vitro monitoring systems.

Example Embodiment of In Vivo Analyte Monitoring System

FIG. 1 is a conceptual diagram depicting an example embodiment of an analyte monitoring system 100 that includes a sensor applicator 150, a sensor control device 102, and a reader device 120. Here, sensor applicator 150 can be used to deliver sensor control device 102 to a monitoring location on a user's skin where a sensor 104 is maintained in position for a period of time by an adhesive patch 105. Sensor control device 102 is further described in FIGS. 2B and 2C, and can communicate with reader device 120 via a communication path 140 using a wired or wireless technique. Example wireless protocols include Bluetooth, Bluetooth Low Energy (BLE, BTLE, Bluetooth SMART, etc.), Near Field Communication (NFC) and others. Users can monitor applications installed in memory on reader device 120 using screen 122 and input 121 and the device battery can be recharged using power port 123. More detail about reader device 120 is set forth with respect to FIG. 2A below. Reader device 120 can communicate with local computer system 170 via a communication path 141 using a wired or wireless technique. Local computer system 170 can include one or more of a laptop, desktop, tablet, phablet, smartphone, set-top box, video game console, or other computing device and wireless communication can include any of a number of applicable wireless networking protocols including Bluetooth, Bluetooth Low Energy (BTLE), Wi-Fi or others. Local computer system 170 can communicate via communications path 143 with a network 190 similar to how reader device 120 can communicate via a communications path 142 with network 190, by wired or wireless technique as described previously. Network 190 can be any of a number of networks, such as private networks and public networks, local area or wide area networks, and so forth. A trusted computer system 180 can include a server and can provide authentication services and secured data storage and can communicate via communications path 144 with network 190 by wired or wireless technique.

Example Embodiment of Reader Device

Figure 2A:
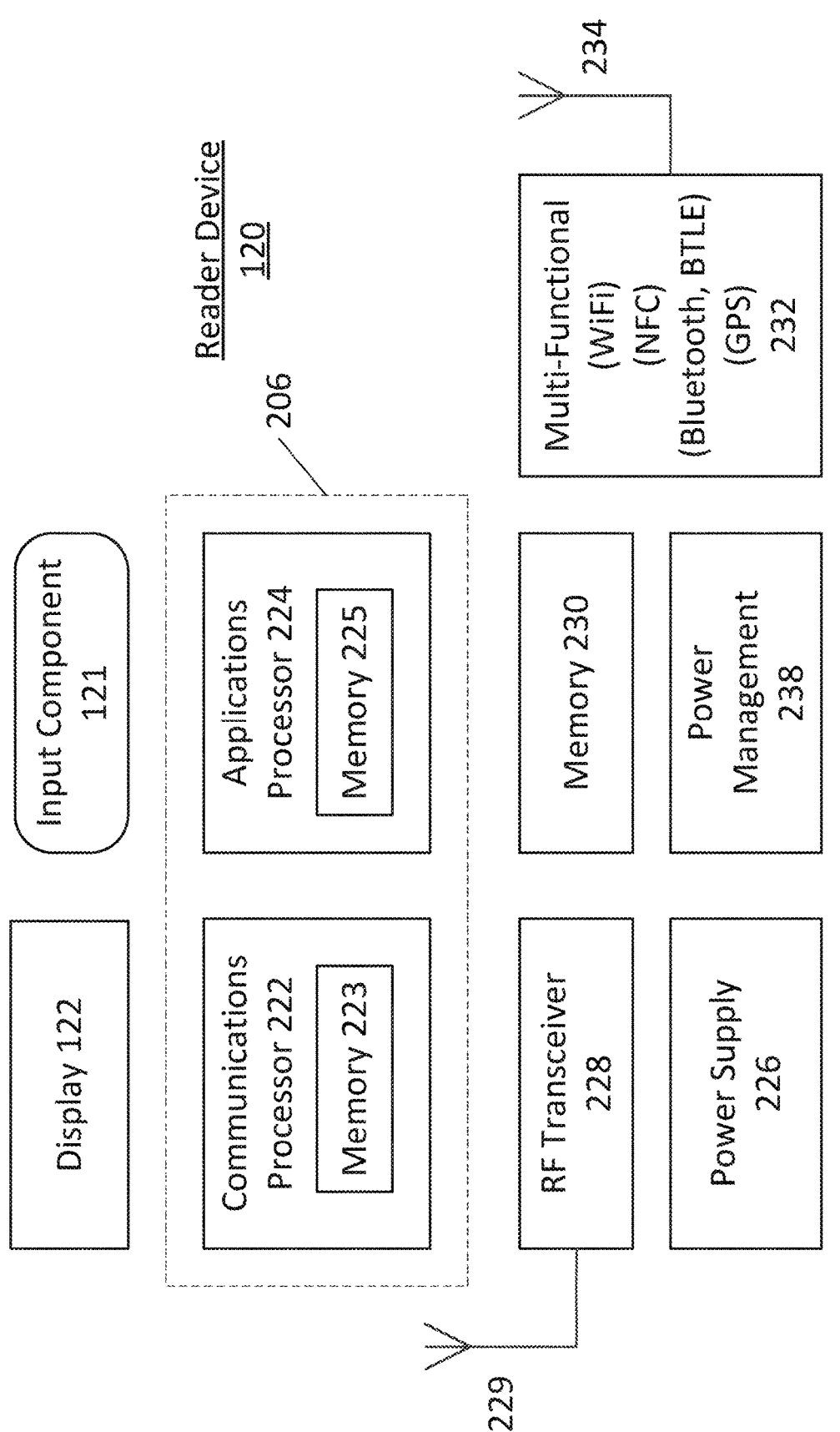
FIG. 2A is a block diagram depicting an example embodiment of a reader device.

FIG. 2A is a block diagram depicting an example embodiment of a reader device configured as a smartphone. Here, reader device 120 can include a display 122, input component 121, and a processing core 206 including a communications processor 222 coupled with memory 223 and an applications processor 224 coupled with memory 225. Also included can be separate memory 230, RF transceiver 228 with antenna 229, and power supply 226 with power management module 238. Further included can be a multifunctional transceiver 232 which can communicate over Wi-Fi, NFC, Bluetooth, BTLE, and GPS with an antenna 234. As understood by one of skill in the art, these components are electrically and communicatively coupled in a manner to make a functional device.

Example Embodiments of Sensor Control Device

FIGS. 2B and 2C are block diagrams depicting example embodiments of sensor control device 102 having analyte sensor 104 and sensor electronics 160 (including analyte monitoring circuitry) that can have the majority of the processing capability for rendering end-result data suitable for display to the user. In FIG. 2B, a single semiconductor chip 161 is depicted that can be a custom application specific integrated circuit (ASIC). Shown within ASIC 161 are certain high-level functional units, including an analog front end (AFE) 162, power management (or control) circuitry 164, processor 166, and communication circuitry 168 (which can be implemented as a transmitter, receiver, transceiver, passive circuit, or otherwise according to the communication protocol). In this embodiment, both AFE 162 and processor 166 are used as analyte monitoring circuitry, but in other embodiments either circuit can perform the analyte monitoring function. Processor 166 can include one or more processors, microprocessors, controllers, and/or microcontrollers, each of which can be a discrete chip or distributed amongst (and a portion of) a number of different chips.

A memory 163 is also included within ASIC 161 and can be shared by the various functional units present within ASIC 161, or can be distributed amongst two or more of them. Memory 163 can also be a separate chip. Memory 163 can be volatile and/or non-volatile memory. In this embodiment, ASIC 161 is coupled with power source 170, which can be a coin cell battery, or the like. AFE 162 interfaces with in vivo analyte sensor 104 and receives measurement data therefrom and outputs the data to processor 166 in digital form, which in turn processes the data to arrive at the end-result glucose discrete and trend values, etc. This data can then be provided to communication circuitry 168 for sending, by way of antenna 171, to reader device 120 (not shown), for example, where minimal further processing is needed by the resident software application to display the data.

FIG. 2C is similar to FIG. 2B but instead includes two discrete semiconductor chips 162 and 174, which can be packaged together or separately. Here, AFE 162 is resident on ASIC 161. Processor 166 is integrated with power management circuitry 164 and communication circuitry 168 on chip 174. AFE 162 includes memory 163 and chip 174 includes memory 165, which can be isolated or distributed within. In one example embodiment, AFE 162 is combined with power management circuitry 164 and processor 166 on one chip, while communication circuitry 168 is on a separate chip. In another example embodiment, both AFE 162 and communication circuitry 168 are on one chip, and processor 166 and power management circuitry 164 are on another chip. It should be noted that other chip combinations are possible, including three or more chips, each bearing responsibility for the separate functions described, or sharing one or more functions for fail-safe redundancy.

Example Embodiment of Assembly Process for Sensor Control Device

The components of sensor control device 102 can be acquired by a user in multiple packages requiring final assembly by the user before delivery to an appropriate user location. FIGS. 3A-3D depict an example embodiment of an assembly process for sensor control device 102 by a user, including preparation of separate components before coupling the components in order to ready the sensor for delivery. FIGS. 3E-3F depict an example embodiment of delivery of sensor control device 102 to an appropriate user location by selecting the appropriate delivery location and applying device 102 to the location.

FIG. 3A is a proximal perspective view depicting an example embodiment of a user preparing a container 810, configured here as a tray (although other packages can be used), for an assembly process. The user can accomplish this preparation by removing lid 812 from tray 810 to expose platform 808, for instance by peeling a non-adhered portion of lid 812 away from tray 810 such that adhered portions of lid 812 are removed. Removal of lid 812 can be appropriate in various embodiments so long as platform 808 is adequately exposed within tray 810. Lid 812 can then be placed aside.

FIG. 3B is a side view depicting an example embodiment of a user preparing an applicator device 150 for assembly. Applicator device 150 can be provided in a sterile package sealed by a cap 708. Preparation of applicator device 150 can include uncoupling housing 702 from cap 708 to expose sheath 704 (FIG. 3C). This can be accomplished by unscrewing (or otherwise uncoupling) cap 708 from housing 702. Cap 708 can then be placed aside.

FIG. 3C is a proximal perspective view depicting an example embodiment of a user inserting an applicator device 150 into a tray 810 during an assembly. Initially, the user can insert sheath 704 into platform 808 inside tray 810 after aligning housing orienting feature 1302 (or slot or recess) and tray orienting feature 924 (an abutment or detent). Inserting sheath 704 into platform 808 temporarily unlocks sheath 704 relative to housing 702 and also temporarily unlocks platform 808 relative to tray 810. At this stage, removal of applicator device 150 from tray 810 will result in the same state prior to initial insertion of applicator device 150 into tray 810 (i.e., the process can be reversed or aborted at this point and then repeated without consequence).

Sheath 704 can maintain position within platform 808 with respect to housing 702 while housing 702 is distally advanced, coupling with platform 808 to distally advance platform 808 with respect to tray 810. This step unlocks and collapses platform 808 within tray 810. Sheath 704 can contact and disengage locking features (not shown) within tray 810 that unlock sheath 704 with respect to housing 702 and prevent sheath 704 from moving (relatively) while housing 702 continues to distally advance platform 808. At the end of advancement of housing 702 and platform 808, sheath 704 is permanently unlocked relative to housing 702. A sharp and sensor (not shown) within tray 810 can be coupled with an electronics housing (not shown) within housing 702 at the end of the distal advancement of housing 702. Operation and interaction of the applicator device 150 and tray 810 are further described below.

FIG. 3D is a proximal perspective view depicting an example embodiment of a user removing an applicator device 150 from a tray 810 during an assembly. A user can remove applicator 150 from tray 810 by proximally advancing housing 702 with respect to tray 810 or other motions having the same end effect of uncoupling applicator 150 and tray 810. The applicator device 150 is removed with sensor control device 102 (not shown) fully assembled (sharp, sensor, electronics) therein and positioned for delivery.

FIG. 3E is a proximal perspective view depicting an example embodiment of a patient applying sensor control device 102 using applicator device 150 to a target area of skin, for instance, on an abdomen or other appropriate location. Advancing housing 702 distally collapses sheath 704 within housing 702 and applies the sensor to the target location such that an adhesive layer on the bottom side of sensor control device 102 adheres to the skin. The sharp is automatically retracted when housing 702 is fully advanced, while the sensor (not shown) is left in position to measure analyte levels.

FIG. 3F is a proximal perspective view depicting an example embodiment of a patient with sensor control device 102 in an applied position. The user can then remove applicator 150 from the application site.

System 100, described with respect to FIGS. 3A-3F and elsewhere herein, can provide a reduced or eliminated chance of accidental breakage, permanent deformation, or incorrect assembly of applicator components compared to prior art systems. Since applicator housing 702 directly engages platform 808 while sheath 704 unlocks, rather than indirect engagement via sheath 704, relative angularity between sheath 704 and housing 702 will not result in breakage or permanent deformation of the arms or other components. The potential for relatively high forces (such as in conventional devices) during assembly will be reduced, which in turn reduces the chance of unsuccessful user assembly.

Example Embodiment of Sensor Applicator Device

FIG. 4A is a side view depicting an example embodiment of an applicator device 150 coupled with screw cap 708. This is an example of how applicator 150 is shipped to and received by a user, prior to assembly by the user with a sensor. FIG. 4B is a side perspective view depicting applicator 150 and cap 708 after being decoupled. FIG. 4C is a perspective view depicting an example embodiment of a distal end of an applicator device 150 with electronics housing 706 and adhesive patch 105 removed from the position they would have retained within sensor electronics carrier 710 of sheath 704, when cap 708 is in place.

Example Embodiment of Tray and Sensor Module Assembly

Figure 5:
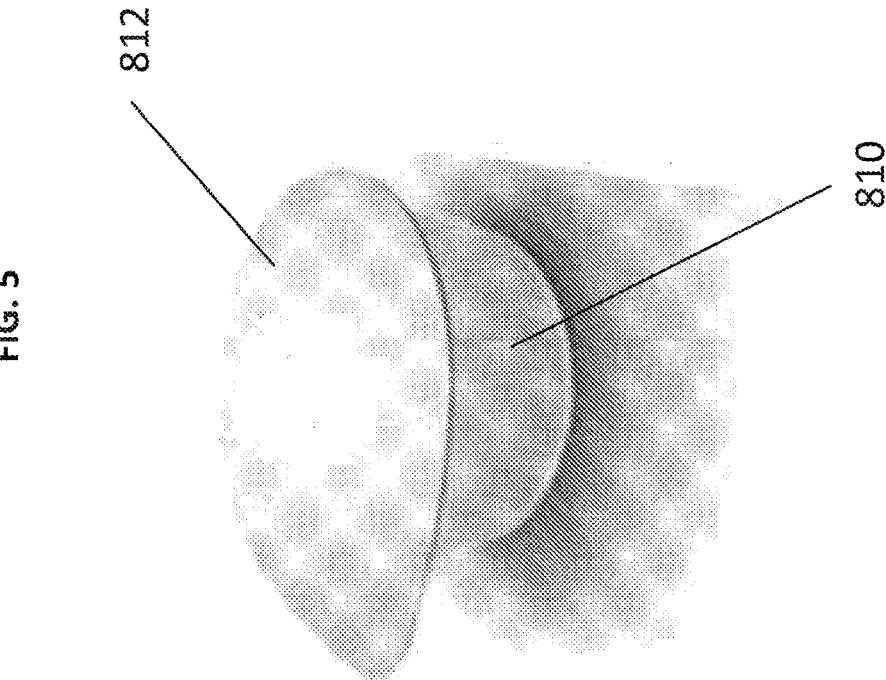
FIG. 5 is a proximal perspective view depicting an example embodiment of a tray with sterilization lid coupled.

FIG. 5 is a proximal perspective view depicting an example embodiment of a tray 810 with sterilization lid 812 removably coupled thereto, which may be representative of how the package is shipped to and received by a user prior to assembly.

Figure 6A:
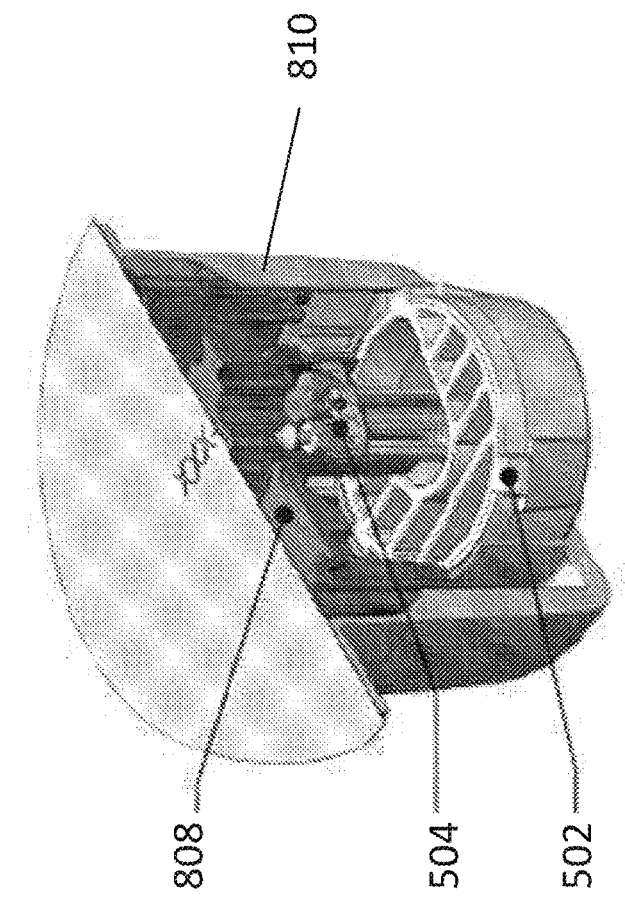
FIG. 6A is a proximal perspective cutaway view depicting an example embodiment of a tray with sensor delivery components.

FIG. 6A is a proximal perspective cutaway view depicting sensor delivery components within tray 810. Platform 808 is slidably coupled within tray 810. Desiccant 502 is stationary with respect to tray 810. Sensor module 504 is mounted within tray 810.

Figure 6B:
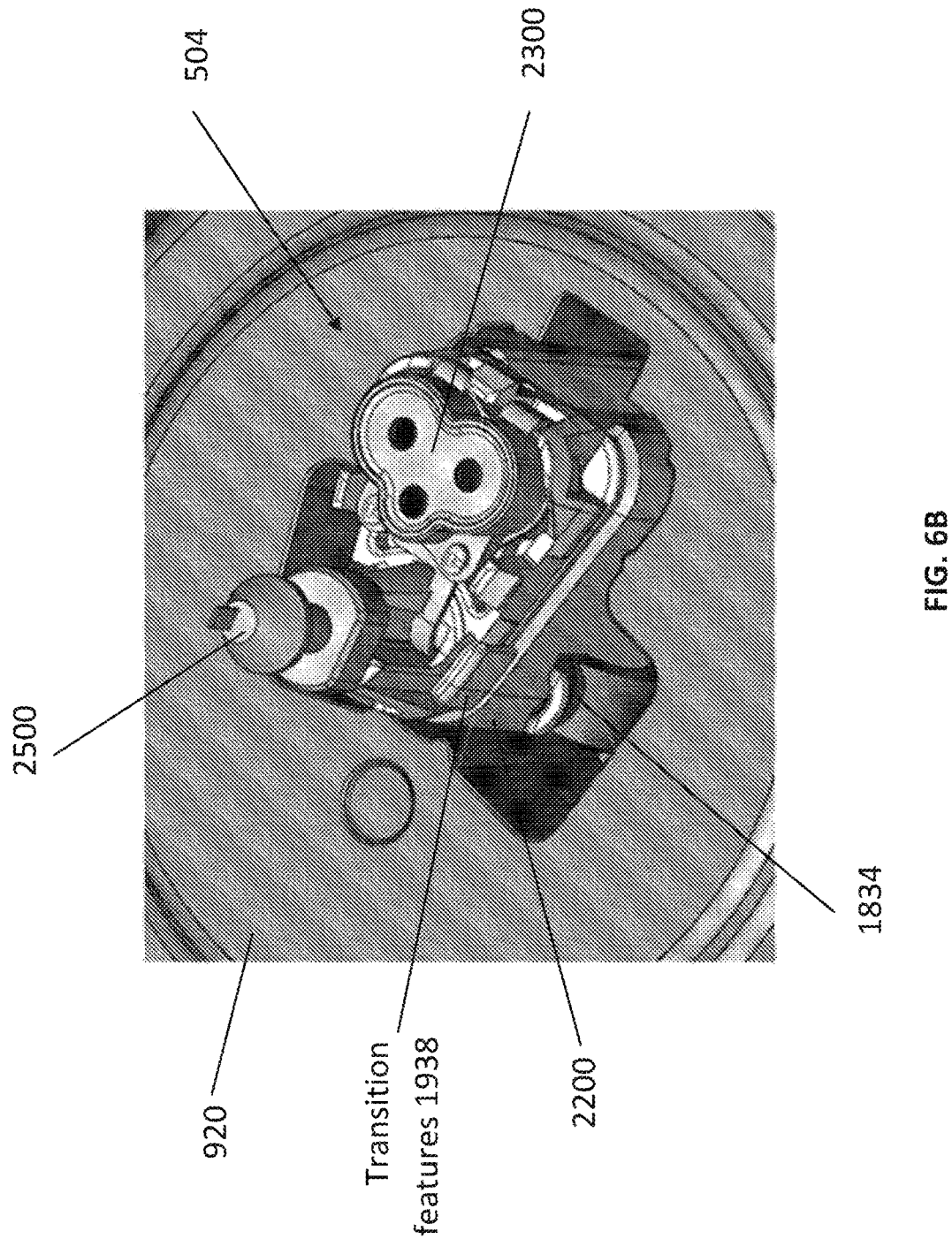
FIG. 6B is a proximal perspective view depicting sensor delivery components.

FIG. 6B is a proximal perspective view depicting sensor module 504 in greater detail. Here, retention arm extensions 1834 of platform 808 releasably secure sensor module 504 in position. Module 2200 is coupled with connector 2300, sharp module 2500 and sensor (not shown) such that during assembly they can be removed together as sensor module 504.

Example Embodiment of Applicator Housing

Figure 7A:
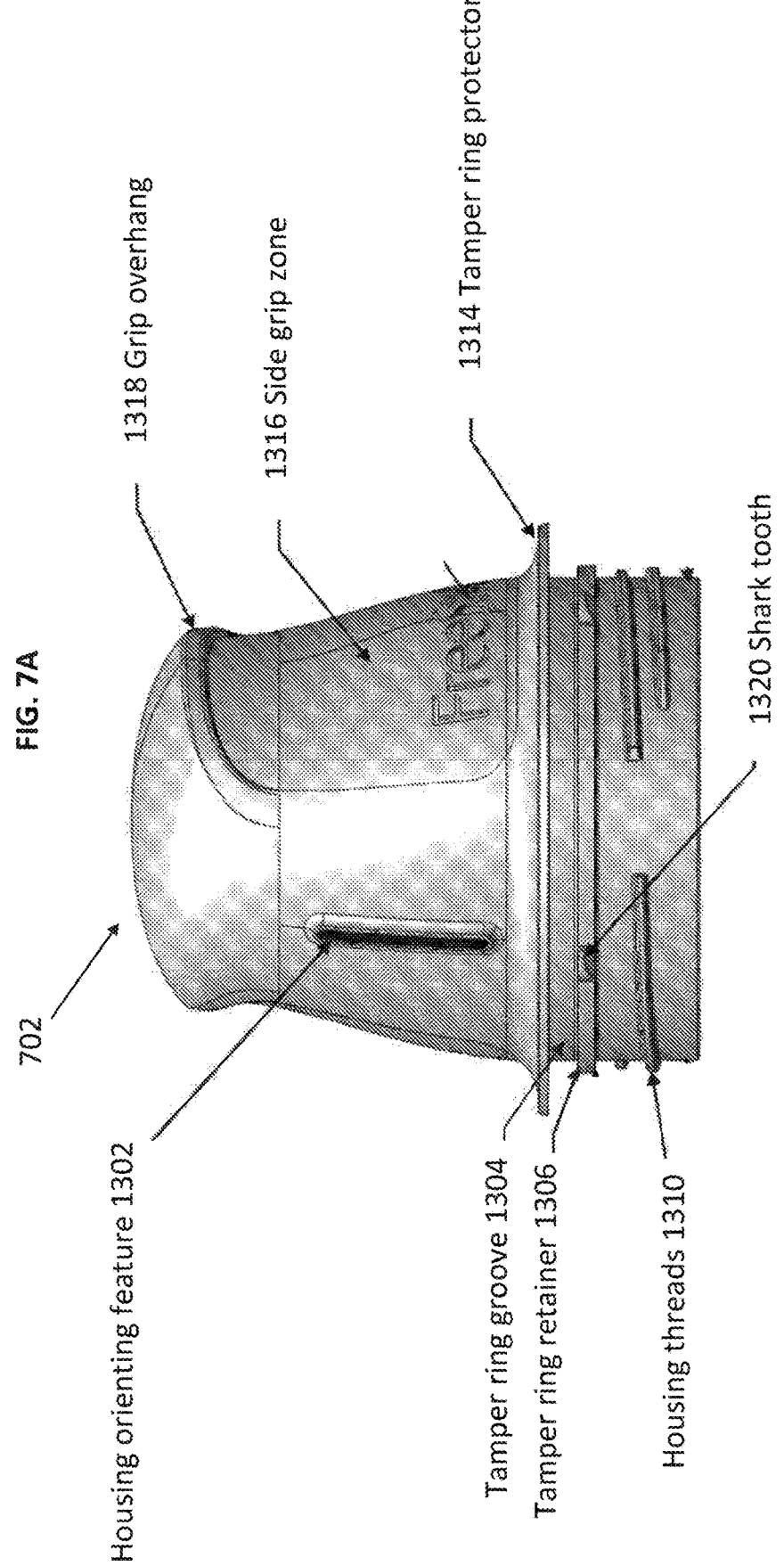
FIG. 7A is side view depicting an example embodiment of a housing.

FIG. 7A is side view depicting an example embodiment of the applicator housing 702 that can include an internal cavity with support structures for applicator function. A user can push housing 702 in a distal direction to activate the applicator assembly process and then also to cause delivery of sensor control device 102, after which the cavity of housing 702 can act as a receptacle for a sharp. In the example embodiment, various features are shown including housing orienting feature 1302 for orienting the device during assembly and use. Tamper ring groove 1304 can be a recess located around an outer circumference of housing 702, distal to a tamper ring protector 1314 and proximal to a tamper ring retainer 1306. Tamper ring groove 1304 can retain a tamper ring so users can identify whether the device has been tampered with or otherwise used. Housing threads 1310 can secure housing 702 to complimentary threads on cap 708 (FIGS. 4A and 4B) by aligning with complimentary cap threads and rotating in a clockwise or counterclockwise direction. A side grip zone 1316 of housing 702 can provide an exterior surface location where a user can grip housing 702 in order to use it. Grip overhang 13 18 is a slightly raised ridge with respect to side grip zone 1316 which can aid in ease of removal of housing 702 from cap 708. A shark tooth 1320 can be a raised section with a flat side located on a clockwise edge to shear off a tamper ring (not shown), and hold tamper ring in place after a user has unscrewed cap 708 and housing 702. In the example embodiment four shark teeth 1320 are used, although more or less can be used as desired.

Figure 7B:
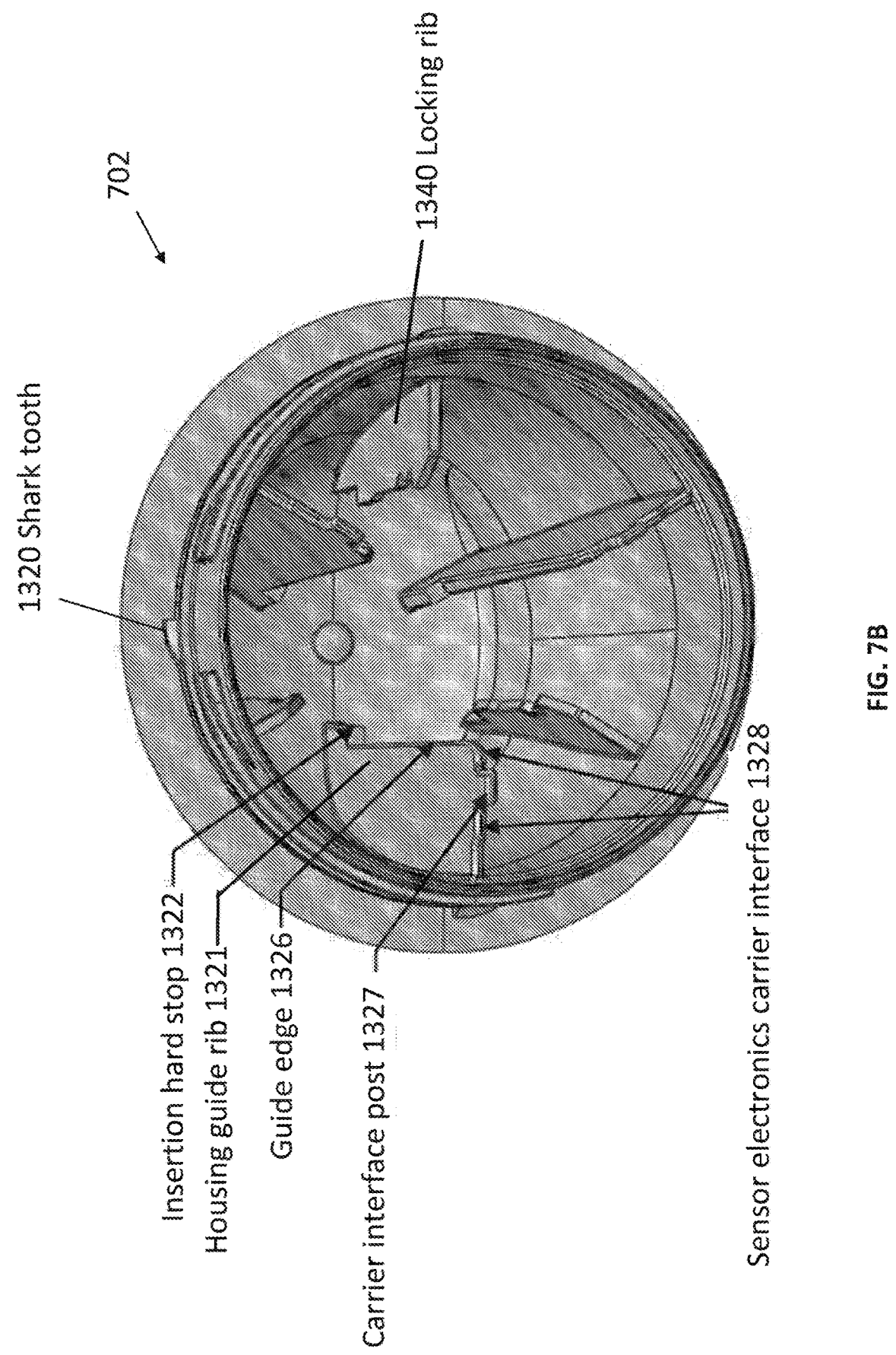
FIG. 7B is a perspective view depicting an example embodiment of a distal end of a housing.

FIG. 7B is a perspective view depicting a distal end of housing 702. Here, three housing guide structures (or "guide ribs") 1321 are located at 120 degree angles with respect to each other and at 60 degree angles with respect to locking structures (or "locking ribs") 1340, of which there are also three at 120 degree angles with respect to each other. Other angular orientations, either symmetric or asymmetric, can be used, as well as any number of one or more structures 1321 and 1340. Here, each structure 1321 and 1340 is configured as a planar rib, although other shapes can be used. Each guide rib 1321 includes a guide edge (also called a "sheath guide rail") 1326 that can pass along a surface of sheath 704 (e.g., guide rail 1418 described with respect to FIG. 8A). An insertion hard stop 1322 can be a flat, distally facing surface of housing guide rib 1321 located near a proximal end of housing guide rib 1321. Insertion hard stop 1322 provides a surface for a sensor electronics carrier travel limiter face 1420 of a sheath 704 (FIG. 8B) to abut during use, preventing sensor electronics carrier travel limiter face 1420 from moving any further in a proximal direction. A carrier interface post 1327 passes through an aperture 1510 (FIG. 9A) of sensor electronics carrier 710 during an assembly. A sensor electronics carrier interface 1328 can be a rounded, distally facing surface of housing guide ribs 1321 which interfaces with sensor electronics carrier 710.

Figure 7C:
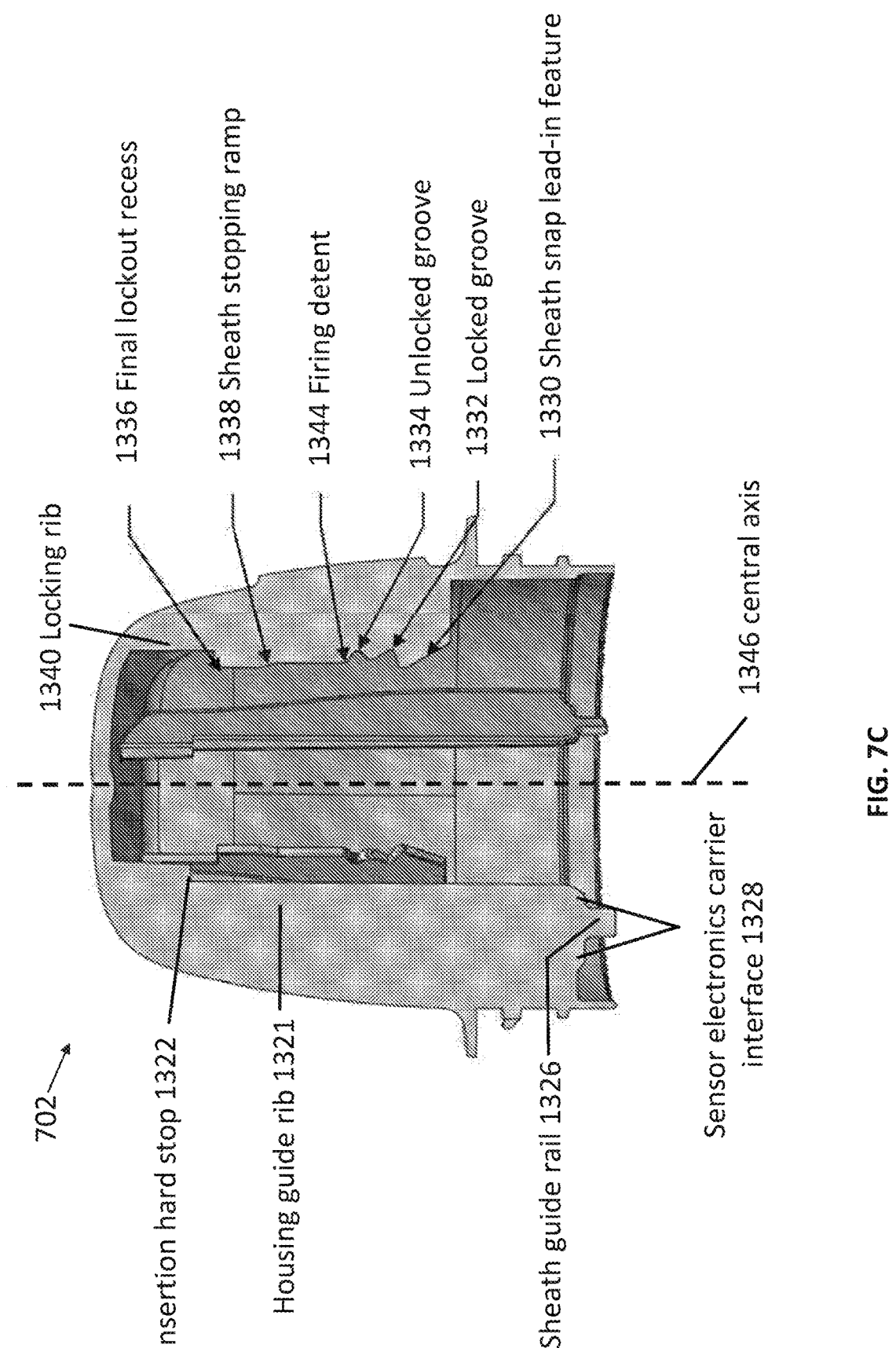
FIG. 7C is a side cross-sectional view depicting an example embodiment of a housing.

FIG. 7C is a side cross-section depicting an example embodiment of a housing. In the example embodiment, side cross-sectional profiles of housing guide rib 1321 and locking rib 1340 are shown. Locking rib 1340 includes sheath snap lead-in feature 1330 near a distal end of locking rib 1340 which flares outward from central axis 1346 of housing 702 distally. Each sheath snap lead-in feature 1330 causes detent snap round 1404 of detent snap 1402 of sheath 704 as shown in FIG. 8C to bend inward toward central axis 1346 as sheath 704 moves towards the proximal end of housing 702. Once past a distal point of sheath snap lead-in feature 1330, detent snap 1402 of sheath 704 is locked into place in locked groove 1332. As such, detent snap 1402 cannot be easily moved in a distal direction due to a surface with a near perpendicular plane to central axis 1346, shown as detent snap flat 1406 in FIG. 8C.

As housing 702 moves further in a proximal direction toward the skin surface, and as sheath 704 advances toward the distal end of housing 702, detent snaps 1402 shift into the unlocked grooves 1334, and applicator 150 is in an "armed" position, ready for use. When the user further applies force to the proximal end of housing 702, while sheath 704 is pressed against the skin, detent snap 1402 passes over firing detent 1344. This begins a firing sequence (as described, for example, with respect to FIGS. 12A-12D) due to release of stored energy in the deflected detent snaps 1402, which travel in a proximal direction relative to the skin surface, toward sheath stopping ramp 1338 which is slightly flared outward with respect to central axis 1346 and slows sheath 704 movement during the firing sequence. The next groove encountered by detent snap 1402 after unlocked groove 1334 is final lockout groove 1336 which detent snap 1402 enters at the end of the stroke or pushing sequence performed by the user. Final lockout recess 1336 can be a proximally-facing surface that is perpendicular to central axis 1346 which, after detent snap 1402 passes, engages a detent snap flat 1406 and prevents reuse of the device by securely holding sheath 704 in place with respect to housing 702. Insertion hard stop 1322 of housing guide rib 1321 prevents sheath 704 from advancing proximally with respect to housing 702 by engaging sensor electronics carrier travel limiter face 1420.

Figure 7D:
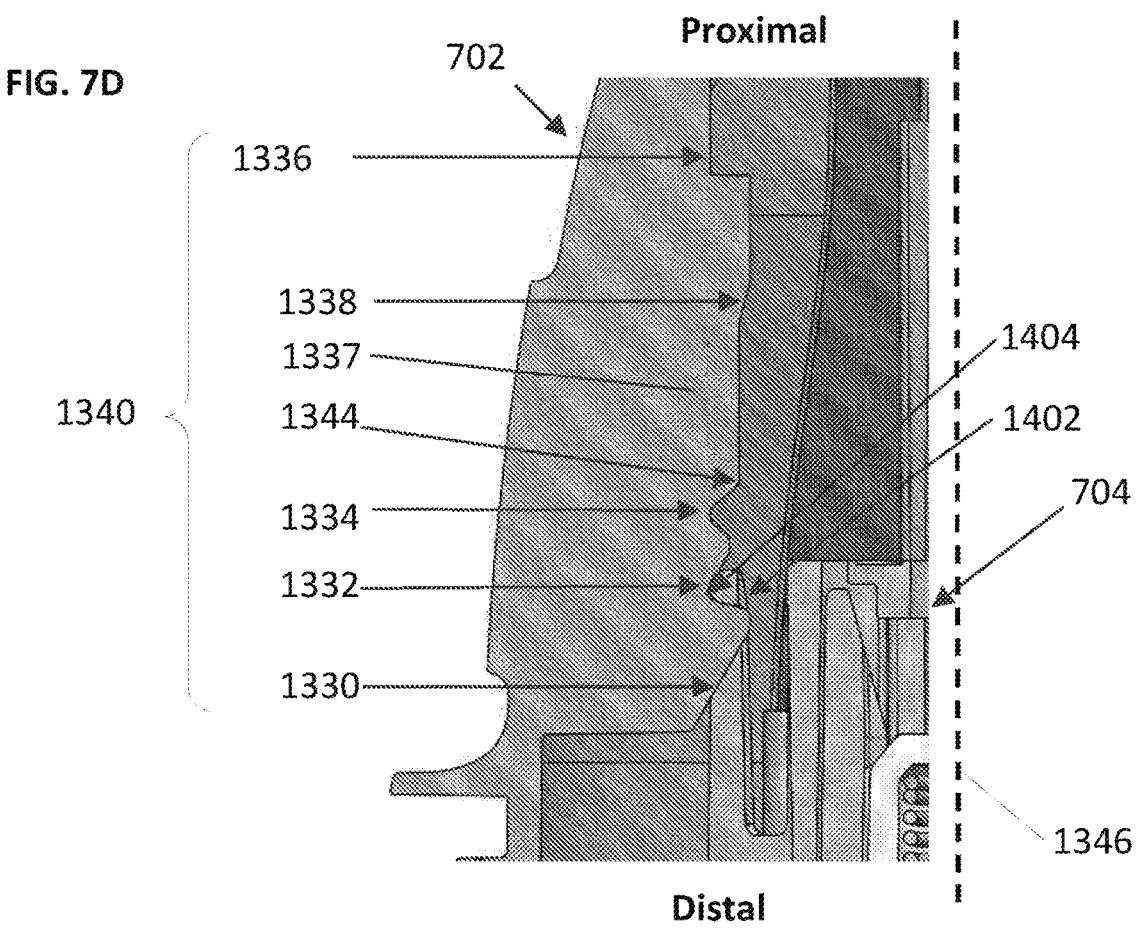
FIGS. 7D and 7E are side cross-sectional views depicting a locking rib portion of an example embodiment of a housing with a portion of a sheath.
Figure 7E:
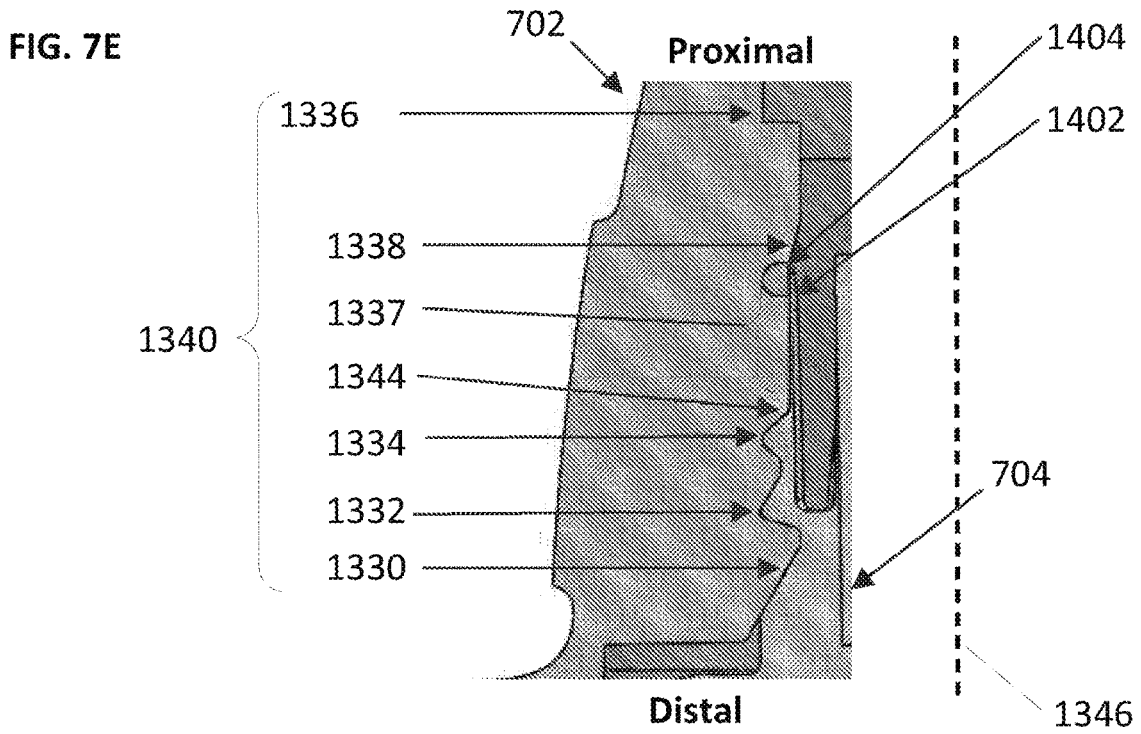

FIGS. 7D and 7E are close-up side views of an example embodiment of locking rib 1340 of applicator housing 702, as detent snap 1402 of sheath 704 moves toward the proximal end of housing 702. FIG. 7D shows sheath 704 in a "locked" state, in which detent round 1404 of detent snap 1402 has already passed over sheath snap lead-in feature 1330 and is positioned in locked groove 1332 of locking rib 1340. As force is applied to the proximal end of housing 702, detent round 1404 is advanced proximally into unlocked groove 1334, placing applicator 150 into an "armed" position. When force is further applied to the proximal end of housing 702, applicator 150 is "fired," as detent round 1404 is advanced proximally from the unlocked groove 1334 and passes over firing detent 1344. Thereafter, sheath 704 is further advanced proximally such that detent round 1404 is slidably advanced over firing surface 1337, as shown in FIG. 7E. In this embodiment, firing surface 1337 is substantially parallel to central axis 1346. As sheath 704 continues to advance proximally, detent round 1404 reaches sheath stopping ramp 1338 which slows the movement of sheath 704. Upon detent round 1404 reaching final lockout recess 1336, detent snap flat 1406 (not shown) is engaged and securely holds sheath 704 in place with respect to housing 702.

Figure 7F:
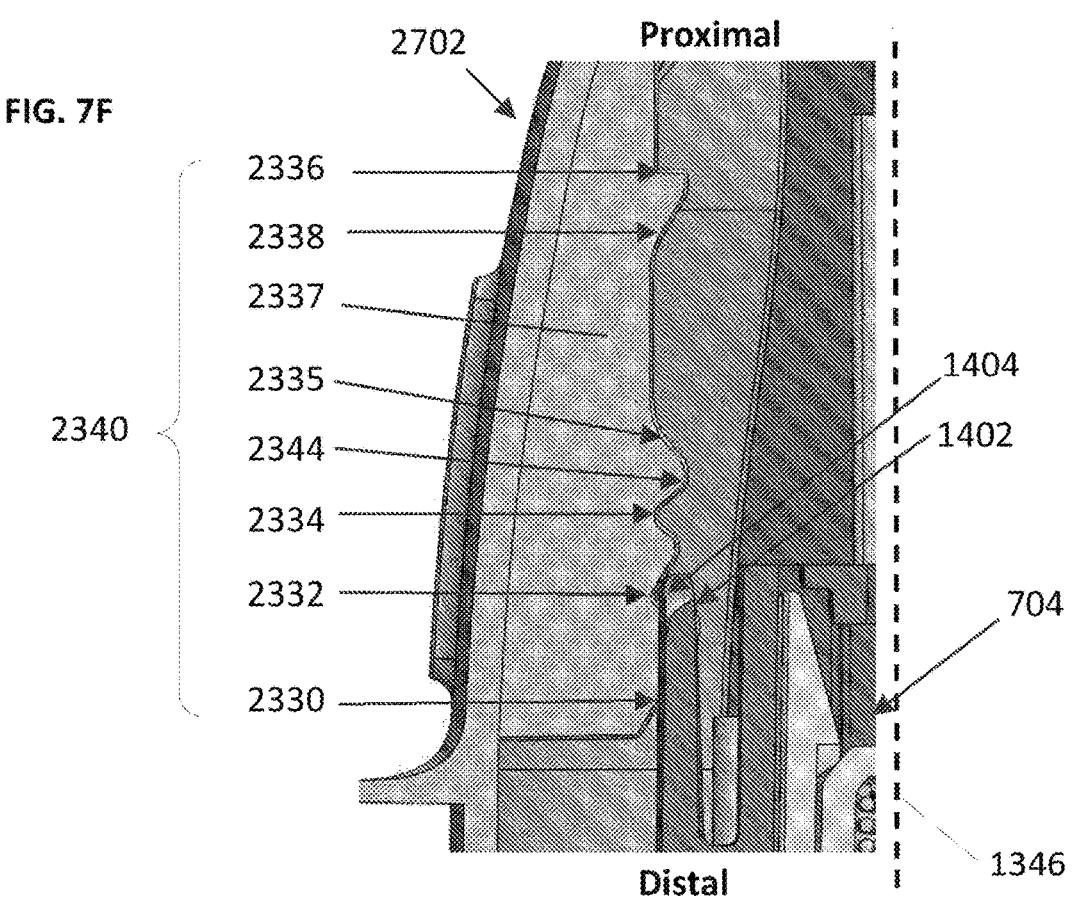
FIGS. 7F and 7G are side cross-sectional views depicting a locking rib portion of another example embodiment of a housing and a portion of a sheath.
Figure 7G:
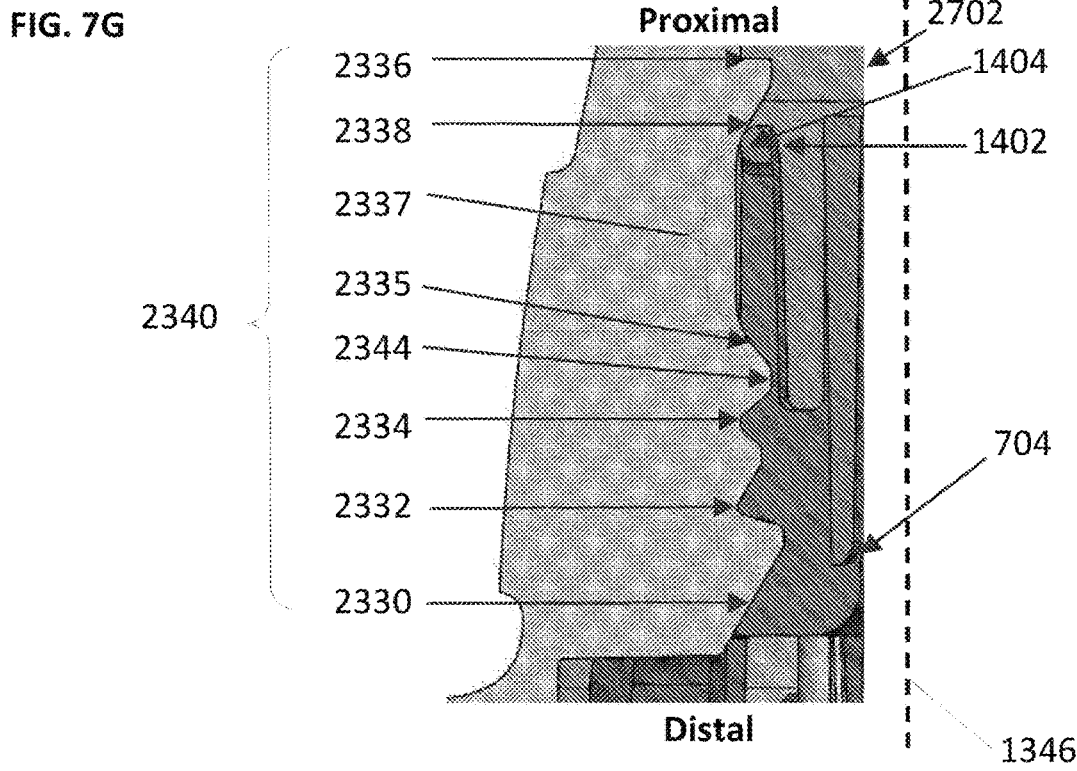

FIGS. 7F and 7G are close-up side views of an alternative embodiment of locking rib 2340 that is designed to improve the firing velocity of the sharp from the sensor applicator. Here, locking rib 2340 includes an inward detent ramp 2335 to reduce friction between sheath 704 and housing 2702 during firing. Locking rib 2340 also includes a sheath stopping ramp 2338 at the proximal end of firing surface 2337. In FIG. 7F, sheath 704 is initially shown in a "locked" state, in which detent round 1404 of detent snap 1402 has already passed over sheath snap lead-in feature 2330, and is positioned in locked groove 2332. As force is applied to the proximal end of housing 2702, detent round 1404 is advanced into unlocked groove 2334, placing applicator 150 into the "armed" position. When force is further applied to the proximal end of housing 2702, applicator 150 is "fired," as detent round 1404 passes over firing detent 2344.

As shown in FIG. 7G, detent round 1404 then advances toward the proximal end of housing 2702 in a "free flight" state, in which detent round 1404 passes over inward detent ramp 2335. While advancing proximally in the "free flight" state, detent round 1404 can be in non-continuous, or have no contact with, inward detent ramp 2335 and firing surface 2337. In this regard, detent round 1404 can be easily and quickly advanced, as there is little to no frictional force between detent round 1404 and inward detent ramp 2335 and firing surface 2337, and as such, improves upon the firing velocity of the sharp from the applicator. Sheath stopping ramp 2338, which is positioned proximally further along the locking rib 2340 relative to the embodiment shown in FIGS. 7D and 7E, provides an edge portion to frictionally engage the detent round 1404 and slow the movement of sheath 704. The sheath stopping ramp 2338 can have a sloped shape and provide for increasing frictional contact as the detent round 1404 advances in a proximal direction. Finally, upon detent round 1404 reaching final lockout recess 2336, detent snap flat 1406 (not shown) is engaged and securely holds sheath 704 in place with respect to housing 2702. Lockout recess 2336 prevents detent round 1404 and sheath 704 from backwards, or distal movement. This embodiment reflects a higher firing velocity relative to the embodiment depicted in FIGS. 7D and 7E, which also assists in prevention of a premature withdrawal of sharp.

Figures 7H, 7I:
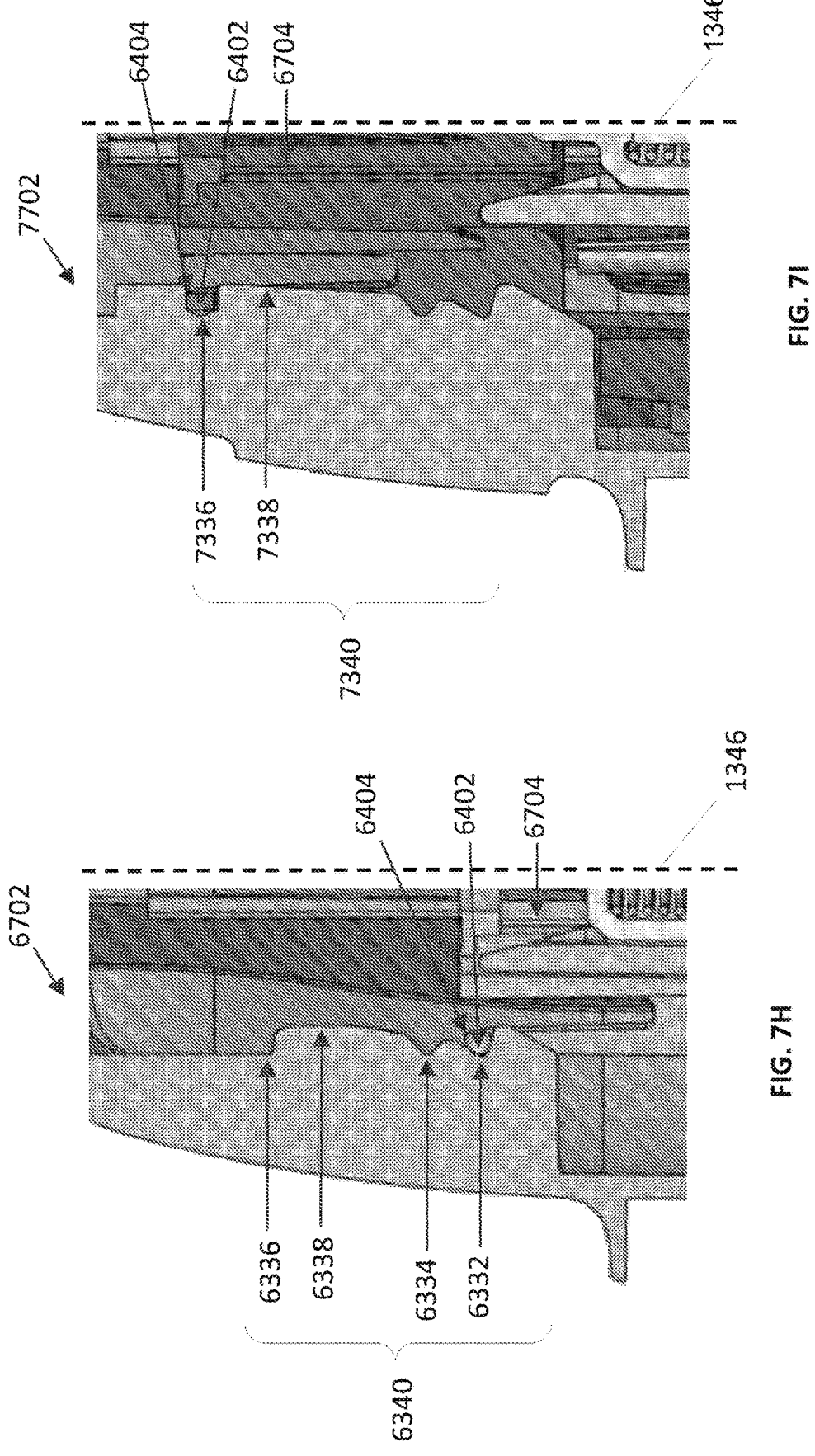
FIG. 7H is a side cross-sectional view depicting a locking rib portion of another example embodiment of a housing and a portion of a sheath.
FIG. 7I is a side cross-sectional view depicting a locking rib portion of another example embodiment of a housing and a portion of a sheath.

FIG. 7H is a close-up side view of an alternative embodiment of locking rib 6340 designed to maintain a downward force on sheath 6704 during firing which, in turn, can prevent sheath 6704 from unwanted movement during the sensor insertion process. Here, sheath 6704 is shown in a "locked" state, in which detent round 6404 of detent snap 6402 is positioned in locked groove 6332. As force is applied to the proximal end of housing 6702, detent round 6404 is advanced into unlocked groove 6334, placing applicator in the "armed" position. When force is further applied to the proximal end of housing 6702, applicator is "fired," and detent round 6404 advances over sloped firing surface 6338 toward the proximal end of housing 6702. Sloped firing surface 6338 can be angled toward central axis 1346 such that the resulting downward force upon sheath 6704 increases as detent round 6404 advances in a proximal direction. In the depicted embodiment, detent round 6404 is in continuous contact with sloped firing surface 6338. Lockout recess 6336 prevents detent round 6404 and sheath 6704 from backwards, or distal movement. This embodiment reflects a slower firing velocity relative to the previously described embodiments, and can be used, for example, with the motion-actuated sharp retraction process that is described with respect to FIGS. 14A-14C and 15A-15B.

FIG. 7I is a close-up side view of still another alternative embodiment of locking rib 7340, also designed to maintain a downward force on sheath 6704 during firing which, in turn, can prevent sheath 6704 from unwanted movement during a sensor insertion process. Here, sheath 6704 is shown in a "fired" state, in which detent round 6404 of detent snap 6402 is positioned in a two-way lockout recess 7336. Upon detent round 6404 advancing into two-way lockout recess 7336, sheath 6704 can be prevented from further movement in either a proximal or distal direction. This can reduce unwanted movement of sheath 6704 during the sensor insertion process. Furthermore, in some embodiments, as described with respect to FIGS. 14A-14C and 15A-15B, two-way lockout recess 7336 can provide for the immobilization of sheath 6704 during a motion-actuated sharp retraction process. As can be seen in FIG. 7I, sloped firing surface 7338 is angled toward central axis 1346 such that a resulting downward force upon sheath 6704 increases as detent round 6404 advances in a proximal direction. In the depicted embodiment, detent round 6404 is in continuous contact with sloped firing surface 7338. This embodiment reflects a slower firing velocity and can be used, for example, with the motion-actuated sharp retraction process that is described with respect to FIGS. 14A-14C and 15A-15B.

Example Embodiment of Applicator Sheath

Figure 8A:
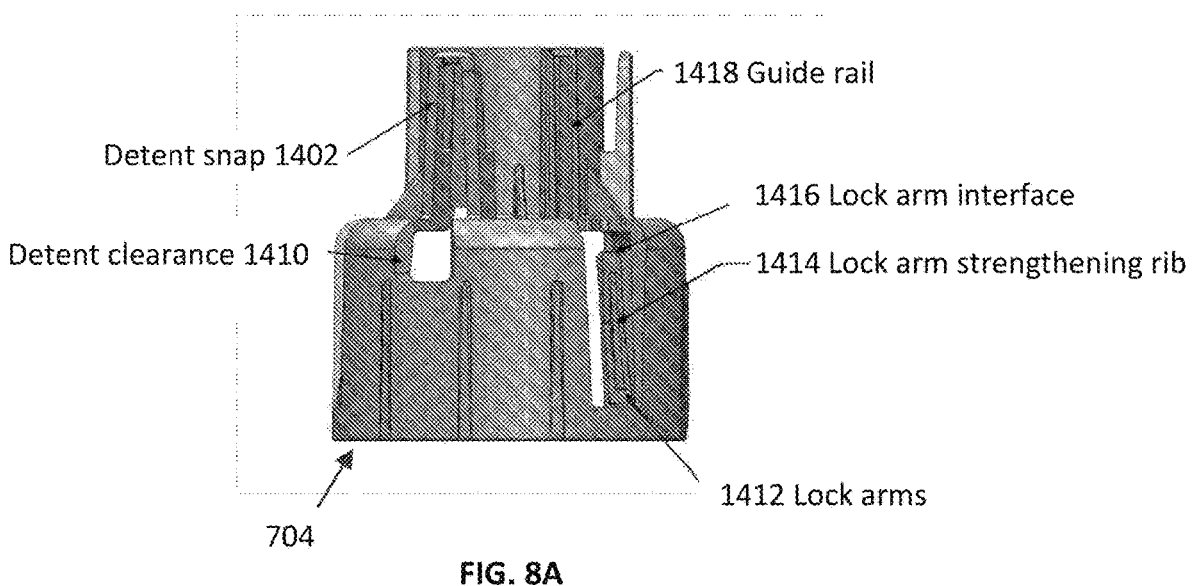
FIG. 8A is a side view depicting an example embodiment of a sheath.
Figure 8B:
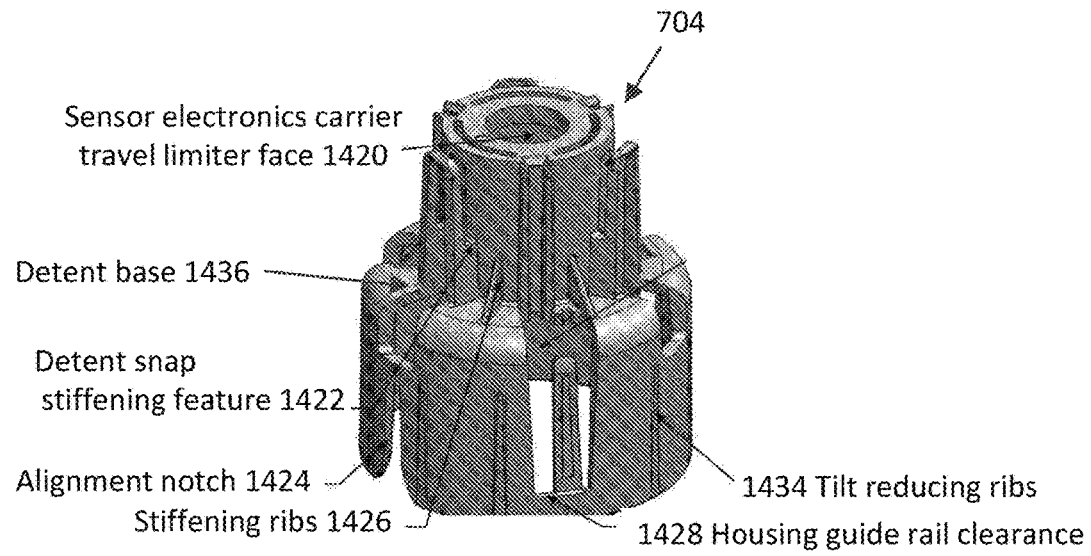
FIG. 8B is a perspective view depicting an example embodiment of a proximal end of a sheath.
Figures 8C, 8D:
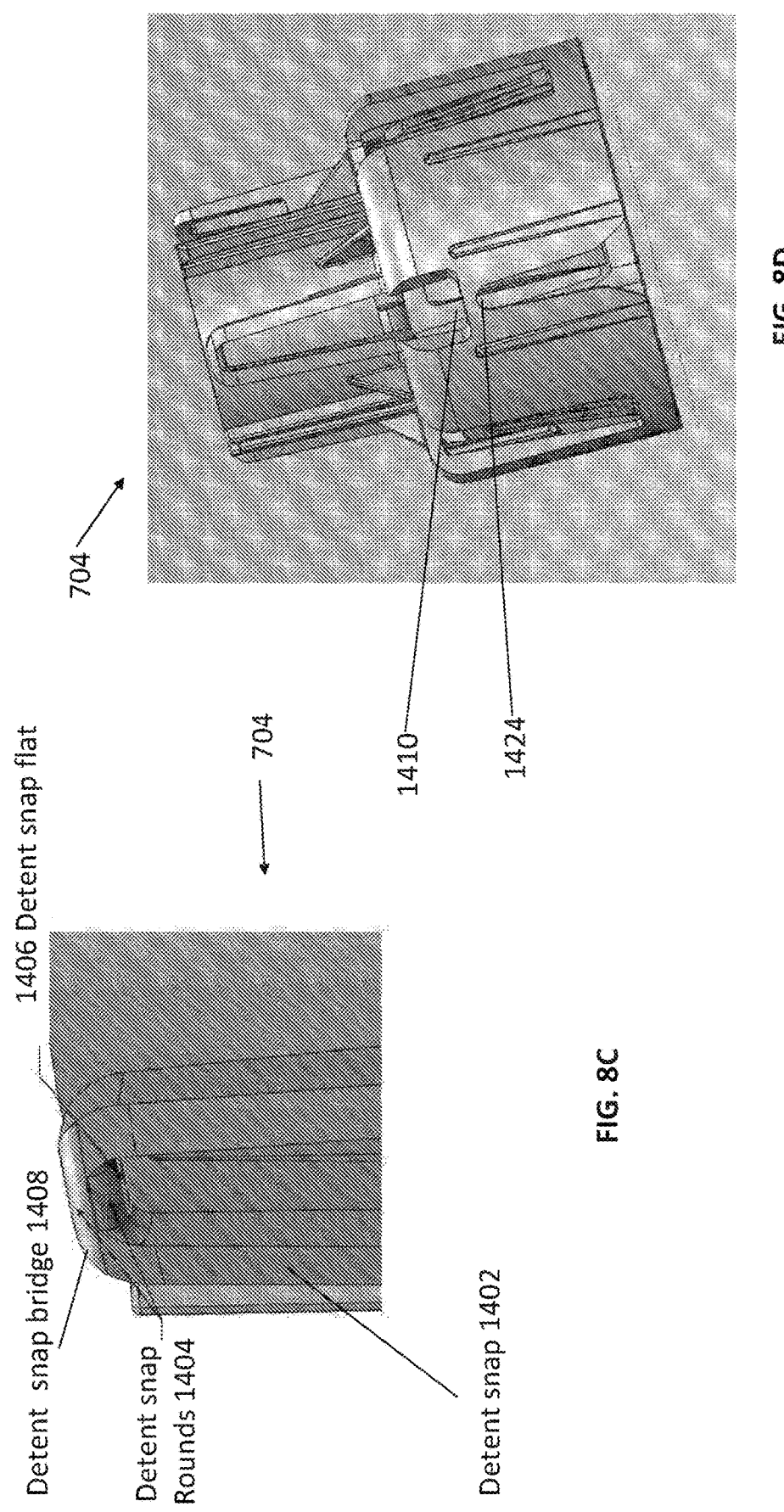
FIG. 8C is a close-up perspective view depicting an example embodiment of a distal side of a detent snap of a sheath.
FIG. 8D is a side view depicting an example embodiment of features of a sheath.

FIGS. 8A and 8B are a side view and perspective view, respectively, depicting an example embodiment of sheath 704. In this example embodiment, sheath 704 can stage sensor control device 102 above a user's skin surface prior to application. Sheath 704 can also contain features that help retain a sharp in a position for proper application of a sensor, determine the force required for sensor application, and guide sheath 704 relative to housing 702 during application. Detent snaps 1402 are near a proximal end of sheath 704, described further with respect to FIG. 8C below. Sheath 704 can have a generally cylindrical cross section with a first radius in a proximal section (closer to top of figure) that is shorter than a second radius in a distal section (closer to bottom of figure). Also shown are a plurality of detent clearances 1410, three in the example embodiment. Sheath 704 can include one or more detent clearances 1410, each of which can be a cutout with room for sheath snap lead-in feature 1330 to pass distally into until a distal surface of locking rib 1340 contacts a proximal surface of detent clearance 1410.

Guide rails 1418 are disposed between sensor electronics carrier traveler limiter face 1420 at a proximal end of sheath 704 and a cutout around lock arms 1412. Each guide rail 1418 can be a channel between two ridges where the guide edge 1326 of housing guide rib 1321 can slide distally with respect to sheath 704.

Lock arms 1412 are disposed near a distal end of sheath 704 and can include an attached distal end and a free proximal end, which can include lock arm interface 1416. Lock arms 1412 can lock sensor electronics carrier 710 to sheath 704 when lock arm interface 1416 of lock arms 1412 engage lock interface 1502 of sensor electronics carrier 710. Lock arm strengthening ribs 1414 can be disposed near a central location of each lock arm 1412 and can act as a strengthening point for an otherwise weak point of each lock arm 1412 to prevent lock arm 1412 from bending excessively or breaking.

Detent snap stiffening features 1422 can be located along the distal section of detent snaps 1402 and can provide reinforcement to detent snaps 1402. Alignment notch 1424 can be a cutout near the distal end of sheath 704, which provides an opening for user alignment with sheath orientation feature of platform 808. Stiffening ribs 1426 can include buttresses, that are triangularly shaped here, which provide support for detent base 1436. Housing guide rail clearance 1428 can be a cutout for a distal surface of housing guide rib 1321 to slide during use.

FIG. 8C is a close-up perspective view depicting an example embodiment of detent snap 1402 of sheath 704. Detent snap 1402 can include a detent snap bridge 1408 located near or at its proximal end. Detent snap 1402 can also include a detent snap flat 1406 on a distal side of detent snap bridge 1408. An outer surface of detent snap bridge 1408 can include detent snap rounds 1404 which are rounded surfaces that allow for easier movement of detent snap bridge 1408 across interior surfaces of housing 702 such as, for example, locking rib 1340.

FIG. 8D is a side view depicting an example embodiment of sheath 704. Here, alignment notch 1424 can be relatively close to detent clearance 1410. Detent clearance 1410 is in a relatively proximal location on distal portion of sheath 704.

Figure 8E:
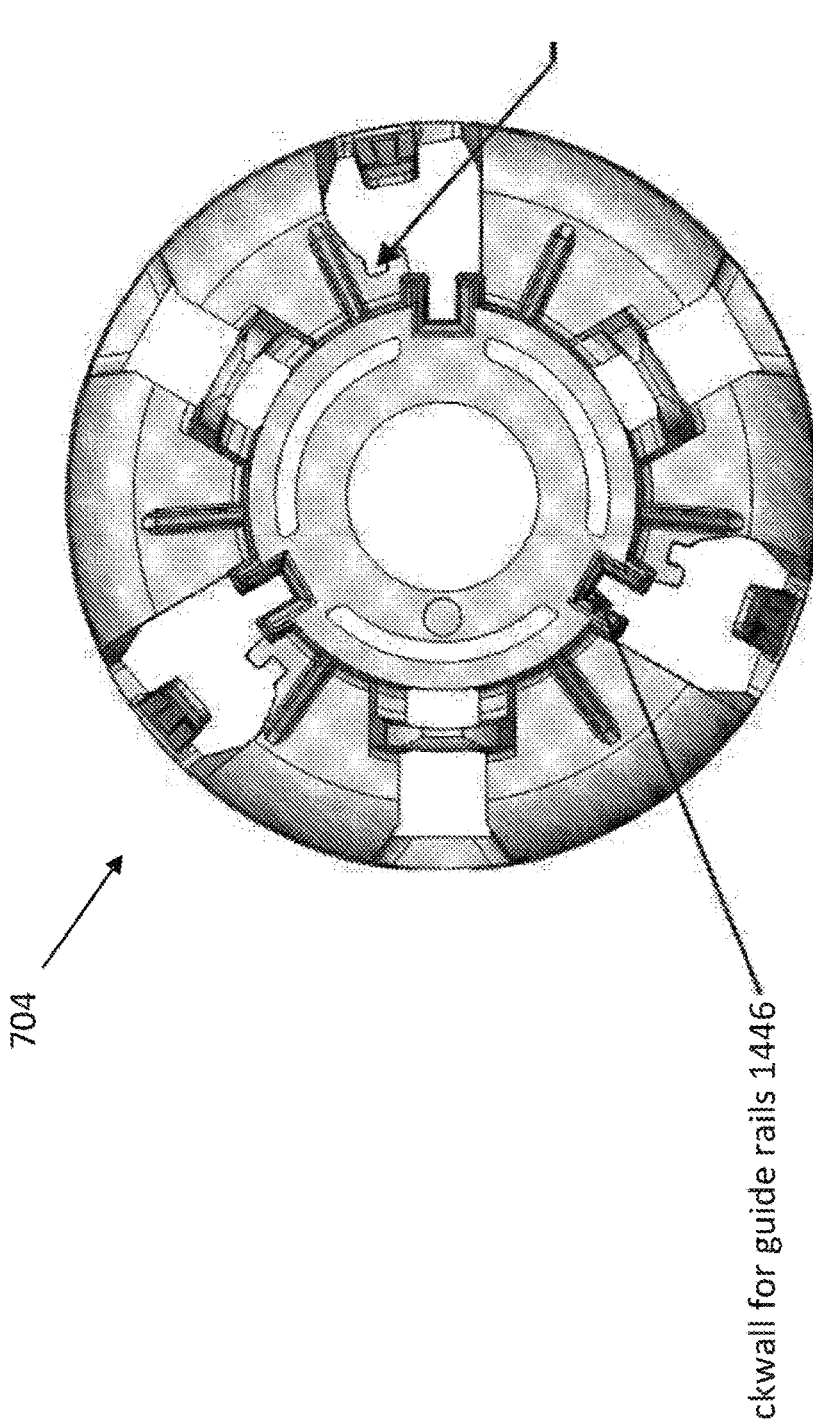
FIG. 8E is an end view of an example embodiment of a proximal end of a sheath.

FIG. 8E is an end view depicting an example embodiment of a proximal end of sheath 704. Here, a back wall for guide rails 1446 can provide a channel to slidably couple with housing guide rib 1321 of housing 702. Sheath rotation limiter 1448 can be notches which reduce or prevent rotation of the sheath 704.

Figures 8F, 8G, 8H:
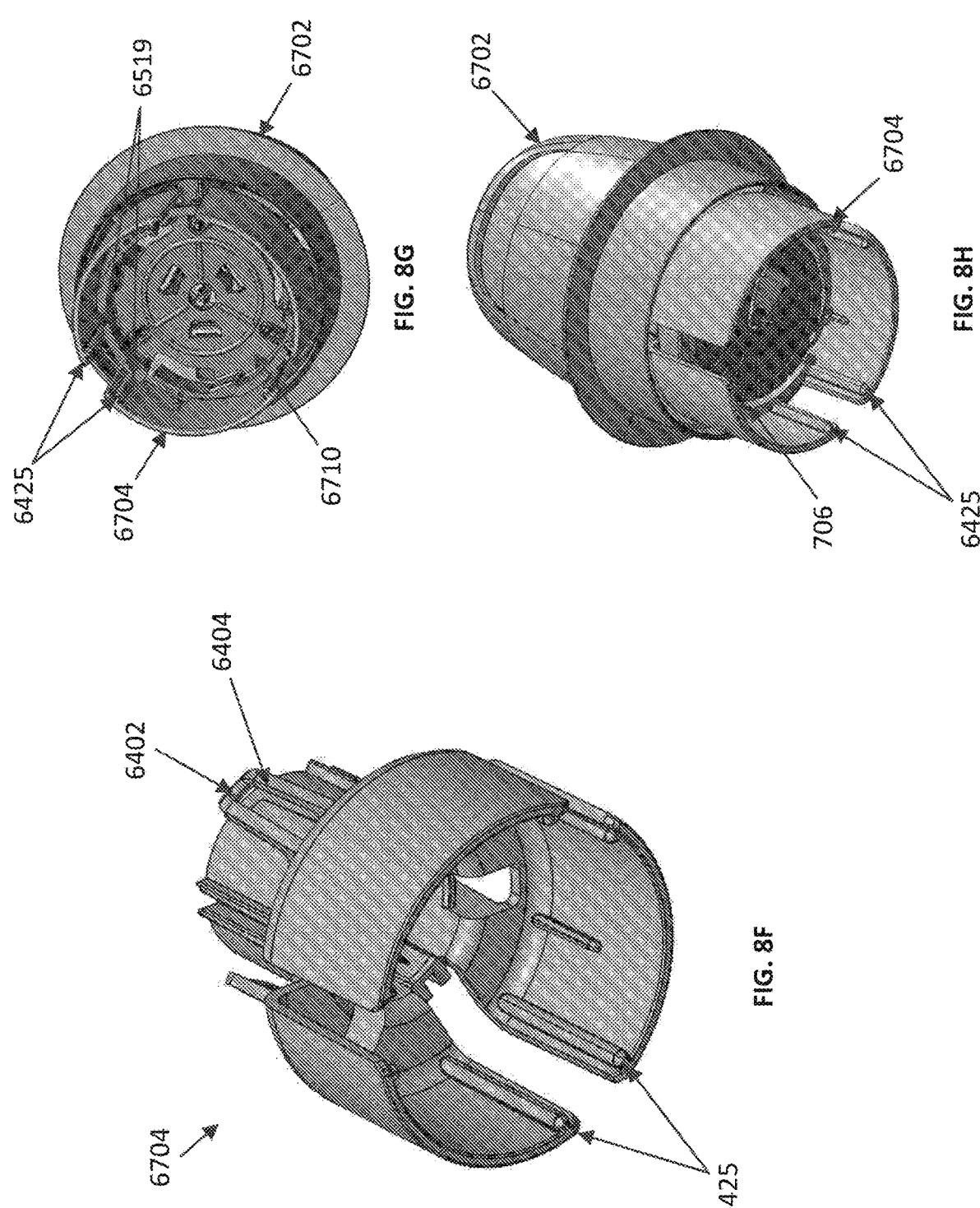
FIGS. 8F to 8H are perspective views depicting another example embodiment of a sheath in various stages of assembly with other applicator components.

FIGS. 8F-8H are perspective views of an alternative example embodiment of sheath 6704 in various stages of assembly with other components of the applicator. As shown in FIG. 8F, sheath 6704 can have many of the same features as sheath 704, previously described with respect to FIGS. 8A-8C. Sheath 6704, for example, can include one or more detent snaps 6404 having one or more detent rounds 6402 attached thereto. Sheath 6704, however, can be shorter in overall length as compared to sheath 702. In addition, sheath 6704 can include one or more inner sheath ribs 6425 disposed on the inner surface of sheath 6704, and which protrude in an inward direction towards the central axis of sheath 6704.

Turning to FIG. 8G, sheath 6704 is shown in perspective view in a stage of assembly with applicator housing 6702 and sensor electronics carrier 6710. One or more inner sheath ribs 6425 of sheath 6704 can interface with one or more corresponding rib notches 6519 in sensor electronics carrier 6710. The fitted interface between corresponding ribs 6425 and notches 6519 can help maintain axial alignment of the sheath 6704 and sensor electronics carrier 6710 during the sensor insertion process. Furthermore, the interface between ribs 6425 and notches 6519 can reduce lateral and rotational movement between the applicator components, which can, in turn, reduce the chance of improper sensor insertion.

Turning to FIG. 8H, sheath 6704 is shown in perspective view in a stage of assembly with applicator housing 6702 and sensor electronics housing 706, which has been inserted into sensor electronics carrier 6710. Inner sheath ribs 6425 are also shown.

It should be noted that although six inner sheath ribs 6425 and six corresponding rib notches 65 19 are depicted, any number of ribs and notches are fully within the scope of the present disclosure. Moreover, while ribs 6425 are depicted with a rounded surface edge, in other embodiments, ribs 6425 can have a rectangular or triangular shape, and rib notches 6519 can have a corresponding receiving shape for interfacing with ribs 6425. In addition, although ribs 6425 are depicted as being disposed on an inner circumferential surface of sheath 6704, ribs 6425 can also be disposed on any other surface of sheath 6704, or portion thereof, that comes into contact with sensor electronics carrier 6710.

Example Embodiments of Sensor Electronics Carriers

Figure 9A:
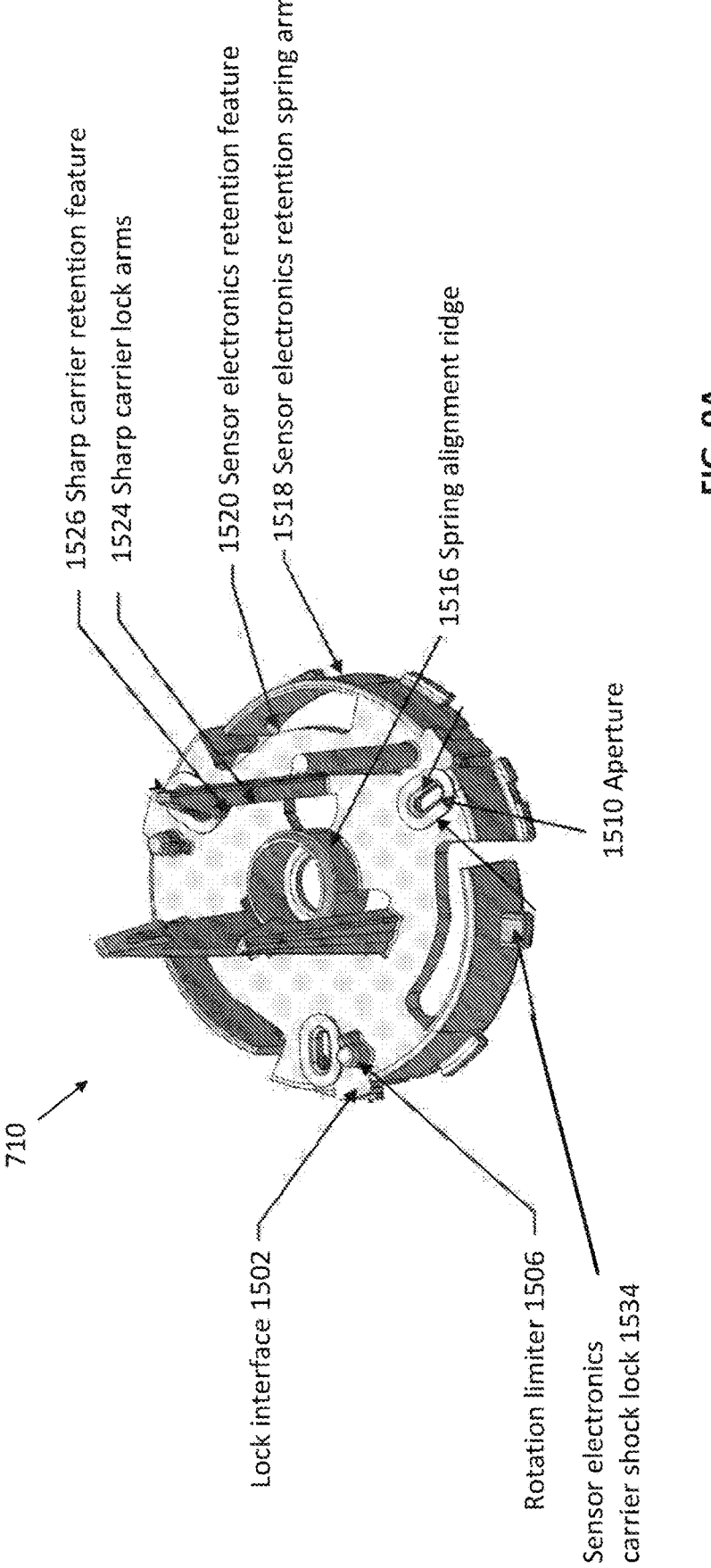
FIG. 9A is a proximal perspective view depicting an example embodiment of a sensor electronics carrier.

FIG. 9A is a proximal perspective view depicting an example embodiment of sensor electronics carrier 710 that can retain sensor electronics within applicator 150. It can also retain sharp carrier 1102 with sharp module 2500. In this example embodiment, sensor electronics carrier 710 generally has a hollow round flat cylindrical shape, and can include one or more deflectable sharp carrier lock arms 1524

(e.g., three) extending proximally from a proximal surface surrounding a centrally located spring alignment ridge 1516 for maintaining alignment of spring 1104. Each lock arm 1524 has a detent or retention feature 1526 located at or near its proximal end. Shock lock 1534 can be a tab located on an outer circumference of sensor electronics carrier 710 extending outward and can lock sensor electronics carrier 710 for added safety prior to firing. Rotation limiter 1506 can be a proximally extending relatively short protrusion on a proximal surface of sensor electronics carrier 710 which limits rotation of carrier 710. Sharp carrier lock arms 1524 can interface with sharp carrier 1102 as described with reference to FIGS. 10A-10E below.

Figure 9B:
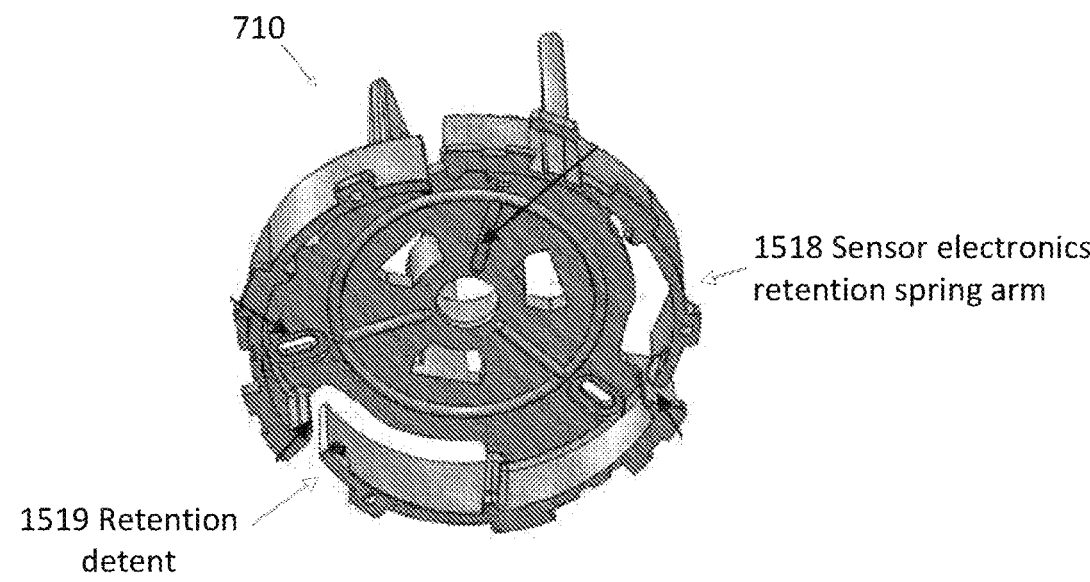
FIG. 9B is a distal perspective view depicting an example embodiment of a sensor electronics carrier.

FIG. 9B is a distal perspective view of sensor electronics carrier 710. Here, one or more sensor electronics retention spring arms 1518 (e.g., three) are normally biased towards the position shown and include a detent 1519 that can pass over the distal surface of electronics housing 706 of device 102 when housed within recess or cavity 1521. In certain embodiments, after sensor control device 102 has been adhered to the skin with applicator 150, the user pulls applicator 150 in a proximal direction, i.e., away from the skin. The adhesive force retains sensor control device 102 on the skin and overcomes the lateral force applied by spring arms 1518. As a result, spring arms 1518 deflect radially outwardly and disengage detents 1519 from sensor control device 102 thereby releasing sensor control device 102 from applicator 150.

Figure 9C:
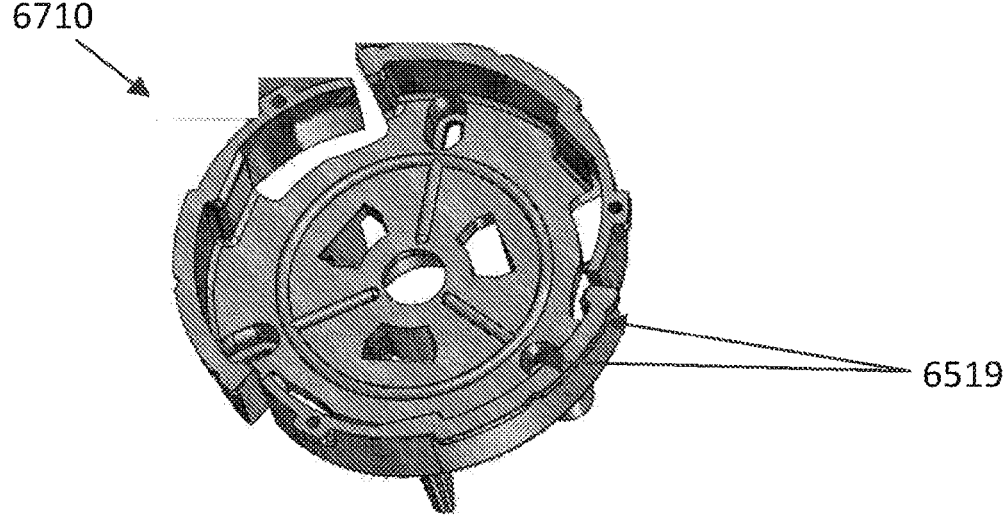
FIG. 9C is a distal perspective view depicting another example embodiment of a sensor electronics carrier.

FIG. 9C is a perspective view of an alternative example embodiment of sensor electronics carrier 6710. As shown in FIG. 9C, sensor electronics carrier 6710 can have many of the same features as sensor electronics carrier 710, previously described with respect to FIGS. 9A-9B. In addition, sensor electronics carrier 6710 also includes one or more notch ribs 6519 disposed along an outer circumferential surface. As best seen in FIGS. 8F-8H, notch ribs 6519 are configured to interface with inner sheath ribs 6425 in order to maintain axial alignment of the sheath and sensor electronics carrier, and reduce lateral and rotational movement between applicator components during the sensor insertion process.

Example Embodiments of Sharp Carriers

Figure 10A:
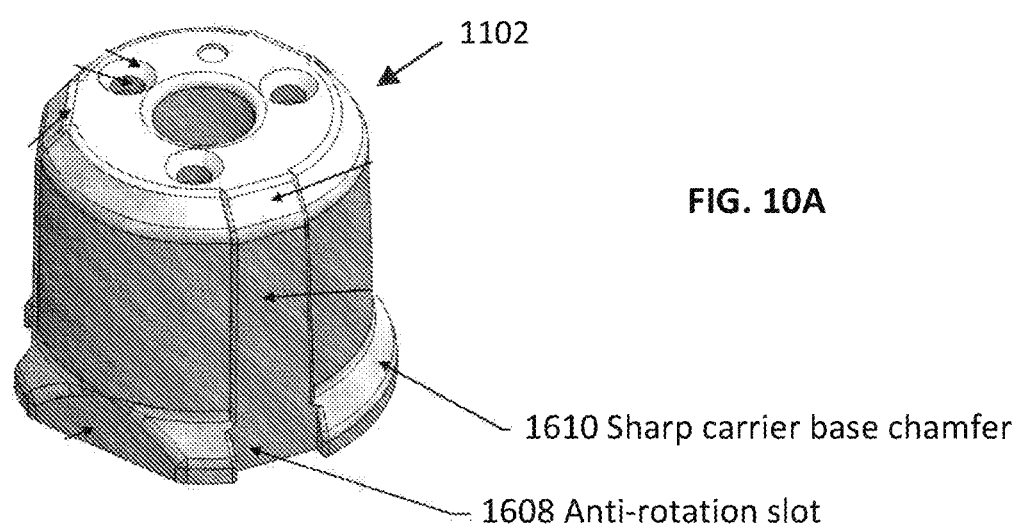
FIG. 10A is a perspective view of a sharp carrier in accordance with the disclosed subject matter.
Figure 10B:
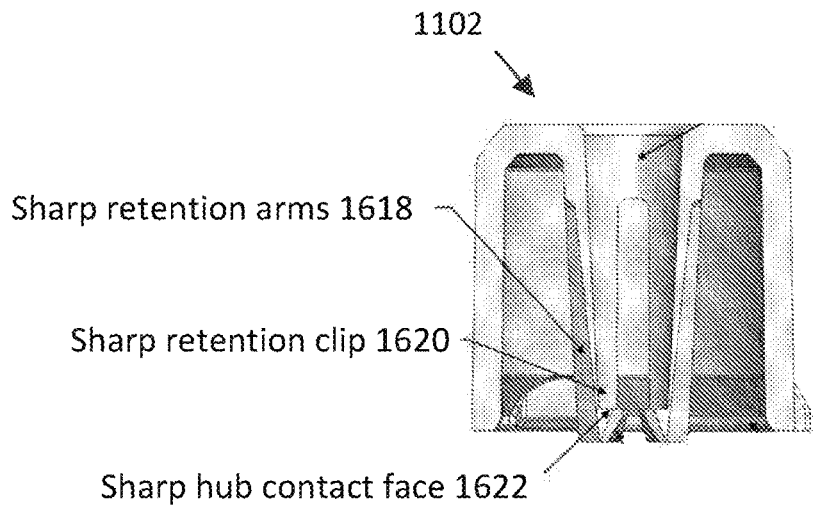
FIG. 10B is a side cutaway view of the sharp carrier of FIG. 10A.

FIGS. 10A and 10B are a proximal perspective view and a side cross-sectional view, respectively, depicting an example embodiment of sharp carrier 1102. Sharp carrier 1102 can grasp and retain sharp module 2500 within applicator 150. It can also automatically retract as a result of one or more springs changing from a preloaded, compressed state to an expanded state during an insertion process, as described with respect to FIGS. 40A-40F. Near a distal end of sharp carrier 1102 can be anti-rotation slots 1608 which prevent sharp carrier 1102 from rotating when located within a central area of sharp carrier lock arms 1524 (as shown in FIG. 9A). Anti-rotation slots 1608 can be located between sections of sharp carrier base chamfer 1610, which can ensure full retraction of sharp carrier 1102 through sheath 704 upon retraction of sharp carrier 1102 at the end of the deployment procedure.

As shown in FIG. 10B, sharp retention arms 1618 can be located in an interior of sharp carrier 1102 about a central axis and can include a sharp retention clip 1620 at a distal end of each arm 1618. Sharp retention clip 1620 can have a proximal surface which can be nearly perpendicular to the central axis and can abut a distally facing surface of sharp hub 2516 (FIG. 11A).

Example Embodiments of Sensor Modules

Figures 11A, 11B:
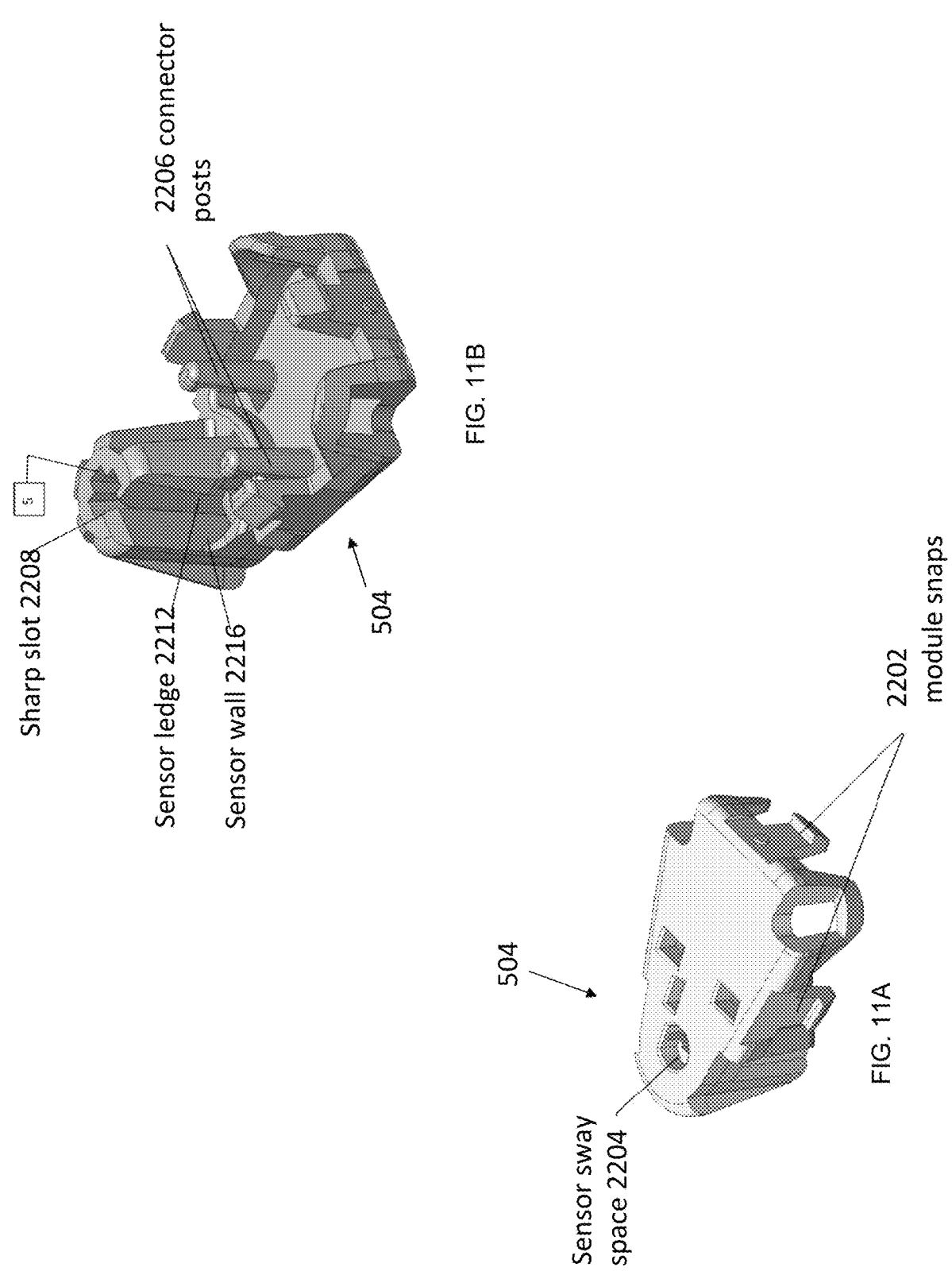
FIGS. 11A to 11B are top and bottom perspective views, respectively, depicting an example embodiment of a sensor module.

FIGS. 11A and 11B are a top perspective view and a bottom perspective view, respectively, depicting an example embodiment of sensor module 504. Module 504 can hold a connector 2300 (FIGS. 12A and 12B) and a sensor 104 (FIG. 13). Module 504 is capable of being securely coupled with electronics housing 706. One or more deflectable arms or module snaps 2202 can snap into the corresponding features 2010 of housing 706. A sharp slot 2208 can provide a location for sharp tip 2502 to pass through and sharp shaft 2504 to temporarily reside. A sensor ledge 2212 can define a sensor position in a horizontal plane, prevent a sensor from lifting connector 2300 off of posts and maintain sensor 104 parallel to a plane of connector seals. It can also define sensor bend geometry and minimum bend radius. It can limit sensor travel in a vertical direction and prevent a tower from protruding above an electronics housing surface and define a sensor tail length below a patch surface. A sensor wall 2216 can constrain a sensor and define a sensor bend geometry and minimum bend radius.

Figures 12A, 12B:
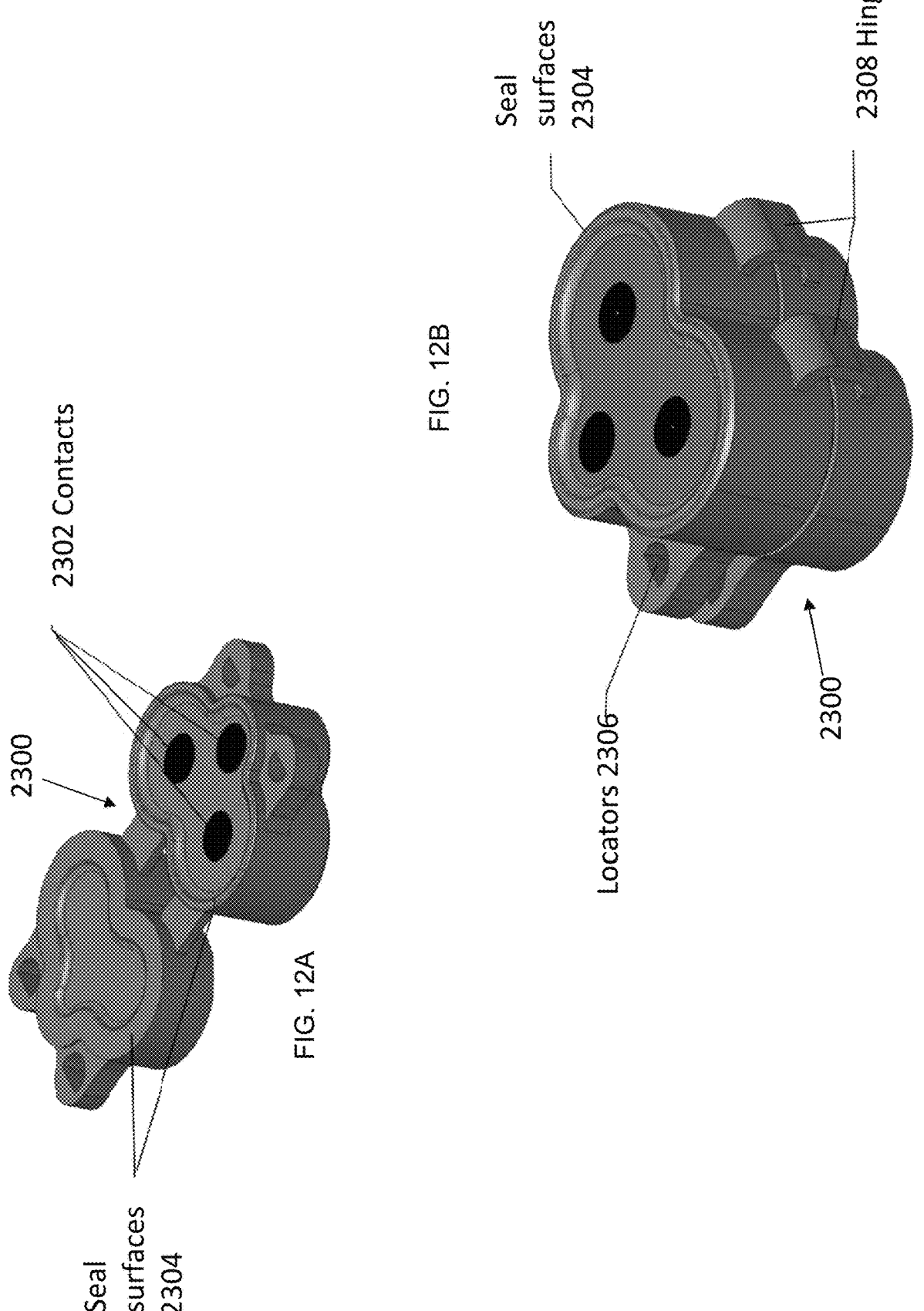
FIGS. 12A and 12B are perspective and compressed views, respectively, depicting an example embodiment of a sensor connector.
Figure 13:
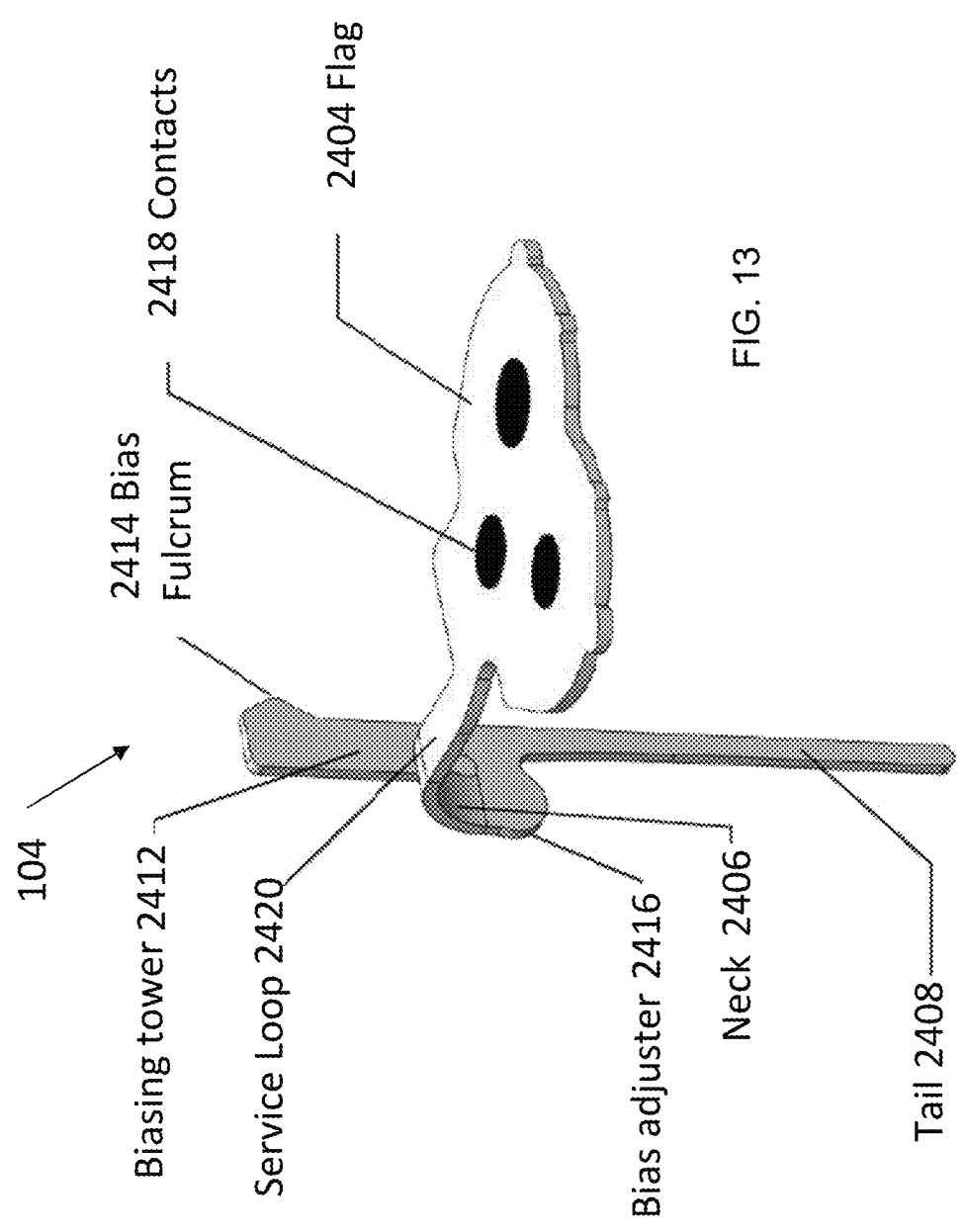
FIG. 13 is a perspective view depicting an example embodiment of a sensor.

FIGS. 12A and 12B are perspective views depicting an example embodiment of connector 2300 in an open state and a closed state, respectively. Connector 2300 can be made of silicone rubber that encapsulates compliant carbon impregnated polymer modules that serve as electrical conductive contacts 2302 between sensor 104 and electrical circuitry contacts for the electronics within housing 706. The connector can also serve as a moisture barrier for sensor 104 when assembled in a compressed state after transfer from a container to an applicator and after application to a user's skin. A plurality of seal surfaces 2304 can provide a watertight seal for electrical contacts and sensor contacts. One or more hinges 2208 can connect two distal and proximal portions of connector 2300.

FIG. 13 is a perspective view depicting an example embodiment of sensor 104. A neck 2406 can be a zone which allows folding of the sensor, for example ninety degrees. A membrane on tail 2408 can cover an active analyte sensing element of the sensor 104. Tail 2408 can be the portion of sensor 104 that resides under a user's skin after insertion. A flag 2404 can contain contacts and a sealing surface. A biasing tower 2412 can be a tab that biases the tail 2408 into sharp slot 2208. A bias fulcrum 2414 can be an offshoot of biasing tower 2412 that contacts an inner surface of a needle to bias a tail into a slot. A bias adjuster 2416 can reduce a localized bending of a tail connection and prevent sensor trace damage. Contacts 2418 can electrically couple the active portion of the sensor to connector 2300. A service loop 2420 can translate an electrical path from a vertical direction ninety degrees and engage with sensor ledge 2212 (FIG. 11B).

Referring again to FIG. 13, the sensor 104 can be configured with a neck 2406, interconnecting the flag 2404 and the tail 2408, that allows bending of the sensor 104 between the flag 2404 and the tail 2408. In one example, the neck 2406 can be bent about ninety degrees to facilitate the contacts 2418 of the flag 2404 making contact with a sensor ledge 2212 (FIG. 11B). The sensor 104, however, can be manufactured, and in some embodiments even shipped, or stored, in a relatively flat configuration where there is substantially no bend in the neck 2406 of the sensor 104, such that the flag 2404, neck 2406, and tail 2408 can form a substantially planar surface. To configure the sensor 104 in the illustrated embodiment, the neck 2406 must be bent. However, bending the neck 2406 subjects the sensor 104 generally, and the neck 2404 in particular, to stresses that may weaken or damage the sensor 104, cause microfactures, or otherwise reduce its efficiency and efficacy. Techniques described herein below can ensure that the neck 2404 can be bent to a desired angle while reducing damage to the sensor 104 and its constituent parts.

One exemplary technique to reduce damage caused by bending the neck 2406 of the sensor 104 is to apply a sufficient amount of heat for a sufficient amount of time in temporal proximity to the time when the neck 2406 will be bent. These factors of the degree of heat, the length of time of exposure, and the nearness of the application of heat to the time when the bend is conducted, can be determined based on the type of material comprising the sensor 104 generally and the neck 2406 in particular with suitable examples provided below. Care must be taken, for example, to avoid damaging the contacts 2418 and the membrane covering the tail 2408.

The application of heat can be controlled by the manufacturing components used to bend the neck 2406. In one embodiment, the neck 2406 can be bent, or folded, by heating a portion of the neck 2406 of the sensor 104 to a predetermined temperature and bending the neck 2406 of the sensor 104 to form an angle between the tail 2408 of the sensor 104 and the flag 2404 of the sensor. As mentioned, the predetermined temperature and length of heating can be determined based on properties of one or more of the materials comprising the neck 2406 of the sensor 104. The temperature and length of heating can be chosen based on being sufficient to improve malleability of the neck 2406 of the sensor 104 without damaging the rest of the sensor. In some embodiments, a suitable temperature can in the temperature range of between 50 and 60° C., inclusive, and a suitable length of heating can be specified at or around 1.8 seconds, nominally. As an example, the temperature can be specified as a target temperature within a suitable range, e.g., 53, 55, or 57° C., etc., with a specified degree of variance, e.g., ±2° C. Heating the neck 2406 of the sensor 104 can include heating only a region of the neck 2406 of the sensor 104, heating substantially all of the neck 2406, or heating one or more other components of the sensor 104.

The heating and bending can be performed by one or more heating and bending apparatuses. For example, the sensor 104 can be inserted in to a first configuration of a heading-bending apparatus that includes separate, dedicated components for heating the neck 2406 and bending the neck 2406. Configuring the sensor 104, then, includes heating the neck 2406 with the first component for heating the neck 2406 before passing the sensor 104 to the second component for bending the neck 2406 to the desired angle. Heating the neck 2406 can be performed by a heating element of a heating apparatus. The heating element can be raised to a desired temperature and can be made to contact, or be brought into close proximity with, the designated portion of the neck 2406 for a set period of time, causing the temperature of the neck 2406 to rise. Additionally, the local temperature around the sensor 104 can be raised to indirectly heat the neck 2406 without contacting the neck 2406 with a heating element directly.

Additionally, the heating and bending can be performed by a unified heated-bending apparatus where the necessary components to the heat the neck 2406 are integrated into the components to bend the neck 2406. Heat, therefore, can be applied during the bending in addition to before or after the bending process is complete. The degree of heat, e.g., the temperature being applied to the neck 2406 can remain consistent during the heating and/or heated-bending process by ensuring that the temperature of the heating element remains substantially consistent and that the distance between the heating element and the neck 2406 remains substantially consistent. Alternatively, the temperature of the neck 2406 can be caused to vary during the bending process. For example, the temperature of the next can be raised to a set threshold temperature, allowed to fall to a set threshold before bending is applied, and can be raised again after the bending process (e.g., to avoid microfractures). Where the heating element is integrated into the bending apparatus, the process can involve increasing or decreasing the temperature of the neck 2406 while the neck 2406 is being bent.

In addition, after bending the neck 2406 to form the desired angle, a step in manufacturing or manipulating the sensor 104 can include verifying the integrity of the sensor 104 after the bending by checking the neck 2406 for microfractures. In some embodiments, the neck 2406 can be tested for microfractures using a capacitance test to determine if the capacitance of a neck 2406 under examination varies from a benchmark capacitance. If the number or intensity of microfractures exceeds a predetermined threshold, the sensor can be discarded. Other integrity checks can include check the sensitive components of the sensor 104 to ensure that they remain in a form that is consistent with their intended functions and have not been compromised by the bending process.

Figure 14B:
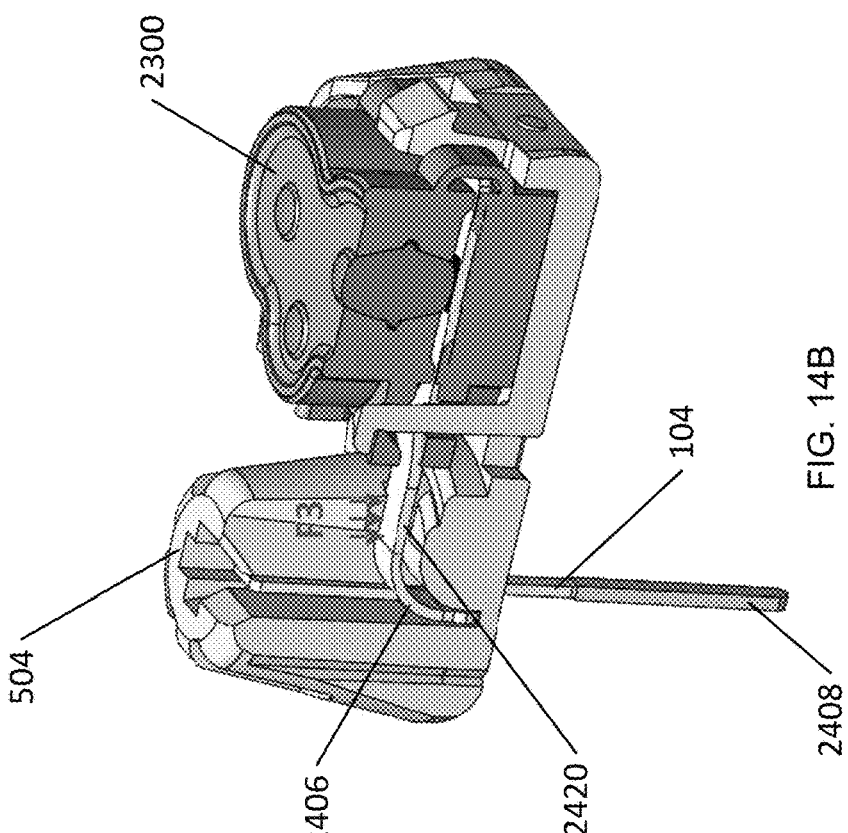
FIGS. 14A and 14B are bottom and top perspective views, respectively, of an example embodiment of a sensor module assembly.
Figure 14A:
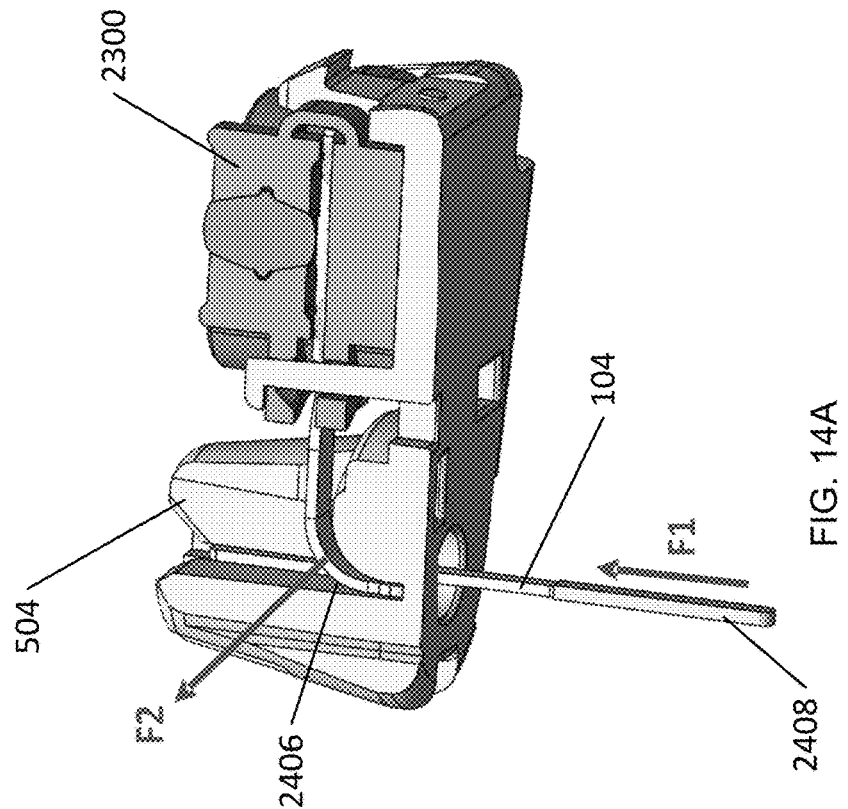

FIGS. 14A and 14B are bottom and top perspective views, respectively, depicting an example embodiment of a sensor module assembly comprising sensor module 504, connector 2300, and sensor 104. According to one aspect of the aforementioned embodiments, during or after insertion, sensor 104 can be subject to axial forces pushing up in a proximal direction against sensor 104 and into the sensor module 105, as shown by force, F1, of FIG. 14A. According to some embodiments, this can result in an adverse force, F2, being applied to neck 2406 of sensor 104 and, consequently, result in adverse forces, F3, being translated to service loop 2420 of sensor 104. In some embodiments, for example, axial forces, F1, can occur as a result of a sensor insertion mechanism in which the sensor is designed to push itself through the tissue, a sharp retraction mechanism during insertion, or due to a physiological reaction created by tissue surrounding sensor 104 (e.g., after insertion).

Figures 15A, 15B:
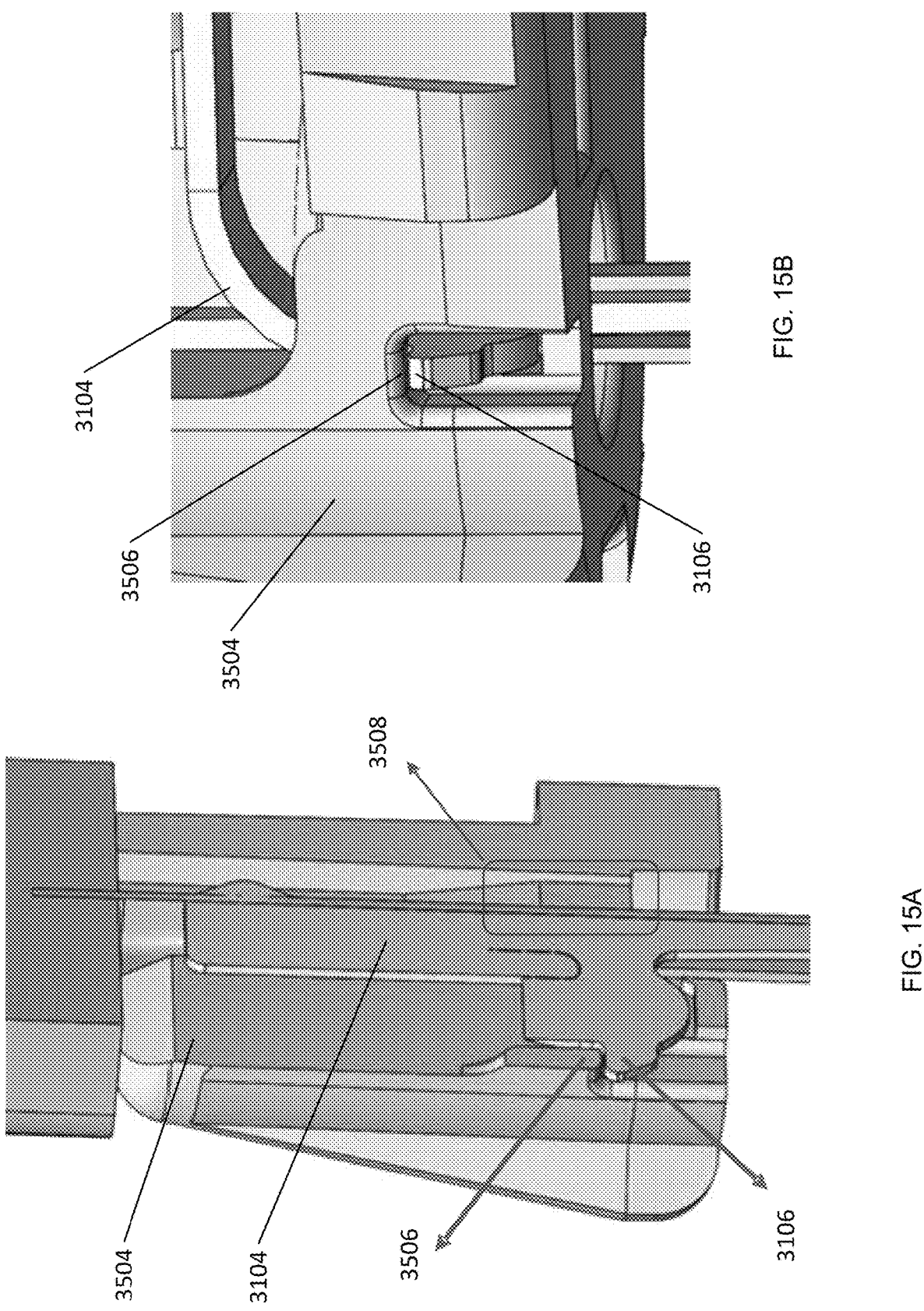
FIGS. 15A and 15B are close-up partial views of an example embodiment of a sensor module assembly.

FIGS. 15A and 15B are close-up partial views of an example embodiment of a sensor module assembly having certain axial stiffening features. In a general sense, the embodiments described herein are directed to mitigating the effects of axial forces on the sensor as a result of insertion and/or retraction mechanisms, or from a physiological reaction to the sensor in the body. As can be seen in FIGS. 15A and 15B, according to one aspect of the embodiments, sensor 3104 comprises a proximal portion having a hook feature 3106 configured to engage a catch feature 3506 of the sensor module 3504. In some embodiments, sensor module 3504 can also include a clearance area 3508 to allow a distal portion of sensor 3104 to swing backwards during assembly to allow for the assembly of the hook feature 3106 of sensor 3104 over and into the catch feature 3506 of sensor module 3504.

According to another aspect of the embodiments, the hook and catch features 3106, 3506 operate in the following manner. Sensor 3104 includes a proximal sensor portion, coupled to sensor module 3504, as described above, and a distal sensor portion that is positioned beneath a skin surface in contact with a bodily fluid. As seen in FIGS. 15A and 15B, the proximal sensor portion includes a hook feature 3106 adjacent to the catch feature 3506 of sensor module 3504. During or after sensor insertion, one or more forces are exerted in a proximal direction along a longitudinal axis of sensor 3104. In response to the one or more forces, hook feature 3106 engages catch feature 3506 to prevent displacement of sensor 3104 in a proximal direction along the longitudinal axis.

According to another aspect of the embodiments, sensor 3104 can be assembled with sensor module 3504 in the following manner. Sensor 3104 is loaded into sensor module 3504 by displacing the proximal sensor portion in a lateral direction to bring the hook feature 3106 in proximity to the catch feature 3506 of sensor module 3504. More specifically, displacing the proximal sensor portion in a lateral direction causes the proximal sensor portion to move into clearance area 3508 of sensor module 3504.

Although FIGS. 15A and 15B depict hook feature 3106 as a part of sensor 3104, and catch feature 3506 as a part of sensor module 3504, those of skill in the art will appreciate that hook feature 3106 can instead be a part of sensor module 3504, and, likewise, catch feature 3506 can instead be a part of sensor 3106. Similarly, those of skill in the art will also recognize that other mechanisms (e.g., detent, latch, fastener, screw, etc.) implemented on sensor 3104 and sensor module 3504 to prevent axial displacement of sensor 3104 are possible and within the scope of the present disclosure.

Figure 15C:
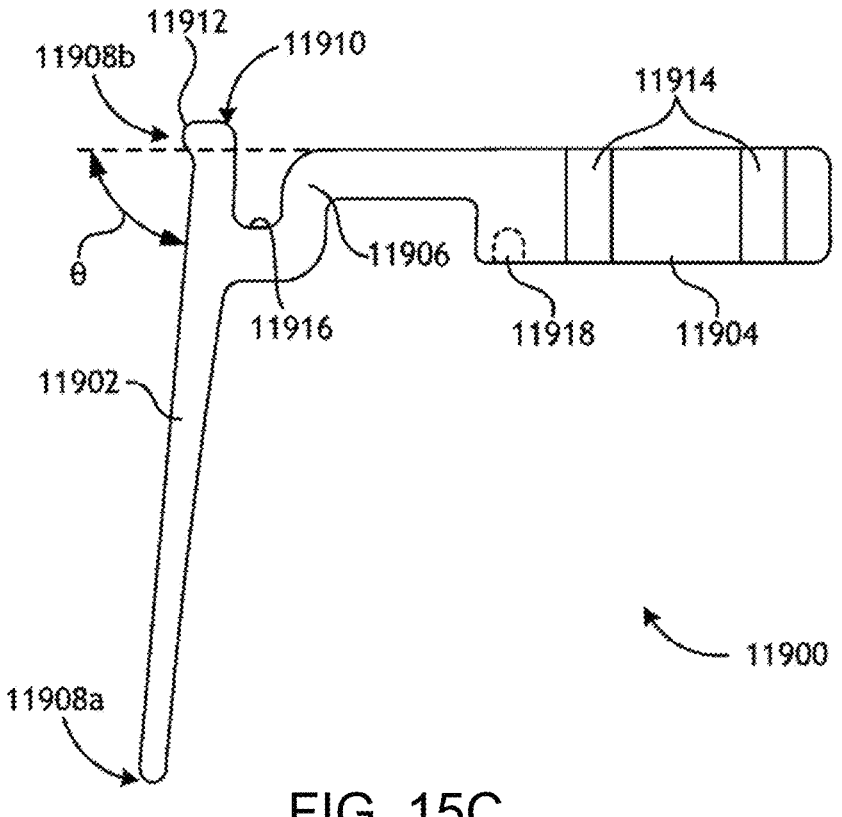
FIGS. 15C-G are side views of example sensors, according to one or more embodiments of the disclosure.

FIG. 15C is a side view of an example sensor 11900, according to one or more embodiments of the disclosure. The sensor 11900 may be similar in some respects to any of the sensors described herein and, therefore, may be used in an analyte monitoring system to detect specific analyte concentrations. As illustrated, the sensor 11900 includes a tail 11902, a flag 11904, and a neck 11906 that interconnects the tail 11902 and the flag 11904. The tail 11902 includes an enzyme or other chemistry or biologic and, in some embodiments, a membrane may cover the chemistry. In use, the tail 11902 is transcutaneously received beneath a user's skin, and the chemistry included thereon helps facilitate analyte monitoring in the presence of bodily fluids.

The tail 11902 may be received within a hollow or recessed portion of a sharp (not shown) to at least partially circumscribe the tail 11902 of the sensor 11900. As illustrated, the tail 11902 may extend at an angle Q offset from horizontal. In some embodiments, the angle Q may be about 85°. Accordingly, in contrast to other sensor tails, the tail 11902 may not extend perpendicularly from the flag 11904, but instead at an angle offset from perpendicular. This may prove advantageous in helping maintain the tail 11902 within the keep the recessed portion of the sharp.

The tail 11902 includes a first or bottom end 11908a and a second or top end 11908b opposite the top end 11908a. A tower 11910 may be provided at or near the top end 11908b and may extend vertically upward from the location where the neck 11906 interconnects the tail 11902 to the flag 11904. During operation, if the sharp moves laterally, the tower 11910 will help picot the tail 11902 toward the sharp and otherwise stay within the recessed portion of the sharp. Moreover, in some embodiments, the tower 11910 may provide or otherwise define a protrusion 11912 that extends laterally therefrom. When the sensor 11900 is mated with the sharp and the tail 11902 extends within the recessed portion of the sharp, the protrusion 11912 may engage the inner surface of the recessed portion. In operation, the protrusion 11912 may help keep the tail 11902 within the recessed portion.

The flag 11904 may comprise a generally planar surface having one or more sensor contacts 11914 arranged thereon. The sensor contact(s) 11914 may be configured to align with a corresponding number of compliant carbon impregnated polymer modules encapsulated within a connector.

In some embodiments, as illustrated, the neck 11906 may provide or otherwise define a dip or bend 11916 extending between the flag 11904 and the tail 11902. The bend 11916 may prove advantageous in adding flexibility to the sensor 11900 and helping prevent bending of the neck 11906.

In some embodiments, a notch 11918 (shown in dashed lines) may optionally be defined in the flag near the neck 11906. The notch 11918 may add flexibility and tolerance to the sensor 11900 as the sensor 11900 is mounted to the mount. More specifically, the notch 11918 may help take up interference forces that may occur as the sensor 11900 is mounted within the mount.

In some embodiments, as illustrated in FIGS. 15D-15G, the neck may comprise or otherwise define a non-linear configuration such as a dip or bend 11920a-11920d with a plurality of turns, e.g., 11921a, 11921b, extending between the flag 11904 and the tail 11902. The bend 11920a-11920d can be advantageous in reducing in-place stiffness of the sensor 11900 by adding flexibility to the sensor 11900 in both a vertically-oriented and horizontally-oriented direction. The added flexibility can provide a multi-directional spring-like structure in the sensor 11900 that helps to limit deformation of the neck 11906 while ensuring that the tail 11902 and the flag 11904 can remain in their expected or fixed positions. The spring-like structure also increases compliance of the sensor 11900 while reducing stress on the overall structure.

Generally, the sensor can be understood as including a tail, a flag, and a neck aligned along a planar surface having a vertical axis and a horizontal axis. The spring-like structure can be formed by various orientations of turns in the bend of the neck of a sensor. Between the tail and the flag, the neck can include at least two turns in relation to the vertical axis providing a spring-like structure. The at least two turns can provide, in relation to an axis of the planar surface shared by the tail, the flag, and the neck, overlapping layers of the structure of the neck, where the neck itself remains unbroken. These overlapping turns make up the spring-like structure. In some embodiments, the overlapping layers of the neck are vertically-oriented. In some embodiments, the overlapping layers of the neck are horizontally-oriented.

Figure 15D:
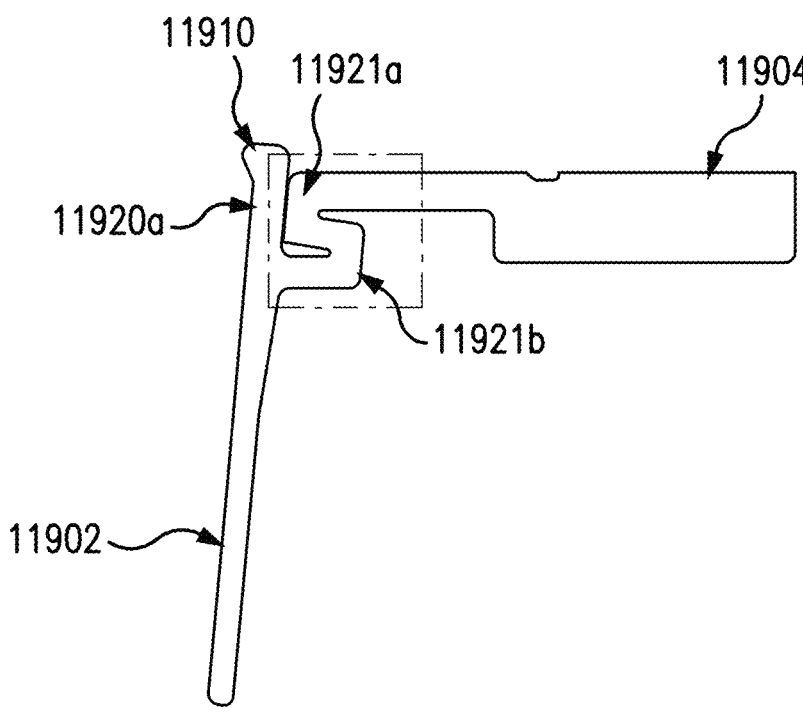

FIG. 15D illustrates one embodiment of a sensor 11900 including a neck between the flag 11904 and tail 11902 with a bend 11920a including turns 11921a and 11921b. In the illustrated embodiment, at least one turn 11921a abuts the top end of the tail or possibly the tower 11910 of the sensor 11900. This orientation can be advantageous in that it reduces the overall footprint of the sensor, even considering the additional material used to generate the bend 11920a. The arrangement can provide multiple overlapping, vertically-aligned horizontal layers between the turns.

Figure 15E:
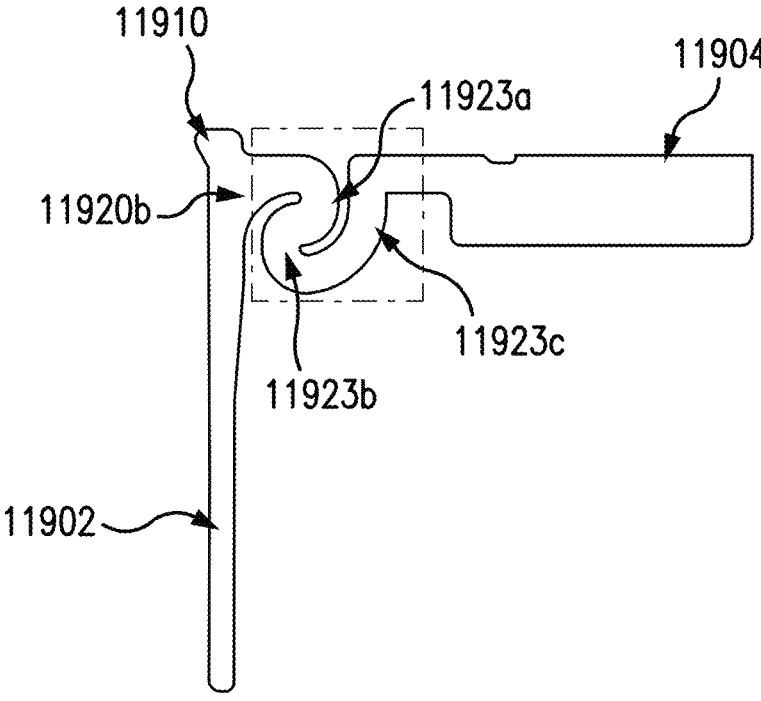

FIG. 15E illustrates another embodiment of a sensor 11900 including a neck between the flag 11904 and tail 11902 with a bend 11920b that generally forms a swirl pattern including at least turn turns 11923a, 11923b, and 11923c. In this embodiment, the turns again abut the top end of the tail or the tower 11910 of the sensor 11900. In addition to maintaining the overall footprint of the sensor, this orientation may provide for additional balancing of the horizontally-oriented and vertically-oriented stresses. The overlapping layers in this arrangement of turns are substantially balanced in along both the horizontal and vertical axes.

Figures 15F, 15G:
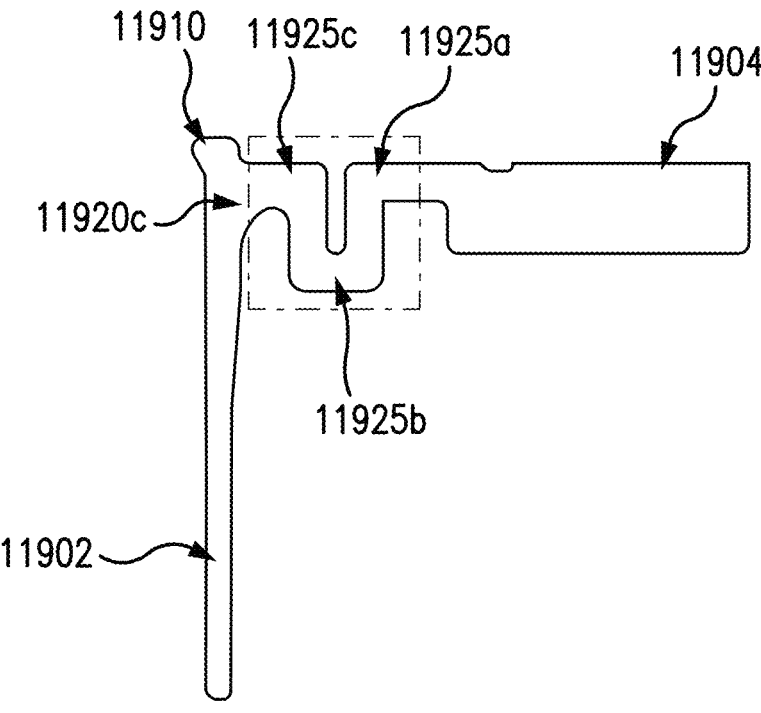

FIG. 15F illustrates another embodiment of a sensor 11900 including a neck between the flag 11904 and tail 11902 with a bend 11920c including turns 11925a, 11925b, and 11925c. In the illustrated embodiment, the turn 11925c connects a region of the tail 11902 near the top end of the tail or the tower 11910 of the sensor to the rest of the bend 11920*c*. In addition to reducing the overall footprint of the sensor, this orientation can provide additional flexibility in the horizontally-oriented axis. The arrangement can provide multiple overlapping, horizontally-aligned vertical layers between the turns.

FIG. 15G illustrates another embodiment of a sensor 11900 including a neck between the flag 11904 and tail 11902 with a bend 11920*d* including turn 11927*a*, 11927*b*, and 11927*c*. In the illustrated embodiment, the bend 11920*d* occurs primarily in the tail 11902 of the sensor, connecting the tail 11902 and the tower 11910, while the stretch of the sensor between the tower 11910 and the flag 11904 is generally uninterrupted. The turn 11927*a* generally connects the tower 11910 to the rest of the bend 11920*d*, while the turn 11927*c* connects the tail 11902 to the rest of the bend 11920*d*. This orientation can provide additional flexibility in the vertically-oriented axis. The arrangement can provide multiple overlapping, horizontally-aligned vertical layers between the turns.

The turns of the neck can be formed by folding or bending the neck of the sensor from a larger neck structure, laser cutting the sensor from a sheet of the material or layers of material comprising the sensor, printing the sensor having the configuration with turns from a sheet of the material or layers of material of which the sensor is composed, stamping the sensor from a sheet of material or layers of material of which the sensor is composed, or other suitable manufacturing processes for providing precision bends in the neck.

Figure 16A:
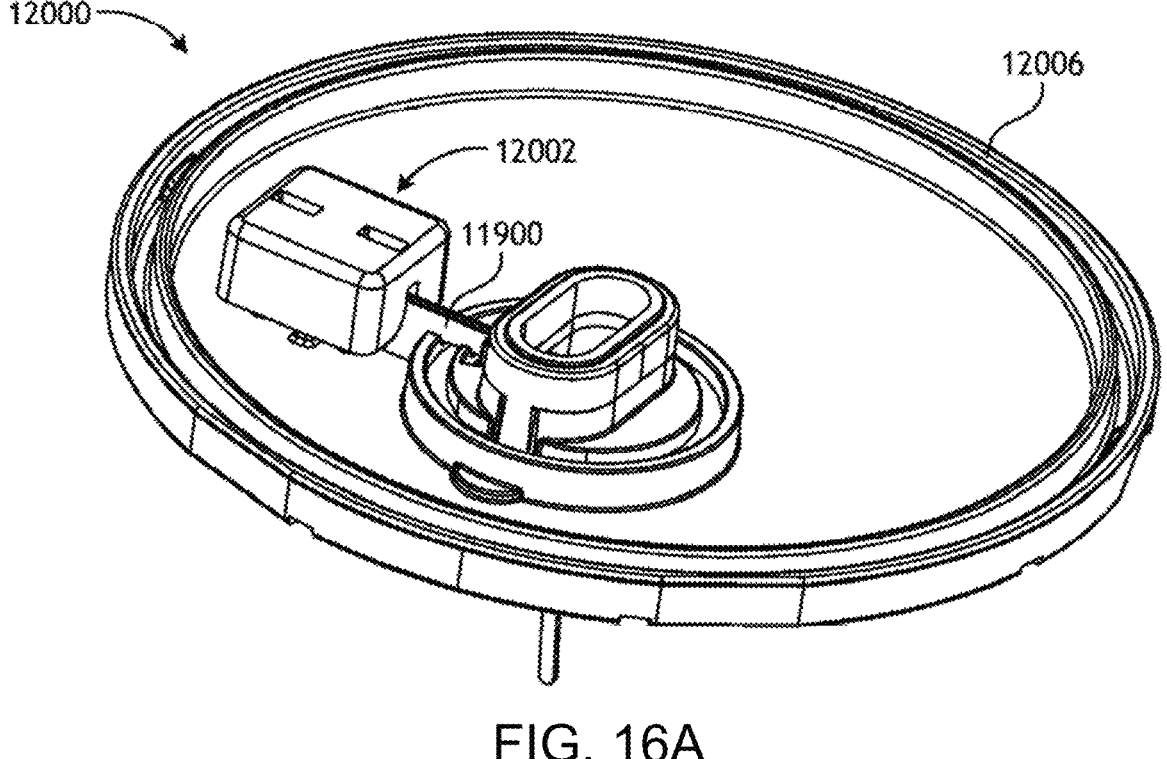

FIGS. 16A and 16B are isometric and partially exploded isometric views of an example connector assembly 12000, according to one or more embodiments. As illustrated, the connector assembly 12000 may include a connector 12002, and FIG. 17C is an isometric bottom view of the connector 12002. The connector 12002 may comprise an injection molded part used to help secure one or more compliant carbon impregnated polymer modules 12004 (four shown in FIG. 16B) to a mount 12006. More specifically, the connector 12002 may help secure the modules 12004 in place adjacent the sensor 11900 and in contact with the sensor contacts 11914 (FIG. 15C) provided on the flag 11904 (FIG. 15C). The modules 12004 may be made of a conductive material to provide conductive communication between the sensor 11900 and corresponding circuitry contacts (not shown) provided within the mount 12006.

As best seen in FIG. 16C, the connector 12002 may define pockets 12008 sized to receive the modules 12004. Moreover, in some embodiments, the connector 12002 may further define one or more depressions 12010 configured to mate with one or more corresponding flanges 12012 (FIG. 16B) on the mount 12006. Mating the depressions 12010 with the flanges 12012 may secure the connector 12002 to the mount 12006 via an interference fit or the like. In other embodiments, the connector 12002 may be secured to the mount 12006 using an adhesive or via sonic welding.

FIGS. 16D and 16E are isometric and partially exploded isometric views of another example connector assembly 12100, according to one or more embodiments. As illustrated, the connector assembly 12100 may include a connector 12102, and FIG. 16F is an isometric bottom view of the connector 12102. The connector 12102 may comprise an injection molded part used to help keep one or more compliant metal contacts 12104 (four shown in FIG. 16E) secured against the sensor 11900 on a mount 12106. More specifically, the connector 12102 may help secure the contacts 12104 in place adjacent the sensor 11900 and in contact with the sensor contacts 11914 (FIG. 15C) provided on the flag 11904. The contacts 12104 may be made of a stamped conductive material that provides conductive communication between the sensor 11900 and corresponding circuitry contacts (not shown) provided within the mount 12106. In some embodiments, for example, the contacts 12104 may be soldered to a PCB (not shown) arranged within the mount 12106.

As best seen in FIG. 16F, the connector 12102 may define pockets 12108 sized to receive the contacts 12104. Moreover, in some embodiments, the connector 12102 may further define one or more depressions 12110 configured to mate with one or more corresponding flanges 12112 (FIG. 120B) on the mount 12006. Mating the depressions 12110 with the flanges 12112 may help secure the connector 12102 to the mount 12106 via an interference fit or the like. In other embodiments, the connector 12102 may be secured to the mount 12106 using an adhesive or via sonic welding.

Example Embodiments of Sharp Modules

Figure 17A:
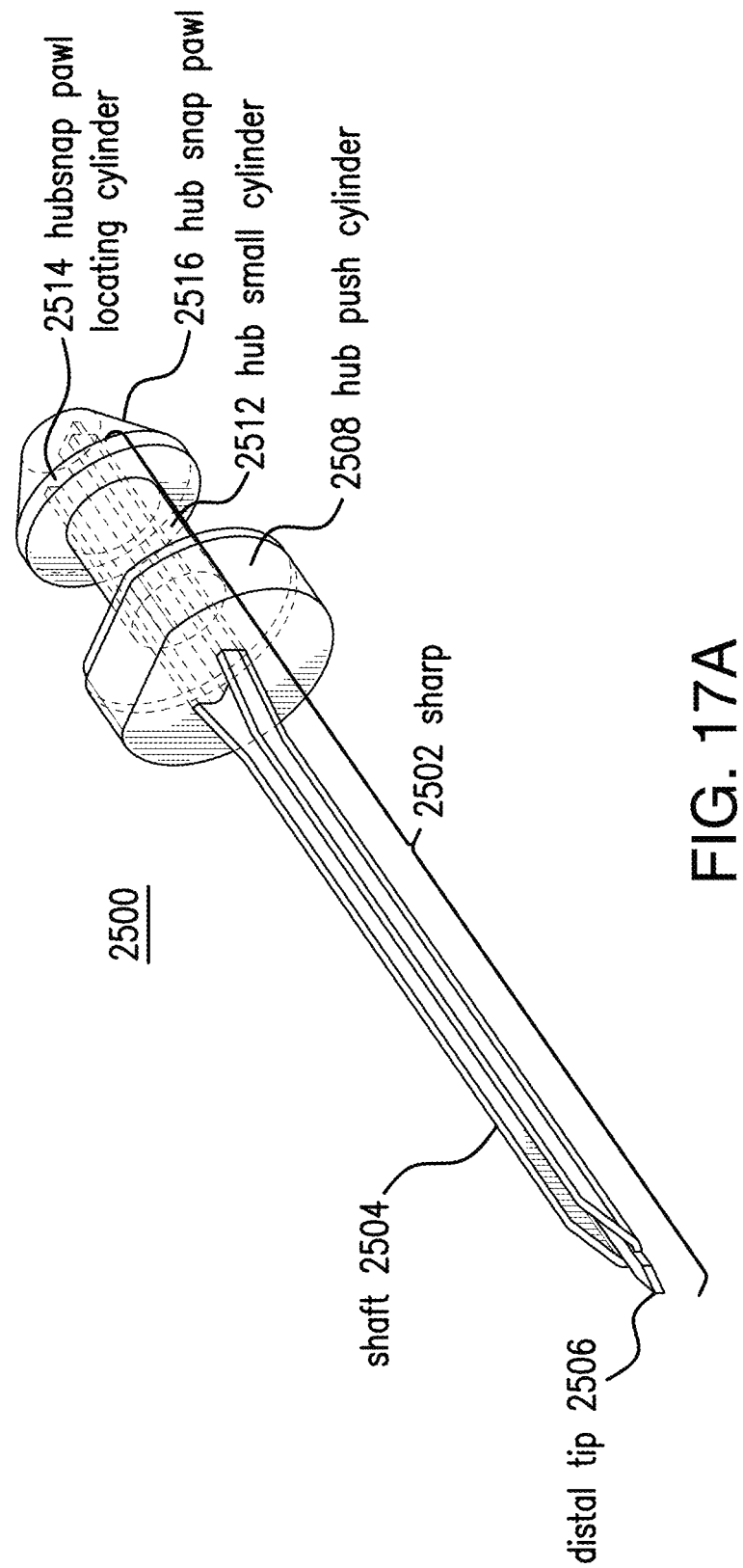
FIG. 17A is a perspective view depicting an example embodiment of a sharp module.

FIG. 17A is a perspective view depicting an example embodiment of sharp module 2500 prior to assembly within sensor module 504 (FIG. 6B). Sharp 2502 can include a distal tip 2506 which can penetrate the skin while carrying sensor tail in a hollow or recess of sharp shaft 2504 to put the active surface of the sensor tail into contact with bodily fluid. A hub push cylinder 2508 can provide a surface for a sharp carrier to push during insertion. A hub small cylinder 2512 can provide a space for the extension of sharp hub contact faces 1622 (FIG. 10B). A hub snap pawl locating cylinder 2514 can provide a distal-facing surface of hub snap pawl 2516 for sharp hub contact faces 1622 to abut. A hub snap pawl 2516 can include a conical surface that opens clip 1620 during installation of sharp module 2500.

FIGS. 17B to 17H show example embodiments of sharp modules, in various stages of assembly, for use in the insertion of dermal analyte sensors. According to one aspect of the embodiments, angling the sensor and/or insertion sharp relative to a reference point can enable co-localization of the tip of the insertion needle and the tip of the sensor, and furthermore, can create a single contact point at the surface of the skin. As such, the sharp can create a leading edge at the surface of the skin to form an insertion path into the dermal layer for the sensor, as the sensor is inserted into a subject. In some embodiments, for example, the sharp and/or dermal sensor may be angled relative to a reference point (e.g., each other, surface of the skin, or the base of the applicator) for insertion, where the angle of the sharp differs from the angle of the sensor. For example, the reference point may be the skin surface to be breached for dermal insertion, or may be a reference or component of the sensor applicator set. In some embodiments, the sharp may be disposed at an angle relative to the sensor. For example, when designed so that that the sharp is angled relative to the sensor, the needle creates a leading edge for the sensor during operation of the applicator set. Furthermore, the needle design itself, and the positioning of the needle with respect to the sensor can be implemented in any desired configuration, including all of those configurations disclosed in U.S. Patent Publication No. 2014/0171771, which is incorporated by reference herein in its entirety for all purposes.

Furthermore, although many of the example embodiments described with respect to FIGS. 17B to 17J make reference to dermal analyte sensors and dermal insertion, it will be understood by those of skill in the art that any of the embodiments can be dimensioned and configured for use with analyte sensors that can be positioned beyond the dermal space, such as into (or even fully through) subcutaneous tissue (e.g., 3 mm to 10 mm beneath the surface of the skin depending on the location of the skin on the body).

Figure 17B:
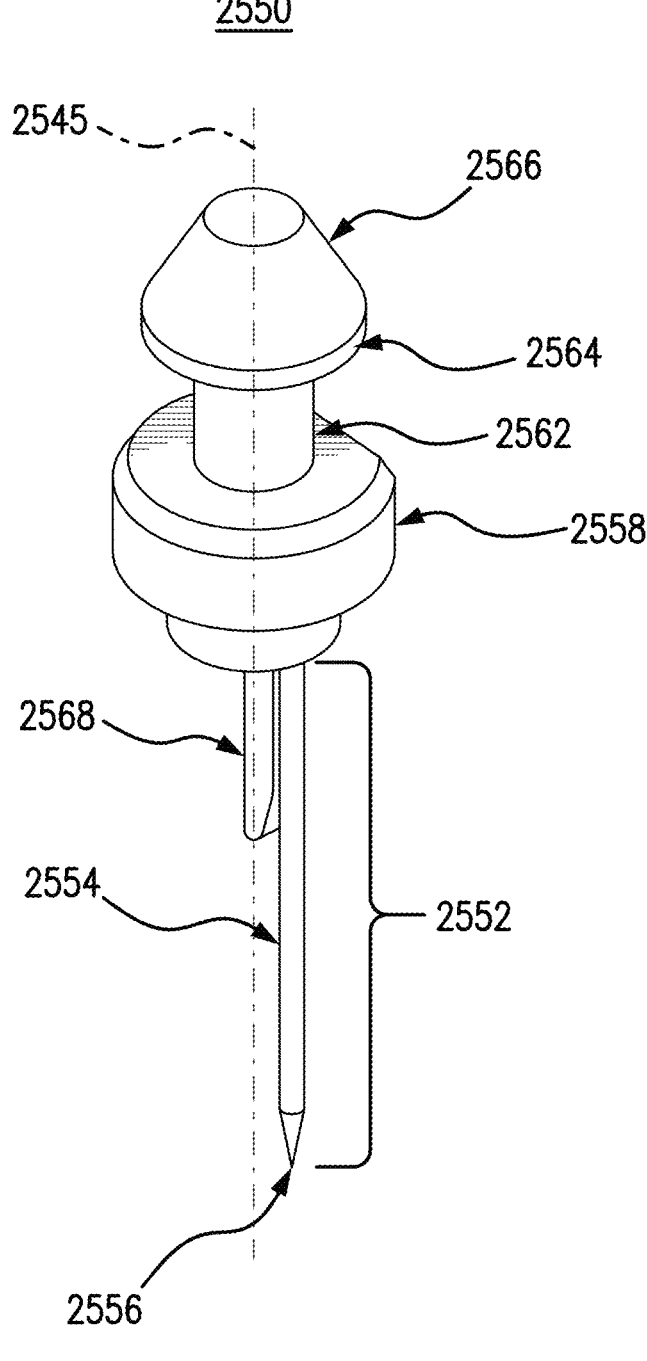
FIG. 17B is a perspective view of another example embodiment of a sharp module.

FIG. 17B is a perspective view depicting an example embodiment of a sharp module 2550 that can be used for the insertion of a dermal sensor. Sharp module 2550 is shown here prior to assembly with sensor module 504 (FIG. 6B), and can include components similar to those of the embodiment described with respect to FIG. 17A, including sharp 2552, sharp shaft 2554, sharp distal tip 2556, hub push cylinder 2558, hub small cylinder 2562, hub snap pawl 2566 and hub snap pawl locating cylinder 2564. Sharp 2552 can be positioned within sharp module 2550 at an off-center location relative to a longitudinal axis 2545 that extends through center of hub snap pawl 2566, hub small cylinder 2562 and hub push cylinder 2558. In addition, sharp module 2550 can include a sharp spacer 2568 that is parallel to and adjacent with a portion of sharp 2552. Sharp spacer 2568 can be positioned in between sensor 104 (not shown) and sharp 2552 along a proximal portion of sharp 2552, and can ensure that sensor 104 and sharp 2552 remain spaced apart at a proximal portion of sharp 2552. Sharp 2552 can be positioned in an off-center location during a molding process with hub components 2558, 2562, 2566, each of which may consist of a rigid plastic material.

Figure 17D:
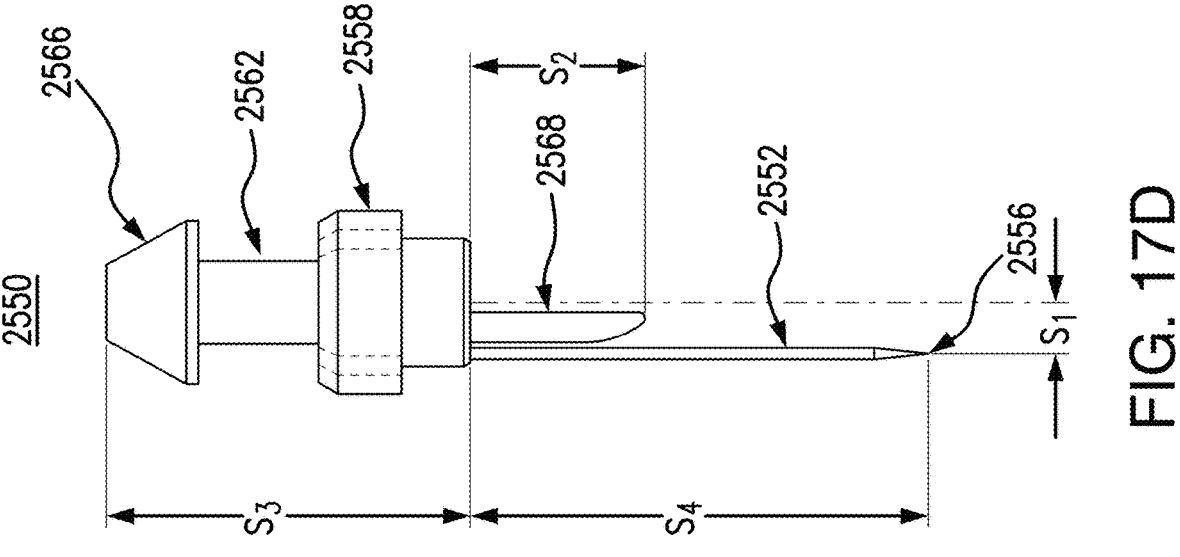
FIGS. 17C and 17D are schematic views depicting the sharp module of FIG. 17B.
Figure 17C:
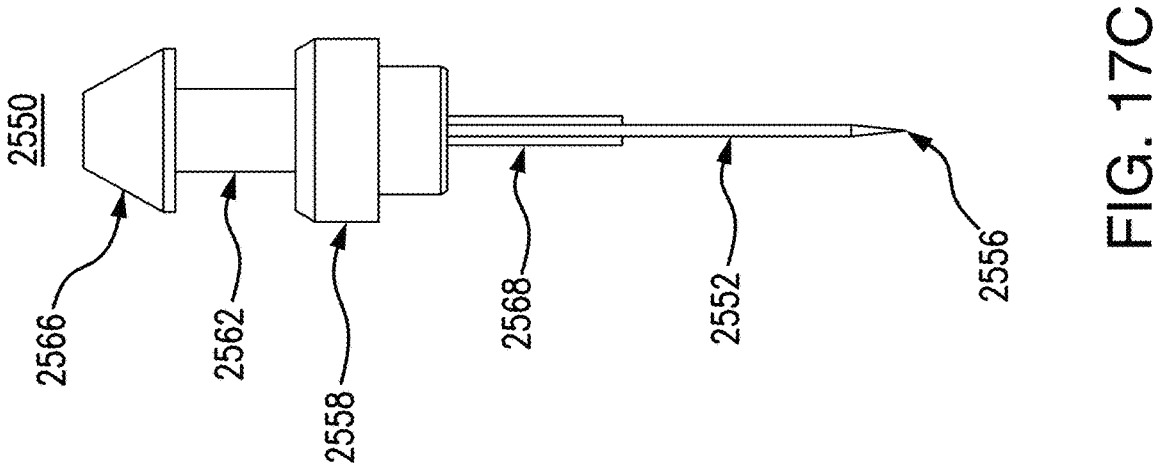

FIGS. 17C and 17D are two side views depicting sharp module 2550 prior to assembly with sensor module 504 (FIG. 6B), and include sharp 2552, spacer 2568, hub push cylinder 2558, hub small cylinder 2562 and hub snap pawl 2566. In some embodiments, the relative distances between the sharp 2552 and hub components can be positioned as follows. For example, distance, Si, between the sharp 2552 and the radial center of hub can range from 0.50 mm to 1 mm (e.g., 0.89 mm). Height, $S_2$, of sharp spacer 2568 can range from 3 to 5 mm (e.g., 3.26 mm). Height, S3, of hub can range from 5 to 10 mm (e.g., 6.77 mm). Length, $S_4$, of sharp 2552 can range from 1.5 mm to 25 mm (e.g., 8.55 mm), and may depend on the location of the insertion site on the subject.

Figures 17E, 17F:
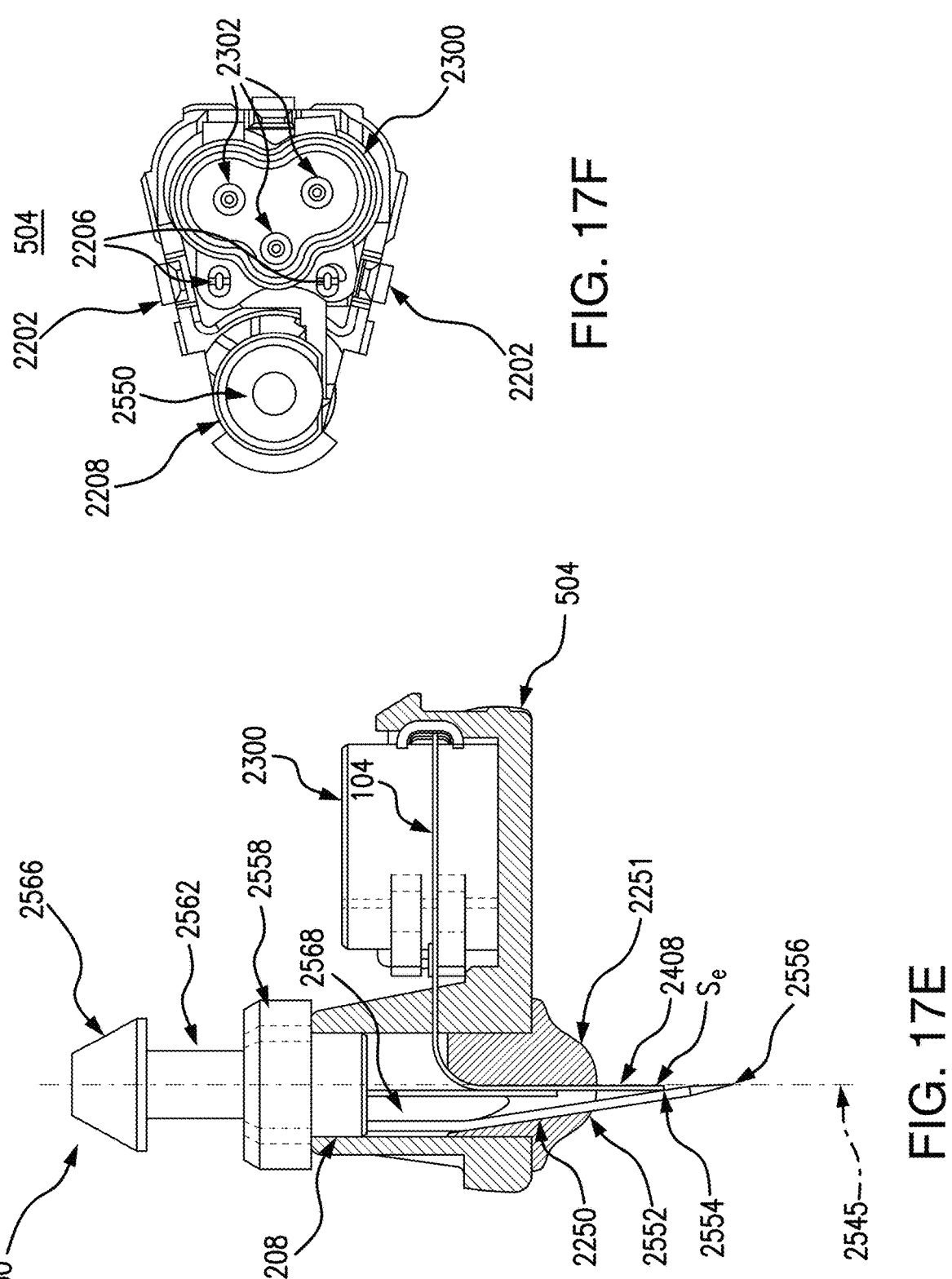
FIGS. 17E and 17F are a side schematic view and a top-down schematic view, respectively, of the sharp module of FIG. 17B, as assembled with a sensor module.
Figures 17G, 17H:
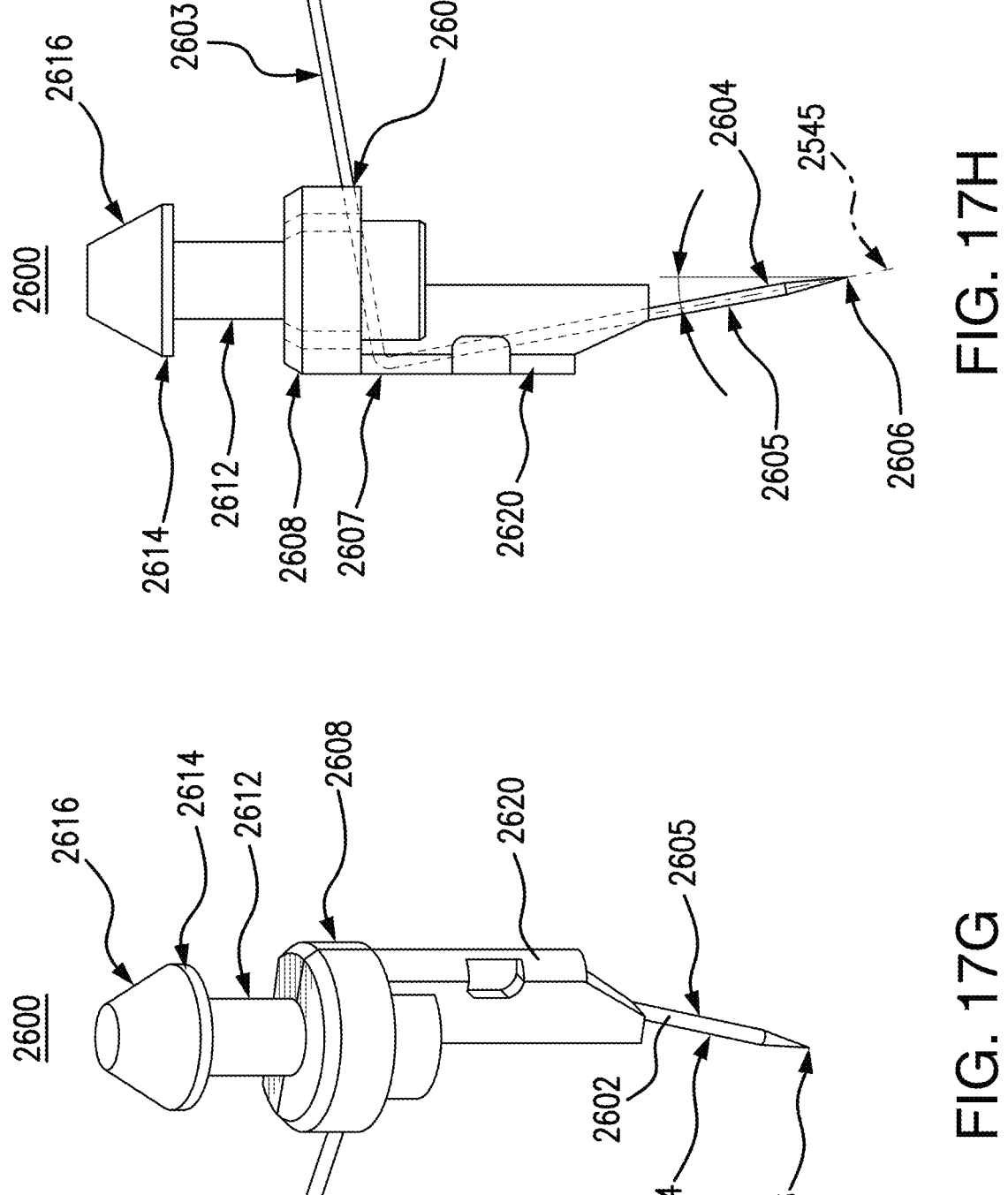
FIG. 17G is a perspective view of another example embodiment of a sharp module.
FIG. 17H is a side schematic view depicting the sharp module of FIG. 17G.

FIG. 17E depicts a side cross-sectional side view of sharp module 2550, including sharp 2552, sharp spacer 2568 and hub components (hub snap pawl 2566, hub small cylinder 2562, and hub push cylinder 2558), as assembled with sensor module 504. As can be seen in FIG. 17E, sharp 2552 is positioned within sharp slot 2208 of sensor module 504 that includes a curved interior surface 2250, located at a distal end. Curved interior surface 2250 of sensor module 504 can be in contact with a portion of sharp 2552 and cause a deflection such that sharp distal tip 2556 is oriented toward central longitudinal axis 2545. As best seen in FIG. 17H, sharp 2552 can be positioned such that the distal portion and central longitudinal axis 2545 form an acute angle, So, that can range between 5° and 20°. In some embodiments, for example, So, can range from 5° to 17°, or 7° to 15°, or 9° to 13°, e.g., 9°, 10°, 11°, 12°, or 13°

Referring still to FIG. 17E, near a distal end of sensor module 504 is protrusion 2251, which can enhance the perfusion of bodily fluid, such as dermal fluid. Although shown as a curved surface in FIG. 17E, protrusion 2251 can be shaped in any desired fashion. In addition, in some embodiments, multiple protrusions can be present. U.S. Patent Publication No. 2014/0275907, which is incorporated by reference herein in its entirety for all purposes, describes sensor devices having different protrusion configurations, each of which can be implemented with the embodiments described herein. Many of the embodiments described herein show the needle exiting from the protrusion, and in other embodiments, the needle can exit from the base of the sensor device adjacent the protrusion, and from that position extend over the tip of sensor 104.

Referring still to FIGS. 17E and 17F, sensor 104 can be a dermal sensor and can include sensor tail 2408, located at a distal end of sensor 104, and which can be positioned in a substantially parallel orientation to central longitudinal axis 2545. Distal end of sensor tail 2408 can be proximal to distal sharp tip 2556, either in a spaced relation with, at rest in, or at rest against a portion of sharp shaft 2554. As further depicted in FIG. 17E, sharp spacer 2568 provides a spaced relation between a proximal portion of sharp 2552 and sensor 104, such that the proximal portion of sharp 2552 and sensor 104 are not in contact. Sensor module 504 can further include sensor connector 2300 for housing a proximal portion of sensor 104 that is relatively perpendicular to a distal end of sensor 104.

FIG. 17F is a top-down cross-sectional view of sensor module 504. Sensor module 504 can include one or more sensor module snaps 2202 for coupling with a housing (not shown) of sensor control device 102. Sensor module 504 can also include sensor connector 2300, which can have sensor contacts 2302 for coupling with a proximal portion of sensor 104. Sensor connector 2300 can be made of silicone rubber that encapsulates compliant carbon impregnated polymer modules that serve as electrical conductive contacts 2302 between sensor 104 and electrical circuitry contacts for the electronics within sensor control device 102. The connector can also serve as a moisture barrier for sensor 104 when assembled in a compressed state after transfer from a container to an applicator and after application to a user's skin. Although three contacts 2302 are depicted, it should be understood that connector 2300 can have fewer contacts (e.g., two) or more contacts (e.g., four, five, six, etc.), depending on the particular type or configuration of sensor 104. Sensor connector 2300 can be further coupled with sensor module 504 by two connector posts 2206 positioned through a like number of apertures in connector 2300. Although two connector posts 2206 are depicted, it should be understood that any number of connector posts 2206 can be used to couple connector 2300 to sensor module 504.

FIGS. 17G and 17H are, respectively, a perspective view and a side view of another example embodiment of sharp module 2600 that can be used for the insertion of a dermal sensor. Sharp module 2600 is shown here prior to assembly with sensor module 504 (FIG. 6B), and can include components similar to those of the embodiments described with respect to FIGS. 17A and 17B, including sharp 2602, sharp shaft 2604, sharp distal tip 2606, hub push cylinder 2608, hub small cylinder 2612, hub snap pawl 2616 and hub snap pawl locating cylinder 2614. In some embodiments, sharp 2602 can be a "pre-bent" needle that includes a proximal portion 2603 that originates from a point external to sharp module 2600 and intersects, at an angle, a central point of the hub (e.g., through hub push cylinder 2608). Sharp 2602 can also include a distal portion 2605 that extends in a distal direction, at an angle, from a point near a distal portion of hub toward the insertion point of the user's skin. As shown in FIG. 17H, sharp 2602 can include an angled portion 2607 located external to hub push cylinder 2608, which can have a substantially 90° angle between proximal portion 2603 and distal portion 2605 of sharp 2602. Sharp module 2600 can also include a bend fin guide 2620 for maintaining "pre-bent" sharp 2602 in position during assembly and/or use, and can prevent lateral or rotational movement of sharp 2602 relative to hub components. Proximal portion 2603 of sharp 2602 can be "trimmed" from the hub after molding process is completed, and prior to assembly of sharp module 2600 with sensor module 504.

Figures 17I, 17J:
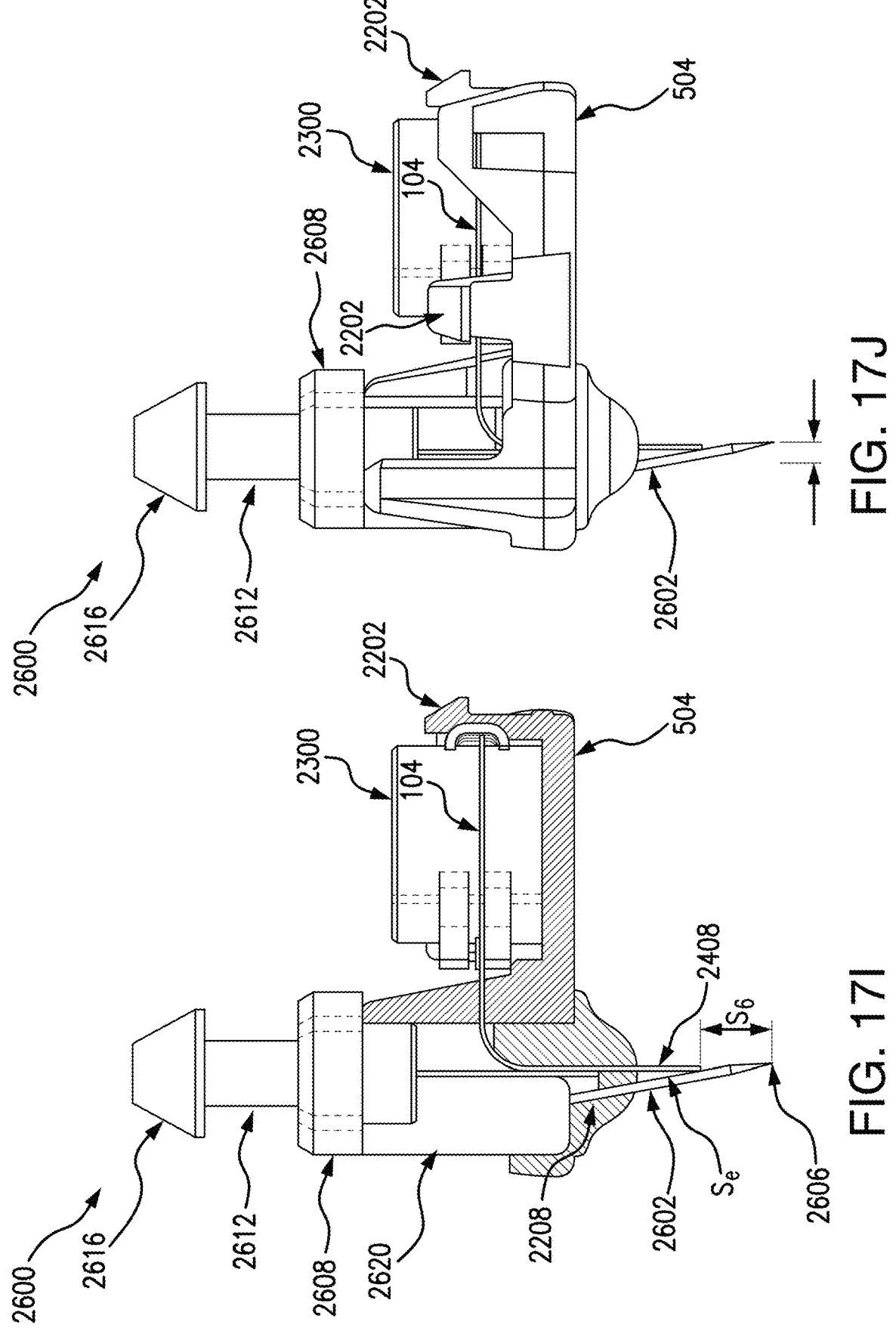
FIGS. 17I and 17J are a side cross-sectional view and a side view, respectively, of the sharp module of FIG. 17G, as assembled with a sensor module.

FIGS. 17I and 17J show, respectively, a side cross-sectional view and a side view of sharp module 2600 (including hub snap pawl 2616, hub small cylinder 2612, and hub push cylinder 2608), as assembled with sensor module 504. As can be seen in FIG. 17I, sensor module 504 includes sharp slot 2208, through which sharp 2602 can extend in an angled and distal direction. As described earlier, a proximal portion of sharp 2602 passes through bend fin guide 2620, which is coupled with a distal portion of sensor module 504. Sensor module 504 can also include sensor 104, which can be a dermal sensor. As seen in FIG. 17I, sharp 2602 and sensor tail 2408 can form an acute angle, So, at a point where their respective longitudinal axes converge. Angle So can range between 5° and 20°. In some embodiments, for example, So, can range from 5° to 17°, or 7° to 15°, or 9° to 13°, e.g., 9°, 10°, 11°, 12°, or 13° In some embodiments, distal sharp tip 2606 is located at a distance, $S_6$, that is proximal to an end of sensor tail 2408. Distance, $S_6$, can range between 0.02 mm to 0.10 mm, e.g., 0.05 mm, 0.06 mm or 0.07 mm.

Referring still to FIGS. 17I and 17J, sensor module 504 can also include sensor connector 2300 for housing a proximal portion of sensor 104 that is relatively perpendicular to a distal end of sensor 104. Sensor module 504 can further include one or more sensor module snaps 2202 for coupling with a housing (not shown) of sensor control device 102. Sensor connector 2300 can include the same structures described with respect to FIG. 17F.

In the above embodiments, the sharp can be made of stainless steel or a like flexible material (e.g., material used to manufacture acupuncture needles), and dimensioned such that the applicator provides for insertion of at least a portion of the dermal sensor into the dermal layer, but not through the dermal layer of the skin. According to certain embodiments, the sharp has a cross sectional diameter (width) of from 0.1 mm to 0.5 mm. For example, the sharp may have a diameter of from 0.1 mm to 0.3 mm, such as from 0.15 mm to 0.25 mm, e.g., 0.16 mm to 0.22 mm in diameter. A given sharp may have a constant, i.e., uniform, width along its entire length, or may have a varying, i.e., changing, width along at least a portion of its length, such as the tip portion used to pierce the surface of the skin. For example, with respect to the embodiment shown in FIG. 17I, width of sharp 2602 can narrow along a distal portion between bend fin guide 1620 and distal sharp tip 2606.

A sharp can also have a length to insert a dermal sensor just into the dermal layer, and no more. Insertion depth may be controlled by the length of the sharp, the configuration of the base and/or other applicator components that limit insertion depth. A sharp may have a length between 1.5 mm and 25 mm. For example, the sharp may have a length of from 1 mm to 3 mm, from 3 mm to 5 mm, from 5 mm to 7 mm, from 7 mm to 9 mm, from 9 mm to 11 mm, from 11 mm to 13 mm, from 13 mm to 15 mm, from 15 mm to 17 mm, from 17 mm to 19 mm, from 19 mm to 21 mm, from 21 mm to 23 mm, from 23 mm to 25 mm, or a length greater than 25 mm. It will be appreciated that while a sharp may have a length up to 25 mm, in certain embodiments the full length of the sharp is not inserted into the subject because it would extend beyond the dermal space. Non-inserted sharp length may provide for handling and manipulation of the sharp in an applicator set. Therefore, while a sharp may have a length up to 25 mm, the insertion depth of the sharp in the skin on a subject in those certain embodiments will be limited to the dermal layer, e.g., about 1.5 mm to 4 mm, depending on the skin location, as described in greater detail below. However, in all of the embodiments disclosed herein, the sharp can be configured to extend beyond the dermal space, such as into (or even fully through) subcutaneous tissue (e.g., 3 mm to 10 mm beneath the surface of the skin depending on the location of the skin on the body). Additionally, in some example embodiments, the sharps described herein can include hollow or partially hollow insertion needles, having an internal space or lumen. In other embodiments, however, the sharps described herein can include solid insertion needles, which do not have an internal space and/or lumen. Furthermore, a sharp of the subject applicator sets can also be bladed or non-bladed.

Likewise, in the above embodiments, a dermal sensor is sized so that at least a portion of the sensor is positioned in the dermal layer and no more, and a portion extends outside the skin in the transcutaneously positioned embodiments. That is, a dermal sensor is dimensioned such that when the dermal sensor is entirely or substantially entirely inserted into the dermal layer, the distal-most portion of the sensor (the insertion portion or insertion length) is positioned within the dermis of the subject and no portion of the sensor is inserted beyond a dermal layer of the subject when the sensor is operably dermally positioned.

The dimensions (e.g., the length) of the sensor may be selected according to the body site of the subject in which the sensor is to be inserted, as the depth and thickness of the epidermis and dermis exhibit a degree of variability depending on skin location. For example, the epidermis is only about 0.05 mm thick on the eyelids, but about 1.5 mm thick on the palms and the soles of the feet. The dermis is the thickest of the three layers of skin and ranges from about 1.5 mm to 4 mm thick, depending on the skin location. For implantation of the distal end of the sensor into, but not through, the dermal layer of the subject, the length of the inserted portion of the dermal sensor should be greater than the thickness of the epidermis, but should not exceed the combined thickness of the epidermis and dermis. Methods may include determining an insertion site on a body of a user and determining the depth of the dermal layer at the site, and selecting the appropriately-sized applicator set for the site.

In certain aspects, the sensor is an elongate sensor having a longest dimension (or "length") of from 0.25 mm to 4 mm. The length of the sensor that is inserted, in the embodiments in which only a portion of a sensor is dermally inserted, ranges from 0.5 mm to 3 mm, such as from 1 mm to 2 mm, e.g., 1.5 mm. The dimensions of the sensor may also be expressed in terms of its aspect ratio. In certain embodiments, a dermal sensor has an aspect ratio of length to width (diameter) of about 30:1 to about 6:1. For example, the aspect ratio may be from about 25:1 to about 10:1, including 20:1 and 15:1. The inserted portion of a dermal sensor has sensing chemistry.

However, all of the embodiments disclosed herein can be configured such that at least a portion of the sensor is positioned beyond the dermal layer, such as into (or through) the subcutaneous tissue (or fat). For example, the sensor can be dimensioned such that when the sensor is entirely or substantially entirely inserted into the body, the distal-most portion of the sensor (the insertion portion or insertion length) is positioned within the subcutaneous tissue (beyond the dermis of the subject) and no portion of the sensor is inserted beyond the subcutaneous tissue of the subject when the sensor is operably positioned. As mentioned, the subcutaneous tissue is typically present in the region that is 3 mm to 10 mm beneath the outer skin surface, depending on the location of the skin on the body.

Example Embodiments of Applicators and Sensor Control Devices for One Piece Architectures Referring briefly again to FIGS. 1 and 3A-3G, for the two-piece architecture system, the sensor tray 202 and the sensor applicator 102 are provided to the user as separate packages, thus requiring the user to open each package and finally assemble the system. In some applications, the discrete, sealed packages allow the sensor tray 202 and the sensor applicator 102 to be sterilized in separate sterilization processes unique to the contents of each package and otherwise incompatible with the contents of the other. More specifically, the sensor tray 202, which includes the plug assembly 207, including the sensor 110 and the sharp 220, may be sterilized using radiation sterilization, such as electron beam (or "e-beam") irradiation. Radiation sterilization, however, can damage the electrical components arranged within the electronics housing of the sensor control device 102. Consequently, if the sensor applicator 102, which contains the electronics housing of the sensor control device 102, needs to be sterilized, it may be sterilized via another method, such as gaseous chemical sterilization using, for example, ethylene oxide. Gaseous chemical sterilization, however, can damage the enzymes or other chemistry and biologies included on the sensor 110. Because of this sterilization incompatibility, the sensor tray 202 and the sensor applicator 102 are commonly sterilized in separate sterilization processes and subsequently packaged separately, which requires the user to finally assemble the components for use.

According to embodiments of the present disclosure, the sensor control device 102 may be modified to provide a one-piece architecture that may be subjected to sterilization techniques specifically designed for a one-piece architecture sensor control device. A one-piece architecture allows the sensor applicator 150 and the sensor control device 102 to be shipped to the user in a single, sealed package that does not require any final user assembly steps. Rather, the user need only open one package and subsequently deliver the sensor control device 102 to the target monitoring location. The one-piece system architecture described herein may prove advantageous in eliminating component parts, various fabrication process steps, and user assembly steps. As a result, packaging and waste are reduced, and the potential for user error or contamination to the system is mitigated.

Figure 18A:
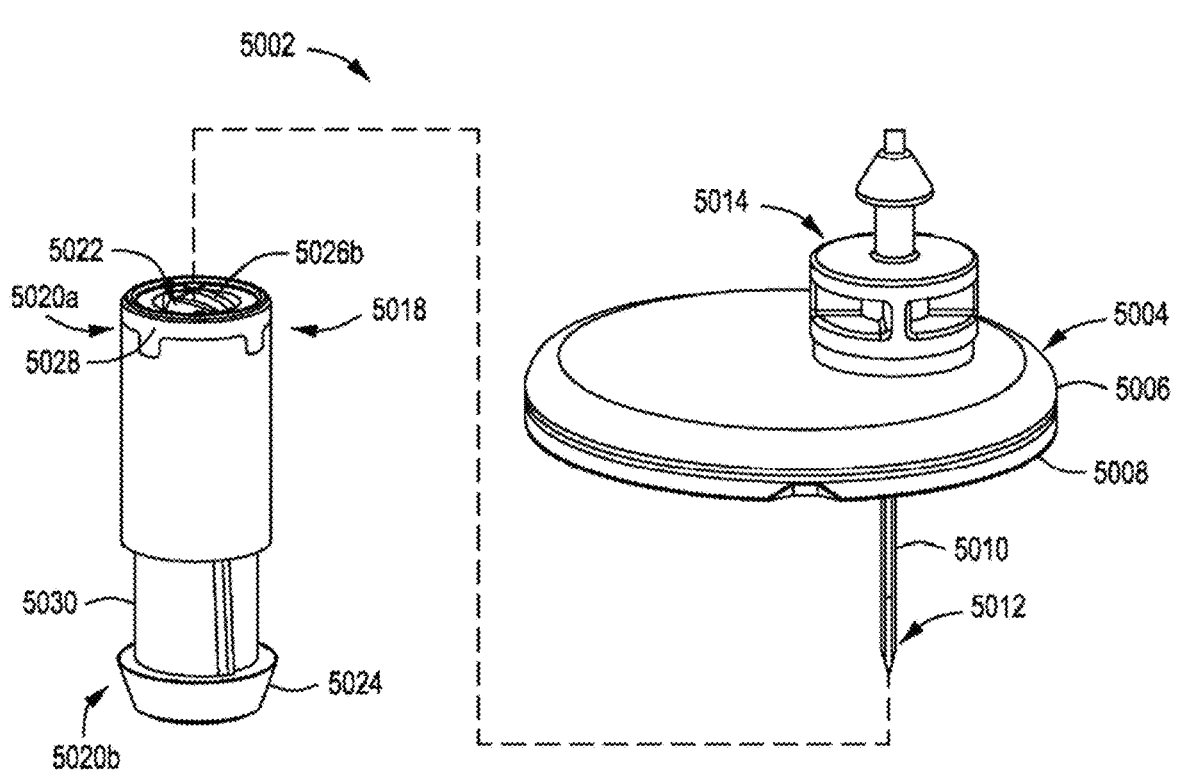
FIGS. 18A and 18B are isometric and side views, respectively, of another example sensor control device.
Figure 18B:
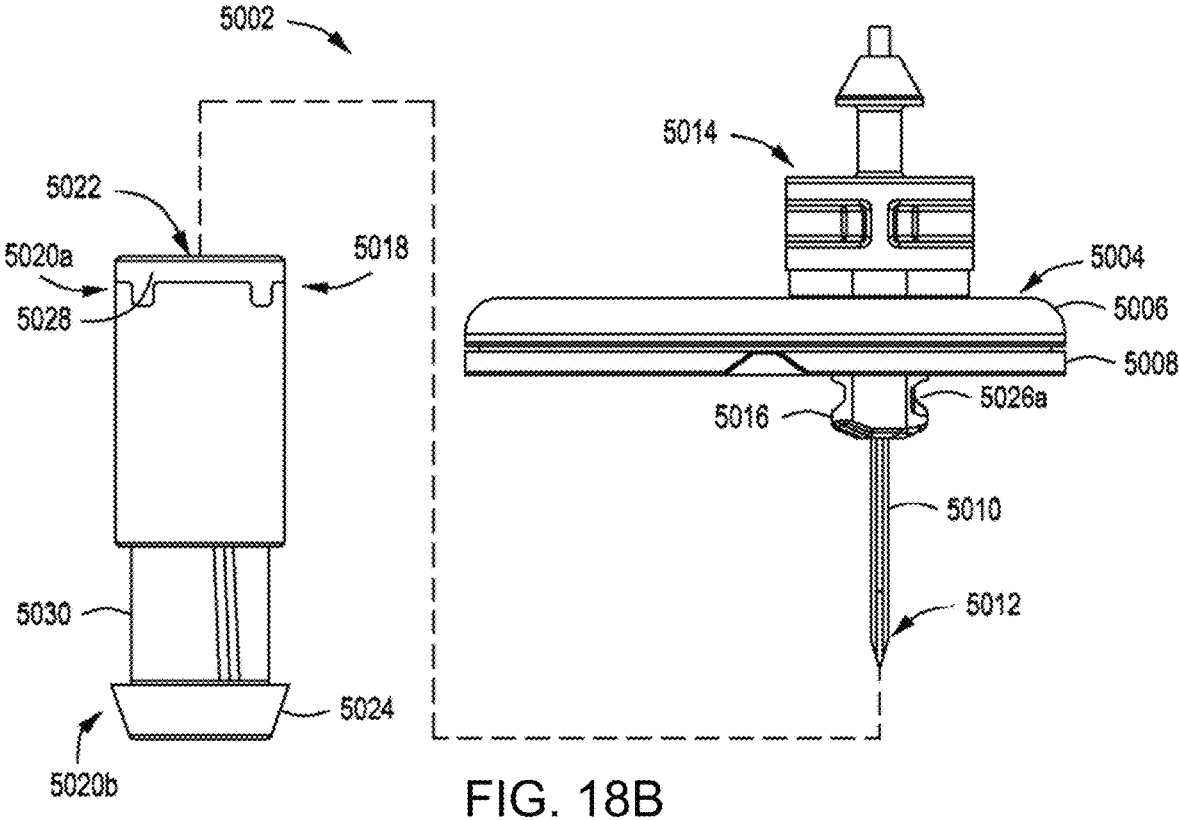

FIGS. 18A and 18B are isometric and side views, respectively, of another example sensor control device 5002, according to one or more embodiments of the present disclosure. The sensor control device 5002 may be similar in some respects to the sensor control device 102 of FIG. 1 and therefore may be best understood with reference thereto. Moreover, the sensor control device 5002 may replace the sensor control device 102 of FIG. 1 and, therefore, may be used in conjunction with the sensor applicator 102 of FIG. 1, which may deliver the sensor control device 5002 to a target monitoring location on a user's skin.

Unlike the sensor control device 102 of FIG. 1, however, the sensor control device 5002 may comprise a one-piece system architecture not requiring a user to open multiple packages and finally assemble the sensor control device 5002 prior to application. Rather, upon receipt by the user, the sensor control device 5002 may already be fully assembled and properly positioned within the sensor applicator 150 (FIG. 1). To use the sensor control device 5002, the user need only open one barrier (e.g., the applicator cap 708 of FIG. 3B) before promptly delivering the sensor control device 5002 to the target monitoring location for use.

As illustrated, the sensor control device 5002 includes an electronics housing 5004 that is generally disc-shaped and may have a circular cross-section. In other embodiments, however, the electronics housing 2004 may exhibit other cross-sectional shapes, such as ovoid or polygonal, without departing from the scope of the disclosure. The electronics housing 5004 may be configured to house or otherwise contain various electrical components used to operate the sensor control device 5002. In at least one embodiment, an adhesive patch (not shown) may be arranged at the bottom of the electronics housing 5004. The adhesive patch may be similar to the adhesive patch 105 of FIG. 1, and may thus help adhere the sensor control device 5002 to the user's skin for use.

As illustrated, the sensor control device 5002 includes an electronics housing 5004 that includes a shell 5006 and a mount 5008 that is matable with the shell 5006. The shell 5006 may be secured to the mount 5008 via a variety of ways, such as a snap fit engagement, an interference fit, sonic welding, one or more mechanical fasteners (e.g., screws), a gasket, an adhesive, or any combination thereof. In some cases, the shell 5006 may be secured to the mount 5008 such that a sealed interface is generated therebetween.

The sensor control device 5002 may further include a sensor 5010 (partially visible) and a sharp 5012 (partially visible), used to help deliver the sensor 5010 transcutaneously under a user's skin during application of the sensor control device 5002. As illustrated, corresponding portions of the sensor 5010 and the sharp 5012 extend distally from the bottom of the electronics housing 5004 (e.g., the mount 5008). The sharp 5012 may include a sharp hub 5014 configured to secure and carry the sharp 5012. As best seen in FIG. 18B, the sharp hub 5014 may include or otherwise define a mating member 5016. To couple the sharp 5012 to the sensor control device 5002, the sharp 5012 may be advanced axially through the electronics housing 5004 until the sharp hub 5014 engages an upper surface of the shell 5006 and the mating member 5016 extends distally from the bottom of the mount 5008. As the sharp 5012 penetrates the electronics housing 5004, the exposed portion of the sensor 5010 may be received within a hollow or recessed (arcuate) portion of the sharp 5012. The remaining portion of the sensor 5010 is arranged within the interior of the electronics housing 5004.

The sensor control device 5002 may further include a sensor cap 5018, shown exploded or detached from the electronics housing 5004 in FIGS. 18A-18B. The sensor cap 5016 may be removably coupled to the sensor control device 5002 (e.g., the electronics housing 5004) at or near the bottom of the mount 5008. The sensor cap 5018 may help provide a sealed barrier that surrounds and protects the exposed portions of the sensor 5010 and the sharp 5012 from gaseous chemical sterilization. As illustrated, the sensor cap 5018 may comprise a generally cylindrical body having a first end 5020a and a second end 5020b opposite the first end 5020a. The first end 5020a may be open to provide access into an inner chamber 5022 defined within the body. In contrast, the second end 5020b may be closed and may provide or otherwise define an engagement feature 5024. As described herein, the engagement feature 5024 may help mate the sensor cap 5018 to the cap (e.g., the applicator cap 708 of FIG. 3B) of a sensor applicator (e.g., the sensor applicator 150 of FIGS. 1 and 3A-3G), and may help remove the sensor cap 5018 from the sensor control device 5002 upon removing the cap from the sensor applicator.

The sensor cap 5018 may be removably coupled to the electronics housing 5004 at or near the bottom of the mount 5008. More specifically, the sensor cap 5018 may be removably coupled to the mating member 5016, which extends distally from the bottom of the mount 5008. In at least one embodiment, for example, the mating member 5016 may define a set of external threads 5026a (FIG. 18B) matable with a set of internal threads 5026b (FIG. 18A) defined by the sensor cap 5018. In some embodiments, the external and internal threads 5026a, b may comprise a flat thread design (e.g., lack of helical curvature), which may prove advantageous in molding the parts. Alternatively, the external and internal threads 5026a,b may comprise a helical threaded engagement. Accordingly, the sensor cap 5018 may be threadably coupled to the sensor control device 5002 at the mating member 5016 of the sharp hub 5014. In other embodiments, the sensor cap 5018 may be removably coupled to the mating member 5016 via other types of engagements including, but not limited to, an interference or friction fit, or a frangible member or substance that may be broken with minimal separation force (e.g., axial or rotational force).

In some embodiments, the sensor cap 5018 may comprise a monolithic (singular) structure extending between the first and second ends 5020a, b. In other embodiments, however, the sensor cap 5018 may comprise two or more component parts. In the illustrated embodiment, for example, the sensor cap 5018 may include a seal ring 5028 positioned at the first end 5020a and a desiccant cap 5030 arranged at the second end 5020b. The seal ring 5028 may be configured to help seal the inner chamber 5022, as described in more detail below. In at least one embodiment, the seal ring 5028 may comprise an elastomeric O-ring. The desiccant cap 5030 may house or comprise a desiccant to help maintain preferred humidity levels within the inner chamber 5022. The desiccant cap 5030 may also define or otherwise provide the engagement feature 5024 of the sensor cap 5018.

Figures 19A, 19B:
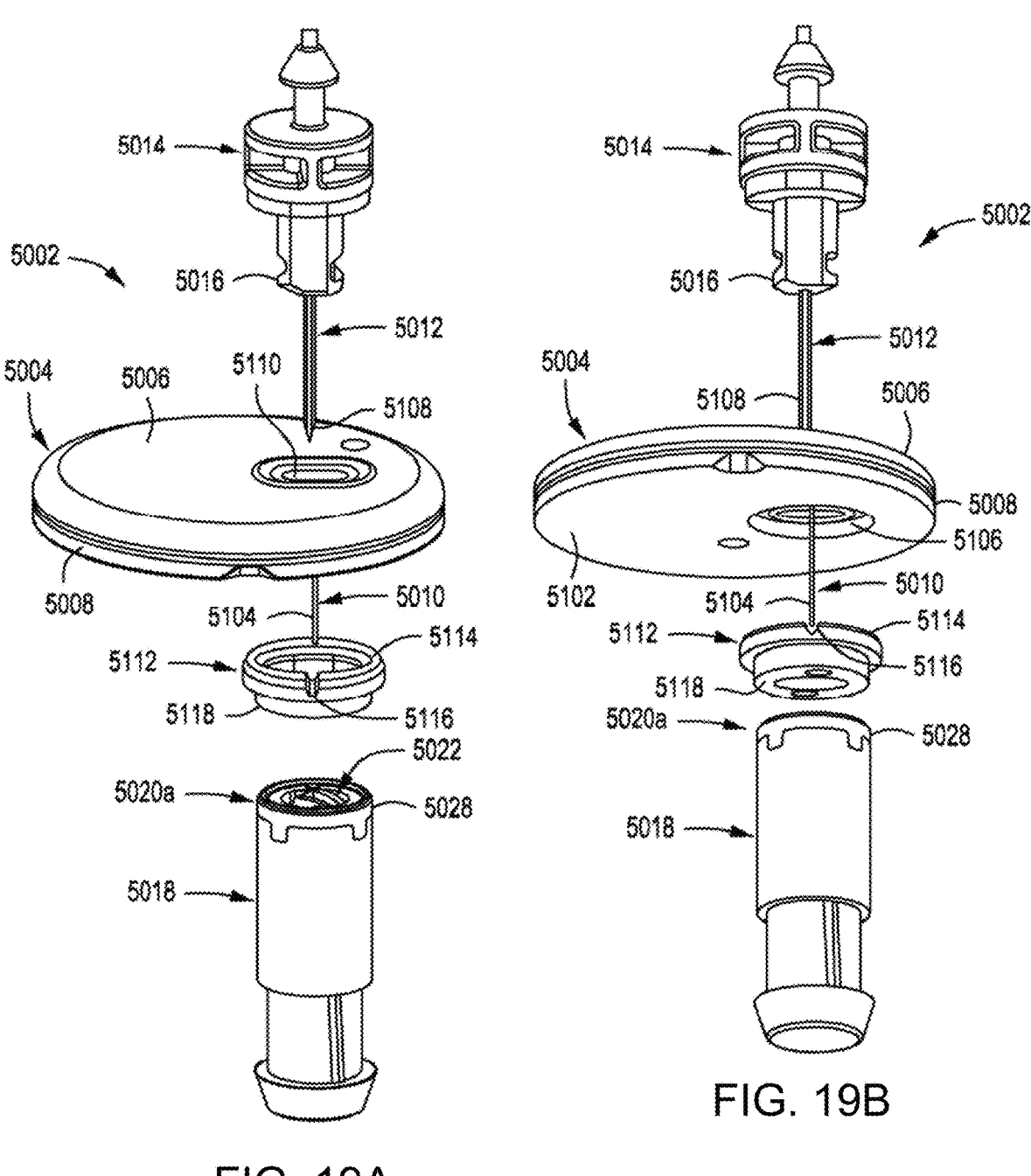
FIGS. 19A and 19B are exploded isometric top and bottom views, respectively of the sensor control device of FIGS. 18A-18B.

FIGS. 19A and 19B are exploded isometric top and bottom views, respectively, of the sensor control device 5002, according to one or more embodiments. The shell 5006 and the mount 5008 operate as opposing clamshell halves that enclose or otherwise substantially encapsulate various electronic components of the sensor control device 5002. More specifically, electronic components may include, but are not limited to, a printed circuit board (PCB), one or more resistors, transistors, capacitors, inductors, diodes, and switches. A data processing unit and a battery may be mounted to or otherwise interact with the PCB. The data processing unit may comprise, for example, an application specific integrated circuit (ASIC) configured to implement one or more functions or routines associated with operation of the sensor control device 5002. More specifically, the data processing unit may be configured to perform data processing functions, where such functions may include, but are not limited to, filtering and encoding of data signals, each of which corresponds to a sampled analyte level of the user. The data processing unit may also include or otherwise communicate with an antenna for communicating with the reader device 120 (FIG. 1). The battery may provide power to the sensor control device 5002 and, more particularly, to the electronic components of the PCB. While not shown, the sensor control device 5002 may also include an adhesive patch that may be applied to the bottom 5102 (FIG. 19B) of the mount 5008, and may help adhere the sensor control device 5002 to the user's skin for use.

The sensor control device 5002 may provide or otherwise include a sealed subassembly that includes, among other component parts, the shell 5006, the sensor 5010, the sharp 5012, and the sensor cap 5018. The sealed subassembly of the sensor control device 5002 may help isolate the sensor 5010 and the sharp 5012 within the inner chamber 5022

(FIG. 19A) of the sensor cap 5018 during a gaseous chemical sterilization process, which might otherwise adversely affect the chemistry provided on the sensor 5010.

The sensor 5010 may include a tail 5104 that extends out an aperture 5106 (FIG. 19B) defined in the mount 5008 to be transcutaneously received beneath a user's skin. The tail 5104 may have an enzyme or other chemistry included thereon to help facilitate analyte monitoring. The sharp 5012 may include a sharp tip 5108 extendable through an aperture 5110 (FIG. 51 A) defined by the shell 5006, and the aperture 5110 may be coaxially aligned with the aperture 5106 of the mount 5008. As the sharp tip 5108 penetrates the electronics housing 5004, the tail 5104 of the sensor 5010 may be received within a hollow or recessed portion of the sharp tip 5108. The sharp tip 5108 may be configured to penetrate the skin while carrying the tail 5104 to put the active chemistry of the tail 5104 into contact with bodily fluids.

The sharp tip 5108 may be advanced through the electronics housing 5004 until the sharp hub 5014 engages an upper surface of the shell 5006 and the mating member 5016 extends out the aperture 5106 in the bottom 5102 of the mount 5008. In some embodiments, a seal member (not shown), such as an O-ring or seal ring, may interpose the sharp hub 5014 and the upper surface of the shell 5006 to help seal the interface between the two components. In some embodiments, the seal member may comprise a separate component part, but may alternatively form an integral part of the shell 5006, such as being a co-molded or overmolded component part.

The sealed subassembly may further include a collar 5112 that is positioned within the electronics housing 5004 and extends at least partially into the aperture 5106. The collar 5112 may be a generally annular structure that defines or otherwise provides an annular ridge 5114 on its top surface. In some embodiments, as illustrated, a groove 5116 may be defined in the annular ridge 5114 and may be configured to accommodate or otherwise receive a portion of the sensor 5010 extending laterally within the electronics housing 5004.

In assembling the sealed subassembly, a bottom 5118 of the collar 5112 may be exposed at the aperture 5106 and may sealingly engage the first end 5020a of the sensor cap 5018 and, more particularly, the seal ring 5028. In contrast, the annular ridge 5114 at the top of the collar 5112 may sealingly engage an inner surface (not shown) of the shell 5006. In at least one embodiment, a seal member (not shown) may interpose the annular ridge 5114 and the inner surface of the shell 5006 to form a sealed interface. In such embodiments, the seal member may also extend (flow) into the groove 5116 defined in the annular ridge 5114 and thereby seal about the sensor 5010 extending laterally within the electronics housing 5004. The seal member may comprise, for example, an adhesive, a gasket, or an ultrasonic weld, and may help isolate the enzymes and other chemistry included on the tail 5104.

Figure 20:
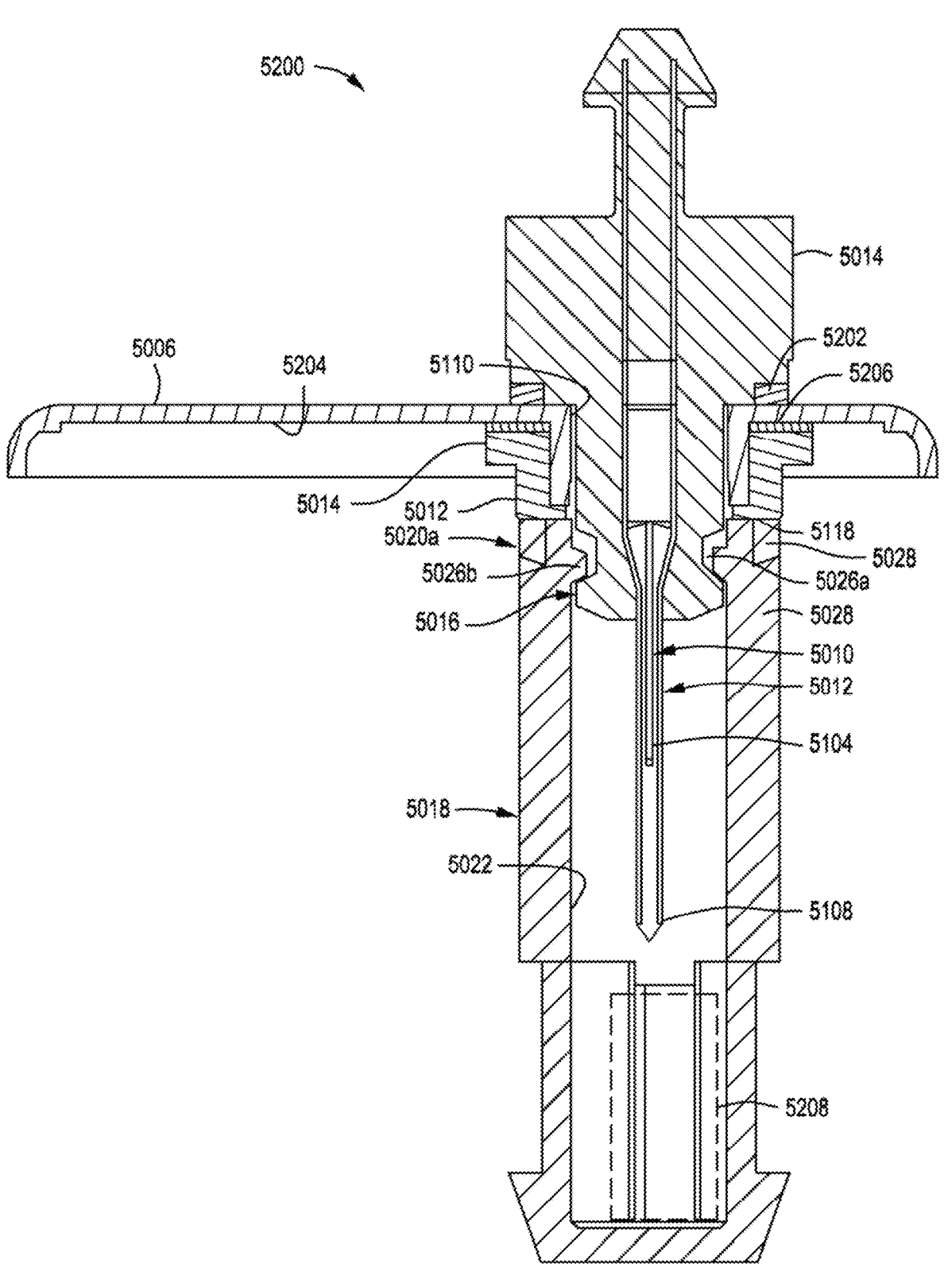
FIG. 20 is a cross-sectional side view of an assembled sealed subassembly, according to one or more embodiments.

FIG. 20 is a cross-sectional side view of an assembled sealed subassembly 5200, according to one or more embodiments. The sealed subassembly 5200 may form part of the sensor control device 5002 of FIGS. 18A-18B and 19A-20B and may include portions of the shell 5006, the sensor 5010, the sharp 5012, the sensor cap 5018, and the collar 5112. The sealed subassembly 5200 may be assembled in a variety of ways. In one assembly process, the sharp 5012 may be coupled to the sensor control device 5002 by extending the sharp tip 5108 through the aperture 5110 defined in the top of the shell 5006 and advancing the sharp 5012 through the shell 5006 until the sharp hub 5014 engages the top of the shell 5006 and the mating member 196 extends distally from the shell 5006. In some embodiments, as mentioned above, a seal member 5202 (e.g., an O-ring or seal ring) may interpose the sharp hub 5014 and the upper surface of the shell 5006 to help seal the interface between the two components.

The collar 5112 may then be received over (about) the mating member 5016 and advanced toward an inner surface 5204 of the shell 5006 to enable the annular ridge 5114 to engage the inner surface 5204. A seal member 5206 may interpose the annular ridge 5114 and the inner surface 5204 and thereby form a sealed interface. The seal member 5206 may also extend (flow) into the groove 5116 (FIGS. 19A-20B) defined in the annular ridge 5114 and thereby seal about the sensor 5010 extending laterally within the electronics housing 5004 (FIGS. 19A-20B). In other embodiments, however, the collar 5112 may first be sealed to the inner surface 5204 of the shell 5006, following which the sharp 5012 and the sharp hub 5014 may be extended through the aperture 5110, as described above.

The sensor cap 5018 may be removably coupled to the sensor control device 5002 by threadably mating the internal threads 5026*b* of the sensor cap 5018 with the external threads 5026*a* of the mating member 5016. Tightening (rotating) the mated engagement between the sensor cap 5018 and the mating member 5016 may urge the first end 5020*a* of the sensor cap 5018 into sealed engagement with the bottom 5118 of the collar 5112. Moreover, tightening the mated engagement between the sensor cap 5018 and the mating member 5016 may also enhance the sealed interface between the sharp hub 5014 and the top of the shell 5006, and between the annular ridge 5114 and the inner surface 5204 of the shell 5006.

The inner chamber 5022 may be sized and otherwise configured to receive the tail 5104 and the sharp tip 5108. Moreover, the inner chamber 5022 may be sealed to isolate the tail 5104 and the sharp tip 5108 from substances that might adversely interact with the chemistry of the tail 5104. In some embodiments, a desiccant 5208 (shown in dashed lines) may be present within the inner chamber 5022 to maintain proper humidity levels.

Figures 40A, 40B:
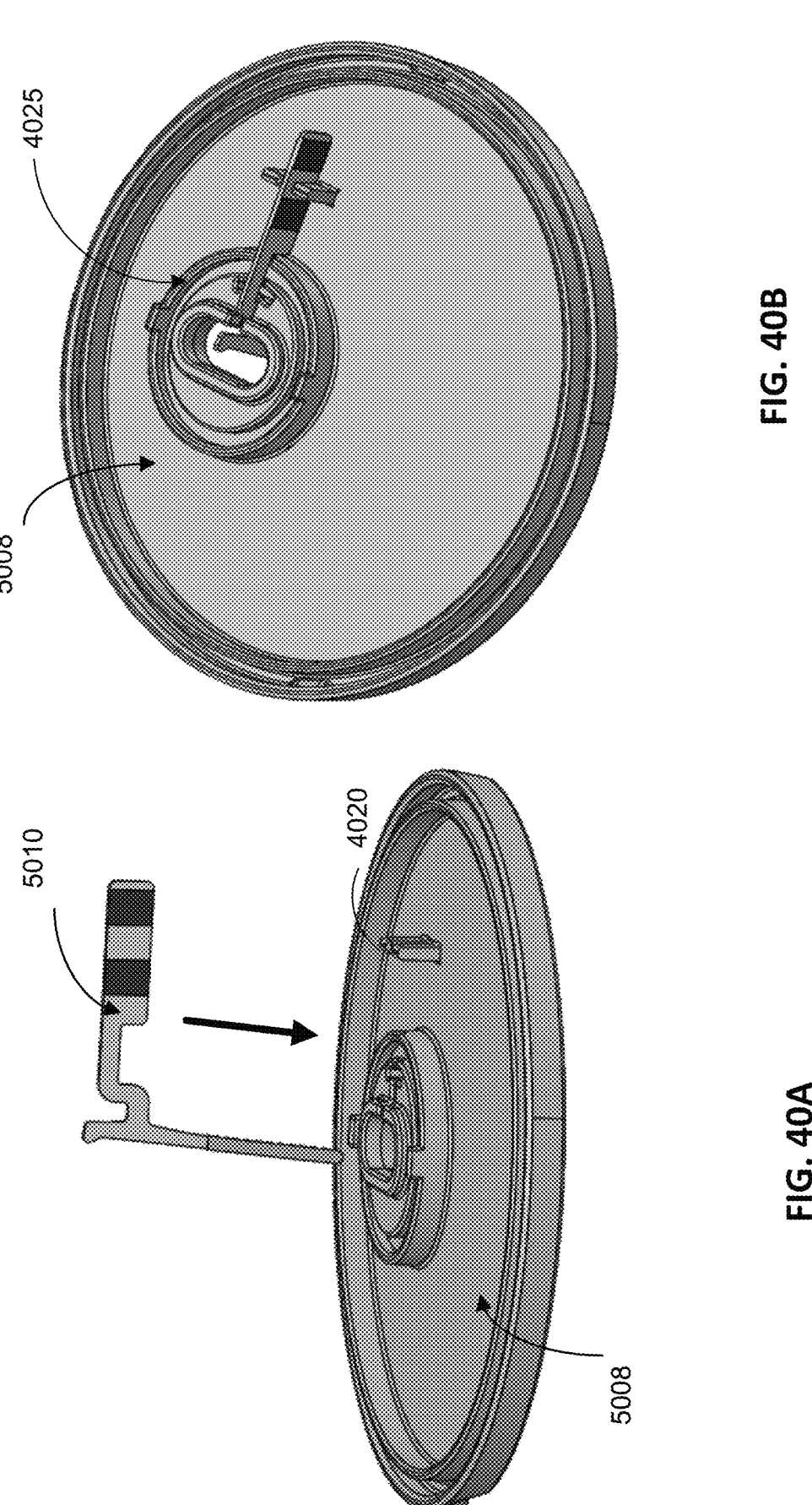
Figure 40F:
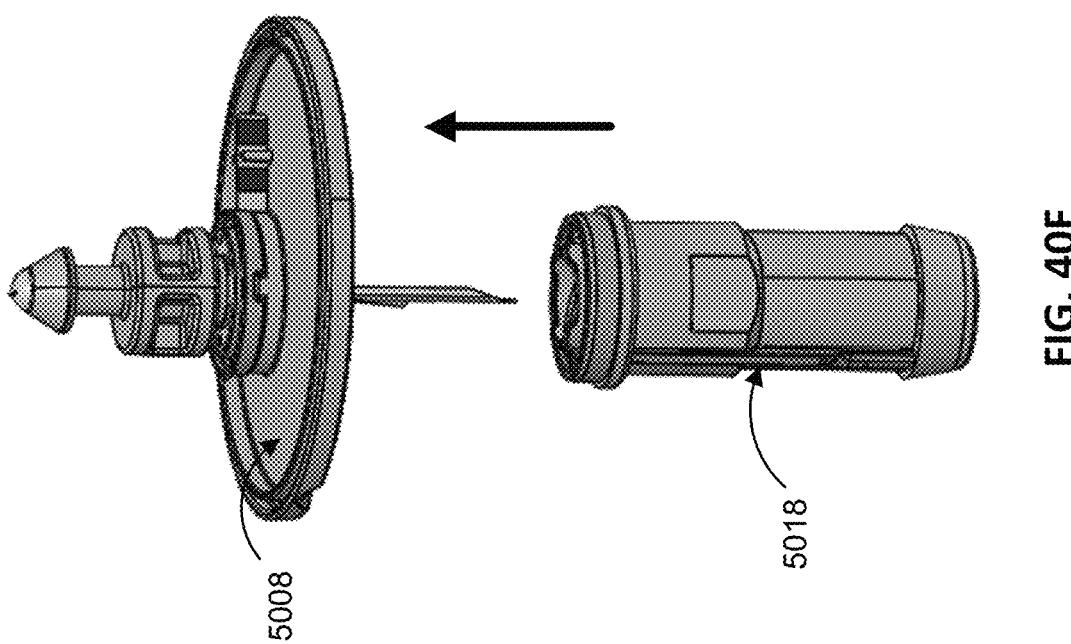
Figure 40E:
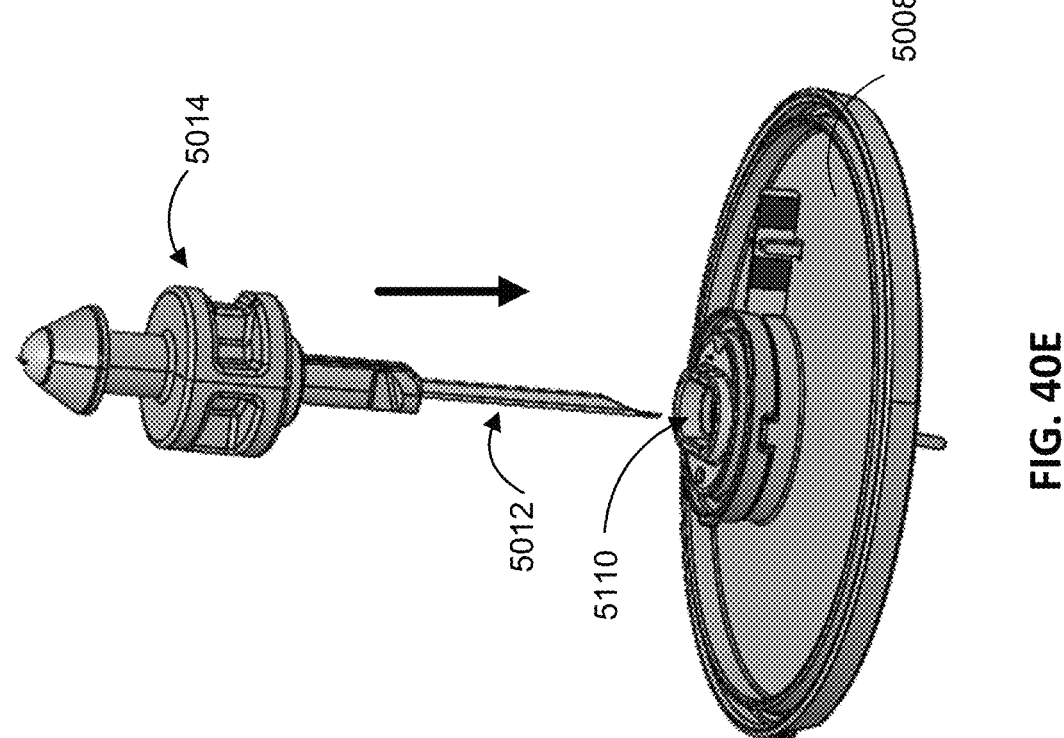
Figure 40H:
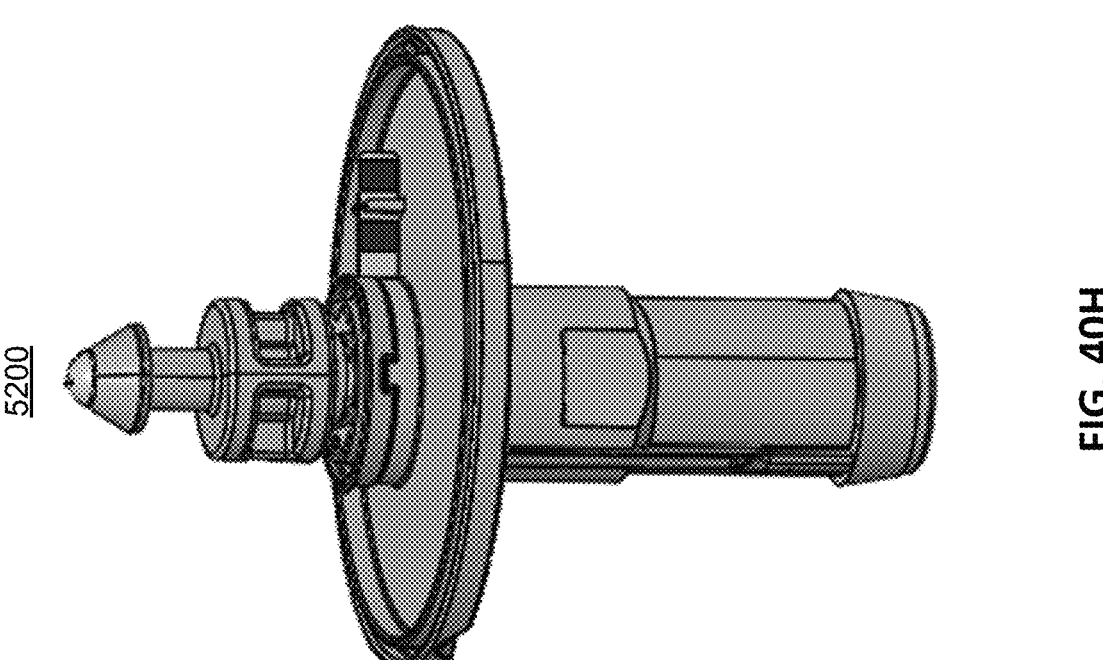

FIGS. 40A-40H illustrate steps of a manufacturing process for manufacturing a sensor subassembly, also referred to as a sealed subassembly such as the sealed subassembly 5200 (see FIGS. 40H, 20). In particular embodiments, assembled sensor subassembly 5200 can include a sensor 5010, sensor mount 5008, collar 5112, sharp 5012, and sensor cap 5018. As described herein, the sensor 5012 can include a body temperature sensor, blood pressure sensor, pulse or heart-rate sensor, glucose level sensor, analyte sensor, or physical activity sensor. Different sensors can be configured and made compatible with the sealed subassembly manufacturing techniques described herein based on the electrical or chemical treatments applied to or used with the sensor of choice.

In an exemplary step of the manufacturing process, as illustrated in FIG. 40A, the sensor 5010 is loaded into the sensor mount 5008. Based on the configuration of the sensor 5010, the sensor mount can include components to interface with and stabilize the sensor 5010 such as flanges 4020, 12112 (see FIG. 16E), 12104, etc. as described herein.

As illustrated in FIG. 40B, the manufacturing process can include dispensing adhesive into a mount channel 4025 of the sensor mount 5008. The adhesive can be dispensed manually or using suitable automation tools. For example, a specially-configured tool having a dispensing valve for dispensing the predetermined adhesive to the mount channel 4025 can be used.

As illustrated in FIG. 40C, the manufacturing process can include loading a collar 5112 onto the sensor mount 5008. In particular, the collar 5112 is loaded to mate with the mount channel 4025 of the sensor 5008. The collar can be loaded manually, or using suitable manufacturing tools, including a manually-operated or robotic loading arm, vacuum or suction gripping arm, magnetic gripping arm, adaptive gripping arm or appendage, or other suitable tool. The collar 5112 can then be clamped to the sensor mount 4025 to ensure the collar 5112 is well-seated within the sensor mount 4025 and disburse the adhesive throughout the sensor mount 4025 and collar 5112. The collar 5112 can be clamped to the sensor mount 4025 using a suitable clamping tool, including a manual clamp, ratcheting clamp, linear slide, including an electric slide, pneumatic slide, ball-screw linear adapter, etc.

The adhesive is then cured to fix the collar 5112 to the sensor mount 5008, as illustrated in FIG. 40D. The adhesive can include a variety of curable adhesive suitable for use in high-throughput manufacturing environments. The adhesive used may be chosen based on cure method and cure time. For example, the adhesive may be chosen to reduce cure time while also limiting exposing the chemistry or electronics of the sensor 5010 to excessive heat, chemicals, etc. that may damage the effectiveness of the sensor, radiation, or excessive infrared or ultra-violet (UV) light. As an example, the adhesive can be a chemically-curable adhesive. Curing the adhesive would then include exposing the adhesive to one or more chemical bonding catalysts. As another example, the adhesive can be an aerobically-curable adhesive. Curing the adhesive would then include exposing the adhesive to air for a sufficient amount before the collar 5112 is mounted or before moving onto the next step. As another example, the adhesive can be a heat-curable adhesive. Curing the adhesive would then include exposing the adhesive to ambient heat or heating elements for a predetermined amount of time. As another example, the adhesive can be a UV-curable adhesive. Curing the adhesive would then include using one or more UV light sources. The UV light sources can include, for example, UV light emitting diodes (LED) arranged to cure the adhesive with a light pipe and multiple angled spot LEDs. FIG. 40D illustrates multiple sources of curing agents 4010 being used to cure the adhesive from above and below the sensor mount 5008.

While curing the adhesive, in certain embodiments, the collar 5112 and sensor mount 5008 can act to shield the sensor 5010 from exposure to curing agents that might otherwise damage the sensor 5010 or other components of the sealed subassembly 5200. Additionally, other temporary components can be used to further protect the sensor 5010. As an example, the collar 5112 can block exposure of chemical agents, heat, or UV light sources while curing the adhesive. Furthermore, depending on the adhesive and curing method, the materials making up the sensor mount 5008 or collar 5112 can be chosen to partially allow curing agents to selectively passthrough to the adhesive.

As illustrated in FIG. 40E, the manufacturing process can include mating the sharp hub 5014 to the sensor mount 5008, covering and mating with the sensor 5010. Mating the sharp hub 5014 to the sensor mount 5008 can include causing some or all of the sharp 5012 to pass through an aperture 5110 in the sensor mount 5008 and collar 5112. In some embodiments, the manufacturing process can further include inspecting the sharp 5012 for imperfections. The inspection can be performed prior to, or after, inserting the sharp hub 5014 into the sensor mount 5008. The inspection can be performed manually, e.g., by loading the sharp into a microscope or other magnifying apparatus and allowing a human operator to confirming condition of the sharp. Alternatively, the inspection can be performed automatically, e.g., by imaging the sharp using high-resolution cameras, x-ray imaging, or similar. Having imaged the sharp 5012, a computer vision system can compare the images to acceptable sharps or apply machine-learned models to the image to confirm the condition of the sharp. If the sharp is deemed to have imperfections, it can be discarded. In some embodiments, imperfections that can cause a sharp to be discarded including, as an example only and not by way of limitation, damage to the sharp tip (e.g., resulting in burrs or bites), debris on the sharp, and other similar damage.

As illustrated in FIG. 40F, the manufacturing process can include attaching a sensor cap 5018 to the sensor mount 5008, covering the sensor 5010 and sharp 5012, to provide a sealed sensor subassembly 5200. In particular embodiments, the sensor cap 5018 can be composed of a singular structure. In other embodiments, the sensor cap 5018 can include multiple component parts. For example, as discussed herein, the sensor cap 5018 can include a desiccant cap 5030 or plug housing a desiccant to control moisture exposure to the sensor 5010 and sharp 5012. The manufacturing process can include assembling the sensor cap 5018 by inserting a desiccant into the desiccant cap 5030 and attaching the desiccant cap 5030 to the sensor cap 5018.

Attaching the sensor cap 5018 to the sensor mount 5008 can be performed by forcibly mating the sensor cap 5018 to the sensor mount 5008. For example, the sensor mount 5008 or sharp hub 5104 may define a set of external threads matable with a set of internal threads defined by the sensor cap 5018. The external and internal threads may comprise a flat thread design (e.g., lack of helical curvature), which may prove advantageous in molding the parts. The sensor cap 5018 may be removably coupled to the sensor mount 5018 via other types of engagements including, but not limited to, an interference or friction fit, or a frangible member or substance that may be broken with minimal separation force (e.g., axial or rotational force). The sensor cap 5018 can be locked into position manually or using machine tools, such as a pneumatic actuator or linear or multi-axis servo motor, to force the sensor cap 5018 to mate with the sensor mount 5008.

Figure 40G:
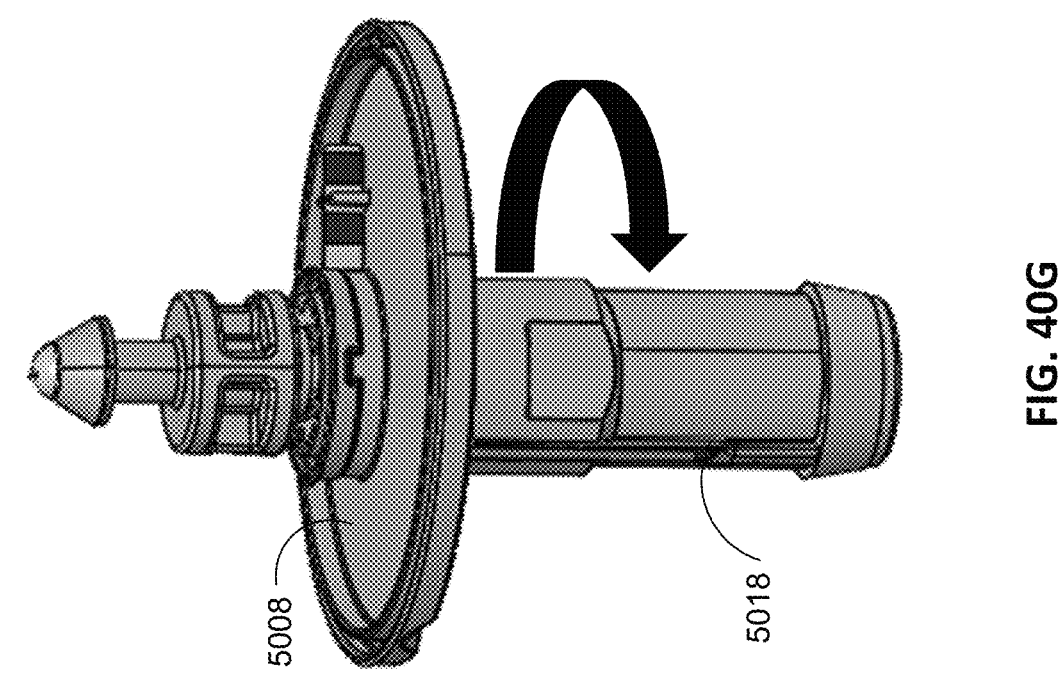

As illustrated in FIG. 40G, attaching the sensor cap 5018 to the sensor mount 5008 can include twisting the sensor cap into position. The external and internal threads may comprise a helical threaded engagement. Accordingly, the sensor cap 5018 may be threadably coupled to the sensor mount 5008 or at a mating member of the sharp hub 5014. FIG. 40G illustrates a completed sensor subassembly 5200.

The manufacturing process can include dispensing adhesive to one or more surfaces of the sharp hub 5014. For example, the manufacturing process can include dispensing adhesive to a top surface of the sharp hub 5014, viewing the sensor subassembly 5200 with the sharp cap 5018 oriented downward. The manufacturing process can include dispensing adhesive to a region of the sharp hub 5014 where the sharp hub 5014 interfaces with the sensor mount 5008. The process can further include curing the adhesive. Curing the adhesive can fix the sharp hub 5014 to the sensor mount 5008. Curing the adhesive can seal the sharp hub to reduce leaks between the sharp hub 5014 and the sharp, improving the barrier between the sharp and environment and thus creating a sterile barrier. The adhesive can be dispensed and cured in a manner similar to how the adhesive is dispensed to the mount channel 4025 and subsequently cured. The adhesive can be used to fix the sharp hub 5014 to the sensor mount 5008. The adhesive, when cured, can further promote the sealing of the sensor subassembly 5200.

The manufacturing process can further include testing the sealed sensor subassembly 5200 for leaks. The testing can be performed using a pressure-decay leak test, vacuum-decay leak test, tracer gas leak test, signature analysis test, or mass-flow leak test. In particular embodiments, the leak test can be automated using dedicated machine tooling to facilitate testing of an individual sealed sensor subassembly 5200 or multiple sealed sensor subassemblies simultaneously. If the sealed sensor subassembly fails the leak test, it can be discarded.

Once properly assembled, the sealed subassembly 5200 may be subjected to a sterilization process such as any of the radiation sterilization processes mentioned herein to properly sterilize the sensor 5010 and the sharp 5012. The sterilization process can further include heat treatment, electronic-beam sterilization, gamma sterilization, x-ray sterilization, ethylene oxide sterilization, autoclave steam sterilization, chlorine dioxide gas sterilization, hydrogen peroxide sterilization. In particular, the sterilization process can be configured using appropriate machine tools to facilitate sterilization of multiple seal subassemblies 5200 simultaneously. For example, a plurality of sealed subassemblies 5200 can be loaded into a tray for subsequent sterilization.

This sterilization step may be undertaken apart from the remaining portions of the sensor control device (FIGS. 18A-18B and 19A-20B) to prevent damage to sensitive electrical components. The sealed subassembly 5200 may be subjected to sterilization prior to or after coupling the sensor cap 5018 to the sharp hub 5014. When sterilized after coupling the sensor cap 5018 to the sharp hub 5014, the sensor cap 5018 may be made of a material that permits the propagation of sterilizing elements therethrough. In some embodiments, the sensor cap 5018 may be transparent or translucent, but can otherwise be opaque, without departing from the scope of the disclosure.

FIGS. 41A-41J illustrate steps of an exemplary process for manufacturing a sensor control device 5002. In particular, FIGS. 41A-41J illustrate steps for manufacturing an electronics housing 5004. As the sensor control device 5002 can be adhered to a user's skin for use with the assistance of an adhesive patch (e.g., adhesive patch 105), while also housing a sensor 5010, the sensor control device 5002 may optionally be referred to as an on-body sensor puck assembly. The electronics housing 5004 shown in FIGS. 41A-41J includes a printed circuit board (PCB) 4100, a shell cap 5006, and a sensor subassembly 5200, the sensor subassembly 5200 including a sensor 5010, a sensor mount 5008 that is matable with the shell cap 5006, a collar 5112, and a sensor cap 5018.

Figure 41B:
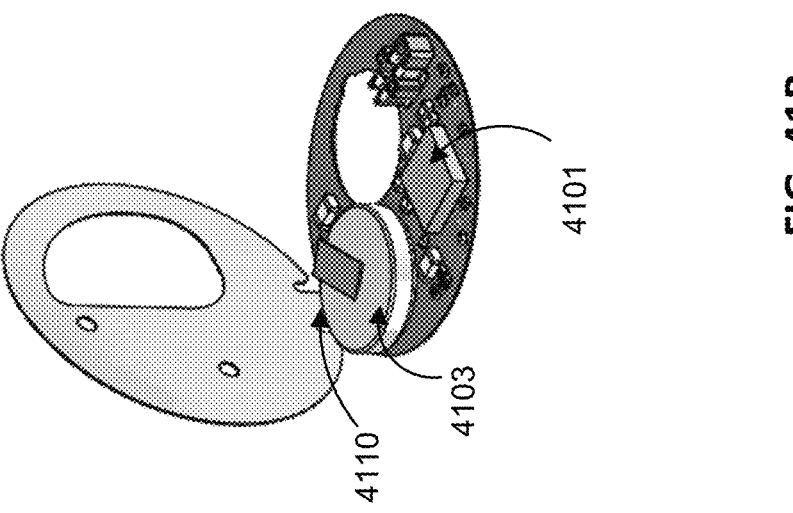
FIGS. 41A-41J illustrate steps of a process for assembling a sensor control device.
Figure 41A:
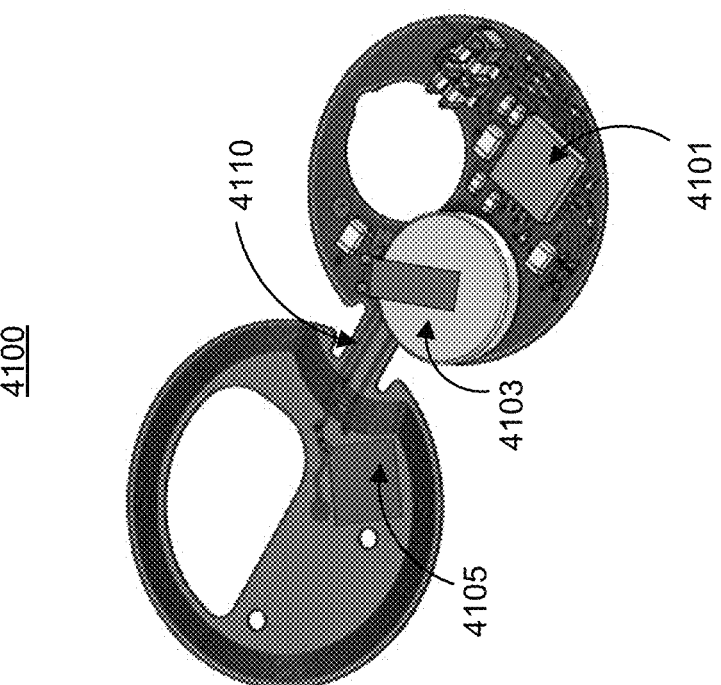

FIGS. 41A-41B illustrate an example PCB 4100 that can be used in the electronics housing 5004 of the on-body sensor puck assembly. The PCB 4100 can include components such as an ASIC 4101, battery 4103, and antenna 4105. As illustrated, the PCB 4100 can be a foldable or flexible PCB, however non-foldable PCBs can also be used In foldable PCB embodiments, the manufacturing process can include folding the PCB 4100 at a fold point 4110 to fit the footprint of the mount 5008 and shell cap 5006 which defines the overall footprint of the electronics housing 5004. FIG. 41B illustrates the PCB 4100 during folding process. Folding the PCB 4100 can also connect components of the PCB 4100, for example connecting the battery 4103 to an appropriate battery terminal.

Figure 41D:
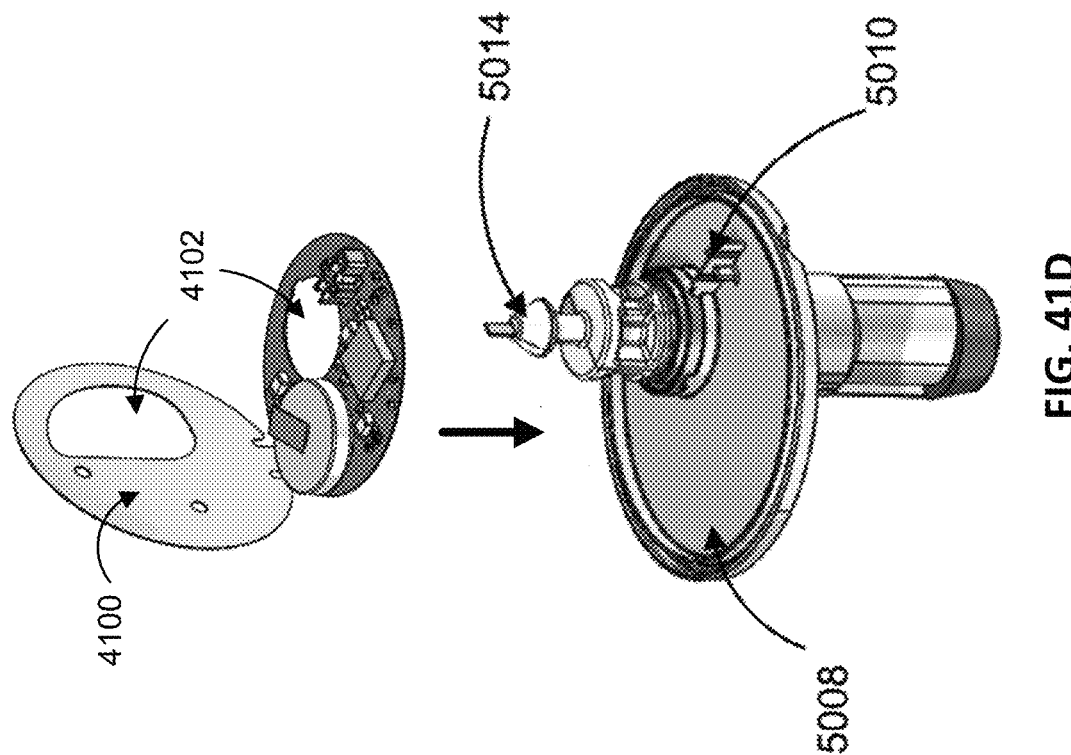
Figure 41C:
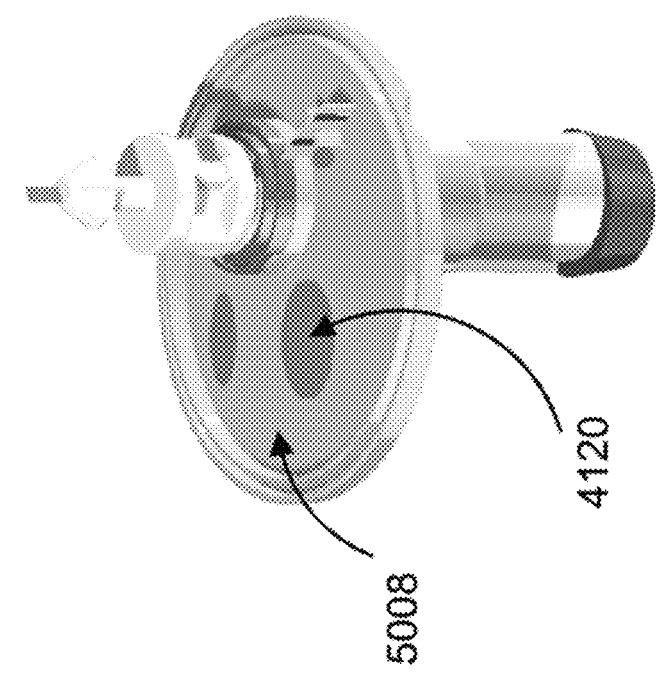

As illustrated in FIG. 41C, the manufacturing process can include dispensing a first adhesive 4120 to a sensor mount 5008 of the sensor subassembly 5200. As an example, the adhesive can be dispensed at locations corresponding to components of the PCB 4100, such as the fold, the battery location, or PCB connectors. The adhesive can be dispensed manually or using suitable automation tools. For example, a specially-configured tool having a dispensing valve for dispensing the predetermined adhesive to the designated locations of the sensor mount 5008 can be used. As described herein, the dispensing valve can be used in combination with other components to manipulate the sensor mount 5008 as appropriate before, during, and after the dispensing. For example, the sensor mount 5008 can be rotated by a rotary motor to facilitate even distribution of the adhesive.

As illustrated in FIG. 41D, the manufacturing process can include loading the PCB 4100 onto the sensor mount 5008 of the sensor subassembly 5200 after aligning the PCB 4100 with the sensor 5010 and the sensor subassembly 5200. For example, the PCB 4100 may include one or more apertures 4102 sized to fit over the sharp hub 5014 of the sealed sensor sharp assembly 5200. FIG. 41E illustrates the PCB 4110 disposed on the sealed subassembly 5200.

Figure 41F:
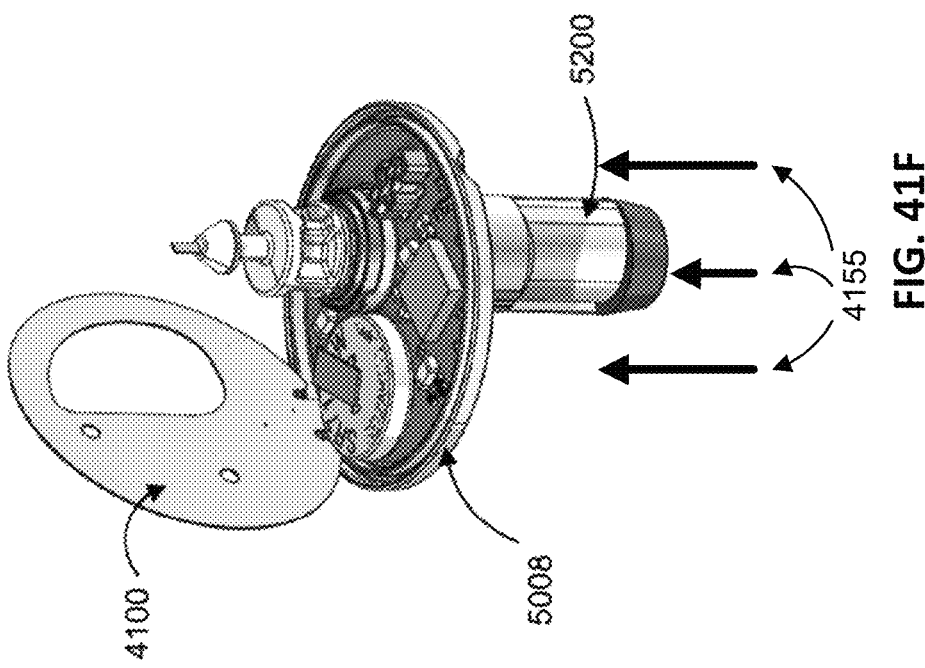
Figure 41E:
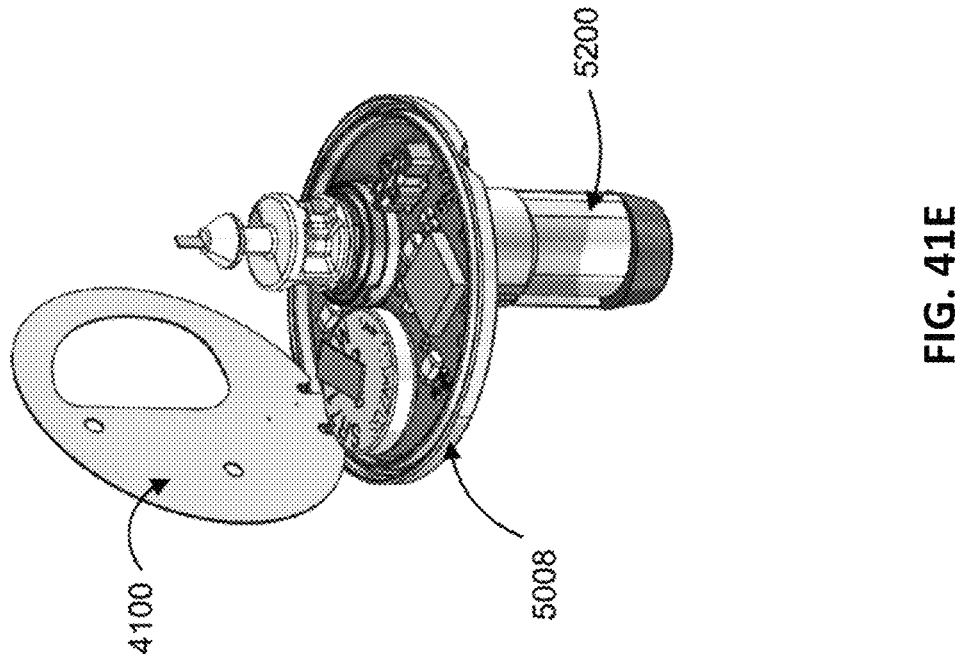

As illustrated in FIG. 41F, the manufacturing process can include curing the first adhesive to fix the PCB to the sensor mount. The adhesive and curing process can include any of the features described herein above. FIG. 41G illustrates the PCB 4100 in a folded state, fixed to the sensor mount 5008.

Figure 33:
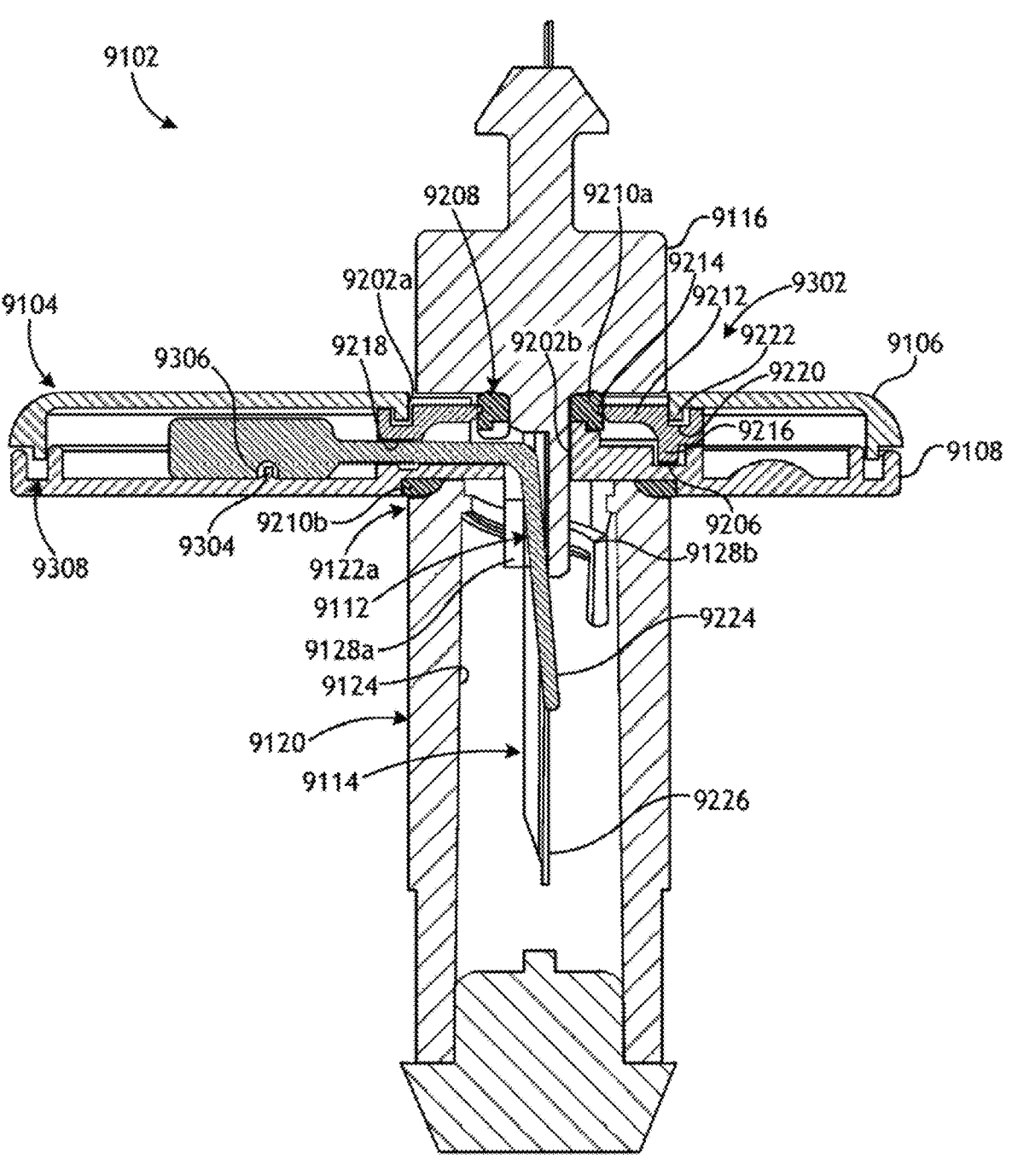
FIG. 33 is a cross-sectional side view of the sensor control device of FIGS. 31A-31B and 32A-32B, according to one or more embodiments.
Figure 41H:
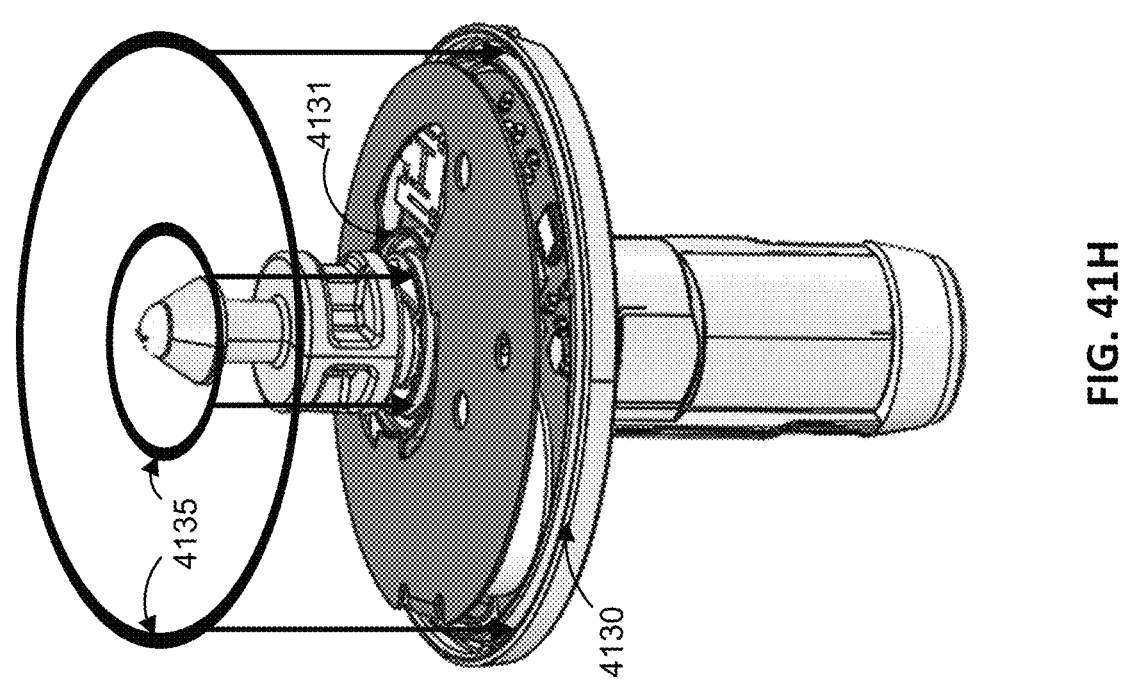
Figure 41G:
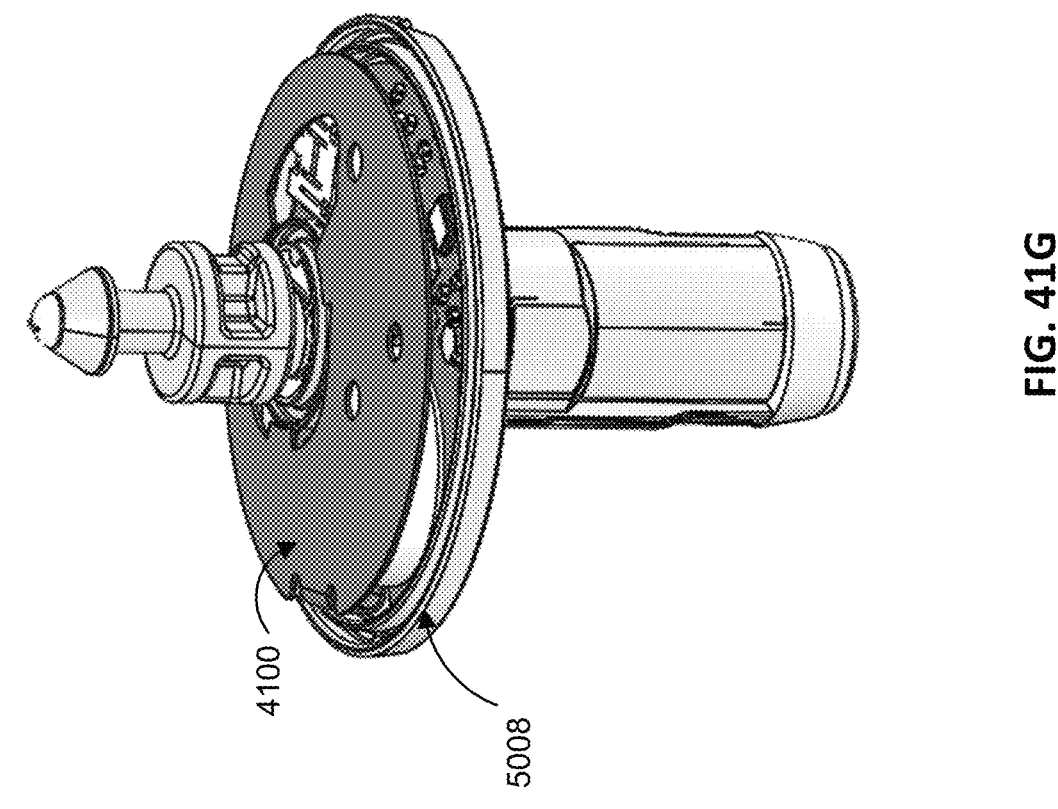

As illustrated in FIG. 41H, the manufacturing process can include dispensing a second adhesive 4135 onto an outer diameter 4130 of the sensor mount 5008 (e.g., channel 9206 shown in FIG. 33) and an inner diameter 4131 of the sensor mount 5008 or collar 5112 of the sensor subassembly 5200 (e.g., collar channel 9220 shown in FIG. 33). The adhesive can be dispensed manually or using suitable automation tools. For example, a specially-configured tool having a dispensing valve for dispensing the predetermined adhesive to the outer diameter 4130 and inner diameter 4131. As described herein, the dispensing valve can be used in combination with other components to manipulate the sensor mount 5008 as appropriate before, during, and after the dispensing.

Figures 2, 41H:
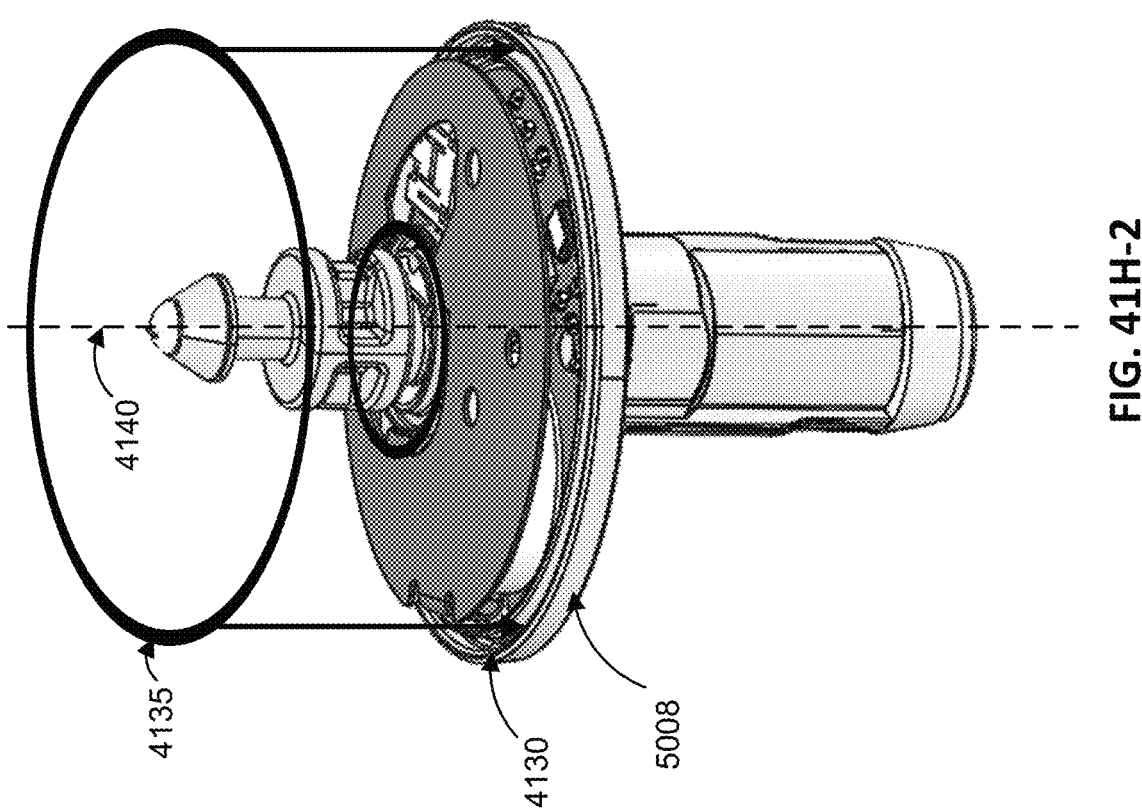
Figures 1, 41H:
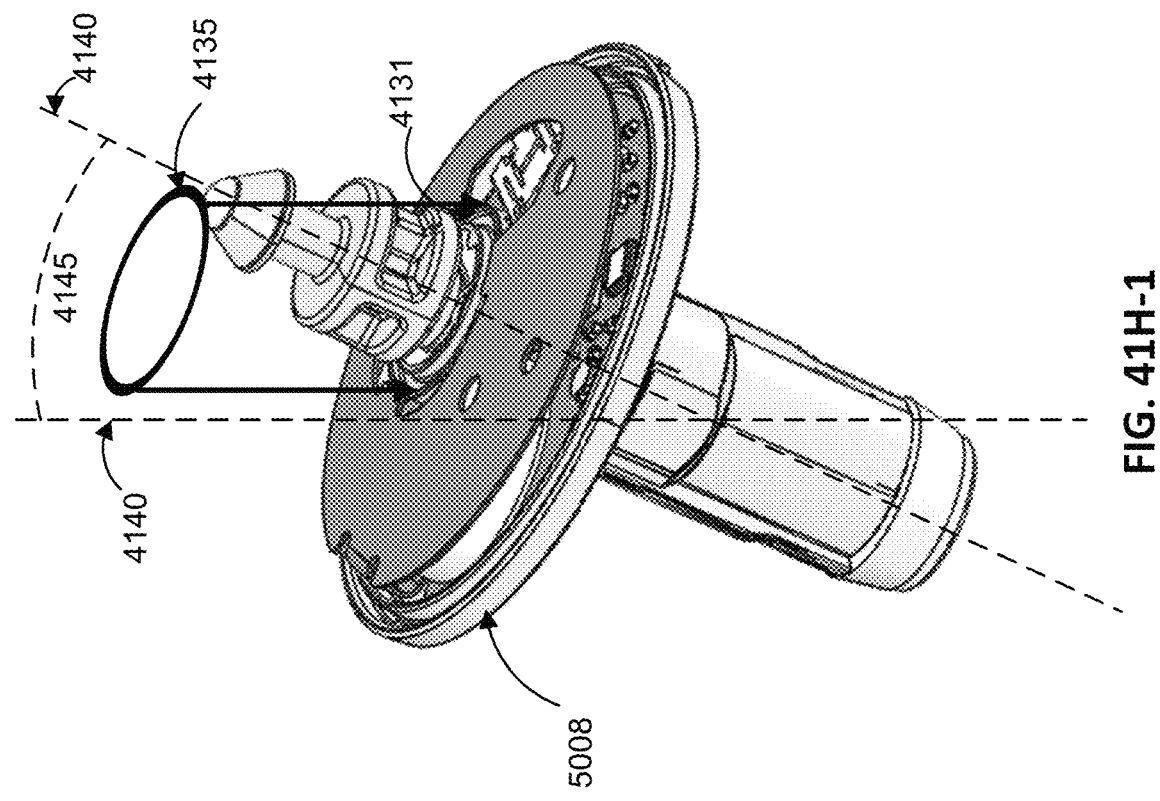

As illustrated in FIG. 41H-1 for the purpose of illustration and not limitation, dispensing the second adhesive 4135 onto the outer diameter 4130 of the sensor mount 5008 and inner diameter 4131 of the sensor mount 5008 or collar 5112 of the sensor subassembly 5200 can include tilting the sensor mount 5200 along an axis 4140 to a predetermined angle 4145 before dispensing the second adhesive 4145 to the inner diameter 4131 of the sensor mount 5008 or collar 5112 of the sensor subassembly 5200. In some embodiments, tilting the sensor mount 520 before dispensing the second adhesive 4145 can allow the nozzle of a dispensing apparatus to more accurately reach the inner diameter 4131 of the sensor mount 5008 or collar 5112 of the sensor subassembly 5200 by facilitating the nozzle, and other actuators used in dispensing the adhesive, to clear the sharp hub. This tilting process can be used for any of the adhesive dispensing steps described herein. As illustrated in FIG. 41H-2, the sensor mount 5008 and sensor subassembly 5200 is returned to a substantially horizontal position by tilting the sensor mount 5008 along the axis 4140 before dispensing the second adhesive 4135 to the outer diameter 4130 of the sensor mount 5008.

Figure 41J:
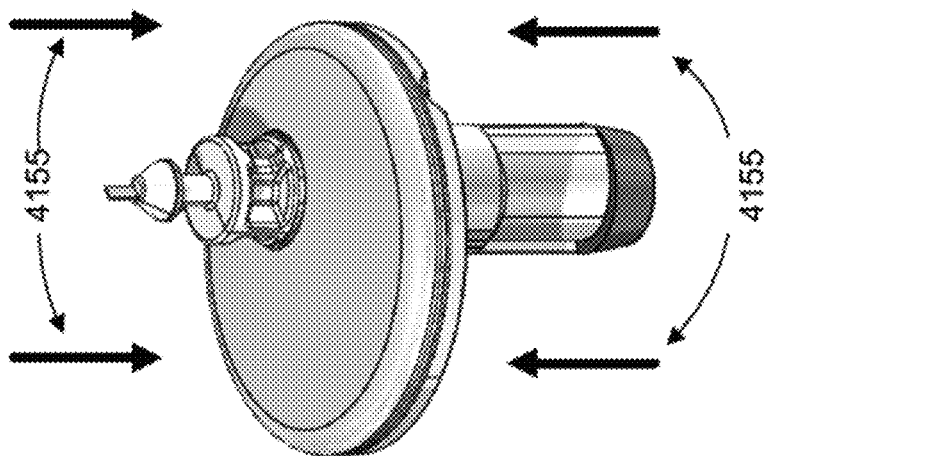
Figure 41I:
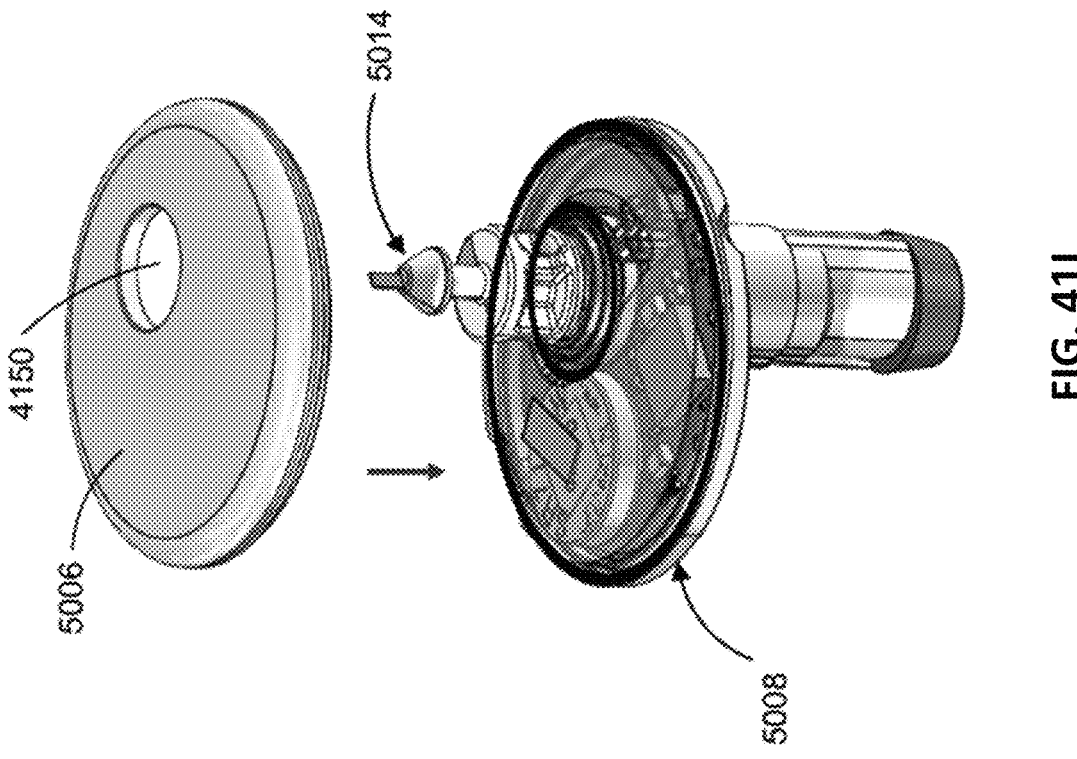

As illustrated in FIG. 41I, the manufacturing process includes attaching the shell cap 5006 to the sensor subassembly 5200 via the sensor mount 5008. An aperture 4150 in the shell cap 5006 is aligned with the sharp hub 5014 before the shell cap 5006 is lowered onto the mount 5008. The shell cap 5006 can be attached to the sensor subassembly 520 manually or using appropriate gripping or clamping tooling, including, but not limited to a manually-operated or robotic loading arm, vacuum or suction gripping arm, magnetic gripping arm, adaptive gripping arm or appendage, or other suitable tool.

As illustrated in FIG. 41J, the manufacturing process includes curing the second adhesive to form the on-body sensor puck assembly. The first adhesive 4130 or second adhesive 4135 can include a variety of curable adhesives suitable for use in high-throughput manufacturing environments. The adhesive(s) used may be chosen based on cure method and cure time. For example, the adhesive(s) may be chosen to reduce cure time while also limit exposing the chemistry or electronics of the sensor subassembly 5200 or PCB 4100 to excessive heat, chemicals, radiation, or excessive infrared or UV light. As an example, the adhesive(s) chosen for the first adhesive 4130 or second adhesive 4135 can be a chemically-curable adhesive. Curing the adhesive would then include exposing the first adhesive 4130 or second adhesive 4135 to one or more chemical bonding catalysts. As another example, the adhesive(s) can be an aerobically-curable adhesive. Curing the first adhesive 4130 or second adhesive 4135 would then include exposing the adhesive(s) to air for a sufficient amount of time before, for example, the shell cap 5006 is lowered to the mount 5008 or before moving onto the next step in the manufacturing process. As another example, the adhesive(s) chosen can be a heat-curable adhesive. Curing the first adhesive 4130 or second adhesive 4135 would then include exposing the adhesive(s) to ambient heat or heating elements for a predetermined amount of time sufficient to cause the adhesive to cure. As another example, the adhesive(s) chosen can be a UV-curable adhesive. Curing the first adhesive 4130 or second adhesive 4135 would then include exposing the adhesive(s) to UV light via one or more UV light sources. The UV light sources can include, for example, UV light emitting diodes (LED) arranged to cure the adhesive with a light pipe and multiple angled spot LEDs. FIGS. 41F and 41J illustrate sources of curing agents 4155 in one embodiment being used to cure the first adhesive 4130 and second adhesive 4135 from above and below the sensor mount 5008.

In certain embodiments, the sensor mount 5008 and shell cap 5006 comprise material that partially allow curing agents to selectively pass through to the first adhesive 4130 and the second adhesive 4135. The sensor mount 5008 and shall cap 5006 can also act to shield the sensor 5010, PCB 4100 and other components of the electronics housing 5004 from exposure to curing agents that might otherwise damage the components of the electronics housing 5004 and sealed subassembly 5200. Additionally, other temporary components can be used to further protect the components.

In some embodiments, the PCB 4100 includes a radio component and the manufacturing process further includes writing data to the radio component of the PCB 4100. For example, data to be written to the radio component of the PCB 4100 can be read from the sensor subassembly 5200, PCB 4100, a shell cap 5004, mount 5006 or other component associated with the electronics housing 5004. The data can then be written to the radio component of the PCB 4100.

In some embodiments, the manufacturing process can further include testing the electronics housing 5004 (e.g., the on-body sensor puck assembly) for leaks. The test can include using a pressure-decay leak test, vacuum-decay leak test, tracer gas leak test, signature analysis test, or mass-flow leak test. If the on-body sensor puck assembly fails the leak test, it can be discarded.

Figures 21A, 21B:
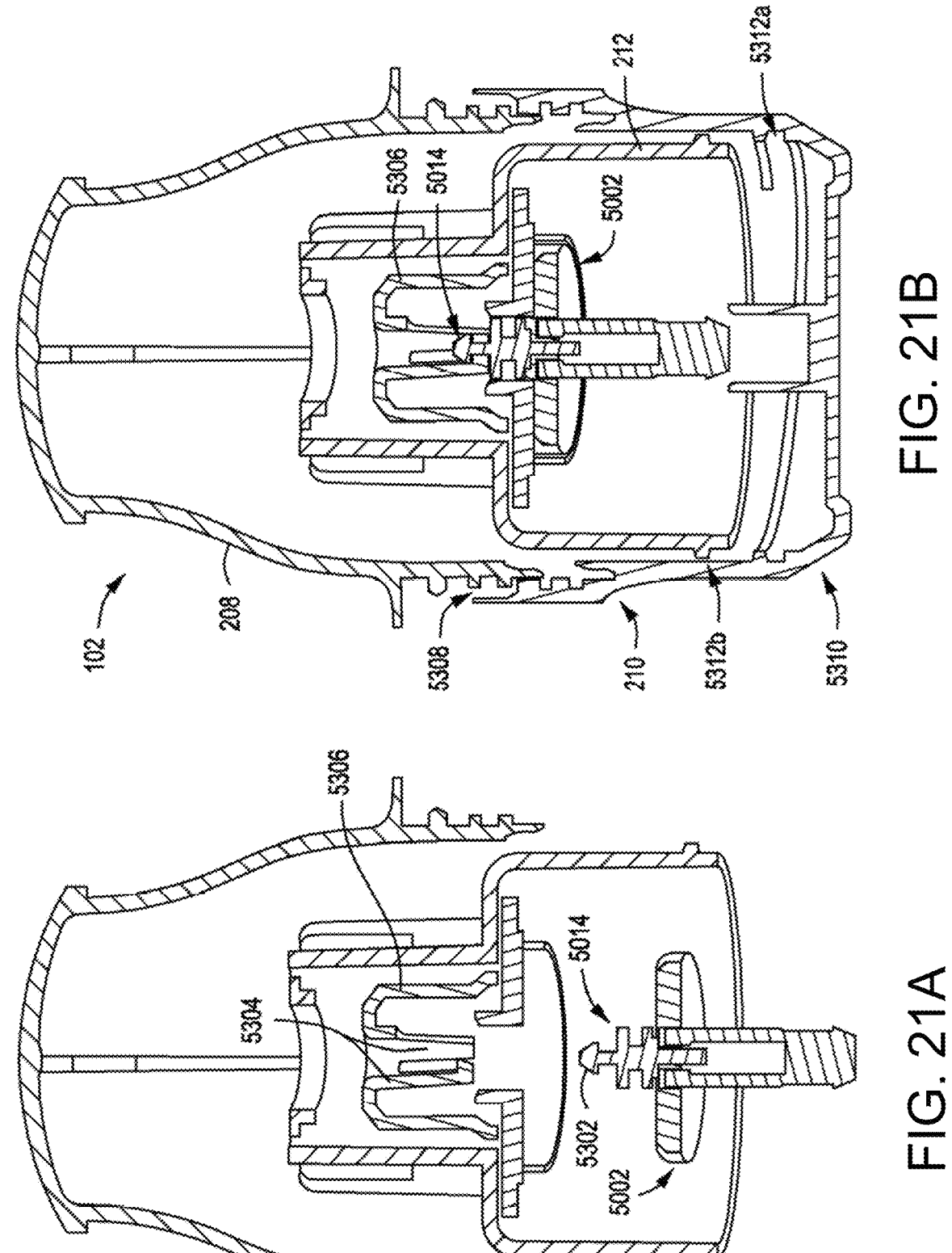
FIGS. 21A-21C are progressive cross-sectional side views showing assembly of the sensor applicator with the sensor control device of FIGS. 18A-18B.
Figure 21C:
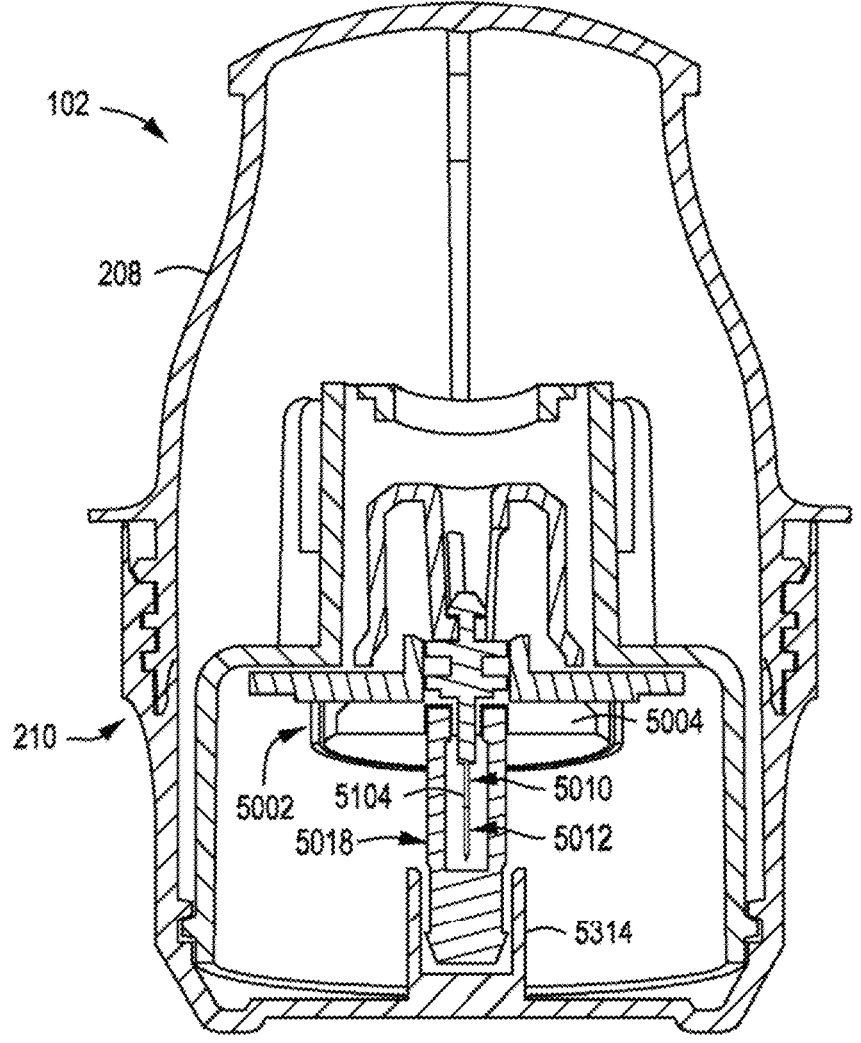

FIGS. 21A-21C are progressive cross-sectional side views showing assembly of the sensor applicator 102 with the sensor control device 5002, according to one or more embodiments. Once the sensor control device 5002 is fully assembled, it may then be loaded into the sensor applicator 102. With reference to FIG. 21A, the sharp hub 5014 may include or otherwise define a hub snap pawl 5302 configured to help couple the sensor control device 5002 to the sensor applicator 102. More specifically, the sensor control device 5002 may be advanced into the interior of the sensor applicator 102 and the hub snap pawl 5302 may be received by corresponding arms 5304 of a sharp carrier 5306 positioned within the sensor applicator 102.

In FIG. 21B, the sensor control device 5002 is shown received by the sharp carrier 5306 and, therefore, secured within the sensor applicator 102. Once the sensor control device 5002 is loaded into the sensor applicator 102, the applicator cap 210 may be coupled to the sensor applicator 102. In some embodiments, the applicator cap 210 and the housing 208 may have opposing, matable sets of threads 5308 that enable the applicator cap 210 to be screwed onto the housing 208 in a clockwise (or counter-clockwise) direction and thereby secure the applicator cap 210 to the sensor applicator 102.

As illustrated, the sheath 212 is also positioned within the sensor applicator 102, and the sensor applicator 102 may include a sheath locking mechanism 5310 configured to ensure that the sheath 212 does not prematurely collapse during a shock event. In the illustrated embodiment, the sheath locking mechanism 5310 may comprise a threaded engagement between the applicator cap 210 and the sheath 212. More specifically, one or more internal threads 53 12*a* may be defined or otherwise provided on the inner surface of the applicator cap 210, and one or more external threads 53 12*b* may be defined or otherwise provided on the sheath 212. The internal and external threads 53 12*a,b* may be configured to threadably mate as the applicator cap 210 is threaded to the sensor applicator 102 at the threads 5308. The internal and external threads 53 12*a,b* may have the same thread pitch as the threads 5308 that enable the applicator cap 210 to be screwed onto the housing 208.

In FIG. 21C, the applicator cap 210 is shown fully threaded (coupled) to the housing 208. As illustrated, the applicator cap 210 may further provide and otherwise define a cap post 5314 centrally located within the interior of the applicator cap 210 and extending proximally from the bottom thereof. The cap post 5314 may be configured to receive at least a portion of the sensor cap 5018 as the applicator cap 210 is screwed onto the housing 208.

With the sensor control device 5002 loaded within the sensor applicator 102 and the applicator cap 210 properly secured, the sensor control device 5002 may then be subjected to a gaseous chemical sterilization configured to sterilize the electronics housing 5004 and any other exposed portions of the sensor control device 5002. Since the distal portions of the sensor 5010 and the sharp 5012 are sealed within the sensor cap 5018, the chemicals used during the gaseous chemical sterilization process are unable to interact with the enzymes, chemistry, and biologies provided on the tail 5104, and other sensor components, such as membrane coatings that regulate analyte influx.

Figure 22A:
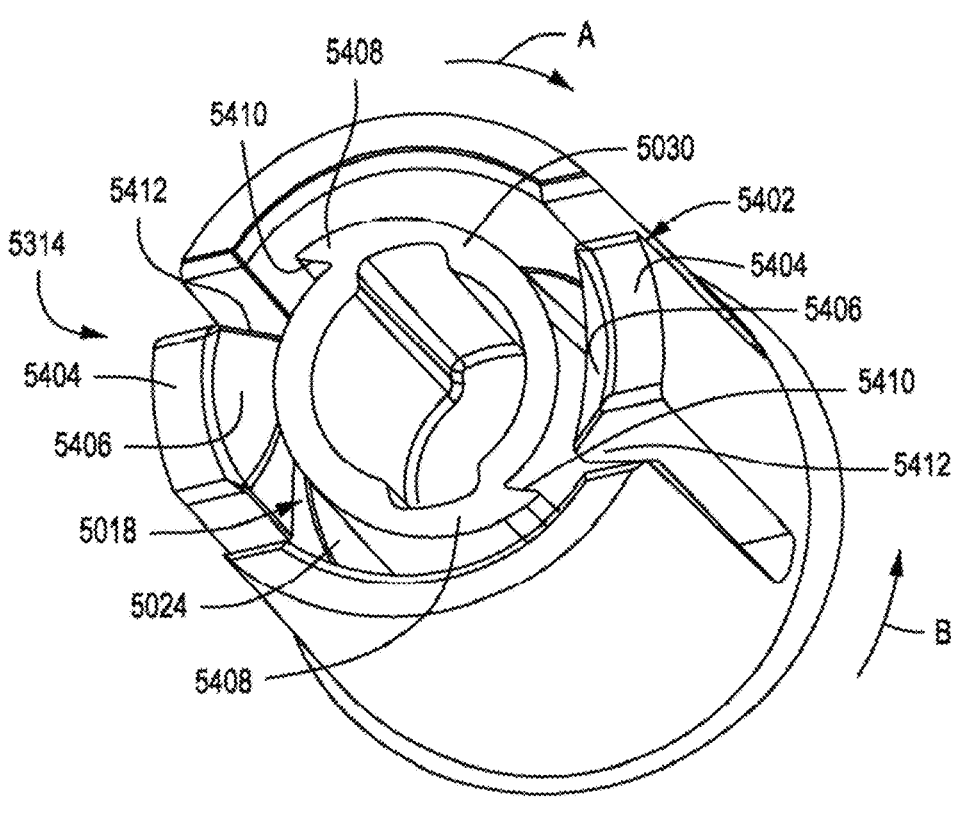
FIGS. 22A and 22B are perspective and top views, respectively, of the cap post of FIG. 21C, according to one or more additional embodiments.
Figure 22B:
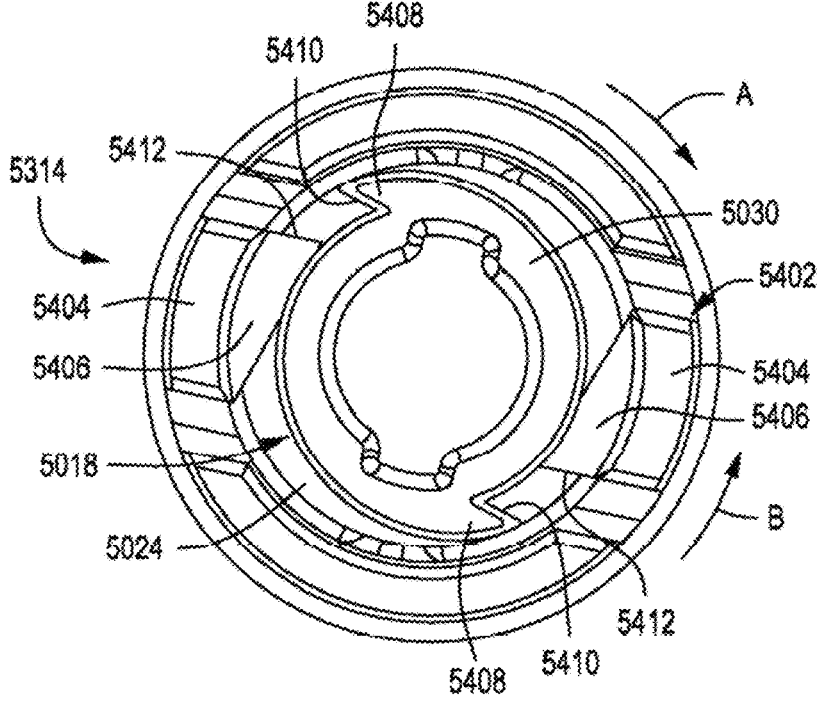

FIGS. 22A and 22B are perspective and top views, respectively, of the cap post 5314, according to one or more additional embodiments. In the illustrated depiction, a portion of the sensor cap 5018 is received within the cap post 5314 and, more specifically, the desiccant cap 5030 of the sensor cap 5018 is arranged within cap post 5314.

As illustrated, the cap post 5314 may define a receiver feature 5402 configured to receive the engagement feature 5024 of the sensor cap 5018 upon coupling (e.g., threading) the applicator cap 210 (FIG. 21C) to the sensor applicator 102 (FIGS. 21A-21C). Upon removing the applicator cap 210 from the sensor applicator 102, however, the receiver feature 5402 may prevent the engagement feature 914 from reversing direction and thus prevent the sensor cap 5018 from separating from the cap post 5314. Instead, removing the applicator cap 210 from the sensor applicator 102 will simultaneously detach the sensor cap 5018 from the sensor control device 5002 (FIGS. 18A-18B and 21A-21C), and thereby expose the distal portions of the sensor 5010 (FIGS. 21A-21C) and the sharp 5012 (FIGS. 21A-21C).

Many design variations of the receiver feature 5402 may be employed, without departing from the scope of the disclosure. In the illustrated embodiment, the receiver feature 5402 includes one or more compliant members 5404 (two shown) that are expandable or flexible to receive the engagement feature 5024 (FIGS. 18A-18B). The engagement feature 5024 may comprise, for example, an enlarged head and the compliant member(s) 5404 may comprise a collet-type device that includes a plurality of compliant fingers configured to flex radially outward to receive the enlarged head.

The compliant member(s) 5404 may further provide or otherwise define corresponding ramped surfaces 5406 configured to interact with one or more opposing camming surfaces 5408 provided on the outer wall of the engagement feature 5024. The configuration and alignment of the ramped surface(s) 5406 and the opposing camming surface(s) 5408 is such that the applicator cap 210 is able to rotate relative to the sensor cap 5018 in a first direction A (e.g., clockwise), but the cap post 5314 binds against the sensor cap 5018 when the applicator cap 210 is rotated in a second direction B (e.g., counter clockwise). More particularly, as the applicator cap 210 (and thus the cap post 5314) rotates in the first direction A, the camming surfaces 5408 engage the ramped surfaces 5406, which urge the compliant members 5404 to flex or otherwise deflect radially outward and results in a ratcheting effect. Rotating the applicator cap 210 (and thus the cap post 5314) in the second direction B, however, will drive angled surfaces 5410 of the camming surfaces 5408 into opposing angled surfaces 5412 of the ramped surfaces 5406, which results in the sensor cap 5018 binding against the compliant member(s) 5404.

Figure 23:
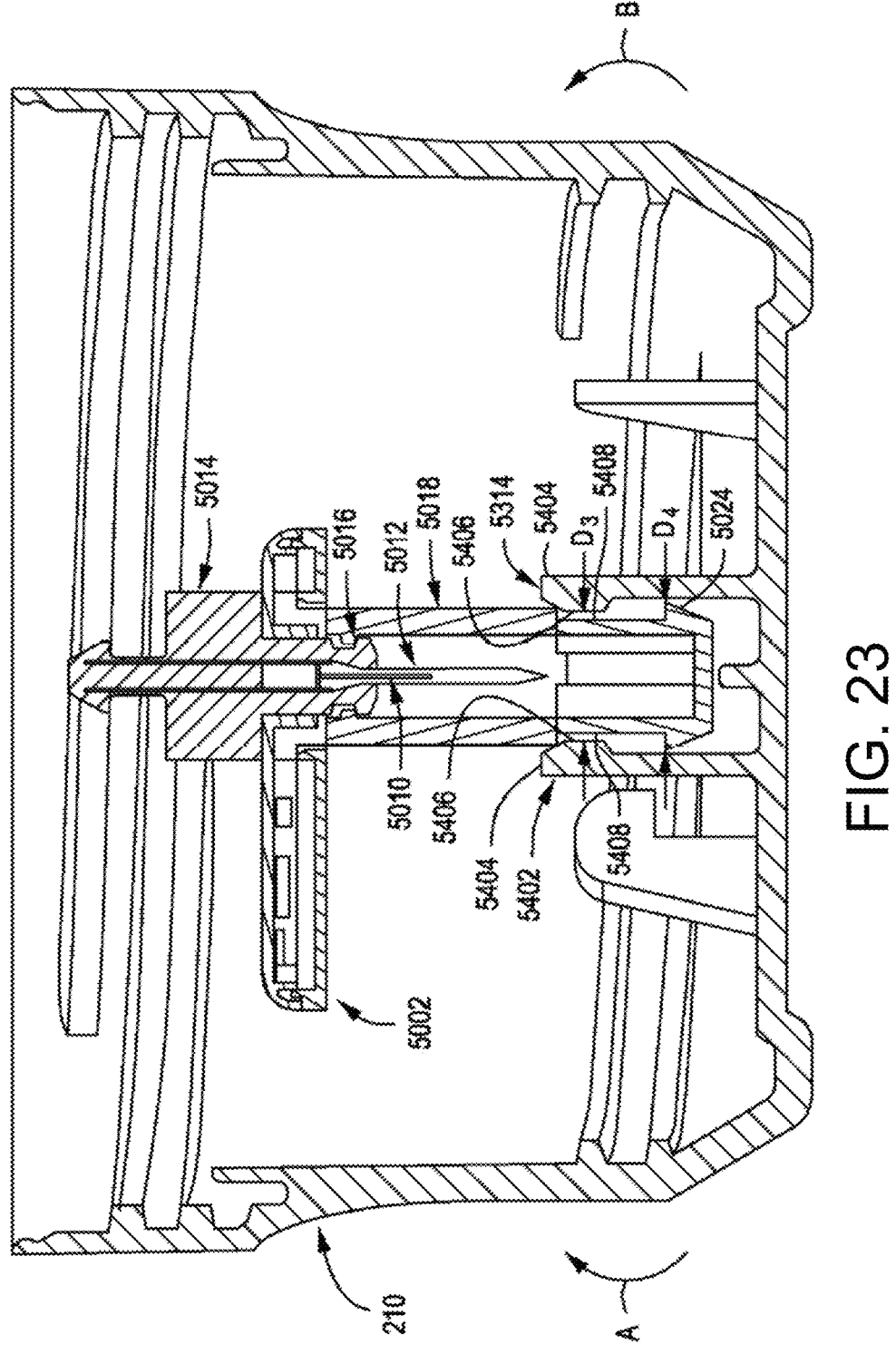
FIG. 23 is a cross-sectional side view of the sensor control device of FIGS. 18A-18B.

FIG. 23 is a cross-sectional side view of the sensor control device 5002 positioned within the applicator cap 210, according to one or more embodiments. As illustrated, the opening to the receiver feature 5402 exhibits a first diameter D3, while the engagement feature 5024 of the sensor cap 5018 exhibits a second diameter D4 that is larger than the first diameter D3 and greater than the outer diameter of the remaining portions of the sensor cap 5018. As the sensor cap 5018 is extended into the cap post 5314, the compliant member(s) 5404 of the receiver feature 5402 may flex (expand) radially outward to receive the engagement feature 5024. In some embodiments, as illustrated, the engagement feature 5024 may provide or otherwise define an angled or frustoconical outer surface that helps bias the compliant member(s) 5404 radially outward. Once the engagement feature 5024 bypasses the receiver feature 5402, the compliant member(s) 5404 are able to flex back to (or towards) their natural state and thus lock the sensor cap 5018 within the cap post 5314.

As the applicator cap 210 is threaded to (screwed onto) the housing 208 (FIGS. 21A-21C) in the first direction A, the cap post 5314 correspondingly rotates in the same direction and the sensor cap 5018 is progressively introduced into the cap post 5314. As the cap post 5314 rotates, the ramped surfaces 5406 of the compliant members 5404 ratchet against the opposing camming surfaces 5408 of the sensor cap 5018. This continues until the applicator cap 210 is fully threaded onto (screwed onto) the housing 208. In some embodiments, the ratcheting action may occur over two full revolutions of the applicator cap 210 before the applicator cap 210 reaches its final position.

To remove the applicator cap 210, the applicator cap 210 is rotated in the second direction B, which correspondingly rotates the cap post 5314 in the same direction and causes the camming surfaces 5408 (i.e., the angled surfaces 5410 of FIGS. 22A-22B) to bind against the ramped surfaces 5406 (i.e., the angled surfaces 5412 of FIGS. 22A-22B). Consequently, continued rotation of the applicator cap 210 in the second direction B causes the sensor cap 5018 to correspondingly rotate in the same direction and thereby unthread from the mating member 5016 to allow the sensor cap 5018 to detach from the sensor control device 5002. Detaching the sensor cap 5018 from the sensor control device 5002 exposes the distal portions of the sensor 5010 and the sharp 5012, and thus places the sensor control device 5002 in position for firing (use).

Figures 24A, 24B:
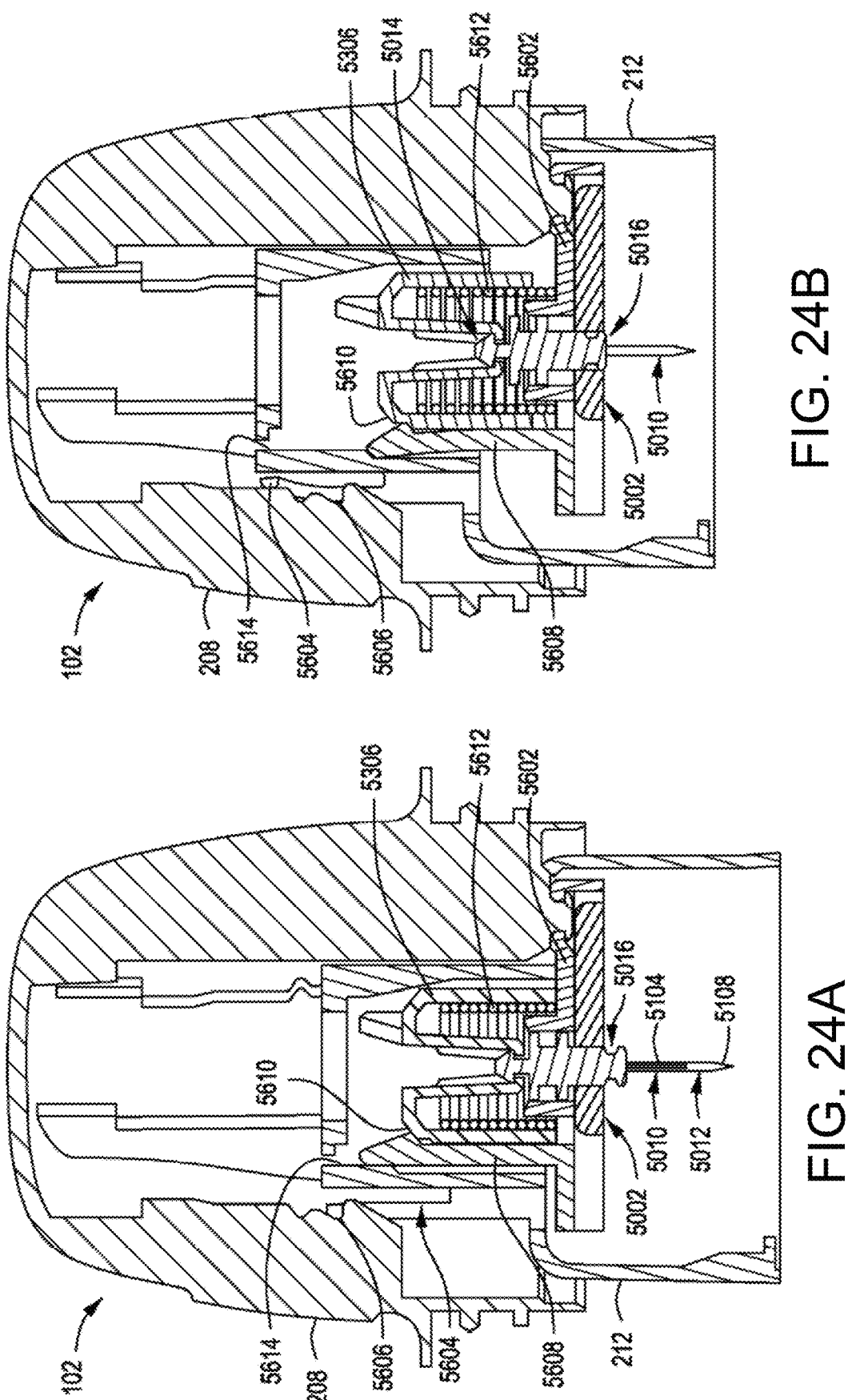
FIGS. 24A and 24B are cross-sectional side views of the sensor applicator ready to deploy the sensor control device to a target monitoring location.

FIGS. 24A and 24B are cross-sectional side views of the sensor applicator 102 ready to deploy the sensor control device 5002 to a target monitoring location, according to one or more embodiments. More specifically, FIG. 24A depicts the sensor applicator 102 ready to deploy (fire) the sensor control device 5002, and FIG. 24B depicts the sensor applicator 102 in the process of deploying (firing) the sensor control device 5002. As illustrated, the applicator cap 210 (FIGS. 21A-21C and 55) has been removed, which correspondingly detaches (removes) the sensor cap 5018 (FIGS. 21A-21C and 55 and thereby exposes the tail 5104 of the sensor 5010 and the sharp tip 5108 of the sharp 5012, as described above. In conjunction with the sheath 212 and the sharp carrier 5306, the sensor applicator 102 also includes a sensor carrier 5602 (alternately referred to as a "puck" carrier) that helps position and secure the sensor control device 5002 within the sensor applicator 102.

Referring first to FIG. 24A, as illustrated, the sheath 212 includes one or more sheath arms 5604 (one shown) configured to interact with a corresponding one or more detents 5606 (one shown) defined within the interior of the housing 208. The detent(s) 5606 are alternately referred to as "firing" detent(s). When the sensor control device 5002 is initially installed in the sensor applicator 102, the sheath arms 5604 may be received within the detents 5606, which places the sensor applicator 102 in firing position. In the firing position, the mating member 5016 extends distally beyond the bottom of the sensor control device 5002. As discussed below, the process of firing the sensor applicator 102 causes the mating member 5016 to retract so that it does not contact the user's skin.

The sensor carrier 5602 may also include one or more carrier arms 5608 (one shown) configured to interact with a corresponding one or more grooves 5610 (one shown) defined on the sharp carrier 5306. A spring 5612 may be arranged within a cavity defined by the sharp carrier 5306 and may passively bias the sharp carrier 5306 upward within the housing 208. When the carrier arm(s) 5608 are properly received within the groove(s) 5610, however, the sharp carrier 5306 is maintained in position and prevented from moving upward. The carrier arm(s) 5608 interpose the sheath 212 and the sharp carrier 5306, and a radial shoulder 5614 defined on the sheath 212 may be sized to maintain the carrier arm(s) 5608 engaged within the groove(s) 5610 and thereby maintain the sharp carrier 5306 in position.

In FIG. 24B, the sensor applicator 102 is in the process of firing. As discussed herein with reference to FIGS. 3F-3G, this may be accomplished by advancing the sensor applicator 102 toward a target monitoring location until the sheath 212 engages the skin of the user. Continued pressure on the sensor applicator 102 against the skin may cause the sheath arm(s) 5604 to disengage from the corresponding detent(s) 5606, which allows the sheath 212 to collapse into the housing 208. As the sheath 212 starts to collapse, the radial shoulder 5614 eventually moves out of radial engagement with the carrier arm(s) 5608, which allows the carrier arm(s) 5608 to disengage from the groove(s) 5610. The passive spring force of the spring 5612 is then free to push upward on the sharp carrier 5306 and thereby force the carrier arm(s) 5608 out of engagement with the groove(s) 5610, which allows the sharp carrier 5306 to move slightly upward within the housing 208. In some embodiments, fewer coils may be incorporated into the design of the spring 5612 to increase the spring force necessary to overcome the engagement between carrier arm(s) 5608 and the groove(s) 5610. In at least one embodiment, one or both of the carrier arm(s) 5608 and the groove(s) 5610 may be angled to help ease disengagement.

As the sharp carrier 5306 moves upward within the housing 208, the sharp hub 5014 may correspondingly move in the same direction, which may cause partial retraction of the mating member 5016 such that it becomes flush, substantially flush, or sub-flush with the bottom of the sensor control device 5002. As will be appreciated, this ensures that the mating member 5016 does not come into contact with the user's skin, which might otherwise adversely impact sensor insertion, cause excessive pain, or prevent the adhesive patch (not shown) positioned on the bottom of the sensor control device 5002 from properly adhering to the skin.

Figure 25B:
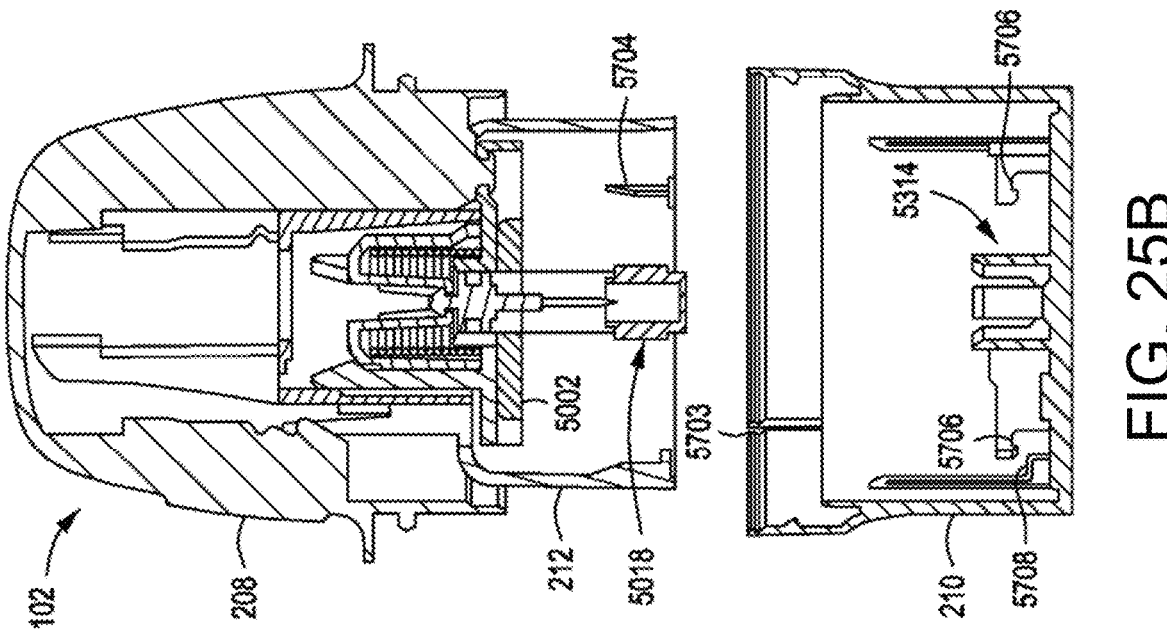
FIGS. 25A-25C are progressive cross-sectional side views showing assembly and disassembly of an example embodiment of the sensor applicator with the sensor control device of FIGS. 18A-18B.
Figure 25A:
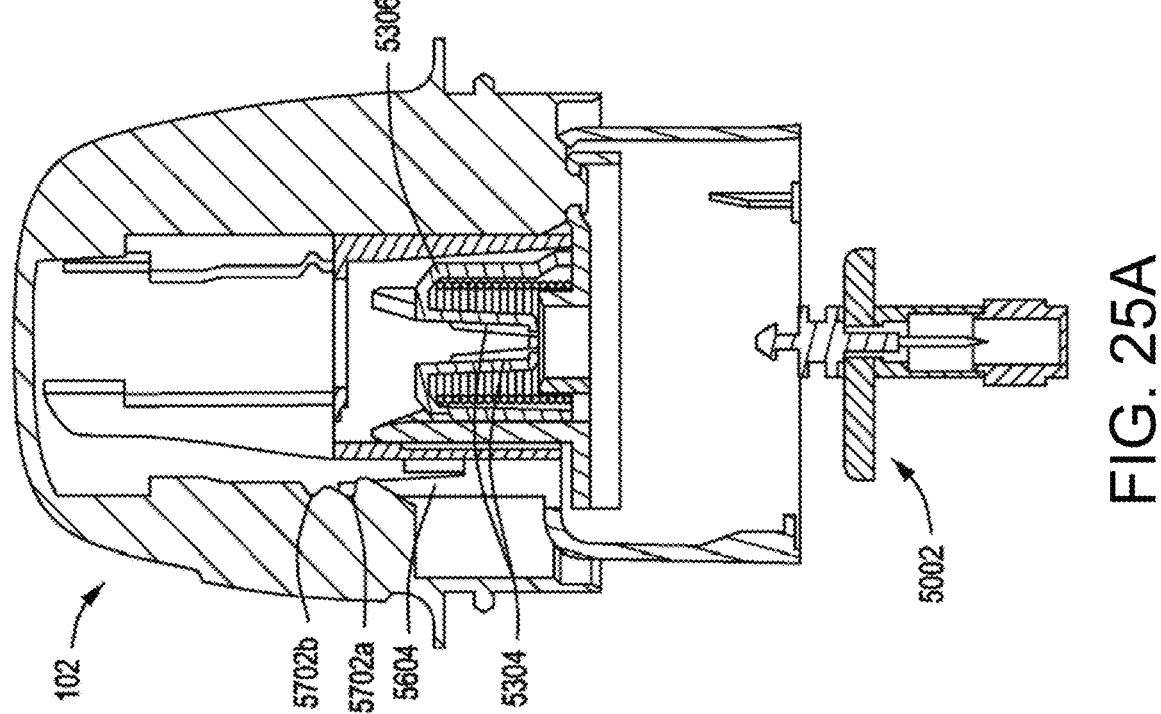
Figure 25C:
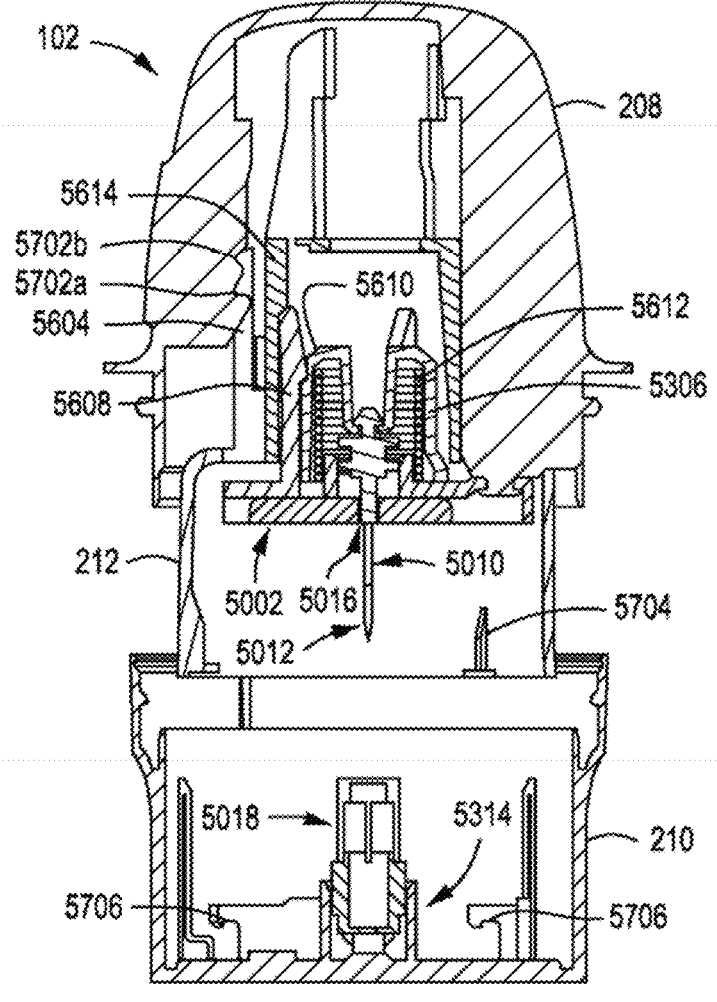

FIGS. 25A-25C are progressive cross-sectional side views showing assembly and disassembly of an alternative embodiment of the sensor applicator 102 with the sensor control device 5002, according to one or more additional embodiments. A fully assembled sensor control device 5002 may be loaded into the sensor applicator 102 by coupling the hub snap pawl 5302 into the arms 5304 of the sharp carrier 5306 positioned within the sensor applicator 102, as generally described above.

In the illustrated embodiment, the sheath arms 5604 of the sheath 212 may be configured to interact with a first detent 5702a and a second detent 5702b defined within the interior of the housing 208. The first detent 5702a may alternately be referred to a "locking" detent, and the second detent 5702b may alternately be referred to as a "firing" detent. When the sensor control device 5002 is initially installed in the sensor applicator 102, the sheath arms 5604 may be received within the first detent 5702a. As discussed below, the sheath 212 may be actuated to move the sheath arms 5604 to the second detent 5702b, which places the sensor applicator 102 in firing position.

In FIG. 25B, the applicator cap 210 is aligned with the housing 208 and advanced toward the housing 208 so that the sheath 212 is received within the applicator cap 210. Instead of rotating the applicator cap 210 relative to the housing 208, the threads of the applicator cap 210 may be snapped onto the corresponding threads of the housing 208 to couple the applicator cap 210 to the housing 208. Axial cuts or slots 5703 (one shown) defined in the applicator cap 210 may allow portions of the applicator cap 210 near its threading to flex outward to be snapped into engagement with the threading of the housing 208. As the applicator cap 210 is snapped to the housing 208, the sensor cap 5018 may correspondingly be snapped into the cap post 5314.

Similar to the embodiment of FIGS. 21A-21C, the sensor applicator 102 may include a sheath locking mechanism configured to ensure that the sheath 212 does not prematurely collapse during a shock event. In the illustrated embodiment, the sheath locking mechanism includes one or more ribs 5704 (one shown) defined near the base of the sheath 212 and configured to interact with one or more ribs 5706 (two shown) and a shoulder 5708 defined near the base of the applicator cap 210. The ribs 5704 may be configured to inter-lock between the ribs 5706 and the shoulder 5708 while attaching the applicator cap 210 to the housing 208. More specifically, once the applicator cap 210 is snapped onto the housing 208, the applicator cap 210 may be rotated (e.g., clockwise), which locates the ribs 5704 of the sheath 212 between the ribs 5706 and the shoulder 5708 of the applicator cap 210 and thereby "locks" the applicator cap 210 in place until the user reverse rotates the applicator cap 210 to remove the applicator cap 210 for use. Engagement of the ribs 5704 between the ribs 5706 and the shoulder 5708 of the applicator cap 210 may also prevent the sheath 212 from collapsing prematurely.

In FIG. 25C, the applicator cap 210 is removed from the housing 208. As with the embodiment of FIGS. 21A-21C, the applicator cap 210 can be removed by reverse rotating the applicator cap 210, which correspondingly rotates the cap post 5314 in the same direction and causes sensor cap 5018 to unthread from the mating member 5016, as generally described above. Moreover, detaching the sensor cap 5018 from the sensor control device 5002 exposes the distal portions of the sensor 5010 and the sharp 5012.

As the applicator cap 210 is unscrewed from the housing 208, the ribs 5704 defined on the sheath 212 may slidingly engage the tops of the ribs 5706 defined on the applicator cap 210. The tops of the ribs 5706 may provide corresponding ramped surfaces that result in an upward displacement of the sheath 212 as the applicator cap 210 is rotated, and moving the sheath 212 upward causes the sheath arms 5604 to flex out of engagement with the first detent 5702a to be received within the second detent 5702b. As the sheath 212 moves to the second detent 5702b, the radial shoulder 5614 moves out of radial engagement with the carrier arm(s) 5608, which allows the passive spring force of the spring 5612 to push upward on the sharp carrier 5306 and force the carrier arm(s) 5608 out of engagement with the groove(s) 5610. As the sharp carrier 5306 moves upward within the housing 208, the mating member 5016 may correspondingly retract until it becomes flush, substantially flush, or sub-flush with the bottom of the sensor control device 5002. At this point, the sensor applicator 102 in firing position. Accordingly, in this embodiment, removing the applicator cap 210 correspondingly causes the mating member 5016 to retract.

Figure 26A:
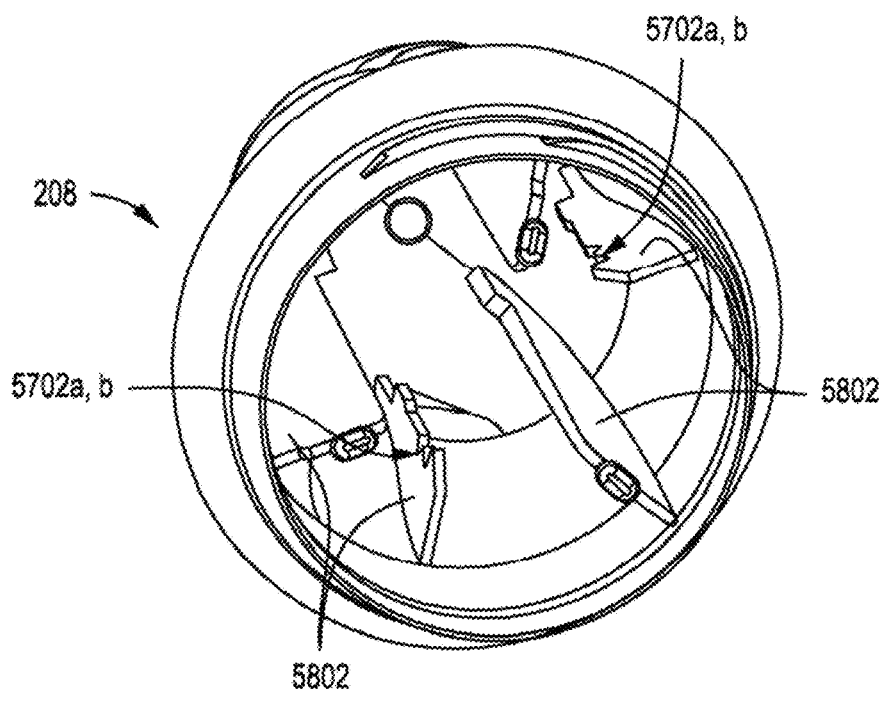
FIG. 26A is an isometric bottom view of the housing, according to one or more embodiments.

FIG. 26A is an isometric bottom view of the housing 208, according to one or more embodiments. As illustrated, one or more longitudinal ribs 5802 (four shown) may be defined within the interior of the housing 208. The ribs 5802 may be equidistantly or non-equidistantly spaced from each other and extend substantially parallel to centerline of the housing 208. The first and second detents 5702a, b may be defined on one or more of the longitudinal ribs 5802.

Figure 27A:
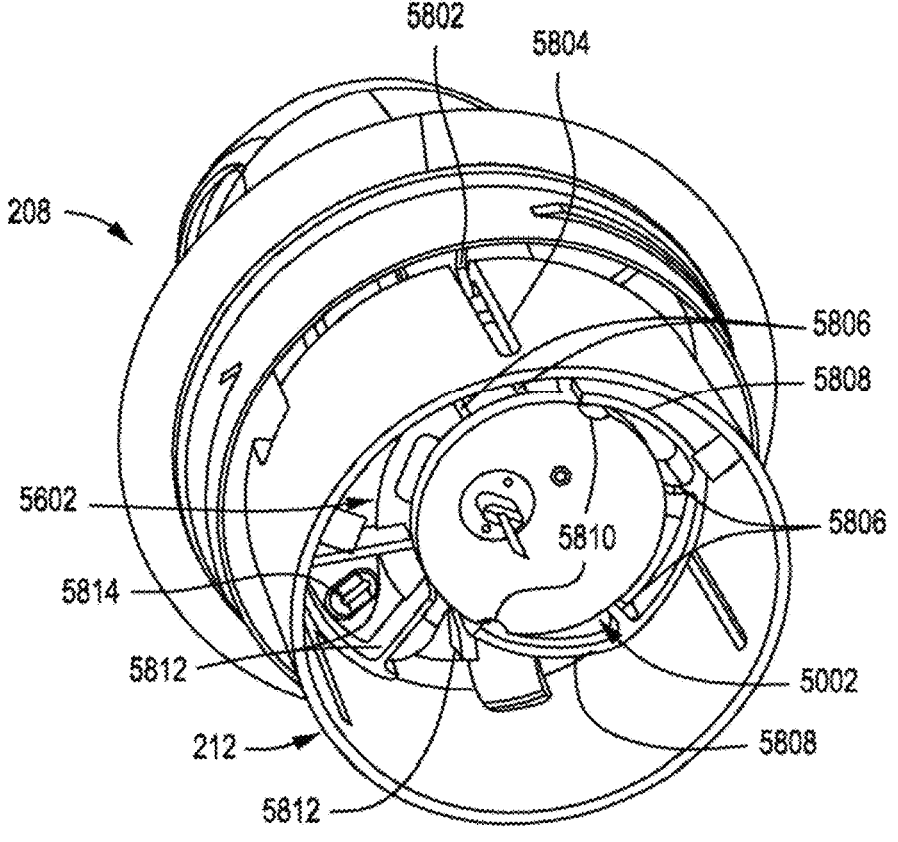
FIG. 27A is an isometric bottom view of the housing with the sheath and other components at least partially positioned therein.

FIG. 27A is an isometric bottom view of the housing 208 with the sheath 212 and other components at least partially positioned within the housing 208. As illustrated, the sheath 212 may provide or otherwise define one or more longitudinal slots 5804 configured to mate with the longitudinal ribs 5802 of the housing 208. As the sheath 212 collapses into the housing 208, as generally described above, the ribs 5802 may be received within the slots 5804 to help maintain the sheath 212 aligned with the housing during its movement. As will be appreciated, this may result in tighter circumferential and radial alignment within the same dimensional and tolerance restrictions of the housing 208.

In the illustrated embodiment, the sensor carrier 5602 may be configured to hold the sensor control device 5002 in place both axially (e.g., once the sensor cap 5018 is removed) and circumferentially. To accomplish this, the sensor carrier 5602 may include or otherwise define one or more support ribs 5806 and one or more flexible arms 5808. The support ribs 5806 extend radially inward to provide radial support to the sensor control device 5002. The flexible arms 5808 extend partially about the circumference of the sensor control device 5002 and the ends of the flexible arms 5808 may be received within corresponding grooves 5810 defined in the side of the sensor control device 5002. Accordingly, the flexible arms 5808 may be able to provide both axial and radial support to the sensor control device 5002. In at least one embodiment, the ends of the flexible arms 5808 may be biased into the grooves 5810 of the sensor control device 5002 and otherwise locked in place with corresponding sheath locking ribs 5812 provided by the sheath 212.

In some embodiments, the sensor carrier 5602 may be ultrasonically welded to the housing 208 at one or more points 5814. In other embodiments, however, the sensor carrier 5602 may alternatively be coupled to the housing 208 via a snap-fit engagement, without departing from the scope of the disclosure. This may help hold the sensor control device 5002 in place during transport and firing.

Figure 28:
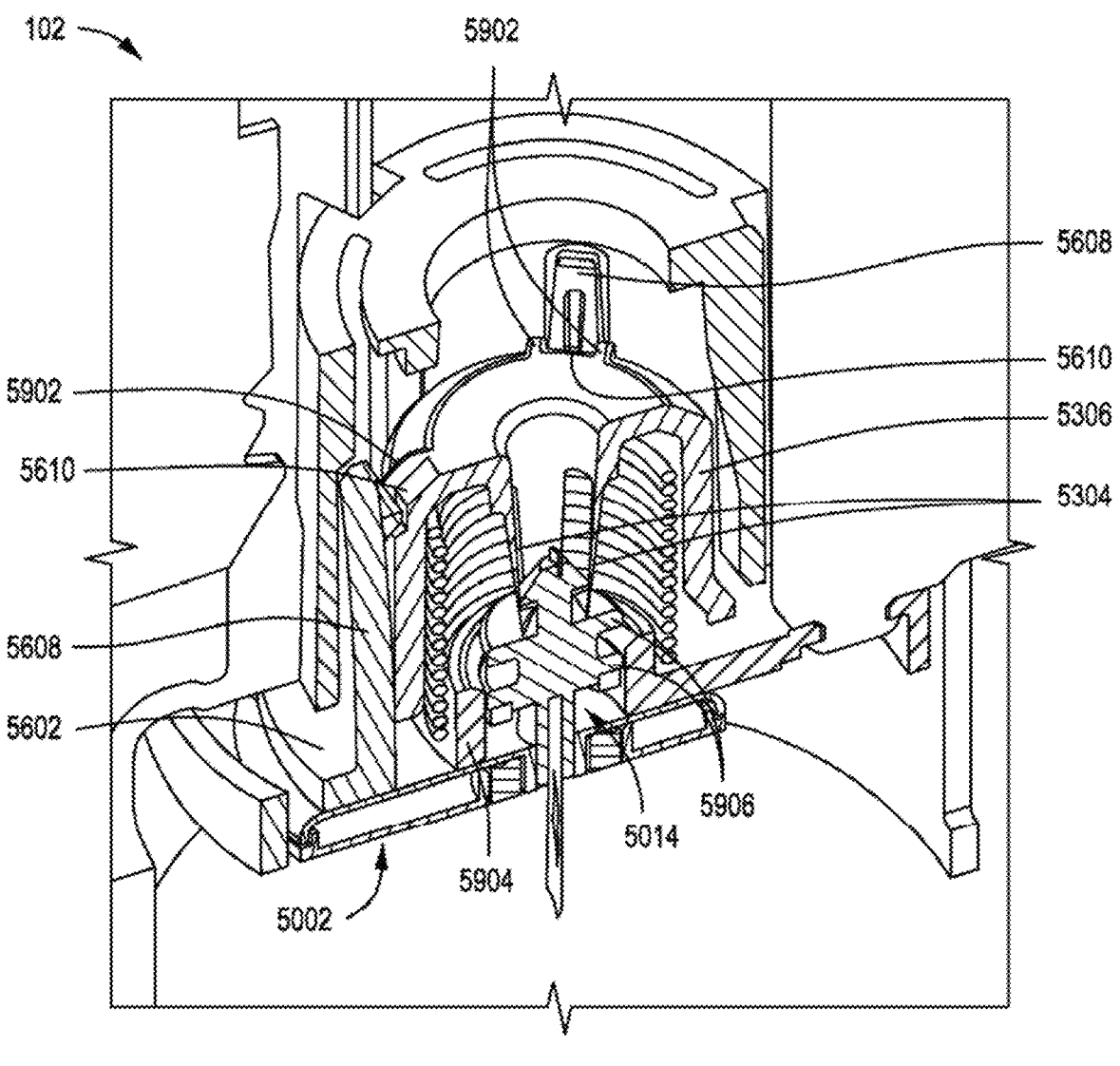
FIG. 28 is an enlarged cross-sectional side view of the sensor applicator with the sensor control device installed therein, according to one or more embodiments.

FIG. 28 is an enlarged cross-sectional side view of the sensor applicator 102 with the sensor control device 5002 installed therein, according to one or more embodiments. As discussed above, the sensor carrier 5602 may include one or more carrier arms 5608 (two shown) engageable with the sharp carrier 5306 at corresponding grooves 5610. In at least one embodiment, the grooves 5610 may be defined by pairs of protrusions 5902 defined on the sharp carrier 5306. Receiving the carrier arms 5608 within the grooves 5610 may help stabilize the sharp carrier 5306 from unwanted tilting during all stages of retraction (firing).

In the illustrated embodiment, the arms 5304 of the sharp carrier 5306 may be stiff enough to control, with greater refinement, radial and bi-axial motion of the sharp hub 5014. In some embodiments, for example, clearances between the sharp hub 5014 and the arms 5304 may be more restrictive in both axial directions as the relative control of the height of the sharp hub 5014 may be more critical to the design.

In the illustrated embodiment, the sensor carrier 5602 defines or otherwise provides a central boss 5904 sized to receive the sharp hub 5014. In some embodiments, as illustrated, the sharp hub 5014 may provide one or more radial ribs 5906 (two shown). In at least one embodiment, the inner diameter of the central boss 5904 helps provide radial and tilt support to the sharp hub 5014 during the life of sensor applicator 102 and through all phases of operation and assembly. Moreover, having multiple radial ribs 5906 increases the length-to-width ratio of the sharp hub 5014, which also improves support against tilting.

Figure 29A:
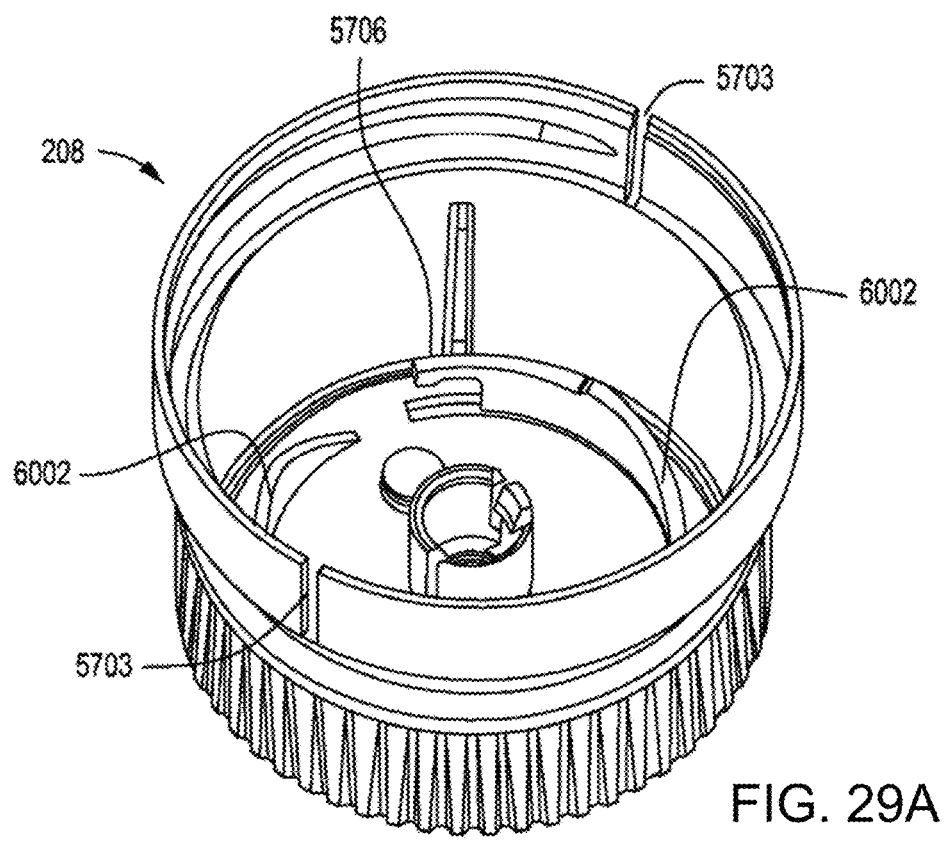
FIG. 29A is an isometric top view of the cap, according to one or more embodiments.

FIG. 29A is an isometric top view of the applicator cap 210, according to one or more embodiments. In the illustrated embodiment, two axial slots 5703 are depicted that separate upper portions of the applicator cap 210 near its threading. As mentioned above, the slots 5703 may help the applicator cap 210 flex outward to be snapped into engagement with the housing 208 (FIG. 25B). In contrast, the applicator cap 210 may be twisted (unthreaded) off the housing 208 by an end user.

FIG. 29A also depicts the ribs 5706 (one visible) defined by the applicator cap 210. By interlocking with the ribs 5704 (FIG. 25C) defined on the sheath 212 (FIG. 25C), the ribs 5706 may help lock the sheath 212 in all directions to prevent premature collapse during a shock or drop event. The sheath 212 may be unlocked when the user unscrews the applicator cap 210 from the housing, as generally described above. As mentioned herein, the top of each rib 5706 may provide a corresponding ramped surface 6002, and as the applicator cap 210 is rotated to unthread from the housing 208, the ribs 5704 defined on the sheath 212 may slidingly engage the ramped surfaces 6002, which results in the upward displacement of the sheath 212 into the housing 208.

In some embodiments, additional features may be provided within the interior of the applicator cap 210 to hold a desiccant component that maintains proper moisture levels through shelf life. Such additional features may be snaps, posts for press-fitting, heat-staking, ultrasonic welding, etc.

Figure 29B:
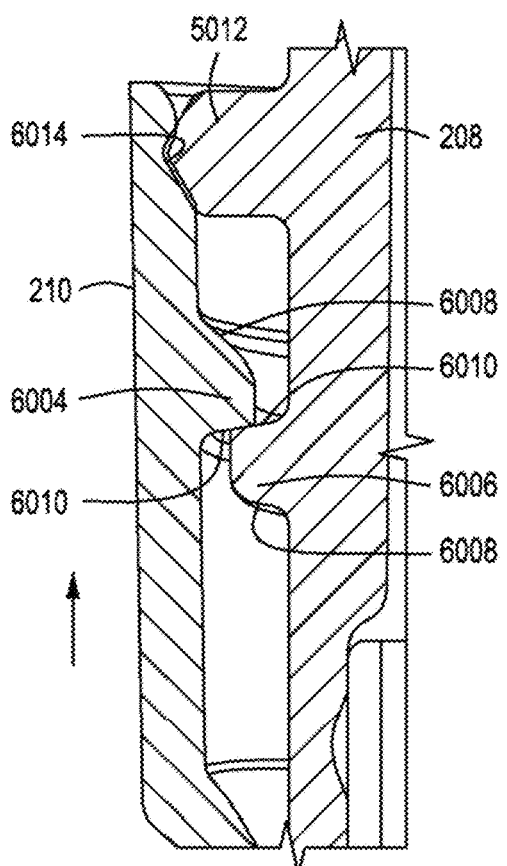
FIG. 29B is an enlarged cross-sectional view of the engagement between the cap and the housing, according to one or more embodiments.

FIG. 29B is an enlarged cross-sectional view of the engagement between the applicator cap 210 and the housing 208, according to one or more embodiments. As illustrated, the applicator cap 210 may define a set of inner threads 6004 and the housing 208 may define a set of outer threads 6006 engageable with the inner threads 6004. As mentioned herein, the applicator cap 210 may be snapped onto the housing 208, which may be accomplished by advancing the inner threads 6004 axially past the outer threads 6006 in the direction indicated by the arrow, which causes the applicator cap 210 to flex outward. To help ease this transition, as illustrated, corresponding surfaces 6008 of the inner and outer threads 6004, 6006 may be curved, angled, or chamfered. Corresponding flat surfaces 6010 may be provided on each thread 6004, 6006 and configured to matingly engage once the applicator cap 210 is properly snapped into place on the housing 208. The flat surfaces 6010 may slidingly engage one another as the user unthreads the applicator cap 210 from the housing 208.

The threaded engagement between the applicator cap 210 and the housing 208 results in a sealed engagement that protects the inner components against moisture, dust, etc. In some embodiments, the housing 208 may define or otherwise provide a stabilizing feature 6012 configured to be received within a corresponding groove 1914 defined on the applicator cap 210. The stabilizing feature 6012 may help stabilize and stiffen the applicator cap 210 once the applicator cap 210 is snapped onto the housing 208. This may prove advantageous in providing additional drop robustness to the sensor applicator 102. This may also help increase the removal torque of the applicator cap 210.

Figure 30A:
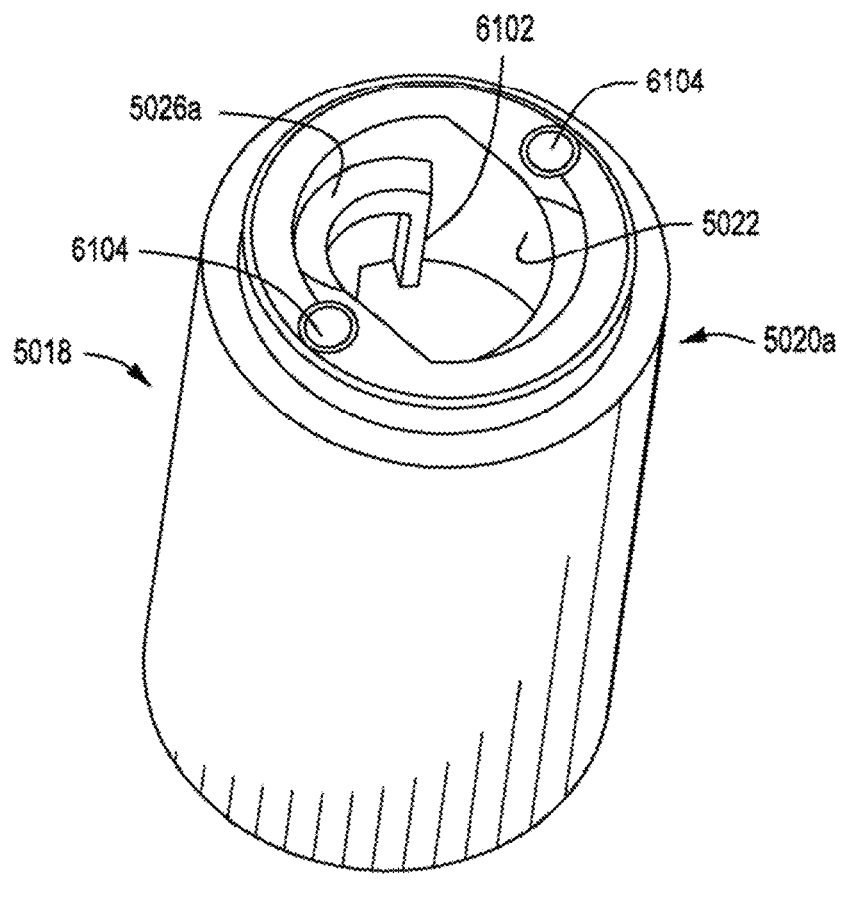
FIGS. 30A and 30B are isometric views of the sensor cap and the collar, respectively, according to one or more embodiments.
Figure 30B:
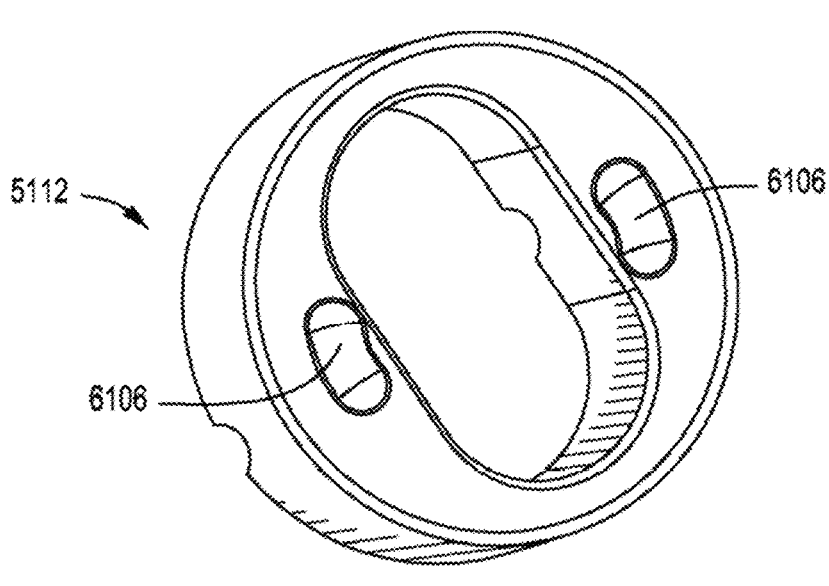

FIGS. 30A and 30B are isometric views of the sensor cap 5018 and the collar 5112, respectively, according to one or more embodiments. Referring to FIG. 30A, in some embodiments, the sensor cap 5018 may comprise an injection molded part. This may prove advantageous in molding the internal threads 5026a defined within the inner chamber 5022, as opposed to installing a threaded core or threading the inner chamber 5022. In some embodiments, one or more stop ribs 6102 (on visible) may be defined within the inner chamber 5022 to prevent over travel relative to mating member 5016 of the sharp hub 5014 (FIGS. 18A-18B).

Referring to both FIGS. 30A and 30B, in some embodiments, one or more protrusions 6104 (two shown) may be defined on the first end 5020a of the sensor cap 5018 and configured to mate with one or more corresponding indentations 6106 (two shown) defined on the collar 5112. In other embodiments, however, the protrusions 6104 may instead be defined on the collar 5112 and the indentations 6106 may be defined on the sensor cap 5018, without departing from the scope of the disclosure.

The matable protrusions 6104 and indentations 6106 may prove advantageous in rotationally locking the sensor cap 5018 to prevent unintended unscrewing of the sensor cap 5018 from the collar 5112 (and thus the sensor control device 5002) during the life of the sensor applicator 102 and through all phases of operation/assembly. In some embodiments, as illustrated, the indentations 6106 may be formed or otherwise defined in the general shape of a kidney bean. This may prove advantageous in allowing for some over-rotation of the sensor cap 5018 relative to the collar 5112. Alternatively, the same benefit may be achieved via a flat end threaded engagement between the two parts.

Embodiments disclosed herein include:

A. A sensor control device that includes an electronics housing, a sensor arranged within the electronics housing and having a tail extending from a bottom of the electronics housing, a sharp extending through the electronics housing and having a sharp tip extending from the bottom of the electronics housing, and a sensor cap removably coupled at the bottom of the electronics housing and defining a sealed inner chamber that receives the tail and the sharp.

B. An analyte monitoring system that includes a sensor applicator, a sensor control device positioned within the sensor applicator and including an electronics housing, a sensor arranged within the electronics housing and having a tail extending from a bottom of the electronics housing, a sharp extending through the electronics housing and having a sharp tip extending from the bottom of the electronics housing, and a sensor cap removably coupled at the bottom of the electronics housing and defining an engagement feature and a sealed inner chamber that receives the tail and the sharp. The analyte monitoring system may further include a cap coupled to the sensor applicator and providing a cap post defining a receiver feature that receives the engagement feature upon coupling the cap to the sensor applicator, wherein removing the cap from the sensor applicator detaches the sensor cap from the electronics housing and thereby exposes the tail and the sharp tip.

C. A method of preparing an analyte monitoring system that includes loading a sensor control device into a sensor applicator, the sensor control device including an electronics housing, a sensor arranged within the electronics housing and having a tail extending from a bottom of the electronics housing, a sharp extending through the electronics housing and having a sharp tip extending from the bottom of the electronics housing, and a sensor cap removably coupled at the bottom of the electronics housing and defining a sealed inner chamber that receives the tail and the sharp. The method further including securing a cap to the sensor applicator, sterilizing the sensor control device with gaseous chemical sterilization while the sensor control device is positioned within the sensor applicator, and isolating the tail and the sharp tip within the inner chamber from the gaseous chemical sterilization.

Each of embodiments A, B, and C may have one or more of the following additional elements in any combination: Element 1: wherein the sensor cap comprises a cylindrical body having a first end that is open to access the inner chamber, and a second end opposite the first end and providing an engagement feature engageable with a cap of a sensor applicator, wherein removing the cap from the sensor applicator correspondingly removes the sensor cap from the electronics housing and thereby exposes the tail and the sharp tip. Element 2: wherein the electronics housing includes a shell matable with a mount, the sensor control device further comprising a sharp and sensor locator defined on an inner surface of the shell, and a collar received about the sharp and sensor locator, wherein the sensor cap is removably coupled to the collar. Element 3: wherein the sensor cap is removably coupled to the collar by one or more of an interference fit, a threaded engagement, a frangible member, and a frangible substance. Element 4: wherein an annular ridge circumscribes the sharp and sensor locator and the collar provides a column and an annular shoulder extending radially outward from the column, and wherein a seal member interposes the annular shoulder and the annular ridge to form a sealed interface. Element 5: wherein the annular ridge defines a groove and a portion of the sensor is seated within the groove, and wherein the seal member extends into the groove to seal about the portion of the sensor. Element 6: wherein the seal member is a first seal member, the sensor control device further comprising a second seal member interposing the annular shoulder and a portion of the mount to form a sealed interface. Element 7: wherein the electronics housing includes a shell matable with a mount, the sensor control device further comprising a sharp hub that carries the sharp and is engageable with a top surface of the shell, and a mating member defined by the sharp hub and extending from the bottom of the electronics housing, wherein the sensor cap is removably coupled to the mating member. Element 8: further comprising a collar at least partially receivable within an aperture defined in the mount and sealingly engaging the sensor cap and an inner surface of the shell. Element 9: wherein a seal member interposes the collar and the inner surface of the shell to form a sealed interface. Element 10: wherein the collar defines a groove and a portion of the sensor is seated within the groove, and wherein the seal member extends into the groove to seal about the portion of the sensor.

Element 11: wherein the receiver feature comprises one or more compliant members that flex to receive the engagement feature, and wherein the one or more compliant members prevent the engagement feature from exiting the cap post upon removing the cap from the sensor applicator. Element 12: further comprising a ramped surface defined on at least one of the one or more compliant members, and one or more camming surfaces provided by the engagement feature and engageable with the ramped surface, wherein the ramped surface and the one or more camming surfaces allow the cap and the cap post to rotate relative to the sensor cap in a first direction, but prevent the cap and the cap post from rotating relative to the sensor cap in a second direction opposite the first direction. Element 13: wherein the electronics housing includes a shell matable with a mount, the sensor control device further comprising a sharp hub that carries the sharp and is engageable with a top surface of the shell, and a mating member defined by the sharp hub and extending from the bottom of the electronics housing, wherein the sensor cap is removably coupled to the mating member and rotating the cap in the second direction detaches the sensor cap from the mating member. Element 14: wherein the electronics housing includes a shell matable with a mount and the sensor control device further includes a sharp and sensor locator defined on an inner surface of the shell, and a collar received about the sharp and sensor locator, wherein the sensor cap is removably coupled to the collar.

Element 15: wherein the cap provides a cap post defining a receiver feature and the sensor cap defines an engagement feature, the method further comprising receiving the engagement feature with the receiver feature as the cap is secured to the sensor applicator. Element 16: further comprising removing the cap from the sensor applicator, and engaging the engagement feature on the receiver feature as the cap is being removed and thereby detaching the sensor cap from the electronics housing and exposing the tail and the sharp tip. Element 17: wherein loading the sensor control device into a sensor applicator is preceded by sterilizing the tail and the sharp tip with radiation sterilization, and sealing the tail and the sharp tip within the inner chamber.

By way of non-limiting example, exemplary combinations applicable to A, B, and C include: Element 2 with Element 3; Element 2 with Element 4; Element 4 with Element 5; Element 4 with Element 6; Element 7 with Element 8; Element 8 with Element 9; Element 9 with Element 10; Element 11 with Element 12; and Element 15 with Element 16.

Example Embodiments of Seal Arrangement for Analyte Monitoring Systems

Figure 31A:
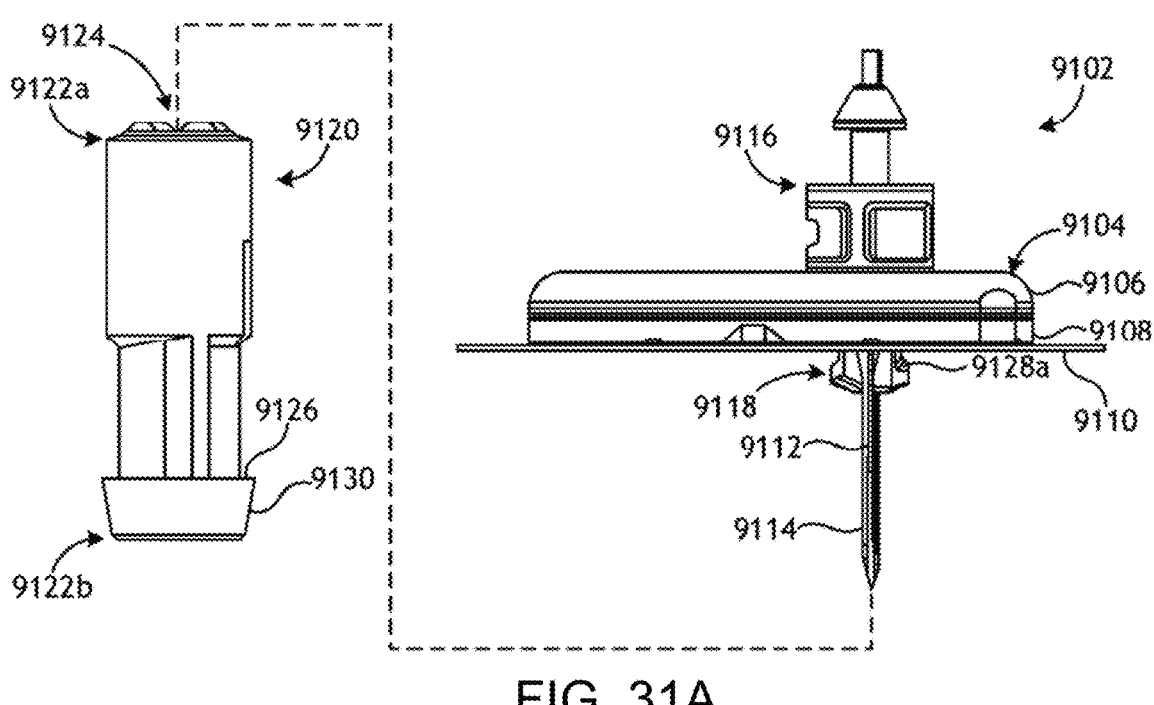
FIGS. 31A and 31B are side and isometric views, respectively, of an example sensor control device, according to one or more embodiments of the present disclosure.
Figure 31B:
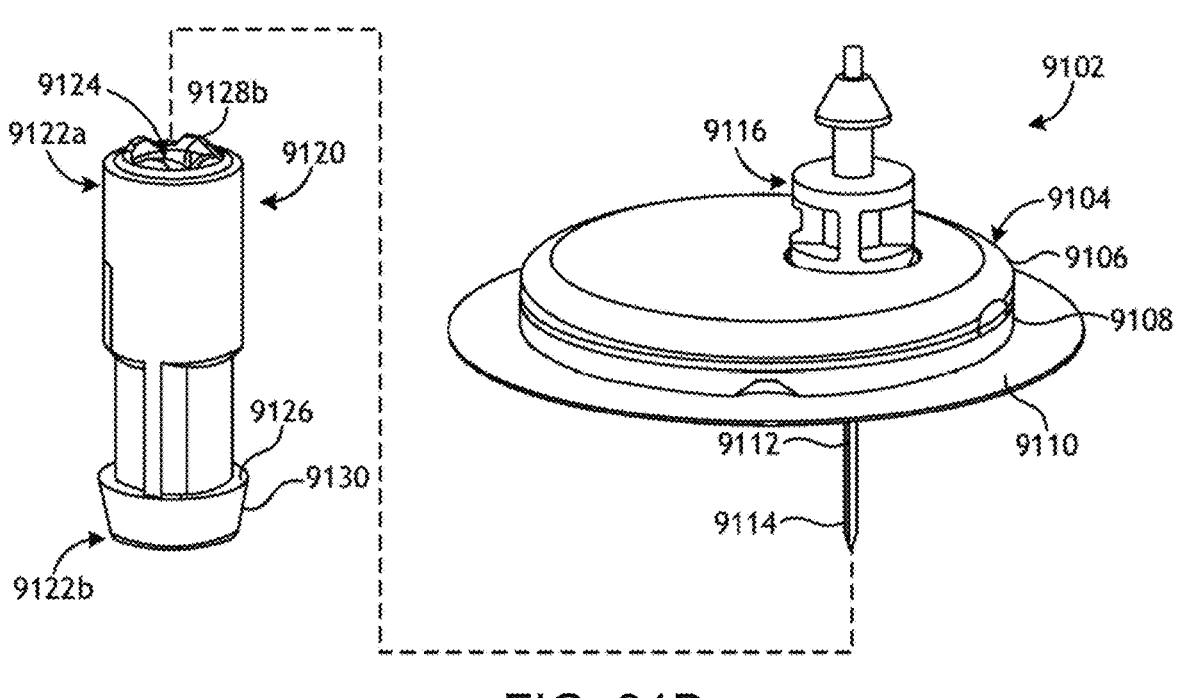

FIGS. 31A and 31B are side and isometric views, respectively, of an example sensor control device 9102, according to one or more embodiments of the present disclosure. The sensor control device 9102 may be similar in some respects to the sensor control device 102 of FIG. 1 and therefore may be best understood with reference thereto. Moreover, the sensor control device 9102 may replace the sensor control device 102 of FIG. 1 and, therefore, may be used in conjunction with the sensor applicator 102 of FIG. 1, which may deliver the sensor control device 9102 to a target monitoring location on a user's skin.

As illustrated, the sensor control device 9102 includes an electronics housing 9104, which may be generally disc-shaped and have a circular cross-section. In other embodiments, however, the electronics housing 9104 may exhibit other cross-sectional shapes, such as ovoid, oval, or polygonal, without departing from the scope of the disclosure. The electronics housing 9104 includes a shell 9106 and a mount 9108 that is matable with the shell 9106. The shell 9106 may be secured to the mount 9108 via a variety of ways, such as a snap fit engagement, an interference fit, sonic welding, laser welding, one or more mechanical fasteners (e.g., screws), a gasket, an adhesive, or any combination thereof. In some cases, the shell 9106 may be secured to the mount 9108 such that a sealed interface is generated therebetween. An adhesive patch 9110 may be positioned on and otherwise attached to the underside of the mount 9108. Similar to the adhesive patch 105 of FIG. 1, the adhesive patch 9110 may be configured to secure and maintain the sensor control device 9102 in position on the user's skin during operation.

The sensor control device 9102 may further include a sensor 9112 and a sharp 9114 used to help deliver the sensor 9112 transcutaneously under a user's skin during application of the sensor control device 9102. Corresponding portions of the sensor 9112 and the sharp 9114 extend distally from the bottom of the electronics housing 9104 (e.g., the mount 9108). A sharp hub 9116 may be overmolded onto the sharp 9114 and configured to secure and carry the sharp 9114. As best seen in FIG. 31A, the sharp hub 9116 may include or otherwise define a mating member 9118. In assembling the sharp 9114 to the sensor control device 9102, the sharp 9114 may be advanced axially through the electronics housing 9104 until the sharp hub 9116 engages an upper surface of the electronics housing 9104 or an internal component thereof and the mating member 9118 extends distally from the bottom of the mount 9108. As described herein below, in at least one embodiment, the sharp hub 9116 may sealingly engage an upper portion of a seal overmolded onto the mount 9108. As the sharp 9114 penetrates the electronics housing 9104, the exposed portion of the sensor 9112 may be received within a hollow or recessed (arcuate) portion of the sharp 9114. The remaining portion of the sensor 9112 is arranged within the interior of the electronics housing 9104.

The sensor control device 9102 may further include a sensor cap 9120, shown detached from the electronics housing 9104 in FIGS. 31A-31B. The sensor cap 9120 may help provide a sealed barrier that surrounds and protects exposed portions of the sensor 9112 and the sharp 9114. As illustrated, the sensor cap 9120 may comprise a generally cylindrical body having a first end 9122a and a second end 9122b opposite the first end 9122a. The first end 9122a may be open to provide access into an inner chamber 9124 defined within the body. In contrast, the second end 9122b may be closed and may provide or otherwise define an engagement feature 9126. As described in more detail below, the engagement feature 9126 may help mate the sensor cap 9120 to an applicator cap of a sensor applicator (e.g., the sensor applicator 102 of FIG. 1), and may help remove the sensor cap 9120 from the sensor control device 9102 upon removing the sensor cap from the sensor applicator.

The sensor cap 9120 may be removably coupled to the electronics housing 9104 at or near the bottom of the mount 9108. More specifically, the sensor cap 9120 may be removably coupled to the mating member 9118, which extends distally from the bottom of the mount 9108. In at least one embodiment, for example, the mating member 9118 may define a set of external threads 9128a (FIG. 31A) matable with a set of internal threads 9128b (FIG. 31B) defined within the inner chamber 9124 of the sensor cap 9120. In some embodiments, the external and internal threads 9128a,b may comprise a flat thread design (e.g., lack of helical curvature), but may alternatively comprise a helical threaded engagement. Accordingly, in at least one embodiment, the sensor cap 9120 may be threadably coupled to the sensor control device 9102 at the mating member 9118 of the sharp hub 9116. In other embodiments, the sensor cap 9120 may be removably coupled to the mating member 9118 via other types of engagements including, but not limited to, an interference or friction fit, or a frangible member or substance (e.g., wax, an adhesive, etc.) that may be broken with minimal separation force (e.g., axial or rotational force).

In some embodiments, the sensor cap 9120 may comprise a monolithic (singular) structure extending between the first and second ends 9122a,b. In other embodiments, however, the sensor cap 9120 may comprise two or more component parts. In the illustrated embodiment, for example, the body of the sensor cap 9120 may include a desiccant cap 9130 arranged at the second end 9122b. The desiccant cap 9130 may house or comprise a desiccant to help maintain preferred humidity levels within the inner chamber 9124. Moreover, the desiccant cap 9130 may also define or otherwise provide the engagement feature 9126 of the sensor cap 9120. In at least one embodiment, the desiccant cap 9130 may comprise an elastomeric plug inserted into the bottom end of the sensor cap 9120.

FIGS. 32A and 32B are exploded, isometric top and bottom views, respectively, of the sensor control device 9102, according to one or more embodiments. The shell 9106 and the mount 9108 operate as opposing clamshell halves that enclose or otherwise substantially encapsulate various electronic components (not shown) of the sensor control device 9102. Example electronic components that may be arranged between the shell 9106 and the mount 9108 include, but are not limited to, a battery, resistors, transistors, capacitors, inductors, diodes, and switches.

The shell 9106 may define a first aperture 9202a and the mount 9108 may define a second aperture 9202b, and the apertures 9202a, b may align when the shell 9106 is properly mounted to the mount 9108. As best seen in FIG. 32A, the mount 9108 may provide or otherwise define a pedestal 9204 that protrudes from the inner surface of the mount 9108 at the second aperture 9202b. The pedestal 9204 may define at least a portion of the second aperture 9202b. Moreover, a channel 9206 may be defined on the inner surface of the mount 9108 and may circumscribe the pedestal 9202. In the illustrated embodiment, the channel 9206 is circular in shape, but could alternatively be another shape, such as oval, ovoid, or polygonal.

The mount 9108 may comprise a molded part made of a rigid material, such as plastic or metal. In some embodiments, a seal 9208 may be overmolded onto the mount 9108 and may be made of an elastomer, rubber, a-polymer, or another pliable material suitable for facilitating a sealed interface. In embodiments where the mount 9108 is made of a plastic, the mount 9108 may be molded in a first "shot" of injection molding, and the seal 9208 may be overmolded onto the mount 9108 in a second "shot" of injection molding. Accordingly, the mount 9108 may be referred to or otherwise characterized as a "two-shot mount."

In the illustrated embodiment, the seal 9208 may be overmolded onto the mount 9108 at the pedestal 9204 and also on the bottom of the mount 9108. More specifically, the seal 9208 may define or otherwise provide a first seal element 9210a overmolded onto the pedestal 9204, and a second seal element 9210b (FIG. 32B) interconnected to (with) the first seal element 9210a and overmolded onto the mount 9108 at the bottom of the mount 9108. In some embodiments, one or both of the seal elements 9210a,b may help form corresponding portions (sections) of the second aperture 9202b. While the seal 9208 is described herein as being overmolded onto the mount 9108, it is also contemplated herein that one or both of the seal elements 9210a,b may comprise an elastomeric component part independent of the mount 9208, such as an O-ring or a gasket.

The sensor control device 9102 may further include a collar 9212, which may be a generally annular structure that defines a central aperture 9214. The central aperture 9214 may be sized to receive the first seal element 9210a and may align with both the first and second apertures 9202a, b when the sensor control device 9102 is properly assembled. The shape of the central aperture 9214 may generally match the shape of the second aperture 9202b and the first seal element 9210a.

In some embodiments, the collar 9212 may define or otherwise provide an annular lip 9216 on its bottom surface. The annular lip 9216 may be sized and otherwise configured to mate with or be received into the channel 9206 defined on the inner surface of the mount 9108. In some embodiments, a groove 9218 may be defined on the annular lip 9216 and may be configured to accommodate or otherwise receive a portion of the sensor 9112 extending laterally within the mount 9108. In some embodiments, the collar 9212 may further define or otherwise provide a collar channel 9220 (FIG. 32A) on its upper surface sized to receive and otherwise mate with an annular ridge 9222 (FIG. 32B) defined on the inner surface of the shell 9106 when the sensor control device 9102 is properly assembled.

The sensor 9112 may include a tail 9224 that extends through the second aperture 9202*b* defined in the mount 9108 to be transcutaneously received beneath a user's skin. The tail 9224 may have an enzyme or other chemistry included thereon to help facilitate analyte monitoring. The sharp 9114 may include a sharp tip 9226 extendable through the first aperture 9202*a* defined by the shell 9106. As the sharp tip 9226 penetrates the electronics housing 9104, the tail 9224 of the sensor 9112 may be received within a hollow or recessed portion of the sharp tip 9226. The sharp tip 9226 may be configured to penetrate the skin while carrying the tail 9224 to put the active chemistry of the tail 9224 into contact with bodily fluids.

The sensor control device 9102 may provide a sealed subassembly that includes, among other component parts, portions of the shell 9106, the sensor 9112, the sharp 9114, the seal 9208, the collar 9212, and the sensor cap 9120. The sealed subassembly may help isolate the sensor 9112 and the sharp 9114 within the inner chamber 9124 (FIG. 32A) of the sensor cap 9120. In assembling the sealed subassembly, the sharp tip 9226 is advanced through the electronics housing 9104 until the sharp hub 9116 engages the seal 9208 and, more particularly, the first seal element 9210*a*. The mating member 9118 provided at the bottom of the sharp hub 9116 may extend out the second aperture 9202*b* in the bottom of the mount 9108, and the sensor cap 9120 may be coupled to the sharp hub 9116 at the mating member 9118. Coupling the sensor cap 9120 to the sharp hub 9116 at the mating member 9118 may urge the first end 9122*a* of the sensor cap 9120 into sealed engagement with the seal 9208 and, more particularly, into sealed engagement with the second seal element 9210*b* on the bottom of the mount 9108. In some embodiments, as the sensor cap 9120 is coupled to the sharp hub 9116, a portion of the first end 9122*a* of the sensor cap 9120 may bottom out (engage) against the bottom of the mount 9108, and the sealed engagement between the sensor hub 9116 and the first seal element 9210*a* may be able to assume any tolerance variation between features.

FIG. 33 is a cross-sectional side view of the sensor control device 9102, according to one or more embodiments. As indicated above, the sensor control device 9102 may include or otherwise incorporate a sealed subassembly 9302, which may be useful in isolating the sensor 9112 and the sharp 9114 within the inner chamber 9124 of the sensor cap 9120. To assemble the sealed subassembly 9302, the sensor 9112 may be located within the mount 9108 such that the tail 9224 extends through the second aperture 9202*b* at the bottom of the mount 9108. In at least one embodiment, a locating feature 9304 may be defined on the inner surface of the mount 9108, and the sensor 9112 may define a groove 9306 that is matable with the locating feature 9304 to properly locate the sensor 9112 within the mount 9108.

Once the sensor 9112 is properly located, the collar 9212 may be installed on the mount 9108. More specifically, the collar 9212 may be positioned such that the first seal element 9210*a* of the seal 9208 is received within the central aperture 9214 defined by the collar 9212 and the first seal element 9210*a* generates a radial seal against the collar 9212 at the central aperture 9214. Moreover, the annular lip 9216 defined on the collar 9212 may be received within the channel 9206 defined on the mount 9108, and the groove 9218 defined through the annular lip 9216 may be aligned to receive the portion of the sensor 9112 that traverses the channel 9206 laterally within the mount 9108. In some embodiments, an adhesive may be injected into the channel 9206 to secure the collar 9212 to the mount 9108. The adhesive may also facilitate a sealed interface between the two components and generate a seal around the sensor 9112 at the groove 9218, which may isolate the tail 9224 from the interior of the electronics housing 9104.

The shell 9106 may then be mated with or otherwise coupled to the mount 9108. In some embodiments, as illustrated, the shell 9106 may mate with the mount 9108 via a tongue-and-groove engagement 9308 at the outer periphery of the electronics housing 9104. An adhesive may be injected (applied) into the groove portion of the engagement 9308 to secure the shell 9106 to the mount 9108, and also to create a sealed engagement interface. Mating the shell 9106 to the mount 9108 may also cause the annular ridge 9222 defined on the inner surface of the shell 9106 to be received within the collar channel 9220 defined on the upper surface of the collar 9212. In some embodiments, an adhesive may be injected into the collar channel 9220 to secure the shell 9106 to the collar 9212, and also to facilitate a sealed interface between the two components at that location. When the shell 9106 mates with the mount 9108, the first seal element 9210*a* may extend at least partially through (into) the first aperture 9202*a* defined in the shell 9106.

The sharp 9114 may then be coupled to the sensor control device 9102 by extending the sharp tip 9226 through the aligned first and second apertures 9202*a, b* defined in the shell 9106 and the mount 9108, respectively. The sharp 9114 may be advanced until the sharp hub 9116 engages the seal 9208 and, more particularly, engages the first seal element 9210*a*. The mating member 9118 may extend (protrude) out the second aperture 9202*b* at the bottom of the mount 9108 when the sharp hub 9116 engages the first seal element 9210*a*.

The sensor cap 9120 may then be removably coupled to the sensor control device 9102 by threadably mating the internal threads 9128*b* of the sensor cap 9120 with the external threads 9128*a* of the mating member 9118. The inner chamber 9124 may be sized and otherwise configured to receive the tail 9224 and the sharp tip 9226 extending from the bottom of the mount 9108. Moreover, the inner chamber 9124 may be sealed to isolate the tail 9224 and the sharp tip 9226 from substances that might adversely interact with the chemistry of the tail 9224. In some embodiments, a desiccant (not shown) may be present within the inner chamber 9124 to maintain proper humidity levels.

Tightening (rotating) the mated engagement between the sensor cap 9120 and the mating member 9118 may urge the first end 9122*a* of the sensor cap 9120 into sealed engagement with the second seal element 9210*b* in an axial direction (e.g., along the centerline of the apertures 9202*a, b*), and may further enhance the sealed interface between the sharp hub 9116 and the first seal element 9210*a* in the axial direction. Moreover, tightening the mated engagement between the sensor cap 9120 and the mating member 9118 may compress the first seal element 9210*a*, which may result in an enhanced radial sealed engagement between the first seal element 9210*a* and the collar 9212 at the central aperture 9214. Accordingly, in at least one embodiment, the first seal element 9210*a* may help facilitate axial and radial sealed engagements.

As mentioned above, the first and second seal elements 9210*a,b* may be overmolded onto the mount 9108 and may be physically linked or otherwise interconnected. Consequently, a single injection molding shot may flow through the second aperture 9202b of the mount 9108 to create both ends of the seal 9208. This may prove advantageous in being able to generate multiple sealed interfaces with only a single injection molded shot. An additional advantage of a two-shot molded design, as opposed to using separate elasto-meric components (e.g., O-rings, gaskets, etc.), is that the interface between the first and second shots is a reliable bond rather than a mechanical seal. Hence, the effective number of mechanical sealing barriers is effectively cut in half. Moreover, a two-shot component with a single elastomeric shot also has implications to minimizing the number of two-shot components needed to achieve all the necessary sterile barriers. Once properly assembled, the sealed subas-sembly 9302 may be subjected to a radiation sterilization process to sterilize the sensor 9112 and the sharp 9114. The sealed subassembly 9302 may be subjected to the radiation sterilization prior to or after coupling the sensor cap 9120 to the sharp hub 9116. When sterilized after coupling the sensor cap 9120 to the sharp hub 9116, the sensor cap 9120 may be made of a material that permits the propagation of radiation therethrough. In some embodiments, the sensor cap 9120 may be transparent or translucent, but can other-wise be opaque, without departing from the scope of the disclosure.

Figure 33A:
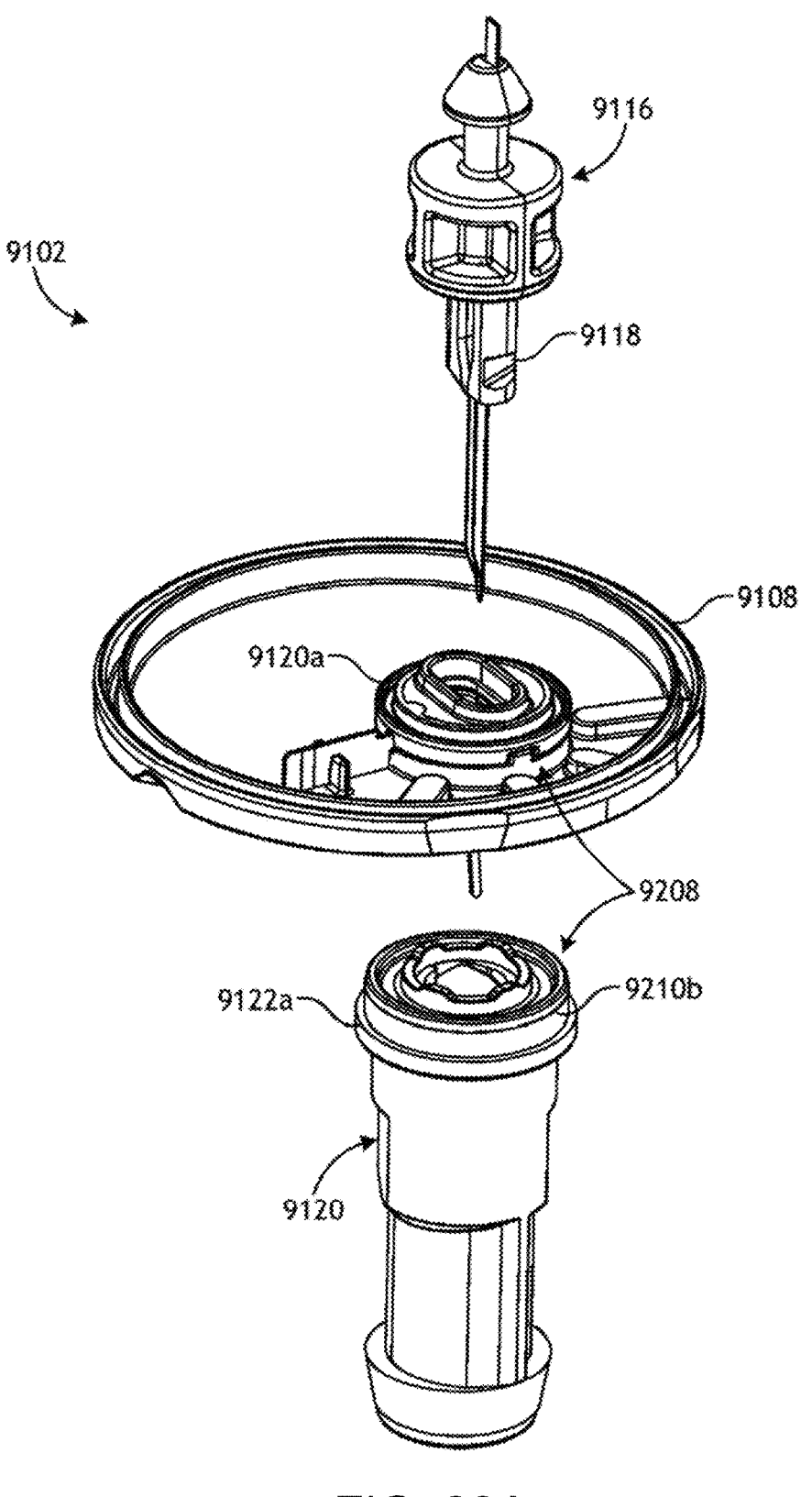
FIG. 33A is an exploded isometric view of a portion of another embodiment of the sensor control device of FIGS. 31A-31B and 32A-32B.

FIG. 33A is an exploded isometric view of a portion of another embodiment of the sensor control device 9102 of FIGS. 31A-31B and 32A-32B. Embodiments included above describe the mount 9108 and the seal 9208 being manufactured via a two-shot injection molding process. In other embodiments, however, as briefly mentioned above, one or both of the seal elements 9210a,b of the seal 9208 may comprise an elastomeric component part independent of the mount 9208. In the illustrated embodiment, for example, the first seal element 9210a may be overmolded onto the collar 9212 and the second seal element 9210b may be overmolded onto the sensor cap 9120. Alternatively, the first and second seal elements 9210a,b may comprise a separate component part, such as a gasket or O-ring posi-tioned on the collar 9212 and the sensor cap 9120, respec-tively. Tightening (rotating) the mated engagement between the sensor cap 9120 and the mating member 9118 may urge the second seal element 9210b into sealed engagement with the bottom of the mount 9108 in an axial direction, and may enhance a sealed interface between the sharp hub 9116 and the first seal element 9210a in the axial direction.

Figure 34A:
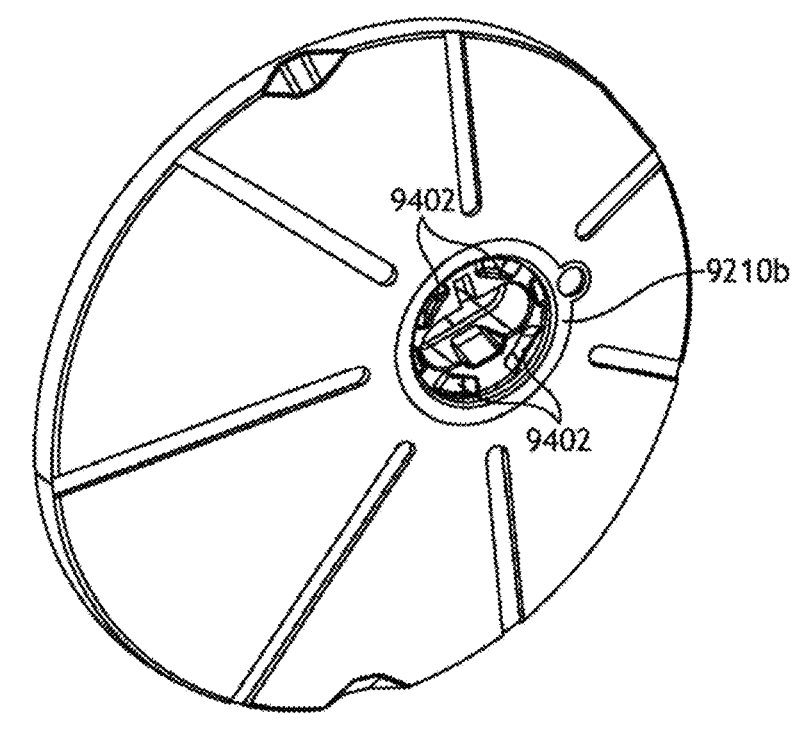
FIG. 34A is an isometric bottom view of the mount of FIGS. 31A-31B and 32A-32B.
Figure 34B:
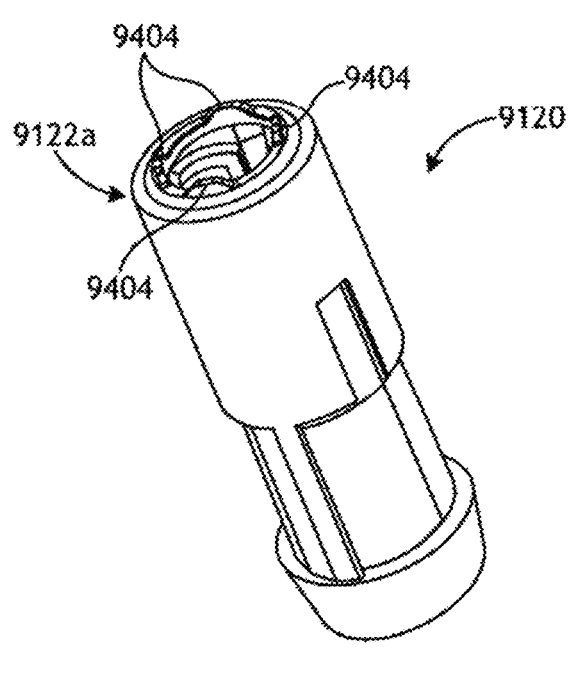
FIG. 34B is an isometric top view of the sensor cap of FIGS. 31A-31B and 32A-32B.

FIG. 34A is an isometric bottom view of the mount 9108, and FIG. 34B is an isometric top view of the sensor cap 9120, according to one or more embodiments. As shown in FIG. 34A, the mount 9108 may provide or otherwise define one or more indentations or pockets 9402 at or near the opening to the second aperture 9202b. As shown in FIG. 34B, the sensor cap 9120 may provide or otherwise define one or more projections 9404 at or near the first end 9122a of the sensor cap 9120. The projections 9404 may be received within the pockets 9402 when the sensor cap 9120 is coupled to the sharp hub 9116 (FIGS. 32A-32B and 93). More specifically, as described above, as the sensor cap 9120 is coupled to the mating member 9118 (FIGS. 32A-32B and 93) of the sensor hub 9116, the first end 9122a of the sensor cap 9120 is brought into sealed engagement with the second seal element 9210b. In this process, the projections 9404 may also be received within the pockets 9402, which may help prevent premature unthreading of the sensor cap 9120 from the sharp hub 9116.

Figure 35B:
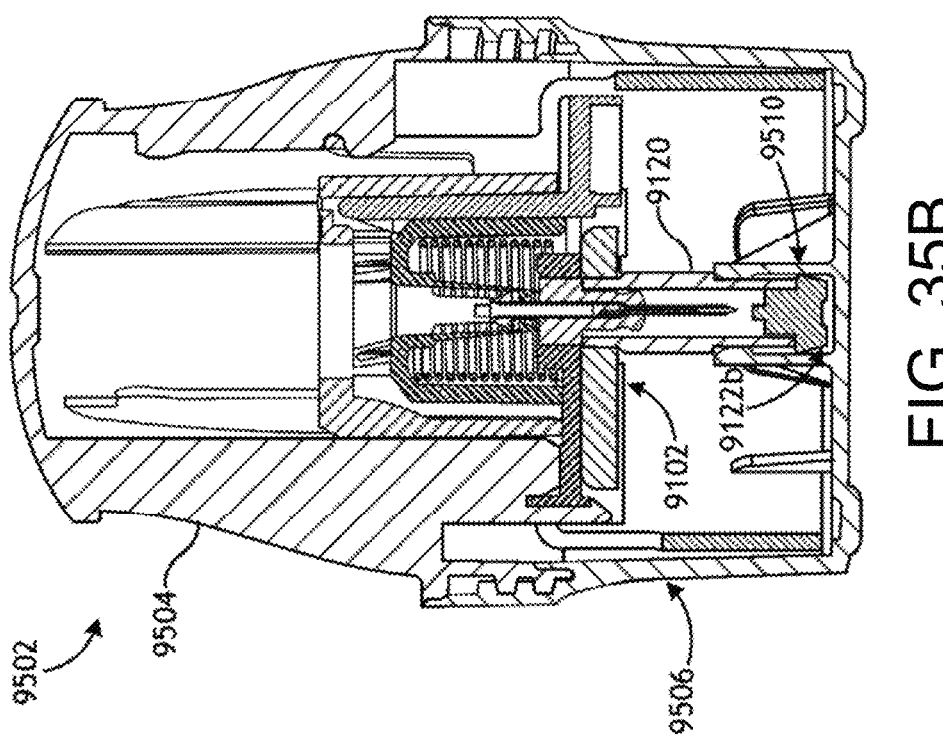
FIGS. 35A and 35B are side and cross-sectional side views, respectively, of an example sensor applicator, according to one or more embodiments.
Figure 35A:
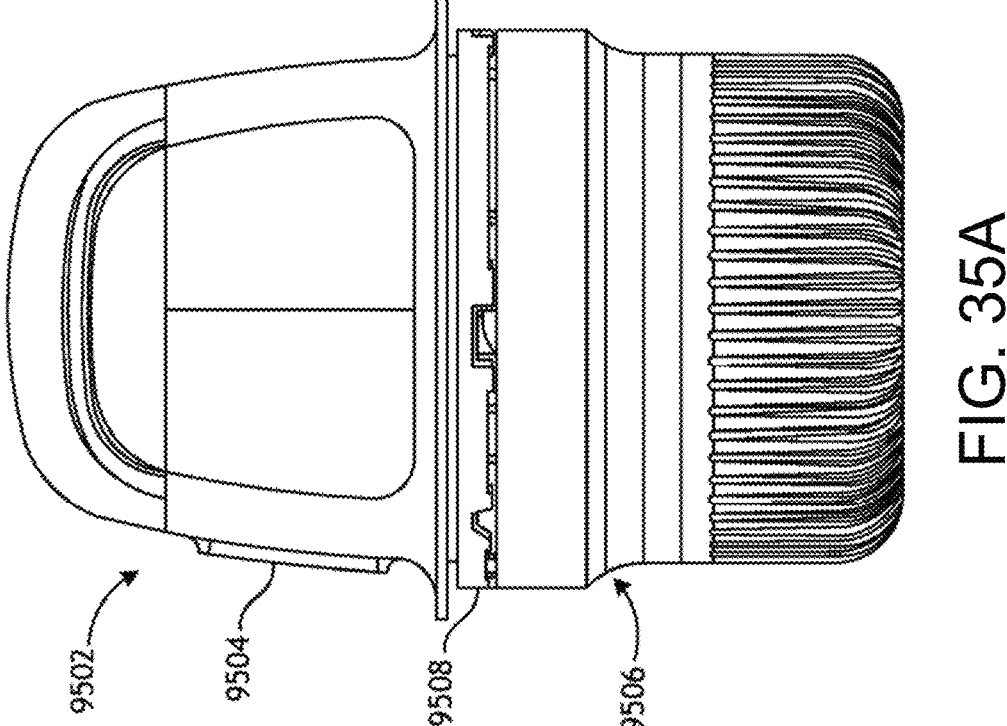

FIGS. 35A and 35B are side and cross-sectional side views, respectively, of an example sensor applicator 9502, according to one or more embodiments. The sensor appli-cator 9502 may be similar in some respects to the sensor applicator 102 of FIG. 1 and, therefore, may be designed to deliver (fire) a sensor control device, such as the sensor control device 9102. FIG. 35A depicts how the sensor applicator 9502 might be shipped to and received by a user, and FIG. 35B depicts the sensor control device 9102 arranged within the interior of the sensor applicator 9502.

As shown in FIG. 35A, the sensor applicator 9502 includes a housing 9504 and an applicator cap 9506 remov-ably coupled to the housing 9504. In some embodiments, the applicator cap 9506 may be threaded to the housing 9504 and include a tamper ring 9508. Upon rotating (e.g., unscrewing) the applicator cap 9506 relative to the housing 9504, the tamper ring 9508 may shear and thereby free the applicator cap 9506 from the sensor applicator 9502.

In FIG. 35B, the sensor control device 9102 is positioned within the sensor applicator 9502. Once the sensor control device 9102 is fully assembled, it may then be loaded into the sensor applicator 9502 and the applicator cap 9506 may be coupled to the sensor applicator 9502. In some embodi-ments, the applicator cap 9506 and the housing 9504 may have opposing, matable sets of threads that enable the applicator cap 9506 to be screwed onto the housing 9504 in a clockwise (or counter-clockwise) direction and thereby secure the applicator cap 9506 to the sensor applicator 9502.

Securing the applicator cap 9506 to the housing 9504 may also cause the second end 9122b of the sensor cap 9120 to be received within a cap post 9510 located within the interior of the applicator cap 9506 and extending proximally from the bottom thereof. The cap post 9510 may be configured to receive at least a portion of the sensor cap 9120 as the applicator cap 9506 is coupled to the housing 9504.

Figure 36A:
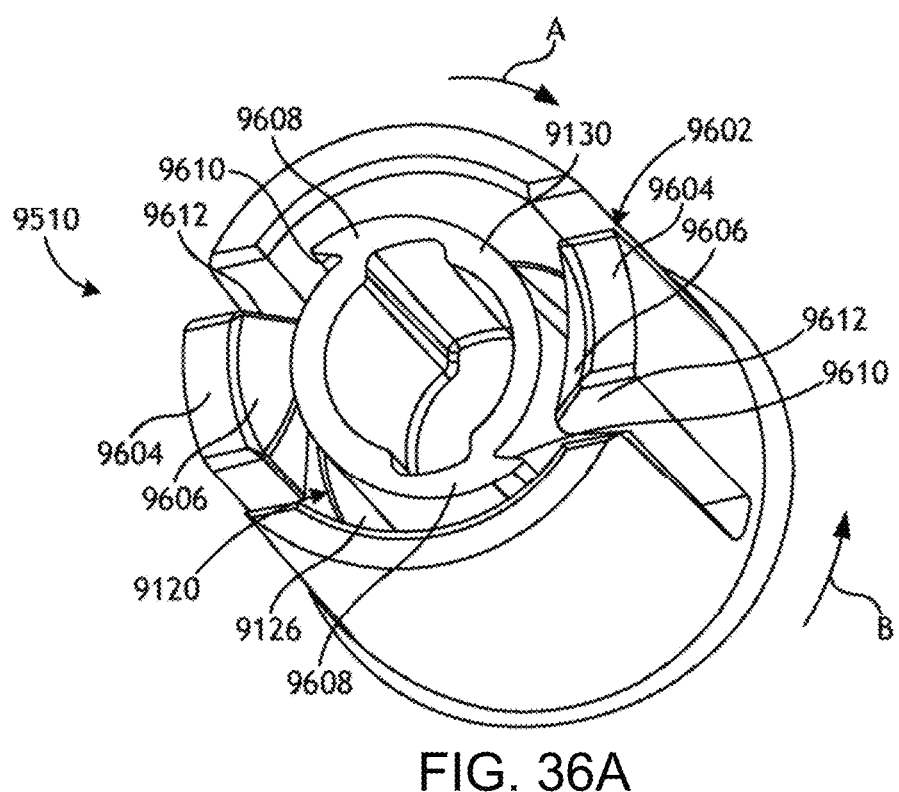
FIGS. 36A and 36B are perspective and top views, respectively, of the cap post of FIG. 35B, according to one or more embodiments.
Figure 36B:
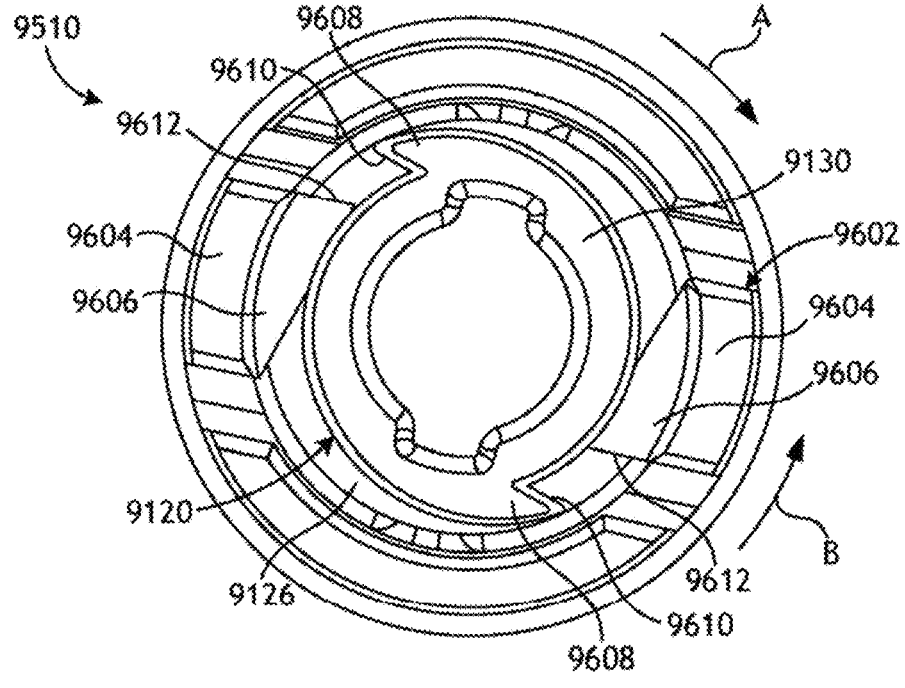

FIGS. 36A and 36B are perspective and top views, respectively, of the cap post 9510, according to one or more additional embodiments. In the illustrated depiction, a por-tion of the sensor cap 9120 is received within the cap post 9510 and, more specifically, the desiccant cap 9130 of the sensor cap 9120 is arranged within cap post 9510. The cap post 9510 may define a receiver feature 9602 configured to receive the engagement feature 9126 of the sensor cap 9120 upon coupling (e.g., threading) the applicator cap 9506 (FIG. 35B) to the sensor applicator 9502 (FIGS. 35A-35B). Upon removing the applicator cap 9506 from the sensor applicator 9502, however, the receiver feature 9602 may prevent the engagement feature 9126 from reversing direc-tion and thus prevent the sensor cap 9120 from separating from the cap post 9510. Instead, removing the applicator cap 9506 from the sensor applicator 9502 will simultaneously detach the sensor cap 9120 from the sensor control device 9102 (FIGS. 31A-31B and 32A-32B), and thereby expose the distal portions of the sensor 9112 (FIGS. 32A-32B) and the sharp 9114 (FIGS. 32A-32B).

Many design variations of the receiver feature 9602 may be employed, without departing from the scope of the disclosure. In the illustrated embodiment, the receiver fea-ture 9602 includes one or more compliant members 9604 (two shown) that are expandable or flexible to receive the engagement feature 9126. The engagement feature 9126 may comprise, for example, an enlarged head and the compliant member(s) 9604 may comprise a collet-type device that includes a plurality of compliant fingers config-ured to flex radially outward to receive the enlarged head.

The compliant member(s) 9604 may further provide or otherwise define corresponding ramped surfaces 9606 con-figured to interact with one or more opposing camming surfaces 9608 provided on the outer wall of the engagement feature 9126. The configuration and alignment of the ramped surface(s) 9606 and the opposing camming surface(s) 9608 is such that the applicator cap 9506 is able to rotate relative to the sensor cap 9120 in a first direction A (e.g., clockwise), but the cap post 9510 binds against the sensor cap 9120 when the applicator cap 9506 is rotated in a second direction B (e.g., counter clockwise). More particularly, as the applicator cap 9506 (and thus the cap post 9510) rotates in the first direction A, the camming surfaces 9608 engage the ramped surfaces 9606, which urge the compliant members 9604 to flex or otherwise deflect radially outward and results in a ratcheting effect. Rotating the applicator cap 9506 (and thus the cap post 9510) in the second direction B, however, will drive angled surfaces 9610 of the camming surfaces 9608 into opposing angled surfaces 9612 of the ramped surfaces 9606, which results in the sensor cap 9120 binding against the compliant member(s) 9604.

Figure 37:
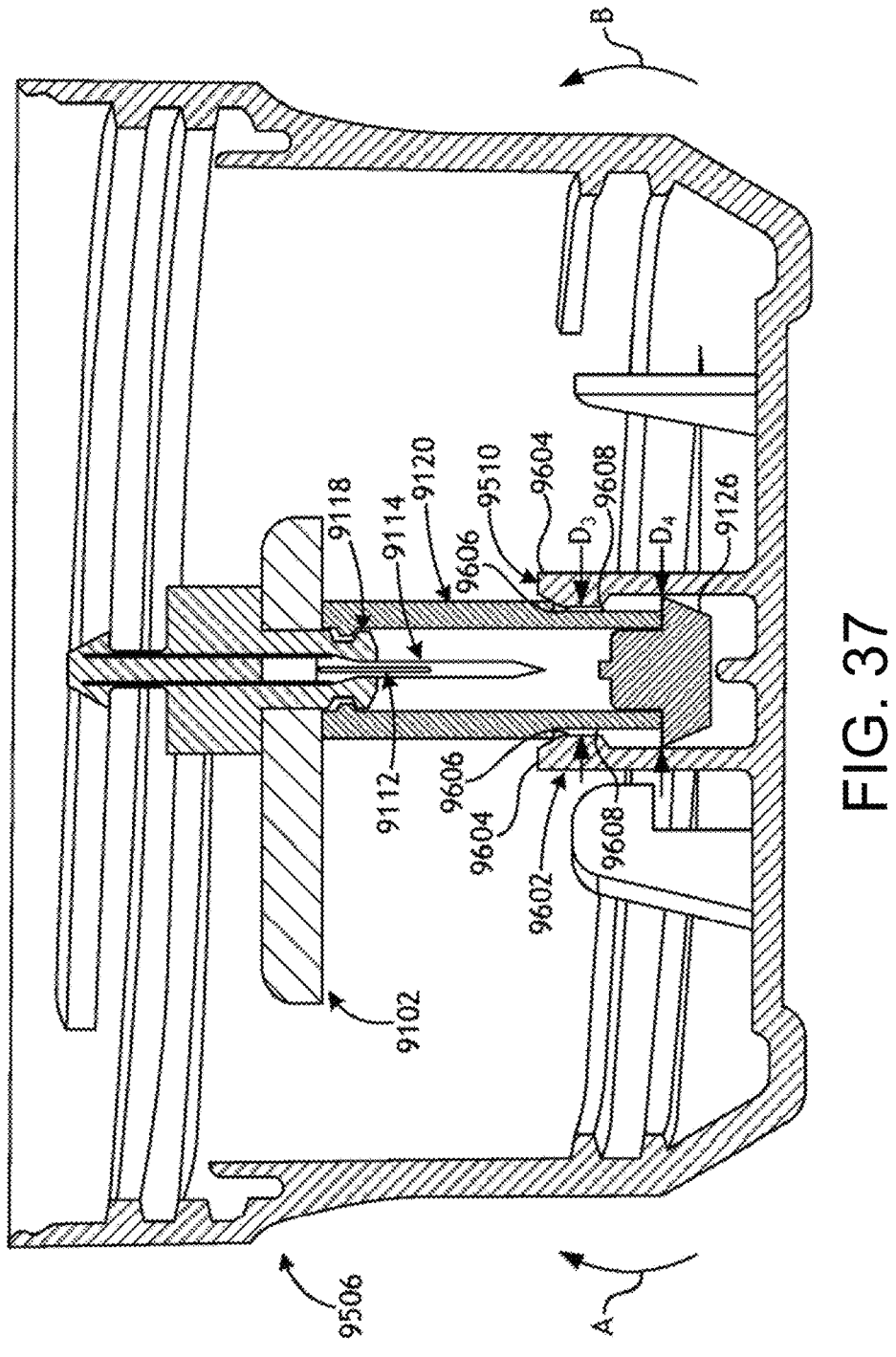
FIG. 37 is a cross-sectional side view of the sensor control device positioned within the applicator cap, according to one or more embodiments.

FIG. 37 is a cross-sectional side view of the sensor control device 9102 positioned within the applicator cap 9506, according to one or more embodiments. As illustrated, the opening to the receiver feature 9602 exhibits a first diameter D3, while the engagement feature 9126 of the sensor cap 9120 exhibits a second diameter D4 that is larger than the first diameter D3 and greater than the outer diameter of the remaining portions of the sensor cap 9120. As the sensor cap 9120 is extended into the cap post 9510, the compliant member(s) 9604 of the receiver feature 9602 may flex (expand) radially outward to receive the engagement feature 9126. In some embodiments, as illustrated, the engagement feature 9126 may provide or otherwise define an angled outer surface that helps bias the compliant member(s) 9604 radially outward. Once the engagement feature 9126 bypasses the receiver feature 9602, the compliant member(s) 9604 are able to flex back to (or towards) their natural state and thus lock the sensor cap 9120 within the cap post 9510.

As the applicator cap 9506 is threaded to (screwed onto) the housing 9504 (FIGS. 35A-35B) in the first direction A, the cap post 9510 correspondingly rotates in the same direction and the sensor cap 9120 is progressively introduced into the cap post 9510. As the cap post 9510 rotates, the ramped surfaces 9606 of the compliant members 9604 ratchet against the opposing camming surfaces 9608 of the sensor cap 9120. This continues until the applicator cap 9506 is fully threaded onto (screwed onto) the housing 9504. In some embodiments, the ratcheting action may occur over two full revolutions of the applicator cap 9506 before the applicator cap 9506 reaches its final position.

To remove the applicator cap 9506, the applicator cap 9506 is rotated in the second direction B, which correspondingly rotates the cap post 9510 in the same direction and causes the camming surfaces 9608 (i.e., the angled surfaces 9610 of FIGS. 36A-36B) to bind against the ramped surfaces 9606 (i.e., the angled surfaces 9612 of FIGS. 36A-36B). Consequently, continued rotation of the applicator cap 9506 in the second direction B causes the sensor cap 9120 to correspondingly rotate in the same direction and thereby unthread from the mating member 9118 to allow the sensor cap 9120 to detach from the sensor control device 9102. Detaching the sensor cap 9120 from the sensor control device 9102 exposes the distal portions of the sensor 9112 and the sharp 9114, and thus places the sensor control device 9102 in position for firing (use).

Figure 38:
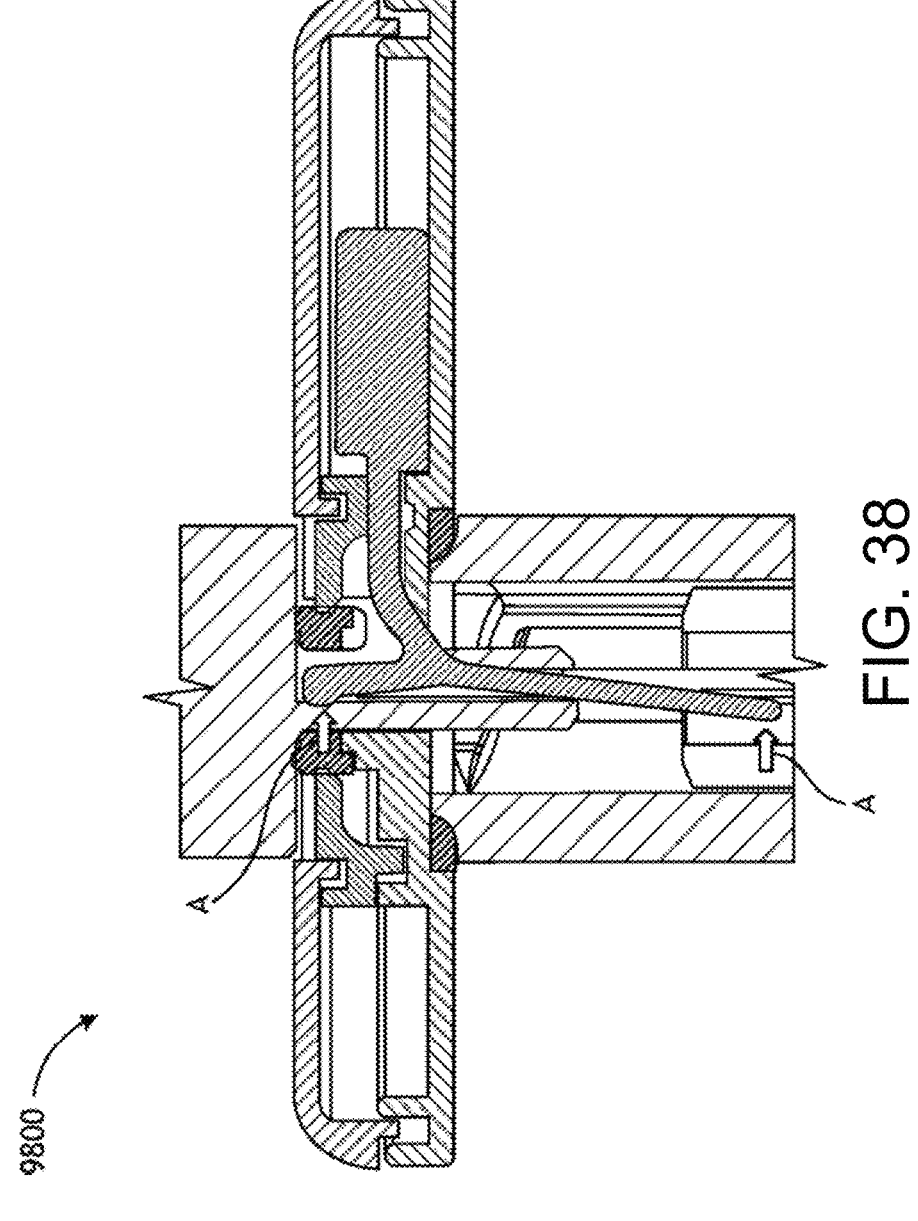
FIG. 38 is a cross-sectional view of a sensor control device showing example interaction between the sensor and the sharp.

FIG. 38 is a cross-sectional view of a sensor control device 9800 showing example interaction between the sensor and the sharp. After assembly of the sharp, the sensor should sit in a channel defined by the sharp. The sensor control device in FIG. 9 does not show the sensor deflected inwards and otherwise aligned fully with the sharp, but such may be the case upon full assembly as slight bias forces may be assumed by the sensor at the locations indicated by the two arrows A. Biasing the sensor against the sharp may be advantageous so that any relative motion between the sensor and the sharp during subcutaneous insertion does not expose the sensor tip (i.e., the tail) outside the sharp channel, which could potentially cause an insertion failure.

FIGS. 42A-42K illustrate steps of an example process for manufacturing an applicator assembly (e.g., an applicator device 150). The applicator assembly includes an inserter 4200, on-body sensor puck assembly (e.g., a sensor control device 5002) coupled to a puck carrier 710 (e.g., sensor electronics carrier 710 of FIG. 4A or sensor carrier 5602 of FIGS. 21A-21C), a sheath 704, an applicator housing 702, and a cap 708.

Figures 42A, 42B:
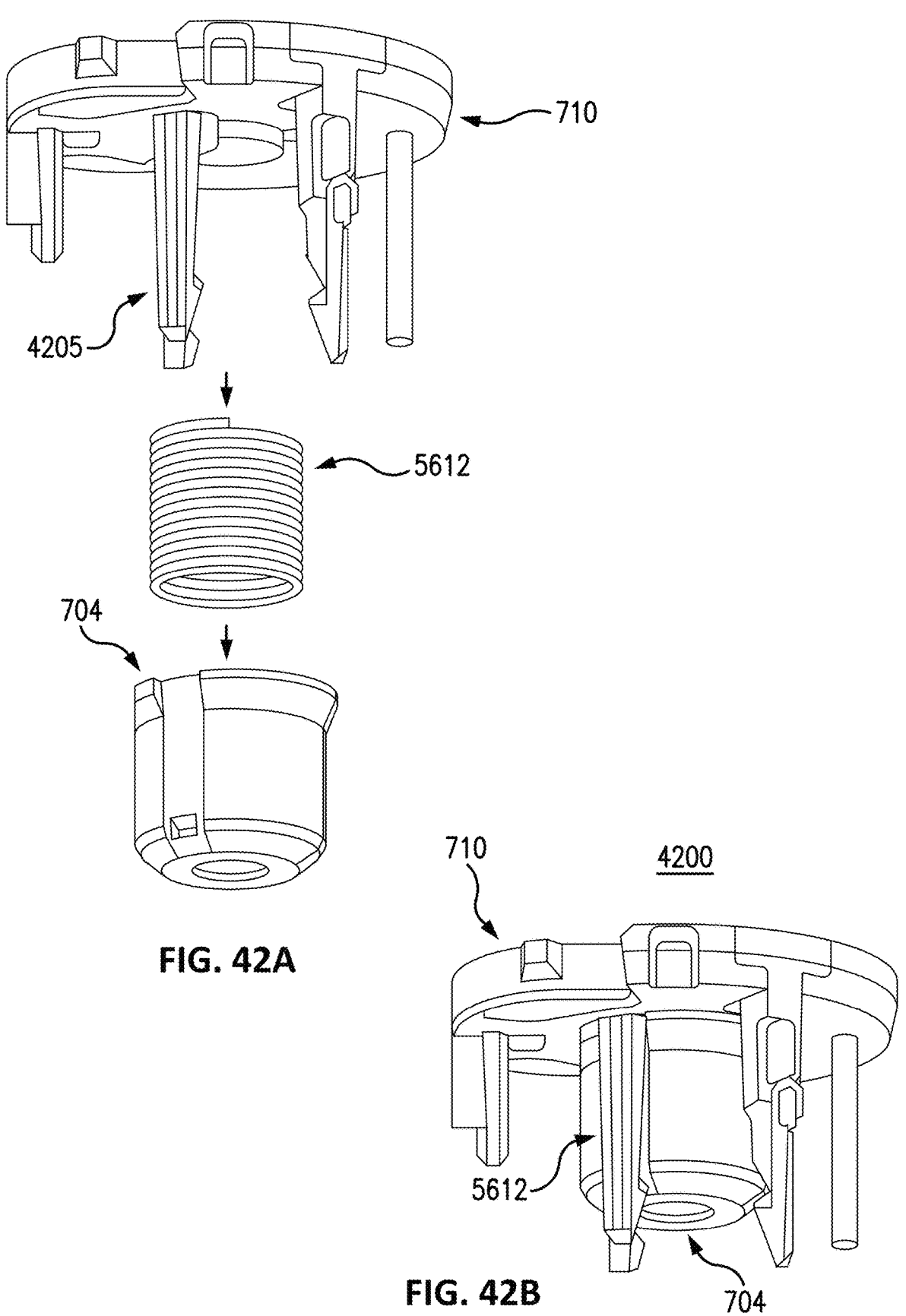
FIGS. 42A-42K illustrate steps of a process for assembling an applicator.

As illustrated in FIGS. 42A-42B, the manufacturing process includes assembling the inserter 4200 by loading a spring 5612 to a sharp carrier 704, lowering a puck carrier 710 to the sharp carrier 704 and compressing the spring 5612 until seated within the sharp carrier 704. The spring 5612 can be compressed manually or using a suitable compression tool, including, but not limited to a manually-operated or robotic loading arm, vacuum or suction gripping arm, magnetic gripping arm, adaptive gripping arm or appendage, pneumatic guided actuator or servo actuator, or other suitable tool. After the spring 5612 is compressed, the process involves locking one or more retention features 4205 of the puck carrier 710 with the sharp carrier 704 to retrain spring compression. The locking may be performed while clamping the puck carrier 710 to the sharp carrier 704 using any suitable clamping mechanism.

Figures 42C, 42D:
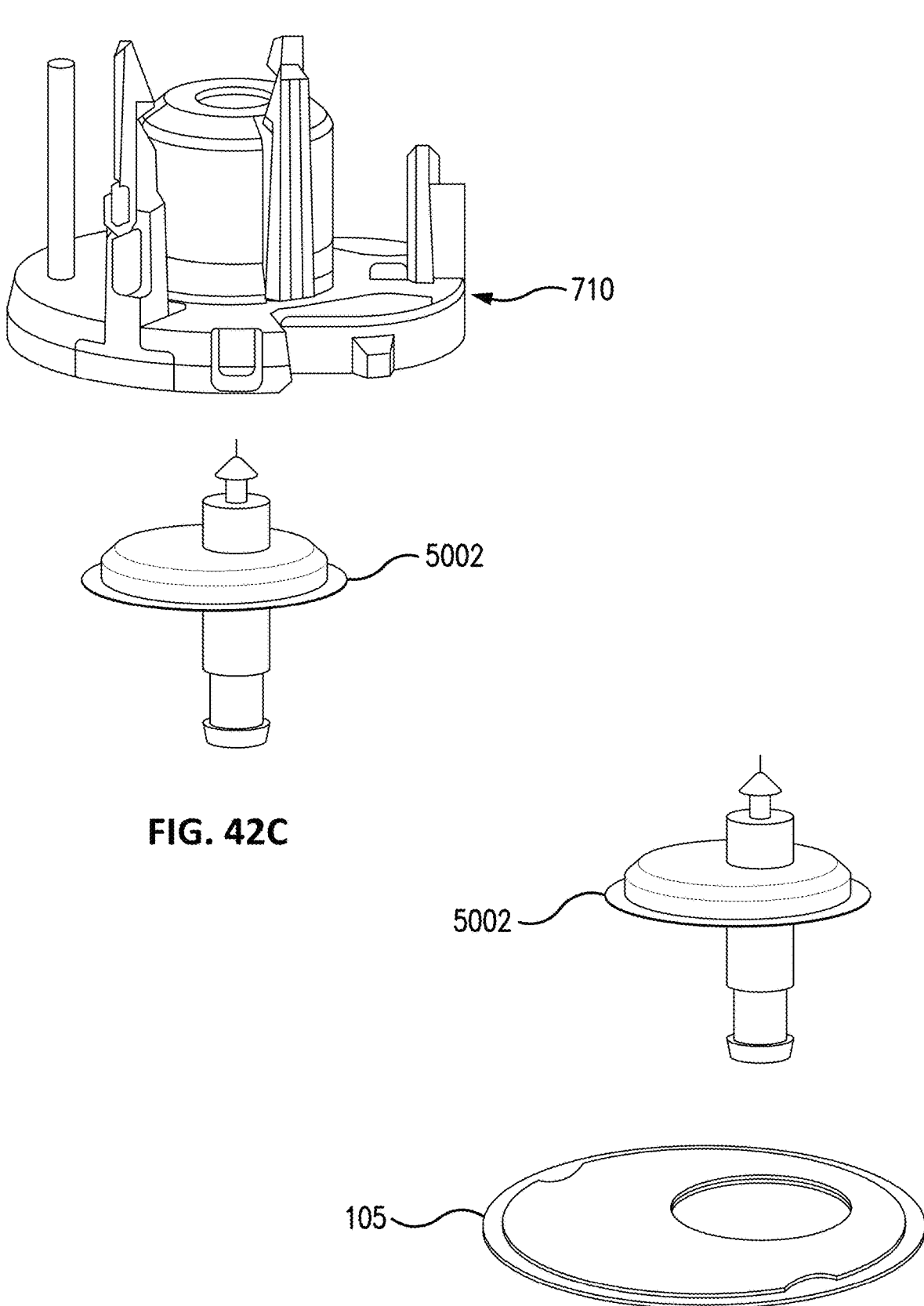
Figure 42F:
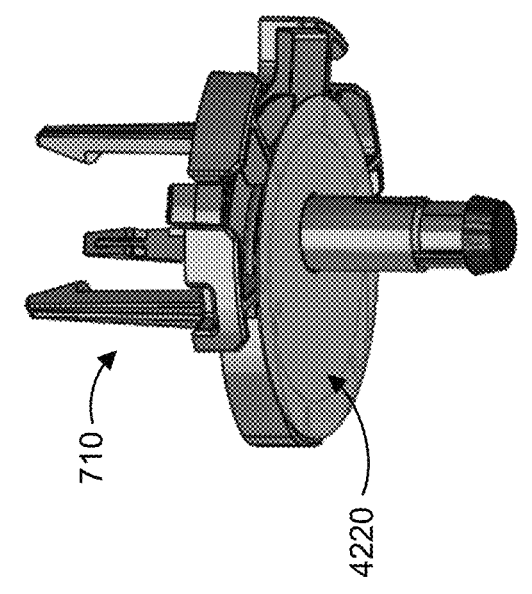
Figure 42E:
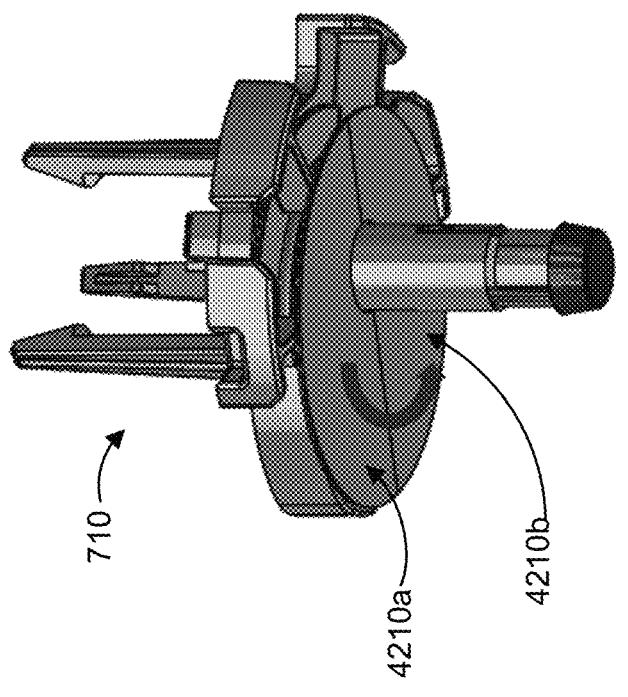

As illustrated in FIG. 42C, the manufacturing process can include coupling the on-body sensor puck assembly 5002 to the puck carrier 710. For example, mount retention features of the can be aligned with arms of the puck carrier 710 and the puck assembly 5002 can be advanced until it snaps into place. As illustrated in FIG. 42D, the manufacturing process can include applying an adhesive patch 105 (or adhesive patch 9110) to the on-body sensor puck assembly or to the puck carrier. The adhesive patch can be applied manually, or using a gripping or applicator machine tooling, vacuum or suction gripping arm, magnetic gripping arm, adaptive gripping arm or appendage, pneumatic guided actuator or servo actuator, or other suitable tool. Prior to applying the adhesive patch, the on-body sensor puck assembly (including puck carrier) and adhesive patch can be loaded into suitable holding tool. The adhesive patch can be configured to fit the contours and components of the on-body sensor puck assembly, for example, the adhesive patch can include a hold to accommodate the sharp cap. The adhesive patch can be aligned with the on-body sensor puck assembly (for example, manually, using optically-guided alignment arms, a spring-loaded alignment tool, etc.) and lowered onto the on-body sensor puck assembly manually or using suitable machine tooling, as described herein. Once the adhesive patch 105 is applied to the on-body sensor puck assembly 5002 or puck carrier 710, as illustrated in FIGS. 42E and 42F, the manufacturing process can include removing tabs 4210*a* and 4210*b* of the adhesive patch 105 to expose a side 4220 of the adhesive patch 150 that will attach, for example, to the body of a wearer, for example by securing an exposed corner of the liner and peeling from the patch manually or using automated equipment.

Figure 42H:
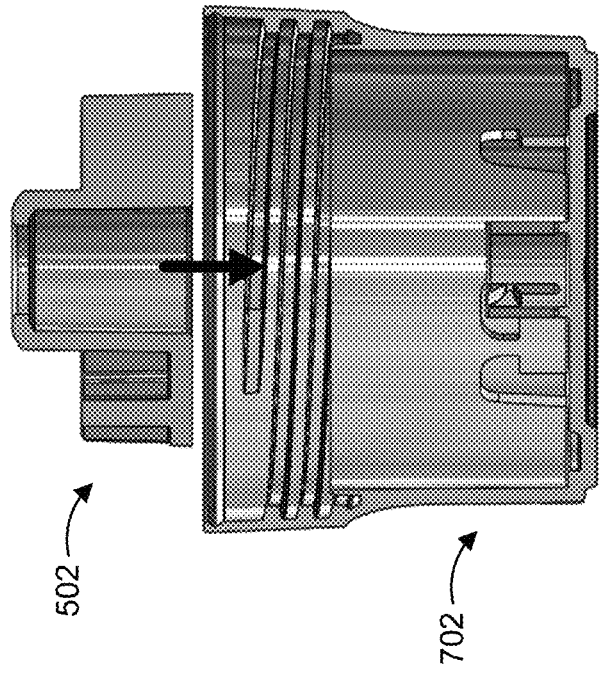
Figure 42G:
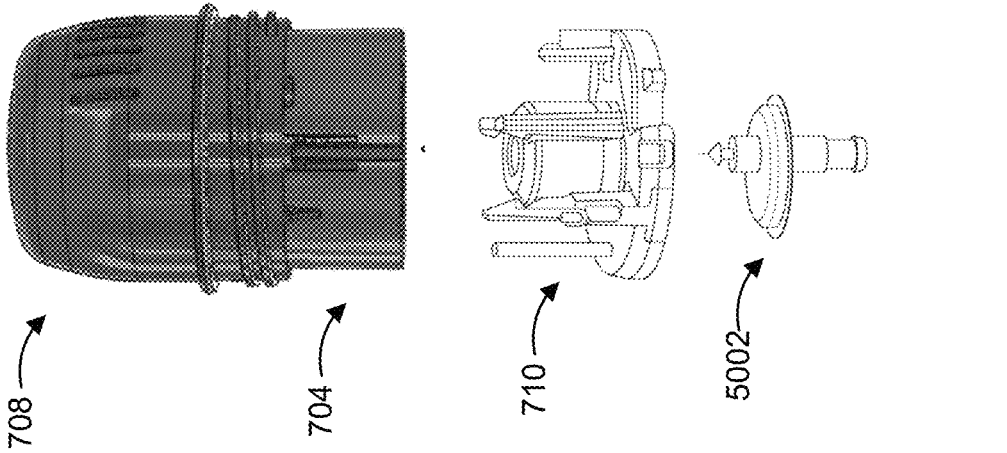

As illustrated in FIG. 42G, the manufacturing process can include attaching a sheath 704 to the puck carrier 710. Attaching the sheath the puck carrier can include loading the sheath into a fixture nest (not illustrated) and lowering the puck carrier 710 with compressed spring into the sheath 704. The manufacturing process can further include attaching the sheath 704 to the applicator housing 708. Attaching the sheath 704 to the applicator housing 708 can include loading the applicator housing 708 into a fixture nest (not illustrated) and engaging an alignment rib of the applicator housing 708 with a notch in the fixture nest. Then, the sheath 704 is lowered onto the applicator housing 708 until it engages the alignment rib of the applicator housing 708. The sheath 704 and puck carrier 710 can be manipulated manually or using suitable machine tooling, e.g., pneumatic guided actuator, to forcibly attach the components, as described herein.

As illustrated in FIG. 42H, the manufacturing process can include loading a desiccant 502 into the cap 702. The desiccant 502 can be used to control moisture exposure of the on-body sensor puck assembly 5002 and adhesive patch 105. The desiccant can be loaded manually or using suitable tooling such as a manually-operated or robotic loading arm, vacuum or suction gripping arm, magnetic gripping arm, adaptive gripping arm or appendage, pneumatic guided actuator, or other suitable tool.

Figure 42J:
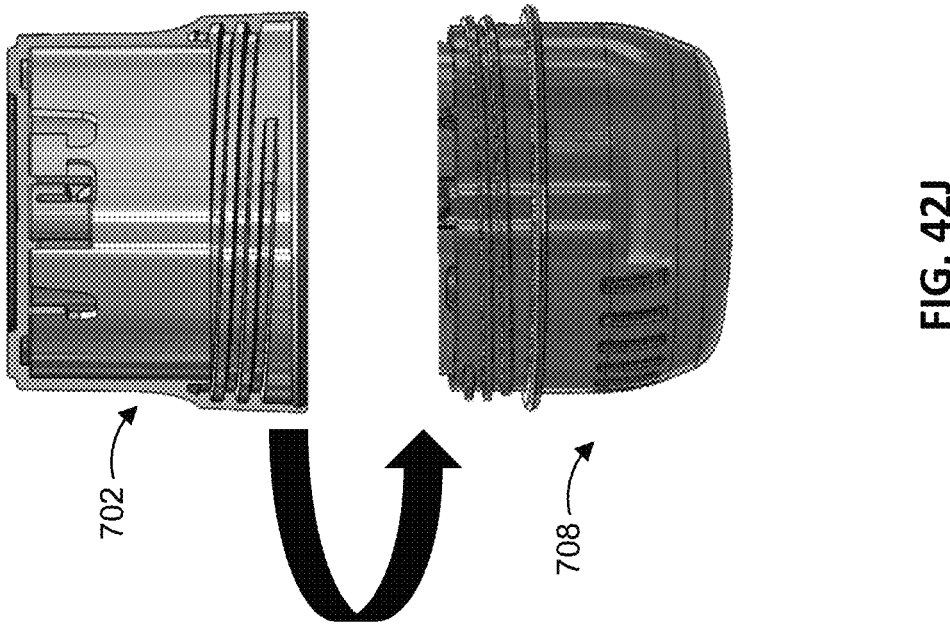
Figure 42I:
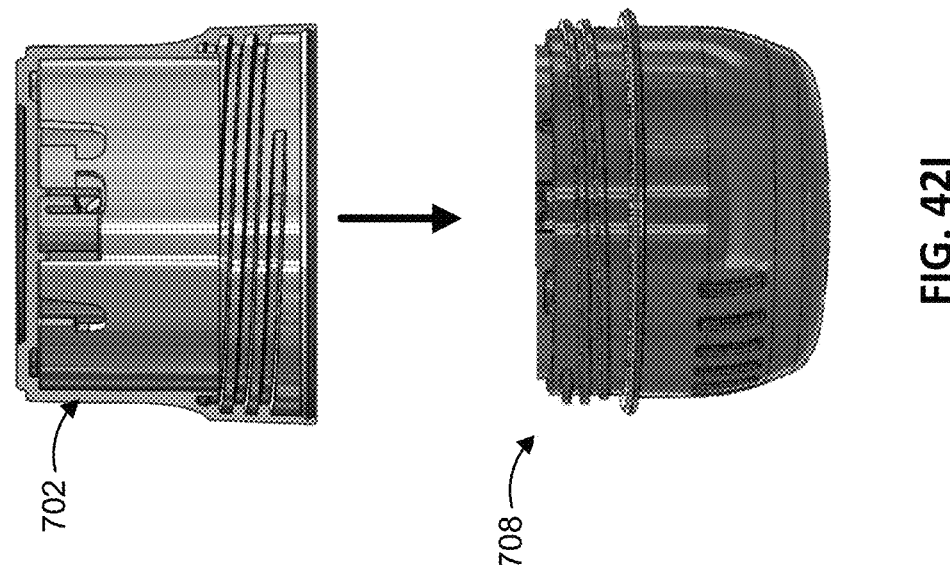

As illustrated in FIG. 42I, the manufacturing process can include coupling the cap 702 to the applicator housing 708. Coupling the cap 702 to the applicator housing 708 can include lowering the cap 702 onto the applicator housing 708. As illustrated in FIG. 42J, coupling the cap 702 to the applicator housing 708 can include lowering the cap 702 onto the applicator housing 708 and screwing the cap 702 to the applicator housing 708 to a pre-determined torque. The cap 702 can be screwed to the applicator housing 708 manually or using suitable automation tooling, for example, a servo rotary actuator can be used to rotate the cap 702 to a suitable motor torque.

Figure 42K:
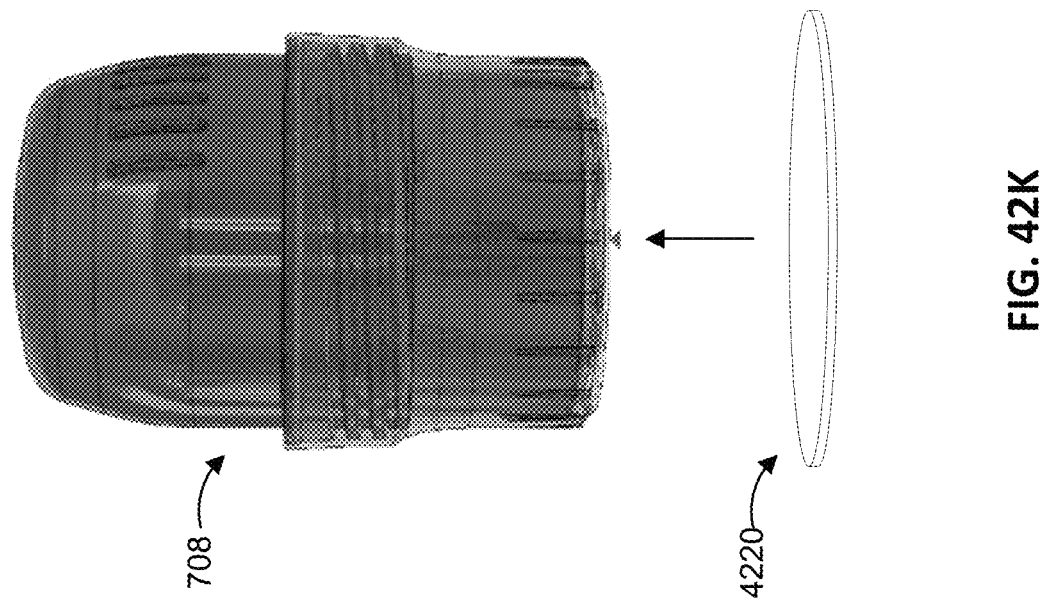

In particular embodiments, a tamper-evident sticker or other method of detecting that the applicator housing 702 has been opened can be applied to the interior or exterior of the applicator housing 708. As illustrated in FIG. 42K, the manufacturing process can include applying a label 4220 to the exterior of the assembled applicator housing 708.

Embodiments disclosed herein include:

D. A sensor control device that includes an electronics housing including a shell that defines a first aperture and a mount that defines a second aperture alignable with the first aperture when the shell is coupled to the mount, a seal overmolded onto the mount at the second aperture and comprising a first seal element overmolded onto a pedestal protruding from an inner surface of the mount, and a second seal element interconnected with the first seal element and overmolded onto a bottom of the mount, a sensor arranged within the electronics housing and having a tail extending through the second aperture and past the bottom of the mount, and a sharp that extends through the first and second apertures and past the bottom of the electronics housing.

E. An assembly that includes a sensor applicator, a sensor control device positioned within the sensor applicator and including an electronics housing including a shell that defines a first aperture and a mount that defines a second aperture alignable with the first aperture when the shell is mated to the mount, a seal overmolded onto the mount at the second aperture and comprising a first seal element overmolded onto a pedestal protruding from an inner surface of the mount, and a second seal element interconnected with the first seal element and overmolded onto a bottom of the mount, a sensor arranged within the electronics housing and having a tail extending through the second aperture and past the bottom of the mount, and a sharp that extends through the first and second apertures and past the bottom of the electronics housing. The assembly further including a sensor cap removably coupled to the sensor control device at the bottom of the mount and defining a sealed inner chamber that receives the tail and the sharp, and an applicator cap coupled to the sensor applicator.

Each of embodiments D and E may have one or more of the following additional elements in any combination: Element 1: wherein the mount comprises a first injection molded part molded in a first shot, and the seal comprises a second injection molded part overmolded onto the first injection molded part in a second shot. Element 2: further comprising a sharp hub that carries the sharp and sealingly engages the first seal element, and a sensor cap removably coupled to the sharp hub at the bottom of the mount and sealingly engaging the second seal element, wherein the sensor cap defines an inner chamber that receives the tail and the sharp. Element 3: wherein the sharp hub provides a mating member that extends past the bottom of the mount and the sensor cap is removably coupled to the mating member. Element 4: further comprising one or more pockets defined on the bottom of the mount at the second aperture, and one or more projections defined on an end of the sensor cap and receivable within the one or more pockets when the sensor cap is coupled to the sharp hub. Element 5: further comprising a collar positioned within the electronics housing and defining a central aperture that receives and sealingly engages the first seal element in a radial direction. Element 6: further comprising a channel defined on the inner surface of the mount and circumscribing the pedestal, an annular lip defined on an underside of the collar and matable with the channel, and an adhesive provided in the channel to secure and seal the collar to the mount at the channel. Element 7: further comprising a groove defined through the annular lip to accommodate a portion of the sensor extending laterally within the mount, wherein the adhesive seals about the sensor at the groove. Element 8: further comprising a collar channel defined on an upper surface of the collar, an annular ridge defined on an inner surface of the shell and matable with the collar channel, and an adhesive provided in the collar channel to secure and seal the shell to the collar. Element 9: wherein one or both of the first and second seal elements define at least a portion of the second aperture. Element 10: wherein the first seal element extends at least partially through the first aperture when the shell is coupled to the mount.

Element 11: wherein the sensor control device further includes a sharp hub that carries the sharp and sealingly engages the first seal element, and wherein the sensor cap is removably coupled to the sharp hub at the bottom of the mount and sealingly engages the second seal element. Element 12: wherein the sensor control device further includes one or more pockets defined on the bottom of the mount at the second aperture, and one or more projections defined on an end of the sensor cap and receivable within the one or more pockets when the sensor cap is coupled to the sharp hub. Element 13: wherein the sensor control device further includes a collar positioned within the electronics housing and defining a central aperture that receives and sealingly engages the first seal element in a radial direction. Element 14: wherein the sensor control device further includes a channel defined on the inner surface of the mount and circumscribing the pedestal, an annular lip defined on an underside of the collar and matable with the channel, and an adhesive provided in the channel to secure and seal the collar to the mount at the channel. Element 15: wherein the sensor control device further includes a groove defined through the annular lip to accommodate a portion of the sensor extending laterally within the mount, and wherein the adhesive seals about the sensor at the groove. Element 16: wherein the sensor control device further includes a collar channel defined on an upper surface of the collar, an annular ridge defined on an inner surface of the shell and matable with the collar channel, and an adhesive provided in the collar channel to secure and seal the shell to the collar. Element 17: wherein one or both of the first and second seal elements define at least a portion of the second aperture. Element 18: wherein the first seal element extends at least partially through the first aperture.

By way of non-limiting example, exemplary combinations applicable to D and E include: Element 2 with Element 3; Element 2 with Element 4; Element 5 with Element 6; Element 6 with Element 7; Element 5 with Element 8; Element 11 with Element 12; Element 13 with Element 14; Element 14 with Element 15; and Element 13 with Element 16.

Additional details of suitable devices, systems, methods, components and the operation thereof along with related features are set forth in International Publication No. WO2018/136898 to Rao et. al., International Publication No. WO2019/236850 to Thomas et. al., International Publication No. WO2019/236859 to Thomas et. al., International Publication No. WO2019/236876 to Thomas et. al., and U.S. patent application Ser. No. 16/433,931, filed Jun. 6, 2019, each of which is incorporated by reference in its entirety herein.

Embodiments disclosed herein include:

F. A method of assembling a sensor subassembly including a sensor, a sensor mount, a collar, a sharp, and a sensor cap. The method includes loading a sensor in a sensor mount, dispensing adhesive into a mount channel of the sensor mount, clamping a collar to the sensor mount, curing the adhesive to fix the collar to the sensor mount, inserting a sharp into the sensor mount over the sensor, and attaching a sensor cap to the sensor and sensor sharp to provide a sealed sensor subassembly.

G. A method of assembling an on-body sensor puck assembly including a printed circuit board (PCB), a puck shell cap, and a sensor subassembly, the sensor subassembly including a sensor, a sensor mount, a collar, and a sensor cap. The method can include dispensing a first adhesive to a sensor mount of the sensor subassembly, loading a PCB onto the sensor mount of the sensor subassembly after aligning the PCB with the sensor and the sensor subassembly, curing the first adhesive to fix the PCB to the sensor mount, dispensing a second adhesive onto an outer diameter of the sensor mount and inner diameter of a collar of the sensor subassembly, attaching the puck shell cap to the sensor subassembly, and curing the second adhesive to form the on-body sensor puck assembly.

H. A method of assembling an applicator assembly comprising an inserter, on-body sensor puck assembly coupled to a puck carrier, a sheath, an applicator housing, and a cap. The method includes assembling the inserter by loading a spring to a sharp carrier, lowering a puck carrier to the sharp carrier and compressing the spring until seated within the sharp carrier, and locking one or more retention features of the sharp carrier to retain spring compression, coupling the on-body sensor puck assembly to the puck carrier, applying an adhesive patch to the on-body sensor puck assembly, attaching a sheath to the puck carrier, attaching the sheath to the applicator housing, and coupling the cap to the applicator housing.

I. A sensor including a tail, a flag, and a neck that interconnects the tail and the flag. The tail, the flag, and the neck are aligned along a planar surface having a vertical axis and a horizontal axis, between the tail and the flag, the neck includes at least two turns in relation to the vertical axis defining a spring structure, and the flag includes a generally planar surface having one or more sensor contacts.

J. A method of configuring a sensor including a tail, a flag, and a neck that interconnects the tail and the flag. The method can include heating a portion of the neck of the sensor to a predetermined temperature and bending the neck of the sensor to form a first angle between the tail of the sensor and the flag of the sensor.

Each of embodiments F, G, H, I, and J may have one or more of the following additional elements in any combination: Element 1: wherein the adhesive is a chemically-curable adhesive, and the method further comprises curing the adhesive by exposing the adhesive to one or more chemical bonding catalysts. Element 2: wherein the adhesive is a heat-curable adhesive, and the method further comprises curing the adhesive by exposing the adhesive to heat suitable to cure the adhesive. Element 3: wherein the adhesive is an ultra-violet (UV)-curable adhesive, and the method further comprises curing the adhesive using one or more UV light sources. Element 4: wherein the sensor is shielded from the one or more UV light sources while curing the adhesive. Element 5: wherein the one or more UV light sources include a UV light emitting diode (LED) with light pipe and multiple angled spot LEDs. Element 6: further comprising loading the collar onto the sensor mount. Element 7: wherein the sharp is attached to a sharp hub and inserting the sharp into the sensor mount comprises coupling the sharp hub to the sensor mount; the method further comprises: dispensing adhesive to a top surface of the sharp hub; and curing the adhesive to seal the sharp hub. Element 8: further comprising testing the sealed sensor subassembly for leaks using a pressure-decay leak test, vacuum-decay leak test, tracer gas leak test, signature analysis test, or mass-flow leak test. Element 9: further comprising discarding the sealed sensor subassembly when leaks are detected that exceed a predetermined threshold. Element 10: further comprising sterilizing the sensor subassembly. Element 11: wherein the sterilizing is performed via heat treatment, radiation, electronic-beam sterilization, gamma sterilization, x-ray sterilization, ethylene oxide sterilization, autoclave steam sterilization, chlorine dioxide gas sterilization, or hydrogen peroxide sterilization. Element 12: wherein the sensor comprises a body temperature sensor, blood pressure sensor, pulse or heart-rate sensor, glucose level sensor, analyte sensor, or physical activity sensor. Element 13: further comprising inspecting the sharp for imperfections prior to inserting the sharp into the sensor mount. Element 14: further comprising discarding the sharp when imperfections are detected that exceed a predetermined threshold. Element 15: wherein attaching the sensor cap to the sensor and sensor sharp to provide a sealed sensor subassembly comprises twisting the sensor cap into position. Element 16: further comprising: inserting a desiccant into a plug; and inserting the plug into the sensor cap prior to attaching the sensor cap to the sensor and sensor sharp.

Element 17: wherein the PCB is a flexible PCB and the method further comprises folding the PCB to fit a footprint of the on-body sensor puck assembly. Element 18: wherein dispensing the first adhesive further comprises dispensing the first adhesive at a location of the fold, a battery location, or a PCB connector location. Element 19: wherein the PCB comprises a radio component and the method further comprises writing data to the radio component of the PCB by: reading sensor data from the sensor subassembly, PCB, a puck shell cap, or a mount carrying the sensor subassembly; and writing the sensor data to the radio component of the PCB. Element 20: wherein dispensing the second adhesive onto the outer diameter of the sensor mount and inner diameter of the collar of the sensor subassembly comprises: tilting the sensor mount along an axis to a predetermined angle; dispensing the second adhesive to the inner diameter of the collar of the sensor subassembly; returning the sensor mount to a substantially horizontal position by tilting the sensor mount along the axis; and dispensing the second adhesive to the outer diameter of the sensor mount. Element 21: further comprising testing the on-body sensor puck assembly for leaks using a pressure-decay leak test, vacuum-decay leak test, tracer gas leak test, signature analysis test, or mass-flow leak test. Element 22: further comprising discarding the on-body sensor puck assembly when leaks are detected that exceed a predetermined threshold. Element 23: wherein the first adhesive or the second adhesive is a chemically-curable adhesive, and the method further comprises curing the first adhesive or the second adhesive by exposing the adhesive to one or more chemical bonding catalysts. Element 24: wherein the first adhesive or the second adhesive is a heat-curable adhesive, and the method further comprises curing the first adhesive or the second adhesive by exposing the adhesive to heat suitable to cure the first adhesive or second adhesive. Element 25: wherein the first adhesive or the second adhesive is an ultra-violet (UV)-curable adhesive, and the method further comprises curing the first adhesive or the second adhesive using one or more UV light sources.

Element 26: wherein attaching the sheath to the puck carrier comprises: loading the sheath into a fixture nest; and lowering the puck carrier with compressed spring into the sheath. Element 27: wherein attaching the sheath to the applicator housing comprises: loading the applicator housing into a fixture nest and engaging an alignment rib of the applicator housing with a notch in the fixture nest; and lowering the sheath onto the applicator housing and engaging the alignment rib of the applicator housing. Element 28: wherein coupling the cap to the applicator housing comprises: lowering the cap onto the applicator housing; and screwing the cap to the applicator housing to a pre-determined torque. Element 29: further comprising loading a desiccant into the cap. Element 30: further comprising applying a tamper-proof sticker to the applicator assembly.

Element 31: wherein the at least two turns of the neck are formed by bending the neck of the sensor. Element 32: wherein the at least two turns of the neck are formed by laser cutting the sensor. Element 33: wherein the at least two turns of the neck are formed by stamping the sensor from a sheet of material comprising the sensor. Element 34: wherein the at least two turns of the neck are formed by printing the sensor to include the at least two turns. Element 35: wherein the at least two turns in relation to the vertical axis provide overlapping layers of the neck. Element 36: wherein the overlapping layers of the neck are vertically-oriented. Element 37: wherein the overlapping layers of the neck are horizontally-oriented.

Element 38: wherein the predetermined temperature is sufficient to improve malleability of the neck of the sensor. Element 39: wherein the predetermined temperature is between 50 and 60° C., inclusive. Element 40: further comprising verifying integrity of the sensor after bending by checking the neck for microfractures in the neck of the sensor. Element 41: further comprising disposing of the sensor if microfractures detected in the neck of the sensor exceed a predetermined threshold of microfractures. Element 42: wherein the heating is performed by a first component of a heated-bending apparatus and the bending is performed by a second component of the heated-bending apparatus. Element 43: wherein the heating the portion of the neck comprises: heating the first component of the heated-bending apparatus with a heating element; and contacting the portion of the neck with the heated first component of the heated-bending apparatus. Element 44: wherein the heating is performed by a heating element integrated into a heated-bending apparatus, wherein heat is applied during the bending. Element 45: wherein an intensity of the heat applied to the neck varies during the bending.

By way of non-limiting example, exemplary combinations applicable to embodiment F include: Element 1 with any of Elements 6-16; Element 2 with any of Elements 6-16; Element 3 with any of Elements 4-16; Element 4 with any of Elements 3 and 5-16; Element 5 with any of Elements 3-4 and 6-16; Element 6 with any of Elements 1-5 and 7-16; Element 7 with any of Elements 1-6 and 8-16; Element 8 with any of Elements 1-7 and 9-16; Element 9 with any of Elements 1-8 and 10-16; Element 10 with any of Elements 1-9 and 11-16; Element 11 with any of Elements 1-10 and 12-16; Element 12 with any of Elements 1-11 and 13-16; Element 13 with any of Elements 1-12 and 14-16; Element 14 with any of Elements 1-13 and 15-16; Element 15 with any of Elements 1-14 and 16; and Element 16 with any of Elements 1-15.

By way of non-limiting example, exemplary combinations applicable to embodiment G include: Element 17 with any of Elements 18-25; Element 18 with any of Elements 17 and 29-25; Element 19 with any of Elements 17-18 and 20-25; Element 20 with any of Elements 17-19 and 21-25; Element 21 with any of Elements 17-20 and 22-25; Element 21 with any of Elements 17-20 and 22-25; Element 22 with any of Elements 17-21 and 23-25; Element 23 with any of Elements 17-22 and 24-25; Element 24 with any of Elements 17-23 and 25; Element 25 with any of Elements 17-24.

By way of non-limiting example, exemplary combinations applicable to embodiment H include: Element 26 with any of Elements 27-30; Element 27 with any of Elements 26 and 28-30; Element 28 with any of Elements 26-27 and 29-30; Element 29 with any of Elements 26-28 and 30; Element 30 with any of Elements 26-29.

By way of non-limiting example, exemplary combinations applicable to embodiment I include: Element 31 with any of Elements 34-37; Element 32 with any of Elements 34-37; Element 33 with any of Elements 34-37; Element 34 with any of Elements 35-37; Element 35 with any of Elements 31-34 and 36-37; Element 36 with any of Elements 31-35 and 37; Element 37 with any of Elements 31-36.

By way of non-limiting example, exemplary combinations applicable to embodiment J include: Element 38 with any of Elements 39-45; Element 39 with any of Elements 38 and 40-45; Element 40 with any of Elements 38-39 and 41-45; Element 41 with any of Elements 38-40 and 42-45; Element 42 with any of Elements 38-41; Element 43 with any of Elements 38-42; Element 44 with any of Elements 38-41 and 45; Element 45 with any of Elements 38-41 and 44.

Additionally or alternatively, any of the elements and combinations applicable to embodiments F, G, H, I, and J are also applicable to any of the other elements and combinations applicable to embodiments F, G, H, I, and J.

Example Embodiments of Firing Mechanism of One Piece and Two-Piece Applicators

FIGS. 39A-39F illustrate example details of embodiments of the internal device mechanics of "firing" the applicator 216 to apply sensor control device 222 to a user and including retracting sharp 1030 safely back into used applicator 216. All together, these drawings represent an example sequence of driving sharp 1030 (supporting a sensor coupled to sensor control device 222) into the skin of a user, withdrawing the sharp while leaving the sensor behind in operative contact with interstitial fluid of the user, and adhering the sensor control device to the skin of the user with an adhesive. Modification of such activity for use with the alternative applicator assembly embodiments and components can be appreciated in reference to the same by those with skill in the art. Moreover, applicator 216 may be a sensor applicator having one-piece architecture or a two-piece architecture as disclosed herein.

Figure 39A:
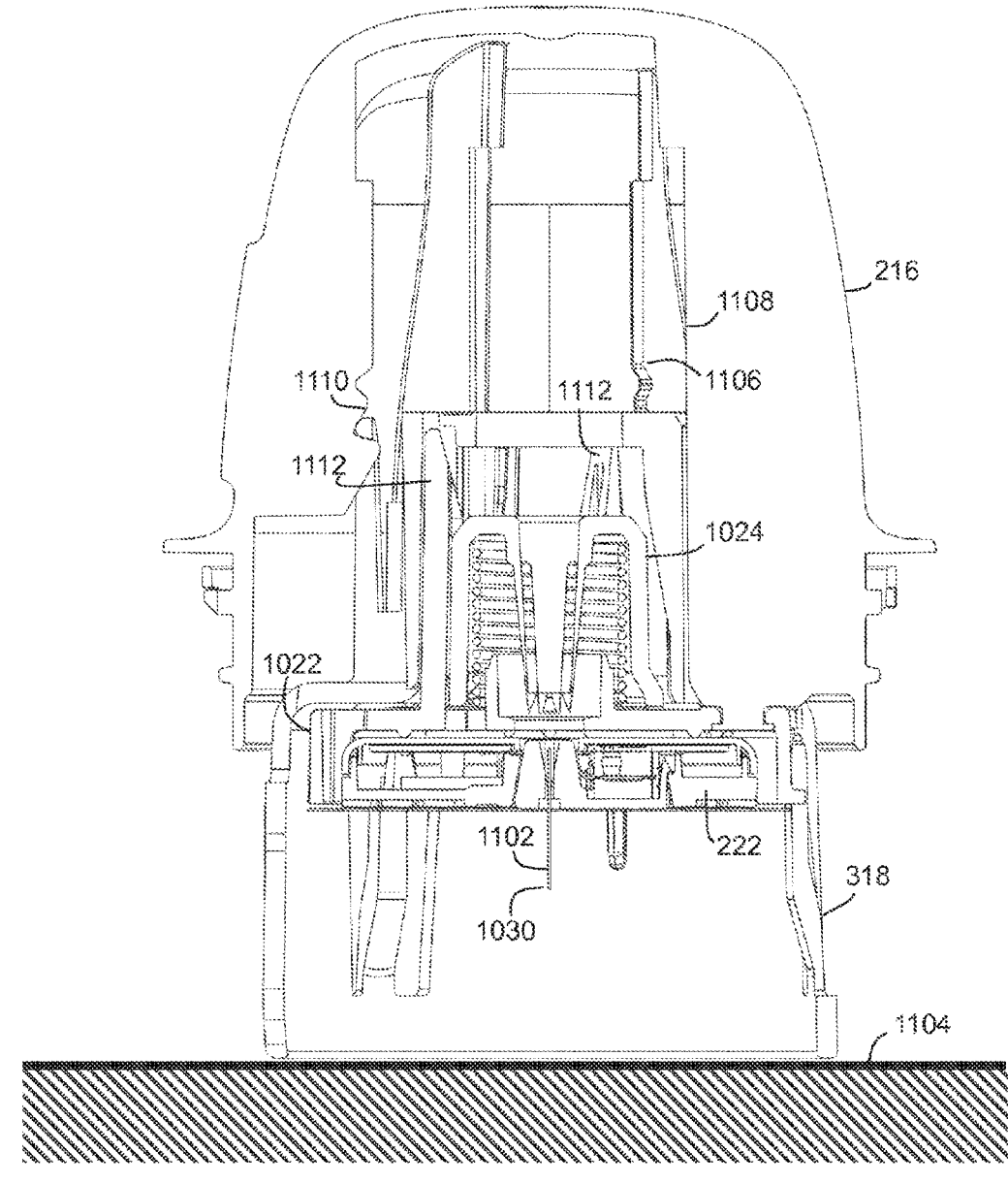
FIGS. 39A-39F illustrate cross-sectional views depicting an example embodiment of an applicator during a stage of deployment.

Turning now to FIG. 39A, a sensor 1102 is supported within sharp 1030, just above the skin 1104 of the user. Rails 1106 (optionally three of them) of an upper guide section 1108 may be provided to control applicator 216 motion relative to sheath 318. The sheath 318 is held by detent features 1110 within the applicator 216 such that appropriate downward force along the longitudinal axis of the applicator 216 will cause the resistance provided by the detent features 1110 to be overcome so that sharp 1030 and sensor control device 222 can translate along the longitudinal axis into (and onto) skin 1104 of the user. In addition, catch arms 1112 of sensor carrier 1022 engage the sharp retraction assembly 1024 to maintain the sharp 1030 in a position relative to the sensor control device 222.

Figure 39B:
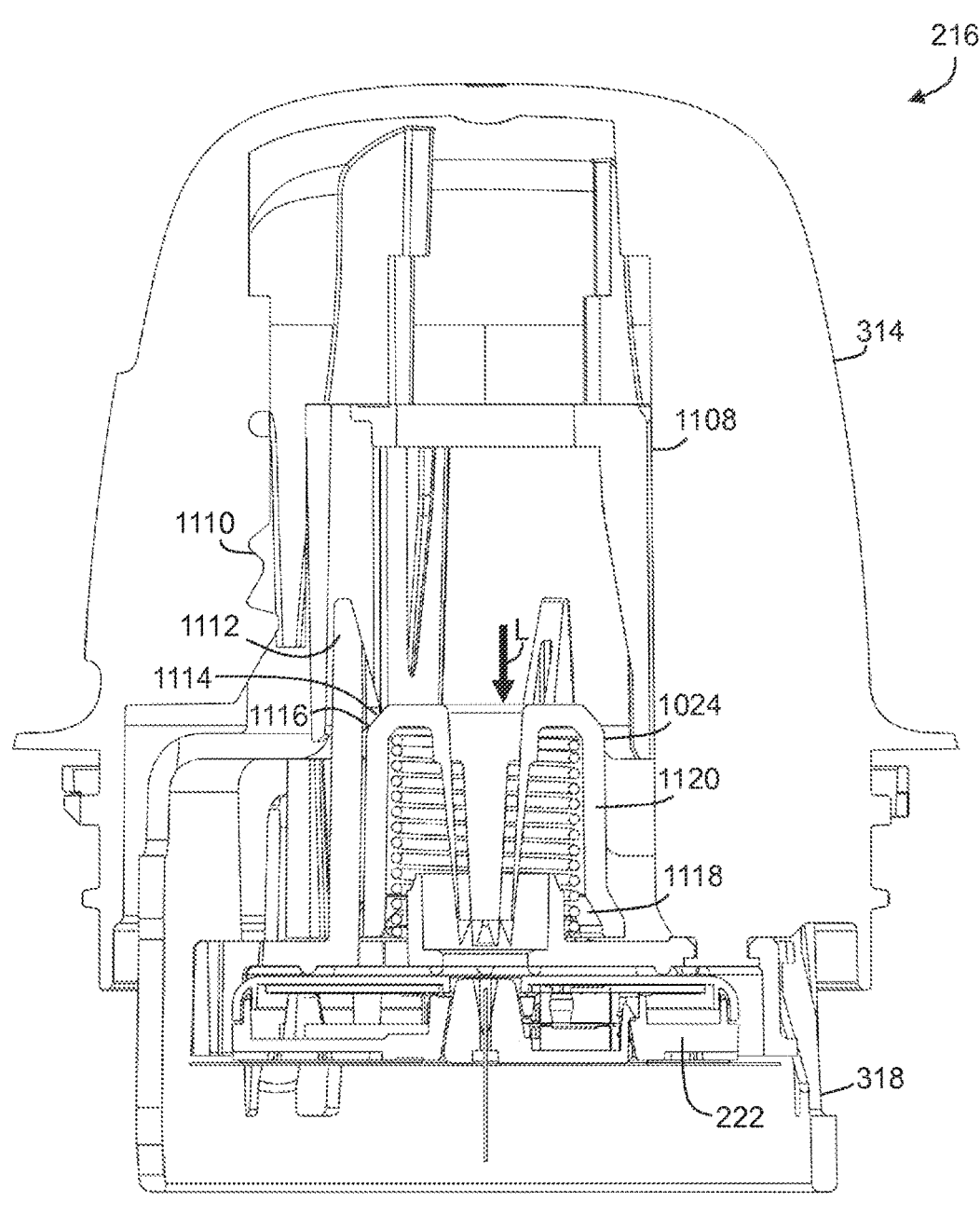

In FIG. 39B, user force is applied to overcome or override detent features 1110 and sheath 318 collapses into housing 314 driving the sensor control device 222 (with associated parts) to translate down as indicated by the arrow L along the longitudinal axis. An inner diameter of the upper guide section 1108 of the sheath 318 constrains the position of carrier arms 1112 through the full stroke of the sensor/sharp insertion process. The retention of the stop surfaces 1114 of carrier arms 1112 against the complimentary faces 1116 of the sharp retraction assembly 1024 maintains the position of the members with return spring 1118 fully energized.

Figure 39C:
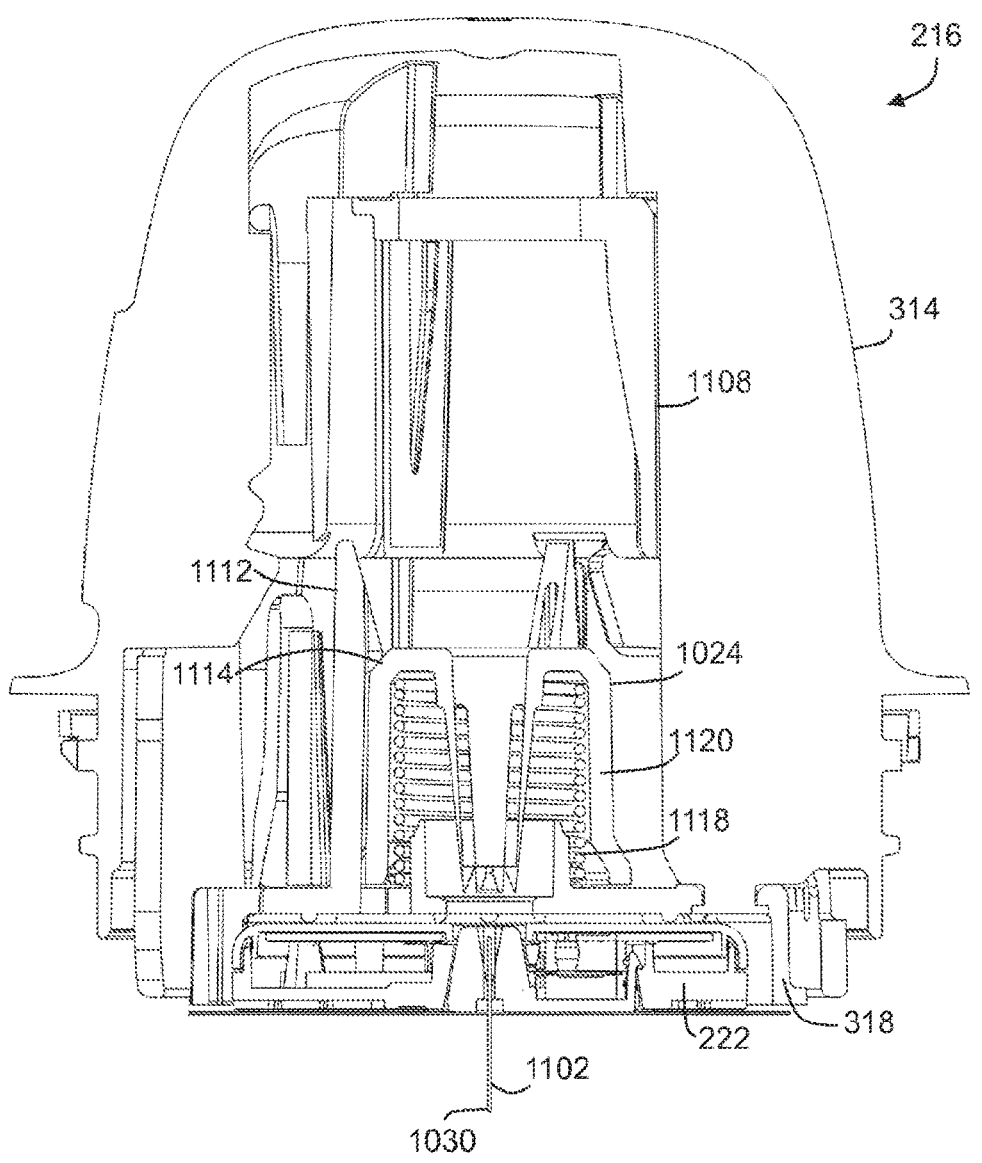
Figure 39D:
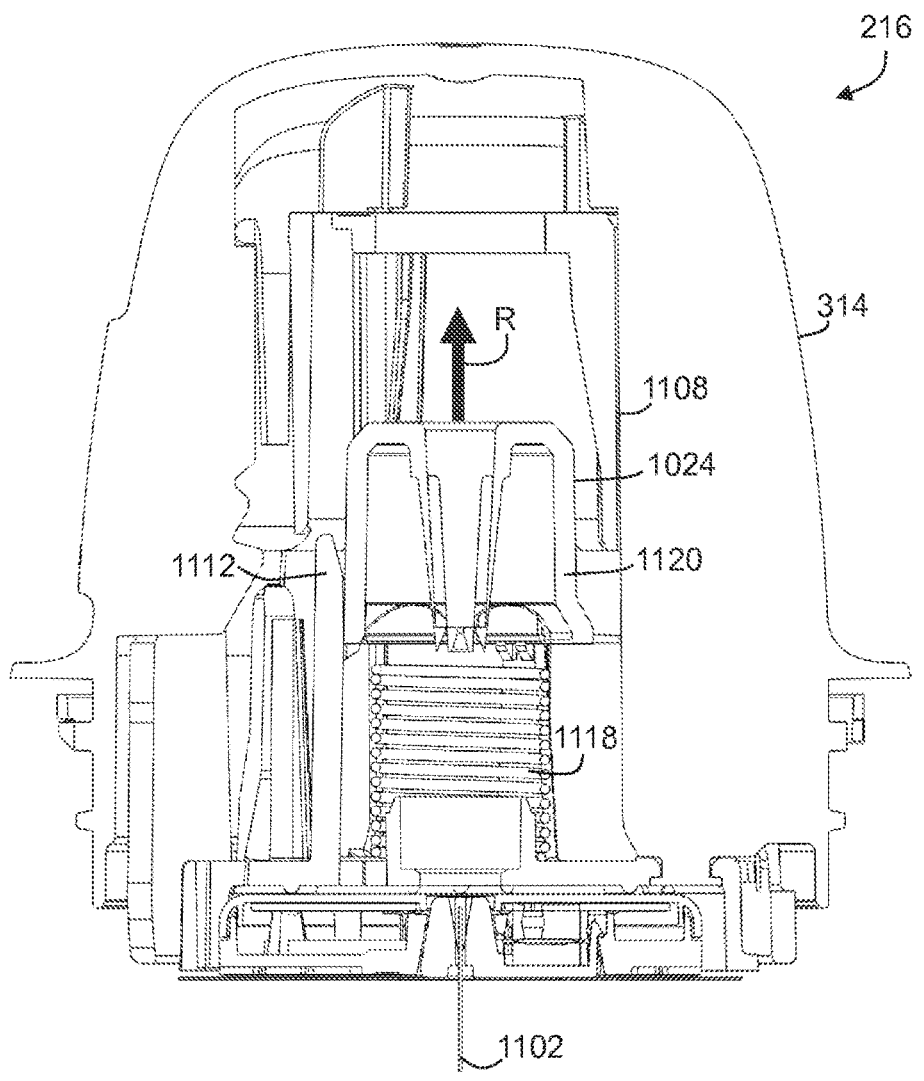

In FIG. 39C, sensor 1102 and sharp 1030 have reached full insertion depth. In so doing, the carrier arms 1112 clear the upper guide section 1108 inner diameter. Then, the compressed force of the coil return spring 1118 drives angled stop surfaces 1114 radially outward, releasing force to drive the sharp carrier 1102 of the sharp retraction assembly 1024 to pull the (slotted or otherwise configured) sharp 1030 out of the user and off of the sensor 1102 as indicated by the arrow R in FIG. 39D.

Figure 39E:
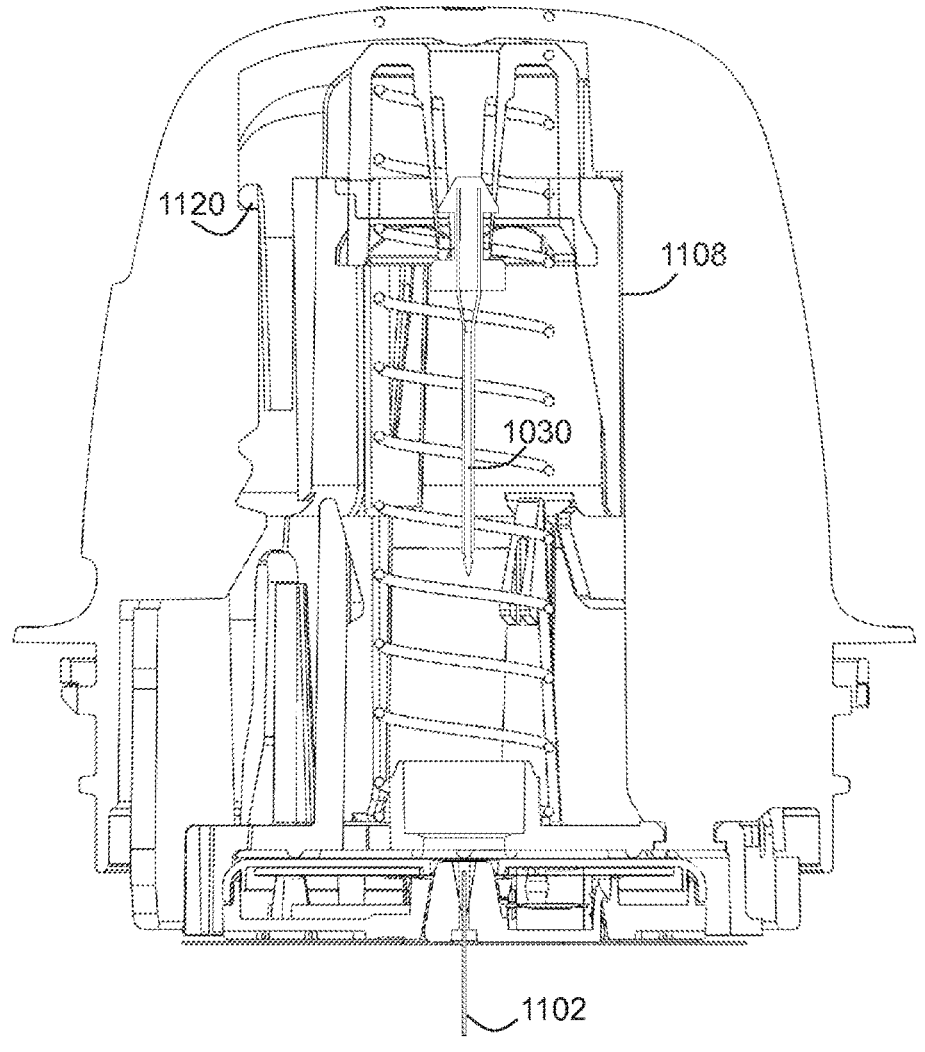
Figure 39F:
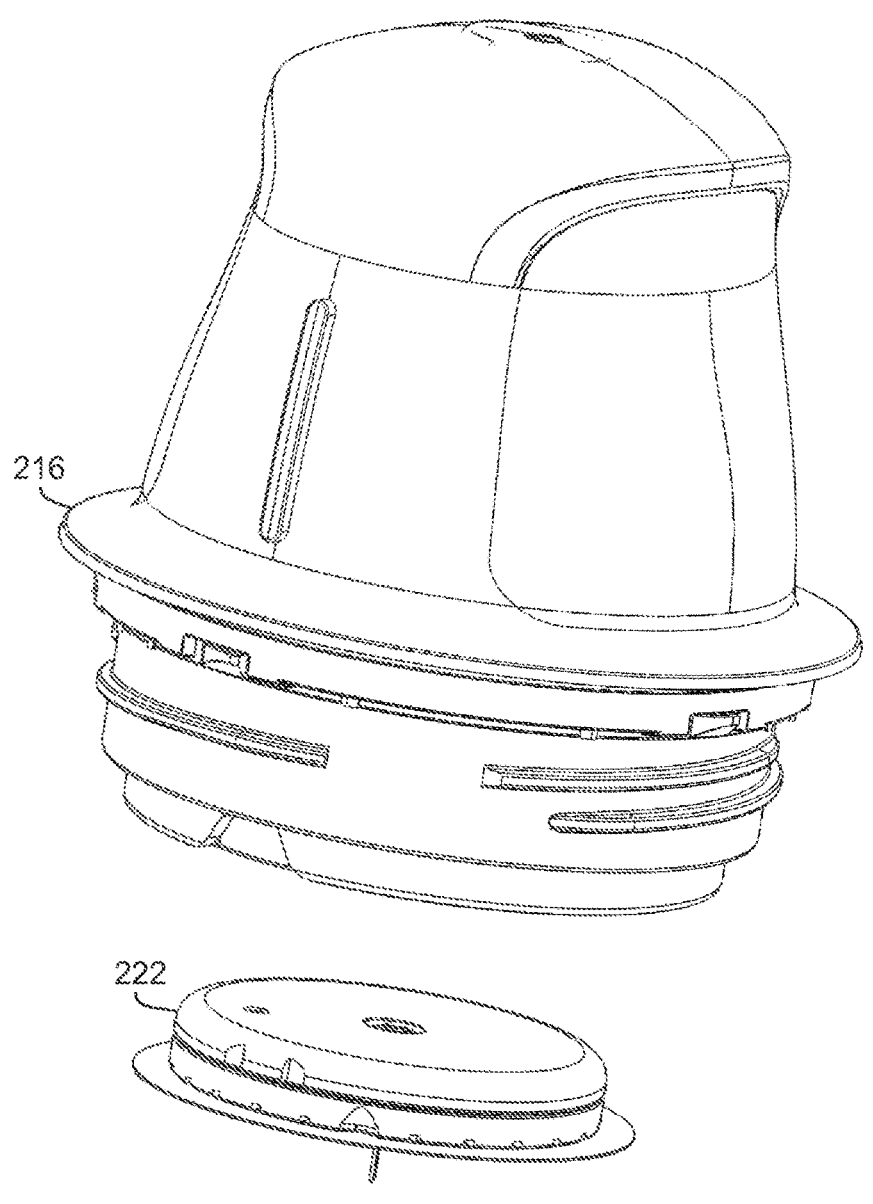

With the sharp 1030 fully retracted as shown in FIG. 39E, the upper guide section 1108 of the sheath 318 is set with a final locking feature 1120. As shown in FIG. 39F, the spent applicator assembly 216 is removed from the insertion site, leaving behind the sensor control device 222, and with the sharp 1030 secured safely inside the applicator assembly 216. The spent applicator assembly 216 is now ready for disposal.

Operation of the applicator 216 when applying the sensor control device 222 is designed to provide the user with a sensation that both the insertion and retraction of the sharp 1030 is performed automatically by the internal mechanisms of the applicator 216. In other words, the present invention avoids the user experiencing the sensation that he is manually driving the sharp 1030 into his skin. Thus, once the user applies sufficient force to overcome the resistance from the detent features of the applicator 216, the resulting actions of the applicator 216 are perceived to be an automated response to the applicator being "triggered." The user does not perceive that he is supplying additional force to drive the sharp 1030 to pierce his skin despite that all the driving force is provided by the user and no additional biasing/driving means are used to insert the sharp 1030. As detailed above in FIG. 39C, the retraction of the sharp 1030 is automated by the coil return spring 1118 of the applicator 216.

With respect to any of the applicator embodiments described herein, as well as any of the components thereof, including but not limited to the sharp, sharp module and sensor module embodiments, those of skill in the art will understand that said embodiments can be dimensioned and configured for use with sensors configured to sense an analyte level in a bodily fluid in the epidermis, dermis, or subcutaneous tissue of a subject. In some embodiments, for example, sharps and distal portions of analyte sensors disclosed herein can both be dimensioned and configured to be positioned at a particular end-depth (i.e., the furthest point of penetration in a tissue or layer of the subject's body, e.g., in the epidermis, dermis, or subcutaneous tissue). With respect to some applicator embodiments, those of skill in the art will appreciate that certain embodiments of sharps can be dimensioned and configured to be positioned at a different end-depth in the subject's body relative to the final end-depth of the analyte sensor. In some embodiments, for example, a sharp can be positioned at a first end-depth in the subject's epidermis prior to retraction, while a distal portion of an analyte sensor can be positioned at a second end-depth in the subject's dermis. In other embodiments, a sharp can be positioned at a first end-depth in the subject's dermis prior to retraction, while a distal portion of an analyte sensor can be positioned at a second end-depth in the subject's subcutaneous tissue. In still other embodiments, a sharp can be positioned at a first end-depth prior to retraction and the analyte sensor can be positioned at a second end-depth, wherein the first end-depth and second end-depths are both in the same layer or tissue of the subject's body.

Additionally, with respect to any of the applicator embodiments described herein, those of skill in the art will understand that an analyte sensor, as well as one or more structural components coupled thereto, including but not limited to one or more spring-mechanisms, can be disposed within the applicator in an off-center position relative to one or more axes of the applicator. In some applicator embodiments, for example, an analyte sensor and a spring mechanism can be disposed in a first off-center position relative to an axis of the applicator on a first side of the applicator, and the sensor electronics can be disposed in a second off-center position relative to the axis of the applicator on a second side of the applicator. In other applicator embodiments, the analyte sensor, spring mechanism, and sensor electronics can be disposed in an off-center position relative to an axis of the applicator on the same side. Those of skill in the art will appreciate that other permutations and configurations in which any or all of the analyte sensor, spring mechanism, sensor electronics, and other components of the applicator are disposed in a centered or off-centered position relative to one or more axes of the applicator are possible and fully within the scope of the present disclosure.

A number of deflectable structures are described herein, including but not limited to deflectable detent snaps 1402, deflectable locking arms 1412, sharp carrier lock arms 1524, sharp retention arms 1618, and module snaps 2202. These deflectable structures are composed of a resilient material such as plastic or metal (or others) and operate in a manner well known to those of ordinary skill in the art. The deflectable structures each has a resting state or position that the resilient material is biased towards. If a force is applied that causes the structure to deflect or move from this resting state or position, then the bias of the resilient material will cause the structure to return to the resting state or position once the force is removed (or lessened). In many instances these structures are configured as arms with detents, or snaps, but other structures or configurations can be used that retain the same characteristics of deflectability and ability to return to a resting position, including but not limited to a leg, a clip, a catch, an abutment on a deflectable member, and the like.

Additional details of suitable devices, systems, methods, components and the operation thereof along with related features are set forth in International Publication No. WO2018/136898 to Rao et. al., International Publication No. WO2019/236850 to Thomas et. al., International Publication No. WO2019/236859 to Thomas et. al., International Publication No. WO2019/236876 to Thomas et. al., and U.S. Patent Publication No. 2020/0196919, filed Jun. 6, 2019, each of which is incorporated by reference in its entirety herein. Further details regarding embodiments of applicators, their components, and variants thereof, are described in U.S. Patent Publication Nos. 2013/0150691, 2016/0331283, and 2018/0235520, all of which are incorporated by reference herein in their entireties and for all purposes. Further details regarding embodiments of sharp modules, sharps, their components, and variants thereof, are described in U.S. Patent Publication No. 2014/0171771, which is incorporated by reference herein in its entirety and for all purposes.

It should be noted that all features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. Thus, the foregoing description of specific embodiments of the disclosed subject matter has been presented for purposes of illustration and description. It is explicitly acknowledged that express recitation of every possible combination and substitution is overly burdensome, especially given that the permissibility of each and every such combination and substitution will be readily recognized by those of ordinary skill in the art.

While the embodiments are susceptible to various modifications and alternative forms, specific examples thereof have been shown in the drawings and are herein described in detail. It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents. Furthermore, any features, functions, steps, or elements of the embodiments may be recited in or added to the claims, as well as negative limitations that define the inventive scope of the claims by features, functions, steps, or elements that are not within that scope.

What is claimed is:

1. A method of assembling an on-body sensor assembly comprising a printed circuit board (PCB), a shell, and a sensor subassembly, the sensor subassembly comprising a sensor, a mount, a collar, and a sensor cap, the method comprising:
    dispensing a first adhesive on an interior surface of the mount, the first adhesive configured to secure the PCB to the mount;
    after dispensing the first adhesive, aligning the PCB with the sensor and the sensor subassembly and loading the PCB onto the mount of the sensor subassembly;
    curing the first adhesive to secure the PCB to the mount;
    dispensing a second adhesive onto an outer diameter of the mount and inner diameter of the collar of the sensor subassembly;
    attaching the shell to the sensor subassembly; and
    curing the second adhesive to form the on-body sensor assembly.

2. The method of claim 1, wherein the PCB is a flexible PCB and the method further comprises folding the PCB to fit a footprint of the on-body sensor assembly.

3. The method of claim 2, wherein dispensing the first adhesive further comprises dispensing the first adhesive at a location of the fold, a battery location, or a PCB connector location.

4. The method of claim 1, wherein the PCB comprises a radio component and the method further comprises writing data to the radio component of the PCB by:
    reading sensor data from the sensor subassembly, PCB, a shell, or a mount carrying the sensor subassembly; and
    writing the sensor data to the radio component of the PCB.

5. The method of claim 1, wherein dispensing the second adhesive onto the outer diameter of the mount and inner diameter of the collar of the sensor subassembly comprises:
    tilting the mount along an axis to a predetermined angle;
    dispensing the second adhesive to the inner diameter of the collar of the sensor subassembly;
    returning the mount to a substantially horizontal position by tilting the mount along the axis; and
    dispensing the second adhesive to the outer diameter of the mount.

6. The method of claim 1, further comprising testing the on-body sensor assembly for leaks using a pressure-decay leak test, vacuum-decay leak test, tracer gas leak test, signature analysis test, or mass-flow leak test.

7. The method of claim 6, further comprising discarding the on-body sensor assembly when leaks are detected that exceed a predetermined threshold.

8. The method of claim 1, wherein the first adhesive or the second adhesive is a chemically-curable adhesive, and the method further comprises curing the first adhesive or the second adhesive by exposing the adhesive to one or more chemical bonding catalysts.

9. The method of claim 1, the first adhesive or the second adhesive is a heat-curable adhesive, and the method further comprises curing the first adhesive or the second adhesive by exposing the adhesive to heat suitable to cure the first adhesive or second adhesive.

10. The method of claim 1, wherein the first adhesive or the second adhesive is an ultraviolet (UV)-curable adhesive, and the method further comprises curing the first adhesive or the second adhesive using one or more UV light sources.

11. The method of claim 10, wherein the one or more UV light sources include a UV light emitting diode (LED) with light pipe and multiple angled spot LEDs.

12. The method of claim 1, further comprising loading the collar onto the mount.

13. The method of claim 1, wherein the method further comprises:

coupling a sharp hub to the mount, the sharp hub including a sharp;

dispensing adhesive to a top surface of the sharp hub; and curing the adhesive to seal the sharp hub.

14. The method of claim 1, wherein the mount is tilted to a first predetermined angle before the first adhesive is dispensed and the mount is tilted to a second predetermined angle before the second adhesive is dispensed.

15. The method of claim 1, wherein the first or second adhesive is an aerobically-curable adhesive.

16. The method of claim 1, wherein aligning the PCB with the sensor and the sensor subassembly comprises aligning an aperture of the PCB with the sensor and a circumference of the PCB with the mount.

* * * * *